(12) United States Patent
Moskowitz et al.

(10) Patent No.: US 12,295,972 B2
(45) Date of Patent: *May 13, 2025

(54) METHODS USING FREEZE-DRIED PLATELET DERIVATIVE COMPOSITIONS FOR RESTORING HEMOSTASIS IN A SUBJECT

(71) Applicant: Cellphire, Inc., Rockville, MD (US)

(72) Inventors: Keith Andrew Moskowitz, Westfield, IN (US); Braden Carl Ishler, Montgomery Village, MD (US); William Matthew Dickerson, Washington, DC (US); Narendra Nath Tandon, Gaithersburg, MD (US); Amber Nicole Lee, Montgomery Village, MD (US); Stephen Edward Amos, Buckeystown, MD (US); Rafael Jorda, Merignac (FR); Michael Alexander Mathews, Arlington, VA (US)

(73) Assignee: Cellphire, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/810,381

(22) Filed: Aug. 20, 2024

(65) Prior Publication Data

US 2024/0408141 A1 Dec. 12, 2024

Related U.S. Application Data

(63) Continuation of application No. 17/674,770, filed on Feb. 17, 2022.

(60) Provisional application No. 63/264,227, filed on Nov. 17, 2021, provisional application No. 63/276,420, filed on Nov. 5, 2021, provisional application No. 63/275,937, filed on Nov. 4, 2021, provisional application No. 63/150,338, filed on Feb. 17, 2021.

(51) Int. Cl.
*A61K 35/19* (2015.01)
*A61K 9/19* (2006.01)
*A61P 7/04* (2006.01)

(52) U.S. Cl.
CPC ............... *A61K 35/19* (2013.01); *A61K 9/19* (2013.01); *A61P 7/04* (2018.01)

(58) Field of Classification Search
None
See application file for complete search history.

(56) References Cited

U.S. PATENT DOCUMENTS

| | | |
|---|---|---|
| 3,928,566 A | 12/1975 | Briggs et al. |
| 3,932,943 A | 1/1976 | Briggs et al. |
| 4,059,967 A | 11/1977 | Rowe et al. |
| 4,157,383 A | 6/1979 | Johannsen et al. |
| 4,455,299 A | 6/1984 | Grode |
| 4,481,189 A | 11/1984 | Prince |
| 4,670,013 A | 6/1987 | Barnes et al. |
| 4,865,871 A | 9/1989 | Livesey et al. |
| 4,994,367 A | 2/1991 | Bode et al. |
| 5,059,518 A | 10/1991 | Kortright et al. |
| 5,213,814 A | 5/1993 | Goodrich, Jr. et al. |
| 5,332,578 A | 7/1994 | Chao |
| 5,364,756 A | 11/1994 | Livesey et al. |
| 5,423,738 A | 6/1995 | Robinson et al. |
| 5,571,801 A | 11/1996 | Segall et al. |
| 5,622,867 A | 4/1997 | Livesey et al. |
| 5,656,498 A | 8/1997 | Iijima et al. |
| 5,656,598 A | 8/1997 | Dunstan et al. |
| 5,723,281 A | 3/1998 | Segall et al. |
| 5,736,313 A | 4/1998 | Spargo et al. |
| 5,759,542 A | 6/1998 | Gurewich |
| 5,800,978 A | 9/1998 | Goodrich, Jr. et al. |
| 5,817,381 A | 10/1998 | Chen et al. |
| 5,827,741 A | 10/1998 | Beattie et al. |
| 5,919,614 A | 7/1999 | Livesey et al. |
| 5,958,670 A | 9/1999 | Goodrich, Jr. et al. |
| 5,993,804 A | 11/1999 | Read et al. |
| 6,127,111 A | 10/2000 | Braun |
| 6,211,575 B1 | 4/2001 | Hansford |
| 6,221,575 B1 | 4/2001 | Roser et al. |

(Continued)

FOREIGN PATENT DOCUMENTS

| | | |
|---|---|---|
| CA | 1261259 A | 9/1989 |
| CA | 2097063 C | 6/1992 |

(Continued)

OTHER PUBLICATIONS

Arruda, V.R., Haematologica. Jul. 2015;100(7):849-850. doi: 10.3324/haematol.2015.129858 PMCID: PMC4486216 PMID: 26130509.*
Ramstrom et al., Platelets. 2010;21(4):289-96. doi: 10.3109/09537101003660564. PMID: 20230207—abstract only.*
Dennison, "A Simple and Universal Method for Making up Buffer Solutions", Biochem Edu., vol. 16, No. 4, 1988, XP023535876, DOI: 10.1016/0307-4412(88)90123-9.
diapharma.com [online], "DiaPhannaProductList," retrieved on Feb. 18, 2021, retrieved from URL, 4 pages.

(Continued)

*Primary Examiner* — Michael Szperka
(74) *Attorney, Agent, or Firm* — Double Helix Law; Emanuel Vacchiano

(57) ABSTRACT

Provided herein are methods and compositions for treating a coagulopathy in a subject. Such methods can include administering to the subject in need thereof, for example because they have been administered an anticoagulant agent, an effective amount of a composition including platelets, or in illustrative embodiments platelet derivatives, and in further illustrative embodiments freeze-dried platelet derivatives (FDPDs). Various properties of exemplary embodiments of such methods and platelet derivatives used therein, as well as numerous additional aspects and embodiments are provided herein.

30 Claims, 86 Drawing Sheets

(56) References Cited

U.S. PATENT DOCUMENTS

| | | |
|---|---|---|
| 6,372,423 B1 | 4/2002 | Braun |
| 6,596,296 B1 | 7/2003 | Nelson et al. |
| 6,653,062 B1 | 11/2003 | DePablo et al. |
| 6,723,497 B2 | 4/2004 | Wolkers et al. |
| 6,770,478 B2 | 8/2004 | Crowe et al. |
| 6,833,236 B1 | 12/2004 | Stienstra |
| 6,858,222 B2 | 2/2005 | Nelson et al. |
| 7,033,603 B2 | 4/2006 | Nelson et al. |
| 7,169,606 B2 | 1/2007 | DePablo et al. |
| 7,514,095 B2 | 4/2009 | Nelson et al. |
| 7,811,558 B2 | 10/2010 | Ho et al. |
| 8,097,403 B2 | 1/2012 | Ho et al. |
| 8,486,617 B2 | 7/2013 | Ho et al. |
| 8,486,619 B2 | 7/2013 | Miller et al. |
| 8,529,961 B2 | 9/2013 | Campbell et al. |
| 8,877,060 B2 | 11/2014 | Sehgal |
| 8,900,209 B2 | 12/2014 | Rosati |
| 9,402,866 B2 | 8/2016 | Radwanski et al. |
| 9,545,379 B2 | 1/2017 | Liu et al. |
| 9,863,699 B2 | 1/2018 | Corbin et al. |
| 9,878,011 B2 | 1/2018 | Landrigan et al. |
| 9,950,035 B2 | 4/2018 | Binder et al. |
| 10,400,017 B2 | 9/2019 | Higgins et al. |
| 10,441,634 B2 | 10/2019 | Landrigan et al. |
| 10,539,367 B2 | 1/2020 | Corbin et al. |
| 10,793,327 B2 | 10/2020 | Weimer et al. |
| 10,843,100 B2 | 11/2020 | Khan et al. |
| 10,969,171 B2 | 4/2021 | Corbin et al. |
| 10,976,105 B2 | 4/2021 | Corbin et al. |
| 11,052,045 B2 | 7/2021 | Liu et al. |
| 11,529,587 B2 | 12/2022 | Montgomery et al. |
| 11,701,388 B2 * | 7/2023 | Moskowitz .......... C12N 5/0644 424/93.72 |
| 11,752,468 B2 | 9/2023 | Montgomery et al. |
| 11,767,511 B2 | 9/2023 | Moskowitz et al. |
| 11,813,572 B2 | 11/2023 | Montgomery et al. |
| 12,208,122 B2 | 1/2025 | Moskowitz et al. |
| 2001/0019819 A1 | 9/2001 | Wolkers et al. |
| 2001/0028880 A1 | 10/2001 | Fisher et al. |
| 2001/0046487 A1 | 11/2001 | Roser et al. |
| 2002/0009500 A1 | 1/2002 | Wolkers et al. |
| 2002/0076445 A1 | 6/2002 | Crowe et al. |
| 2003/0022333 A1 | 1/2003 | Bronshtein |
| 2003/0073238 A1 | 4/2003 | Dzekunov et al. |
| 2003/0148449 A1 | 8/2003 | Kuliopulos et al. |
| 2003/0157475 A1 | 8/2003 | Schenk |
| 2004/0136974 A1 | 7/2004 | Crowe et al. |
| 2004/0147024 A1 | 7/2004 | Crowe et al. |
| 2004/0152964 A1 | 8/2004 | Crowe et al. |
| 2004/0185524 A1 | 9/2004 | Crowe et al. |
| 2004/0265293 A1 | 12/2004 | Crowe et al. |
| 2005/0028559 A1 | 2/2005 | Hiromatsu et al. |
| 2005/0048460 A1 | 3/2005 | Crowe et al. |
| 2005/0074402 A1 | 4/2005 | Cagnolini et al. |
| 2005/0181978 A1 | 8/2005 | Rojkjaer et al. |
| 2005/0191286 A1 | 9/2005 | Gandy |
| 2005/0222029 A1 | 10/2005 | Bartel et al. |
| 2006/0034809 A1 | 2/2006 | Ho et al. |
| 2006/0035383 A1 | 2/2006 | Ho et al. |
| 2006/0051731 A1 | 3/2006 | Ho et al. |
| 2006/0223050 A1 | 10/2006 | Crowe et al. |
| 2007/0087061 A1 | 4/2007 | Drake et al. |
| 2007/0166389 A1 | 7/2007 | Bakaltcheva |
| 2007/0178104 A1 | 8/2007 | Awdalla |
| 2007/0243137 A1 | 10/2007 | Hainfeld |
| 2007/0243178 A1 | 10/2007 | Ho et al. |
| 2007/0248612 A1 | 10/2007 | Wilson |
| 2007/0249047 A1 | 10/2007 | McKenna et al. |
| 2008/0064628 A1 | 3/2008 | Goodall et al. |
| 2008/0145834 A1 | 6/2008 | Ho et al. |
| 2008/0286366 A1 | 11/2008 | Fischer et al. |
| 2008/0299212 A1 | 12/2008 | Kim et al. |
| 2009/0035289 A1 | 2/2009 | Wagner et al. |
| 2009/0111118 A1 | 4/2009 | Mylvaganam et al. |
| 2009/0175905 A1 | 7/2009 | Tseng et al. |
| 2009/0299212 A1 | 12/2009 | Principe et al. |
| 2010/0055067 A1 | 3/2010 | Park |
| 2010/0135969 A1 | 6/2010 | Mishra |
| 2010/0159023 A1 | 6/2010 | Bjornstrup et al. |
| 2010/0190717 A1 | 7/2010 | Bevec et al. |
| 2010/0196461 A1 | 8/2010 | Simpkins |
| 2010/0267928 A1 | 10/2010 | Heckl |
| 2010/0273141 A1 | 10/2010 | Bakaltcheva et al. |
| 2011/0008804 A1 | 1/2011 | Kain et al. |
| 2011/0027257 A1 | 2/2011 | Burnouf et al. |
| 2011/0183311 A1 | 7/2011 | Ho et al. |
| 2011/0189151 A1 | 8/2011 | Stossel et al. |
| 2012/0009221 A1 | 1/2012 | Hoerr et al. |
| 2012/0028236 A1 | 2/2012 | Sehgal |
| 2012/0095085 A1 | 4/2012 | Layzer et al. |
| 2012/0100522 A1 | 4/2012 | Saghbini et al. |
| 2012/0125847 A1 | 5/2012 | Sehgal |
| 2012/0141434 A1 | 6/2012 | Peled et al. |
| 2012/0156306 A1 | 6/2012 | Weissman et al. |
| 2012/0264815 A1 | 10/2012 | Sullenger et al. |
| 2012/0276581 A1 | 11/2012 | Arav et al. |
| 2012/0321722 A1 | 12/2012 | Liu et al. |
| 2013/0059380 A1 | 3/2013 | Ho et al. |
| 2013/0061849 A1 | 3/2013 | Lemper |
| 2013/0122107 A1 | 5/2013 | Bakaltcheva |
| 2013/0195959 A1 | 8/2013 | Patel |
| 2013/0210903 A1 | 8/2013 | Sullenger et al. |
| 2014/0037750 A1 | 2/2014 | Radwanski et al. |
| 2014/0065120 A1 | 3/2014 | Nichols et al. |
| 2014/0329323 A1 | 11/2014 | Nygaard et al. |
| 2014/0330226 A1 | 11/2014 | Coffey |
| 2014/0356948 A1 | 12/2014 | Jeon et al. |
| 2015/0064259 A1 | 3/2015 | Simpkins |
| 2015/0306212 A1 | 10/2015 | Kahvejian et al. |
| 2015/0313943 A1 | 11/2015 | Kishikawa et al. |
| 2015/0313944 A1 | 11/2015 | Feng et al. |
| 2015/0361453 A1 | 12/2015 | Gresele et al. |
| 2016/0082044 A1 | 3/2016 | Liu et al. |
| 2016/0206783 A1 | 7/2016 | Dietz et al. |
| 2016/0219870 A1 | 8/2016 | Wang et al. |
| 2016/0231338 A1 | 8/2016 | Aster et al. |
| 2016/0235781 A1 | 8/2016 | Emanuele |
| 2016/0324897 A1 | 11/2016 | Ingber et al. |
| 2017/0198335 A1 | 7/2017 | Muller et al. |
| 2017/0274012 A1 | 9/2017 | Bode et al. |
| 2017/0333593 A1 | 11/2017 | Willard et al. |
| 2018/0009874 A1 | 1/2018 | Wilcox et al. |
| 2018/0070581 A1 | 3/2018 | Tarrand et al. |
| 2018/0092348 A1 | 4/2018 | She et al. |
| 2018/0169027 A1 | 6/2018 | Zhang et al. |
| 2018/0169139 A1 | 6/2018 | Feuerstein et al. |
| 2018/0235894 A1 | 8/2018 | Gu et al. |
| 2018/0311176 A1 | 11/2018 | Ozsolak et al. |
| 2018/0312903 A1 | 11/2018 | Grölz et al. |
| 2019/0008143 A1 | 1/2019 | Dee et al. |
| 2019/0076478 A1 | 3/2019 | Hale et al. |
| 2019/0192564 A1 | 6/2019 | Hijazi et al. |
| 2020/0046771 A1 | 2/2020 | Kuhn et al. |
| 2020/0060262 A1 | 2/2020 | Stolla |
| 2020/0076455 A1 | 3/2020 | Sharf |
| 2020/0078407 A1 | 3/2020 | Bhattacharya et al. |
| 2020/0093853 A1 | 3/2020 | Feuerstein et al. |
| 2020/0206143 A1 | 7/2020 | Moskowitz et al. |
| 2020/0208109 A1 | 7/2020 | Moskowitz et al. |
| 2020/0208110 A1 | 7/2020 | Lee et al. |
| 2020/0224164 A1 | 7/2020 | Moskowitz et al. |
| 2020/0281980 A1 | 9/2020 | Willard et al. |
| 2020/0291356 A1 | 9/2020 | Jorda et al. |
| 2020/0346167 A1 | 11/2020 | Montgomery et al. |
| 2021/0046120 A1 | 2/2021 | Moskowitz et al. |
| 2021/0046121 A1 | 2/2021 | Moskowitz et al. |
| 2021/0069240 A1 | 3/2021 | Jorda et al. |
| 2021/0100846 A1 | 4/2021 | Lee et al. |
| 2021/0180016 A1 | 6/2021 | Moskowitz et al. |
| 2021/0189341 A1 | 6/2021 | Sheik et al. |
| 2021/0299179 A1 | 9/2021 | Moskowitz et al. |
| 2021/0308066 A1 | 10/2021 | Moskowitz et al. |
| 2021/0308185 A1 | 10/2021 | Moskowitz et al. |
| 2021/0315935 A1 | 10/2021 | Moskowitz et al. |

(56) References Cited

U.S. PATENT DOCUMENTS

| | | |
|---|---|---|
| 2021/0353680 A1 | 11/2021 | Bhattacharya et al. |
| 2021/0368782 A1 | 12/2021 | Dee et al. |
| 2022/0168353 A1 | 6/2022 | Moskowitz et al. |
| 2022/0211029 A1 | 7/2022 | Moskowitz et al. |
| 2022/0273724 A1 | 9/2022 | Moskowitz et al. |
| 2022/0279777 A1 | 9/2022 | Moskowitz et al. |
| 2023/0112136 A1 | 4/2023 | Jorda et al. |
| 2023/0149467 A1 | 5/2023 | Montgomery et al. |
| 2023/0149468 A1 | 5/2023 | Antebi et al. |
| 2023/0158455 A1 | 5/2023 | Montgomery et al. |
| 2023/0226493 A1 | 7/2023 | Montgomery et al. |
| 2023/0248771 A1 | 8/2023 | Moskowitz et al. |
| 2023/0248772 A1 | 8/2023 | Willard |
| 2023/0285465 A1 | 9/2023 | Moskowitz et al. |
| 2023/0346839 A1 | 11/2023 | Bhattacharya et al. |
| 2023/0356150 A1 | 11/2023 | Montgomery et al. |
| 2023/0383258 A1 | 11/2023 | Moskowitz et al. |
| 2024/0066065 A1 | 2/2024 | Moskowitz et al. |
| 2024/0139252 A1 | 5/2024 | Moskowitz et al. |
| 2024/0254443 A1 | 8/2024 | Sheik et al. |
| 2024/0277771 A1 | 8/2024 | Moskowitz et al. |
| 2024/0307453 A1 | 9/2024 | Moskowitz et al. |
| 2025/0000908 A1 | 1/2025 | Moskowitz et al. |

FOREIGN PATENT DOCUMENTS

| | | |
|---|---|---|
| CA | 2136848 A1 | 12/1993 |
| CA | 2393315 A1 | 6/2001 |
| CA | 2840568 A1 | 1/2013 |
| CA | 3053041 A1 | 2/2020 |
| CN | 101072506 A | 11/2007 |
| CN | 103524613 A | 1/2014 |
| CN | 103907595 A | 7/2014 |
| CN | 108715834 A | 10/2018 |
| CN | 109942687 A | 6/2019 |
| EP | 0397890 A1 | 11/1990 |
| EP | 0815866 A2 | 1/1998 |
| EP | 0967862 B1 | 1/2000 |
| EP | 1374890 A2 | 1/2004 |
| EP | 1652538 A2 | 5/2006 |
| EP | 1784639 A2 | 5/2007 |
| EP | 3681518 A1 | 7/2020 |
| EP | 3307283 B1 | 9/2020 |
| EP | 3551198 B1 | 2/2022 |
| JP | H08109136 A | 4/1996 |
| JP | 2005053841 A | 3/2005 |
| JP | 2008509924 A | 4/2008 |
| JP | 2012143554 A | 8/2012 |
| WO | 1990005461 A1 | 5/1990 |
| WO | 9012581 A1 | 11/1990 |
| WO | 1991017655 A1 | 11/1991 |
| WO | 1992008349 A1 | 5/1992 |
| WO | 1993000806 A1 | 1/1993 |
| WO | 1993023997 A1 | 12/1993 |
| WO | 9428950 A1 | 12/1994 |
| WO | 1998034478 A1 | 8/1998 |
| WO | 1999055346 A1 | 11/1999 |
| WO | 2001007921 A2 | 2/2001 |
| WO | 2001058266 A1 | 8/2001 |
| WO | 2003014305 A2 | 2/2003 |
| WO | 2003039582 A1 | 5/2003 |
| WO | 2003090839 A1 | 11/2003 |
| WO | 2004050896 A2 | 6/2004 |
| WO | 2004078187 A1 | 9/2004 |
| WO | 2005002499 A2 | 1/2005 |
| WO | 2005020893 A2 | 3/2005 |
| WO | 2005021706 A2 | 3/2005 |
| WO | 2005077299 A1 | 8/2005 |
| WO | 2005002499 A3 | 11/2005 |
| WO | 2006020773 A2 | 2/2006 |
| WO | 2006059329 A1 | 6/2006 |
| WO | 2004050896 A3 | 12/2006 |
| WO | 2006020773 A3 | 7/2007 |
| WO | 2010046949 A1 | 4/2010 |
| WO | 2011020107 A2 | 2/2011 |
| WO | 2011020107 A3 | 10/2011 |
| WO | 2011149110 A1 | 12/2011 |
| WO | 2012018484 A2 | 4/2012 |
| WO | 2012074637 A2 | 6/2012 |
| WO | 2014051537 A1 | 4/2014 |
| WO | 2014055949 A1 | 4/2014 |
| WO | 2014066142 A1 | 5/2014 |
| WO | 2014084263 A1 | 6/2014 |
| WO | 2014118817 A2 | 8/2014 |
| WO | 2014118817 A3 | 10/2014 |
| WO | 2015073587 A2 | 5/2015 |
| WO | 2015191632 A1 | 12/2015 |
| WO | 2016014854 A1 | 1/2016 |
| WO | 2016057041 A1 | 4/2016 |
| WO | 2016077682 A1 | 5/2016 |
| WO | 2016141325 A1 | 9/2016 |
| WO | 2016201081 A1 | 12/2016 |
| WO | 2016205144 A1 | 12/2016 |
| WO | 2017040238 A1 | 3/2017 |
| WO | 2017123539 A1 | 7/2017 |
| WO | 2018084228 A1 | 5/2018 |
| WO | 2018106250 A1 | 6/2018 |
| WO | 2019055683 A1 | 3/2019 |
| WO | 2020023905 A1 | 1/2020 |
| WO | 2020056009 A1 | 3/2020 |
| WO | 2020112963 A1 | 6/2020 |
| WO | 2020113035 A1 | 6/2020 |
| WO | 2020113090 A1 | 6/2020 |
| WO | 2020113101 A1 | 6/2020 |
| WO | 2020165152 A1 | 8/2020 |
| WO | 2020186193 A1 | 9/2020 |
| WO | 2020219557 A1 | 10/2020 |
| WO | 2020227149 A1 | 11/2020 |
| WO | 2021011857 A1 | 1/2021 |
| WO | 2021034716 A1 | 2/2021 |
| WO | 2021034719 A1 | 2/2021 |
| WO | 2021046409 A1 | 3/2021 |
| WO | 2021108538 A1 | 6/2021 |
| WO | 2021108539 A1 | 6/2021 |
| WO | 2021158622 A1 | 8/2021 |
| WO | 2021158625 A1 | 8/2021 |
| WO | 2021158645 A1 | 8/2021 |
| WO | 2021158646 A1 | 8/2021 |
| WO | 2021232015 A1 | 11/2021 |
| WO | 2022103861 A1 | 5/2022 |
| WO | 2022178177 A1 | 8/2022 |
| WO | 2022178191 A1 | 8/2022 |
| WO | 2022178177 A4 | 10/2022 |
| WO | 2023081804 A1 | 5/2023 |
| WO | 2023220694 A1 | 11/2023 |
| WO | 2023220739 A1 | 11/2023 |
| WO | 2024192173 A1 | 9/2024 |
| WO | 2024249704 A1 | 12/2024 |

OTHER PUBLICATIONS

Dickerson et al., "Lyophilized Human Platelets Restore Hemostasis in the Presence of the P2Y12 Inhibitors Cangrelor, Ticagrelor and Clopidogrel", Cellphire Therapeutics Inc., Rockville, MD, 7 pages, Poster.

Dickerson et al., "Lyophilized Human Platelets Restore Hemostasis in the Presence of the P2Y12 Inhibitors Cangrelor, Ticagrelor and Clopidogre", American Society of Hematology, Blood, 3.22 Disorders of Coagulation or Fibrinolysis, Nov. 5, 2020, 6 pages.

Dickerson et al., "Lyophilized Human Platelets Restore Hemostasis in the Presence of the P2Y12 Inhibitors Cangrelor, Ticagrelor and Clopidogrel", Cellphire, Inc., 2020, 6 pages, Poster.

Dickerson et al., "Lyophilized human platelets support thrombosis unlike normal platelets in the presence of GPIIb/IIIa antagonists", Cellphire Therapeutics, ISth Virtual Congress, Jul. 2021, 1 page, Poster.

Dickerson et al., "Lyophilized human platelets support thrombosis unlike normal platelets in the presence of GPIIb/IIIa antagonists", Cellphire, Inc., AS-ISTH-2021-01436, 2021. 2 pages, Abstract.

Dickerson et al., "Thrombosomes as a Treatment Option for Low-Dose Heparin Reversal", Cellphire, Inc, Oct. 2020. 1 page, Poster.

(56) References Cited

OTHER PUBLICATIONS

Dickson et al., "A scalable, micropore, platelet rich plasma separation device." Biomedical Microdevices, vol. 14(6), Jul. 2012, pp. 1095-1102. DOI:10.1007/s10544-012-9675-2.
Dielis et al., "Coagulation factors and the protein C system as determinants of thrombin generation in a normal population," J. Thromb. Haemost., 2008, 6:125-131.
Diener, "Antiplatelet agents and randomized trials," Review in Neurological Diseases, 2007, 4(4):177-183.
Dinçer et al., "Effect of taurine on wound healing", Amino Acids, vol. 10, Issue 1, Mar. 1996, pp. 59-71, doi: 10.1007/BF00806093.
Dong, et al., "Ristocetin-dependent, but not botrocetin-dependent, binding of von Willebrand factor to the platelet glycoprotein Ib-IX-V complex correlates with shear-dependent interactions," Blood, 2001, 97:162-+168.
Dumont et al, "Feasibility evaluation of two novel systems for the automated preparation and extended storage of DMSO cryopreserved platelets", Transfusion, vol. 63, No. 8, Jun. 26, 2023, pp. 1554-1562, https://doi.org/10.1111/trf.17464.
Dumont, et. al, "A randomized controlled trial evaluating recovery and survival of 6% dimethyl sulfoxide-frozen autologous platelets in healthy volunteers", Transfusion vol. 53(1), Jan. 2013, pp. 128-137.
Duquesnoy, "HLAMatchmaker: a molecularly based algorithm for histocompatibility determination. I. Description of the algorithm", Human Immunology, vol. 63, Issue 5, May 2002, pp. 339-352, doi.org/10.1016/S0198-8859(02)00382-8.
Durbin et al., "Platelet Extracellular Vesicles as a Therapeutic Agent in Hemorrhagic Shock", Oregon Health & Science University Department of Surgery, Division of Trauma, Sep. 20, 2023, 23 pages.
Eikelboom, et. al., "Combined antiplatelet and anticoagulant therapy clinical benefits and risks", Journal of Thrombosis and Haemostasis, vol. 5, Suppl 1, Jul. 2007, pp. 255-263, DOI: 10.1111/j.1538-7836. 2007.02499.
Etchill, et. al., "Platelet Transfusion in Critical Care and Surgery: Evidence-Based Review of Contemporary Practice and Future Directions", Shock, vol. 47, No. 5, May 1, 2017, pp. 537-549.
Extended European Search Report in EP Appln. No. 05784165.2, date Mar. 26, 2008.
Extended European Search Report in EP Appln. No. 16808270.9, date Nov. 22, 2018.
Extended European Search Report in EP Appln. No. 16842662.5, date Jul. 26, 2019.
Extended European Search Report in EP Appln. No. 16923314.5, date Jun. 18, 2020.
Extended European Search Report in EP Appln. No. 17738796.6, date Jul. 23, 2019.
Extended European Search Report in EP Appln. No. 18856149.2, date May 26, 2021.
Extended European Search Report in EP Appln. No. 19840600.1 date Mar. 25, 2022.
Extended European Search Report in EP Appln. No. 19860896.0 date Jun. 14, 2023.
Extended European Search Report in EP Appln. No. 19888909.9 date Sep. 28, 2022.
Extended European Search Report in EP Appln. No. 19888994.1 date Nov. 7, 2022.
Extended European Search Report in EP Appln. No. 19891082.0 date Sep. 30, 2022.
Extended European Search Report in EP Appln. No. 20769409.2 date Dec. 6, 2022.
Extended European Search Report in EP Appln. No. 20802506.4 date Jan. 4, 2023.
Extended European Search Report in EP Appln. No. 20855485.7 date Sep. 15, 2023.
Extended European Search Report in EP Appln. No. 20855619.1 dated Sep. 15, 2023.
Extended European Search Report in EP Appln. No. 20894004.9 date Nov. 8, 2023.
Fijnheer et al., "Platelet activation during preparation of platelet concentrates: a comparison of the platelet-rich plasma and the buffy coat methods," Transfusion, 1990, 30(7):634-638.
Fischer et al., "Primary and secondary hemostatic functionalities of rehydrated, lyophilized platelets," 2006, Transfusion, 46:1943-1950.
Fischer et al., "The interaction of factor VIIa with rehydrated, lyophilized platelets", Platelets, vol. 19 (3), May 2008, pp. 182-191, DOI:10.1080/09537100701493794.
Fischer et. al., "Thrombus Formation with Rehydrated, Lyophilized Platelets", Hematology (Amsterdam, Netherlands), vol. 7 (6), Dec. 2002, pp. 359-369, DOI:10.1080/1024533021000047954.
Fitzpatrick et al., "A Novel Lyophilized Platelet Derivative Produces Effective Hemostasis in Uncontrolled Bleeding/Shock Model without Systemic Thrombosis", Blood, vol. 118, Issue 21, Nov. 18, 2011, pp. 719-722, doi.org/10.1182/blood.V118.21.719.719.
Fitzpatrick et al., "Freeze-dried platelets: Advancing towards clinical use", Cryobiology, vol. 67, Issue 3, Dec. 2013, p. 420, Abstract, doi.org/10.1016/j.cryobiol.2013.09.086.
Fitzpatrick et al., "Stabilization and preservation of a platelet derived hemostatic agent, Thrombosomes", Cryobiology, vol. 63, Issue 3, Dec. 2011, p. 306, Abstract, doi:10.1016/j.cryobiol.2011. 09.005.
Fitzpatrick et al., "Thrombosomes: a platelet-derived hemostatic agent for control of noncompressible hemorrhage", Transfusion, vol. 53, Jan. 2013 Supplement, pp. 100S-106S, doi: 10.1111/trf. 12043.
Fitzpatrick, "Novel platelet products under development for the treatment of thrombocytopenia or acute hemorrhage", Transfusion and Apheresis Science, vol. 58, Issue 1, Feb. 2019, pp. 7-11, doi: 10.1016/j.transci.2018.12.010.
Gaertner et al., "Migrating platelets are mechano-scavengers that collect and bundle bacteria," Cell, Nov. 30, 2017, 171(6):1368-1382.
Gao et al., "Development of Optimal Techniques for Cryopreservation of Human Platelets: I. Platelet activation during cold storage (at 22 and 8° C.) and cryopreservation", Cryobiology vol. 38(3), May 1999, pp. 225-235, DOI: 10.1006/cryo.1999.2162.
Ghaithi et al., "Evaluation of the Total Thrombus-Formation System (T-TAS): application to human and mouse blood analysis", Platelets, vol. 30, Issue 7, 2019, pp. 893-900, doi: 10.1080/09537104. 2018.1535704.
Gilbert et al., "Platelet-derived microparticles express high affinity receptors for factor VIII.", I.Biol. Chem., 1991, 266:17261-17268.
Giles et al., "A combination of factor Xa and phosphatidylcholine-phosphatidylserine vesicles bypasses factor VIII in vivo", Br. J., Haematol., 1988, 69(4):491-497.
Godier et al., "Management of antiplatelet therapy for non elective invasive procedures of bleeding complications: proposals from the French working group on perioperative haemostasis (GIHP), in collaboration with the French Society of Anaesthesia and Intensive Care Medicine (SFAR)" Anaesthesia, Critical Care and Pain Medicine, vol. 38, Issue 3, Jun. 2019, pp. 289-302, doi: 10.1016/j.accpm. 2018.10.004.
Alexander et at., "A Prospective, Multicenter, Randomized, Open-Label, Phase 2, Parallel, Dose Ranging Multidose Study of Thrombosomes® vs Liquid Stored Platelets (LSP) in Bleeding Thrombocytopenic Patients", Celphire Therapeutics, Inc., NCT04631211, Statistical Analysis Plan, Apr. 2, 2024, 22 pages.
Cid et at., "24-h continuous infusion of platelets for patients with platelet transfusion refractoriness", British Journal of Haematology, vol. 181, No. 3, Mar. 14, 2017, pp. 386-389, doi.org/10.1111/bjh. 14572.
Comont et al., "Platelet transfusion refractoriness in patients with acute myeloid leukemia treated by intensive chemotherapy", Leukemia Research, vol. 61, Oct. 2017, pp. 62-67, doi: 10.1016/j. leukres.2017.08.015.
Fitzpatrick et al., "A Phase 1, Multi-Center, Open-Label, Dose Escalation Study of Thrombosomes in Bleeding Thrombocytopenic Patients in Three Cohorts", ClinicalTrials.gov ID NCT03394755, updated, Cellphire Therapeutics, Inc, Apr. 13, 2023, 34 pages.
Fitzpatrick et al., "A Phase 1, Multi-Center, Open-Label, Dose Escalation Study of Thrombosomes in Bleeding Thrombocytopenic

(56) References Cited

OTHER PUBLICATIONS

Patients in Three Cohorts", ClinicalTrials.gov ID NCT03394755, Cellphire Therapeutics, Inc, Jan. 8, 2018, 6 pages.
Fitzpatrick et al., "A Phase 1, Multi-Center, Open-Label, Dose Escalation Study of Thrombosomes in Bleeding Thrombocytopenic Patients in Three Cohorts", Cellphire Therapeutics, Inc., NCT03394755, Statistical Analysis Plan, Jun. 2, 2020, 34 pages.
Fitzpatrick et al., "A Prospective, Multicenter, Randomized, Open-Label, Phase 2, Parallel, Dose Ranging Multidose Study of Thrombosomes® vs Liquid Stored Platelets (LSP) in Bleeding ThrombocytopenicPatients", CellphireTherapeutics, Inc., Clinical Strudy Protocol, NCT04631211, Mar. 28, 2024, 61 pages.
Fitzpatrick et al., "A Prospective, Multicenter, Randomized, Open-Label, Phase 2, Parallel, Dose Ranging Multidose Study of Thrombosomes® vs Liquid Stored Platelets (LSP) in Bleeding ThrombocytopenicPatients", ClinicalTrials.gov NCT 04631211, Cellphire Therapeutics, Inc., Nov. 10, 2020, 8 pages.
Fitzpatrick et al., "A Prospective, Multicenter, Randomized, Open-Lavel Phase 2, Parallel, Dose Ranging Multidose Study of Thrombosomes vs Liquid Stored Platelets (LSP) in Bleeding Thrombocytopenic Patients", ClinicalTrials.gov ID NCT04631211, Cellphire Therapeutics, Inc., Apr. 2, 2024, 44 pages.
Fitzpatrick et al., "A Phase I, Multi-Center, Open-Label, Dose Escalation Study of Thrombosomes® in Bleeding Thrombocytopenic Patients in Three Cohorts", Cellphire Therapeutics, Inc., NCT03394755, Study Protocol, Jun. 2, 2020, 55 pages.
International Search Report and Written Opinion in International Appln. No. PCT/US2024/027563, mailed Oct. 4, 2024, 15 pages.
Moskowitz et al., "A Freeze-Dried Platelet-Derived Hemostatic Agent is Partially Resistant to Fibrinolysis In Vitro", Cellphire Therapeutics, Military Health System Research Symposium, (MHSRS-24-11499), Aug. 2024, 2 pages, abstract.
Moskowitz et al., "A Prospective, Multicenter, Randomized, Open-Label, Phase 2, Parallel, Dose Ranging Multidose Study of Thrombosomes® vs Liquid Stored Platelets (LSP) in Bleeding Thrombocytopenic Patients with Hematological Malignancies", Cellphire Therapeutics, Inc., presented at Association for the Advancement of Blood & Biotherapies, Oct. 19, 2024, 22 pages.
Moskowitz et al., "Freeze-Dried Platelets Decrease Bleeding in Refractory Thrombocytopenic Patients with Hematological Malignancies", AABB Annual Meeting 2024, abstract submission, 2 pages.
Goggs, et. al., "Lyophilized Platelets Versus Cryopreserved Platelets for Management of Bleeding in Thrombocytopenia Dogs: A Multicenter Randomized Clinical Trial", Journal of Veterinary Internal Medicine, Nov. 2020, vol. 34, Issue 6, pp. 2384-2397, doi: 10.1111/jvim.15922.
Greene, et. al., "Chapter 9: Component Preparation and Manufacturing", Transfusion Medicine and Hemostasis, Elsevier Science, 1st edition, 2009, pp. 45-50, doi:10.1016/B978-0-12-374432-6.00009-9, XP009527060.
Grosset et al., "Rapid presymptomatic detection of PrPSc via conformationally responsive palindromic PrP peptides", Peptides, vol. 26, Issue 11, Nov. 2005, pp. 2193-2200, doi: 10.1016/j.peptides. 2005.03.006.
Gybel-Brask et al., "Freeze-dried platelets (Thrombosomes®) reverses CPB-induced platelet dysfunction ex-vivo", RegionH, Rigshospitalet, The Center of Diagnostic Investigations, 2023, 1 page, poster.
Hagedorn, et. al., "Factor XIIa Inhibitor Recombinant Human Albumin Infestin-4 Abolishes Occlusive Arterial Thrombus Formation Without Affecting Bleeding", Circulation, vol. 121, Issue 13, Apr. 6, 2010, pp. 1510-1517, DOI: 10.1161/CIRCULATIONAHA. 109.924761.
Hale et al., "A Novel Use of the NOD SCID Mouse Model for Hemostatic Efficacy", Cellphire, Inc., 2019, 1 page.
Healthline.com [online], "How Many Cells Are in the Human Body? Fast Facts," Jul. 18, 2018, retrieved on May 17, 2021, retrieved from URL, 11 pages.
Heitmeier et al., "Pharmacological profile of asundexian, a novel, orally bioavailable inhibitor of factor XIa", Journal of Thrombosis and Haemostasis, vol. 20, No. 6, Jun. 2022, pp. 1400-1411, https://doi.org/10.1111/jth.15700.
Heitz, et al., "Twenty years of cell-penetrating peptides: from molecular mechanisms to therapeutics," British Journal of Pharmacology, 2009, 157:195-206.
helena.com [online], "Ristocetin Cofactor Assay," retrieved on Feb. 18, 2021, retrieved from URL , 2 pages.
Hemker et al., "Calibrated automated thrombin generation measurement in clotting plasma," Pathophvsiol. Haemost. Thromb., 2003, 33:4-15.
Hoffman et al., "Coagulation Factor IXa Binding to Activated Platelets and Platelet-Derived Microparticles: A Flow Cytometric Study," Thromb. Haemost., 1992, 68:74-78.
Holcomb, et al., "Optimal fluid therapy for traumatic hemorrhagic shock," Crit. Care Clin., 2017, 33(1):15-36.
Holme et al., "Platelet-derived microvesicles and activated platelets express factor Xa activity," Blood Coae:ul. Fibrinolysis, 1995, 6:302-310.
Holmes, et. al., "Combining Antiplatelet and Anticoagulant Therapies", Journal of the American College of Cardiology, vol. 54, No. 2, Jul. 7, 2009, pp. 95-109.
Homepage.haemonetics.com [online], "TEG® 5000 Thrombelastograph® Hemostasis Analyzer System," retrieved Feb. 18, 2021, retrieved from 5000>, 3 pagesURL.
Hong et al., "Transfection of human platelets with short interfering RNA", Clinical and Translational Science, vol. 4, Issue 5, Jun. 2011, pp. 180-182, doi: 10.1111/j.1752-8062.2011.00279.x.
Hrachovinova et al., "Interaction of P-selectin and PSGL-1 generates microparticles that correct hemostasis in a mouse model of hemophilia A," Nat Med., 2003, 9(8): 1020-1025.
Huebner et al., "Freeze-dried plasma enhances clot formation and inhibits fibrinolysis in the presence of tissue plasminogen activator similar to pooled liquid plasma", Transfusion, vol. 57, Issue 8, Aug. 2017, pp. 2007-2015, DOI:10.1111/trf.14149.
Inaba et al., "Dried platelets in a swine model of liver injury", Shock, vol. 41, Issue 5, May 2014, pp. 429-434, doi: 10.1097/SHK. 0000000000000141.
International Partial Search Report and Provisional Opinion in International Appln No. PCT/US2022/079280, mailed Feb. 20, 2023, 14 pages.
International Partial Search Report in International Appln No. PCT/US2022/016866, mailed May 11, 2022, 13 pages.
International Preliminary Report on Patentability in International Appln. No. PCT/US2005/028559, dated May 8, 2007,5 pages.
International Preliminary Report on Patentability in International Appln. No. PCT/US2015/060533, dated May 16, 2017, 5 pages.
International Preliminary Report on Patentability in International Appln. No. PCT/US2016/036657, dated Dec. 12, 2017, 6 pages.
International Preliminary Report on Patentability in International Appln. No. PCT/US2016/048846, dated Mar. 6, 2018,5 pages.
International Preliminary Report on Patentability in International Appln. No. PCT/US2016/065681, dated Jun. 11, 2019, 7 pages.
International Preliminary Report on Patentability in International Appln. No. PCT/US2017/012836, dated Jul. 17, 2018, 7 pages.
International Preliminary Report on Patentability in International Appln. No. PCT/US2018/050924, dated Mar. 26, 2020, 17 pages.
International Preliminary Report on Patentability in International Appln. No. PCT/US2019/043723, dated Feb. 11, 2021, 14 pages.
International Preliminary Report on Patentability in International Appln. No. PCT/US2019/050624, dated Mar. 25, 2021, 10 pages.
International Preliminary Report on Patentability in International Appln. No. PCT/US2019/063549, dated Jun. 10, 2021, 9 pages.
International Preliminary Report on Patentability in International Appln. No. PCT/US2019/063650, mailed Jun. 10, 2021, 9 pages.
International Preliminary Report on Patentability in International Appln. No. PCT/US2019/063736, mailed Jun. 10, 2021, 8 pages.
International Preliminary Report on Patentability in International Appln. No. PCT/US2019/063750, mailed Jun. 10, 2021, 8 pages.
International Search Report and Written Opinion in International Appln No. PCT/US2022/079280, mailed date Apr. 21, 2023, 27 pages.

(56) References Cited

OTHER PUBLICATIONS

International Search Report and Written Opinion in International Appln. No. PCT/US2005/028559, mailed Mar. 23, 2007, 8 pages.
International Search Report and Written Opinion in International Appln. No. PCT/US2015/060553, mailed Jan. 28, 2016, 7 pages.
International Search Report and Written opinion in International Appln. No. PCT/US2016/036657, mailed Aug. 29, 2016,7 pages.
International Search Report and Written Opinion in International Appln. No. PCT/US2016/048846, mailed Nov. 16, 2016, 2 pages.
International Search Report and Written Opinion in International Appln. No. PCT/US2016/065681, mailed Feb. 17, 2017,2 pages.
International Search Report and Written Opinion in International Appln. No. PCT/US2017/012836, mailed Apr. 7, 2017, 8 pages.
International Search Report and Written Opinion in International Appln. No. PCT/US2018/050924, mailed Nov. 20, 2018, 18 pages.
International Search Report and Written Opinion in International Appln. No. PCT/US2019/043723, mailed Oct. 9, 2019, 16 pages.
International Search Report and Written Opinion in International Appln. No. PCT/US2019/050624, mailed Nov. 20, 2019, 23 pages.
International Search Report and Written Opinion in International Appln. No. PCT/US2019/063549, mail date Feb. 4, 2020, 10 pages.
International Search Report and Written Opinion in International Appln. No. PCT/US2019/063650, mail date Feb. 27, 2020, 11 pages.
International Search Report and Written Opinion in International Appln. No. PCT/US2019/063736, mailed Feb. 20, 2020, 10 pages.
International Search Report and Written Opinion in International Appln. No. PCT/US2019/063750, mail date Feb. 19, 2020, 10 pages.
International Search Report and Written Opinion in International Appln. No. PCT/US2020/022705, mailed Jul. 29, 2020, 12 pages.
Lee et al., "Lyophilized Human Platelets Exhibit Adhesive Interactions with *Staphylococcus aureus*", Research adn Practice in Thrombosis and Haemostasis, 2020, 1 page, Poster PB1816.
Lee et al., "Lyophilized Human Platelets Exhibit Adhesive Interactions with *Staphylococcus aureus*", Research adn Practice in Thrombosis and Haemostasis, 2020; 4 (Suppl 1), 2 pages, Abstract PB1816, ISTH 2020 Congress, https://abstracts.isth.org/abstract/lyophilized-human-platelets-exhibit-adhesive-interactions-with-staphylococcus-aureus/.
Lee et al., "Novel treatment modalities: New platelet preparations and subsitutites," British journal of haematology, Sep. 2001, 114(3):496-505.
Li et al., "Extended antiplatelet therapy with clopidogrel alone versus clopidogrel plus aspirin after completion of 9- to 12-month dual antiplatelet therapy for acute coronary syndrome patients with both high bleeding and ischemic risk. Rationale and design of the OPT-BIRISK double-blinded, placebo-controlled randomized trial", American Hear Journal, vol. 228, Oct. 2020, pp. 1-7, https://doi.org/10.1016/j.ahj.2020.07.005.
Lo et al., "Development of a multi-compartment microfiltration device for particle fractionation" 16th International Conference on Miniaturized Systems for Chemistry and Life Sciences, MicroTAS 2012—Okinawa, Japan, Oct. 28, 2012-Nov. 1, 2012, 3 pages.
Lucking et. al., "Characterisation and reproducibility of a human ex vivo model of thrombosis", Thrombosis Research, vol. 126, No. 5, Nov. 2010, pp. 431-435, doi: 10.1016/j.thromres.2010.06.030.
Luo et al., "Construction and in vitro studies of magnetic-apoferritin nanocages conjugated with KGDS peptide targeted at activated platelets for the MRI diagnosis of thrombus," Journal of Nanoparticle Research, vol. 21, Issue 8, Aug. 2019, pp. 1-12.
Mailer et al., "Commentary on "Pharmacological profile of asundexian, a novel, orally bioavailable inhibitor of factor XIa": Small molecule factor XIa inhibitor asundexian allows for safer anticoagulation", Journal of Thrombosis and Haemostasis, vol. 20, Issue 6, Jun. 2022, pp. 1309-1311, https://doi.org/10.1111/jth.15722.
Makielski et al., "Development and implementation of a novel immune thrombocytopenia bleeding score for dogs," J. Vet. Intern. Med., 2018, 32(3):1-10.
Marder, "Bleeding Complications of Thrombolytic Treatment", American Journal of Hospital Pharmacy, vol. 47, Suppl 2, Sep. 1990, pp. S15-S19.
Marris, "The war against wounds", Nature, Mar. 21, 2007, Issue 446, pp. 369-371.
Mathews et al., "Development of Lyophilized Platelet-Derived Extracellular Vesicles for Multiple Indications", Cellphire, Inc., Oct. 2020, 1 page, Poster.
Mathews et al., "Development of Lyophilized Platelet-Derived Extracellular Vesicles for Multiple Indications", Chellphire, Inc., 2020, 1 page, Abstract.
Mazzucco et al., "The use of autologous platelet gel to treat difficult-to-heal wounds: a pilot study," Transfusion, 2004, 44:1013-1018.
McCarrel, et. al., "Temporal Growth Factor Release from Platelet-Rich Plasma, Trehalose Lyophilized Platelets, and Bone Marrow Aspirate and Their Effect on Tendon and Ligament Gene Expression" Journal of Orthopaedic Research : Official Publication of the Orthopaedic Research Society, vol. 27(8), Aug. 1, 2009, pp. 1033-1042,DOI: 10.1002/jor.20853.
MedWow, "Manufacturer Specifications—CS-2000 Plus, Baxter," Apr. 19, 2011, retrieved on Sep. 26, 2019 from http://www.medwow.com/med/apheresis-machine/baxter/cs-3000-plus/5782.model-spec, 2 pages.
Mehendale, et. al., "Platelet Enrichment From Whole Blood in a Clog-Free Microfluidic Radial Pillar Device (RAPID)", Biomedical Microdevices, bioRxiv, Oct. 4, 2017, DOI: https://doi.org/10.1101/197749.
Mehendale, et. at., "Platelet Enrichment in a Continuous and Clog-Free Microfluidic Filter With Sunflower Head Geometry", 20th International Conference on Miniaturized Systems for Chemistry and Life Sciences, Dublin, Ireland, Oct. 9-13, 2016, pp. 272-273.
Meisel et. al., "A Simplified Direct Lipid Mixing Lipoplex Preparation: Comparison of Liposomal-, Dimethylsulfoxide-, and Ethanol-Based Methods", Scientific Reports, vol. 6, Article 27662, Jun. 21, 2016, 12 pages, doi: 10.1038/srep27662.
Merten et al., "Platelet Microparticles Promote Platelet Interaction with Subendothelial Matrix in a Glycoprotein Iib/IIIa Dependent Mechanism", Circulation, 1999, 99:2577-2582.
Miajlovic, et al., "Both complement- and fibrinogen-dependent mechanisms contribute to platelet aggregation mediated by *Staphylococcus aureus* clumping factor B," Infection and Immunity, 2007, 75(7):3335-3343.
Midgett et al., "Combination of freeze-dry microscopy, differential scanning calorimetry, and electron microscopy analysis as a guide for lyophilization cycle optimization to enhance Thrombosomes function", Cryobiology, vol. 63, Issue 3, 2011, p. 320, Abstract, doi:10.1016/j.cryobiol.2011.09.054.
Mihatov, et. al., "Individualizing Dual Antiplatelet Therapy (DAPT) Duration Based on Bleeding Risk, Ischemic Risk, or Both: An Analysis From the DAPT Study", Cardiovascular Revascularization Medicine, vol. 41, Aug. 2022, pp. 105-112, https://doi.org/10.1016/j.carrev.2022.01.006.
Millipore Sigma, "Dulbecco's Modified Eagle's Medium (DMEM)Formulation", Merck KGaA, Sigma-Aldrich Solutions, 2023, 15 pages, retreived from https://www.sigmaaldrich.com/US/en/technical-documents/technical-article/cell-culture-and-cell-culture-analysis/mammalian-cell-culture/dulbecco-modified-eagle-medium-formulation.
Mishra et al., "Cell-penetrating peptides and peptide nucleic acid-coupled MRI contrast agents: evaluation of cellular delivery and target binding." Bioconjugate Chemistry, vol. 20, Issue 10, Oct. 21, 2009, pp. 1860-1868, doi:10.1021/bc9000454.
Mokobi, "Types of Plant Cell—Definition, Structure, Functions, Diagrams," microbenotes.com [online], Feb. 25, 2020, retrieved May 17, 2021, retrieved from URL , 31 pages.
Montague, "Strategies to Improve Haemostasis in Trauma: Evaluation of Thrombosomes in the Presence of Native Platelet Dysfunction", vol. 100, Issue Suppl 3, 2014, pp. A91-A92, DOI:10.1136/heartjnl-2014-306118.158.

(56) References Cited

OTHER PUBLICATIONS

Montecinos et al., "Selective targeting of bioengineered platelets to prostate cancer vasculature: new paradigm for the therapeutic modalities," 2015, 19(7):1530-1537.
Morris, et al., "A peptide carrier for the delivery of biologically active proteins into mammalian cells," Nature Biotechnoloe:v, 2001, 19:1173-1176.
Morrison et al., "Storage of apheresis platelet concentrates after manual replacement of >95% of plasma with PAS 5", Vox Sanguinis, vol. 107; Issue 3, May 7, 2014, pp. 247-253, XP055759704, doi:10.1111/vox.12157.
Moskowitz et al., "A Freeze-Dried Platelet-Derived Hemostatic Agent is Partially Resistant to Fibrinolysis In Vitro", Cellphire Therapeutics, Military Health System Research Symposium, (MHSRS-24-11499), Aug. 2024, 1 page, poster.
Moskowitz et al., "Cryopreserved Platelets Prepared by Novel Allogenic Pooling and Post-thaw Processes are Stable at Elevated Temperatures", Cellphire, Therapeutics, Military Health System Reserach Symposium, (MHSRS-24-11477), Aug. 2024, 1 page, poster.
Moskowitz et al., "Freeze Dried Platelet Derivatives (Thrombosomes®) Retain Hemostatic Properties During Heparin Complexation with Protamine", Research and Practice in Thrombosis and Haemostasis, 2022, 2 pages, ISTH 2022 Congress, Abstract PB0880, https://abstracts.isth.org/abstract/freeze-dried-platelet-derivatives-thrombosomes-retain-hemostatic-properties-during-heparin-complexation-with-protamine/.
Moskowitz et al., "Hemostatic Properties of Infusible Trehalose-Stabilized Lyophilized Platelet Derivatives", Blood, vol. 104, Issue 11, Nov. 16, 2004, p. 834, Abstract, doi.org/10.1182/blood.V104.11.834.834.
Moskowitz et al., "Natural History of Bleeding, Transfusion, and Antibody Prevalence in a Subset of Hermansky-Pudlak Syndrom patients: Effects of Freeze-Dried Lyophilized Platelet Derived Hemostat Ex Vivo", Trombosis & Hemostasis Summit 2024, Cellphire Therapeutics, Inc. Apr. 5, 2024, 1 page, Abstract.
Moskowitz et al., "Natural History of Bleeding, Transfusion, and Antibody Prevalence in a Subset of Hermansky-Pudlak Syndrom patients: Effects of Freeze-Dried Lyophilized Platelet Derived Hemostat Ex Vivo", Trombosis & Hemostasis Summit 2024, Cellphire Therapeutics, Inc. Apr. 5, 2024, 1 page, Poster.
Moskowitz et al., "Stabilized Platelets: A Drug Delivery System for Potential Human Hepatocellular Carcinoma Therapy", Research and Practice in Thrombosis and Haemostasis, vol. 7 (Suppl. 2) Oct. 2023, pp. 709-710, Abstract PB0731, doi.org/10.1016/j.rpth.2023.101329.
Moskowitz, "Thrombosomes for the Treatment of Bleeding Associated with Aggressive Anticoagulation", Cellphire, Inc., Dec. 2021, 40 pages, Posters.
Müller et. al., "Factor XI and XII as antithrombotic targets", Current Opinion in Hematology, vol. 15, No. 5, Sep. 2011, pp. 349-355, doi: 10.1097/MOH.0b013e3283497e61.
Mullin, et.al., "Doxorubicin chemotherapy for presumptive cardiac hemangiosarcoma in dogs", Veterinary and Comparative Oncology, vol. 14, Issue 4, Dec. 18, 2014, 13 pages, doi:10.1111/vco.12131.
Murphy et al., "Platelet transfusions: The problem of refractoriness", Blood Reviews, vol. 4, Issue 1, Mar. 1990, pp. 16-24, doi.org/10.1016/0268-960X(90)90013-I.
NasrEldin, "Effect of cold storage on platelets quality stored in a small containers: Implications for pediatric transfusion", Pediatric Hematology Oncology Journal, vol. 2, Issue 2, Aug. 2017, pp. 29-34, doi.org/10.1016/j.phoj.2017.07.001.
Natan, et al., "Freeze-drying of mononuclear cells derived from umbilical cord blood followed by colony formation", PLoS One, Apr. 21, 2009, vol. 4, Issue 4, e5240, 12 pages, DOI: 10.1371/journal.pone.0005240.
Nieuwland et al., "Cell-Derived Microparticles Generated in Patients During Cardiopulmonary Bypass Are Highly Procoagulant", Circulation, 1997, 96:3534-3541.

Novakowski et al., "Delivery of mRNA to platelets using lipid nanoparticles" Scientific Reports, vol. 9, Article 552, Jan. 24, 2019, 11 pages, doi: 10.1038/s41598-018-36910-2.
O'Brien, et al., "Multiple mechanisms for the activation of human platelet aggregation by *Staphylococcus aureus*: roles for the clumping factors ClfA and ClfB, the serine-aspartate repeat protein SdrE and protein A," Molecular Microbiology, 2002, 44(4):1033-1044.
Ogiwara, et al., "Procoagulant Activity of Antifibrinolytic Agents; A Novel Hemostatic Mechanism of Tranexamic Acid and Epsilon-Aminocaproic Acid", Blood, Nov. 19, 2010, vol. 116, Issue 21, Abstract 1151, 3 pages, https://doi.org/10.1182/blood.V116.21.1151.1151.
Ohanian, et. al., "Freeze-Dried Platelets Are a Promising Alternative in Bleeding Thrombocytopeniatients with Hematological Malignancies", American Journal of Hematology, vol. 97, Issue 3, Mar. 1, 2022, pp. 256-266, doi: 10.1002/ajh.26403.
Oikarinen et al., "Augmentation of the narrow traumatized anterior alveolar ridge to facilitate dental implant placement," Dent. Traumatol., 2003, 19:19-29.
Oliver, "Dry state preservation of nucleated cells: progress and challenge," Cryobiology, Dec. 2011, vol. 63, Issue 3, p. 307, abstract, DOI:10.1016/j.cryobiol.2011.09.007.
"Cryoprotein," The American Heritage® Stedman's Medical Dictionary. Houghton Mifflin Company. Mar. 24, 2010.
"Expose," http://dictionary.reference.com/browse/expose, accessed Jul. 18, 2009.
"Platelet," The American Heritage® Dictionary of the English Language, Fourth Edition. Houghton Mifflin Company, 2004. Mar. 23, 2010.
"Rounding," Dictionary.com. Dictionary.com Unabridged (v 1.1 ). Random House, Inc. http://dictionary.reference.com/browse/rounding (accessed: Oct. 27, 2008).
2.palomar.edu [online], "The Five Kingdoms of Life," Feb. 1998, retrieved on May 17, 2021, retrieved from URL ; 18 pages.
Abdelgawwad, et al., "Transfusion of plateletes loaded with recombinant ADAMTS13 is efficacious for inhibiting arterial thrombosis in mice and in human," Arterioscler. Thromb. Vas. Biol., 2018, 38(11):2731-2743.
Abreu-Blanco et al., "Therapeutic effect of Lyophilized human platelets in an in vitro surrogate model of Bernard-Soulier syndrome and in patient samples", Cellphire, Inc., Oct. 14-17, 2023, 2 pages, abstract.
Abreu-Blanco et al., "Therapeutic effect of Lyophilized human platelets in an in vitro surrogate model of Bernard-Soulier syndrome and in patient samples", Cellphire, Inc., Association for the Advancement of Blood & Biotherapies, Oct. 14-17, 2023, 1 page, poster.
Adams, Ducry et al. ed., "The principles of freeze-drying," DNA Repair Protocols, Methods in Molecular Biology, Humana Press, Clifton, N.J., vol. 368, Chapter 2, 2007, pp. 15-38, doi:10.1007/978-1-59745-362-2_2.
Agam et al. "Passive Participation of Fixed Platelets in Aggregation Facilitated by Covalently Bound Fibrinogen" Blood 61:1, pp. 186-191, 1983.
Ahmadzada, et al., "Fundamentals of siRNA and miRNA therapeutics and a review of targeted nanoparticle delivery systems in breast cancer," Biophysical Reviews, 2018, 10:69-86.
Al Ghaithi et al., "Evaluation of the Total Thrombus-Formation System (T-TAS): application to human and mouse blood analysis", Platelets, vol. 30, Issue 7, Oct. 26, 2018, pp. 893-900, doi: 10.1080/09537104.2018.1535704.
Alquwaizani, et.al., "Anticoagulants: A Review of the Pharmacology, Dosing, and Complications", Current Emergency and Hospital Medicine Reports, vol. 1, No. 2, Apr. 21, 2013, pp. 83-97, DOI: 10.1007/s40138-013-0014-6.
Anonymous, "Bridging Anticoagulation", Circulation, vol. 125, Issue 12, Mar. 27, 2012, pp. e496-e498, doi. org/10.1161/CIRCULATIONAHA.111.084517.
Appleman et al., "Cryopreservation of canine platelets," Journal of Veterinary Internal Medicine, vol. 23, Issue 1, Jan. 2009, pp. 138-145, doi: 10.1111/j.1939-1676.2008.0225.x.
Arav et. al., "Freeze drying (lyophilization) of red blood cells", Journal of Trauma, May 2011, vol. 70, No. 5, pp. S61-S64, DOI: 10.1097/TA.0b013e31821a6083.

(56) References Cited

OTHER PUBLICATIONS

Arnold et al., "The preparation and clinical administration of lyophilized platelet material to children with acute leukemia and aplastic anemia," The Journal of Pediatrics, 1956, 49(5):517-522.
Bannai et al., "The effects of pH and agitation on platelet preservation", The Journal of AABB Transfusion, vol. 25, Jan.-Feb. 1985, pp. 57-59, https://doi.org/10.1046/j.1537-2995.1985.25185116505.x.
Baroletti et al., "Heparin-Induced Thrombocytopenia", Circulation, vol. 114, Issue 8, Aug. 22, 2006, pp. e355-e356, doi.org/10.1161/CIRCULATIONAHA.106.632653.
Barroso, et. al., "Safety Evaluation of a Lyophilized Platelet Derived Hemostatic Product", Transfusion, vol. 58(12), Dec. 2018, pp. 2969-2977, DOI: 10.1111/trf.14972.
Böck et al., "Cryopreservation of human platelets with dimethyl sulfoxide: changes in biochemistry and cell function", Transfusion, vol. 35, No. 11, Nov.-Dec. 1995, pp. 921-924, doi: 10.1046/j.1537-2995.1995.351196110896.x.
Bohoněk, Miloš. "Cryopreservation of Platelets: Advances and Current Practice." Cryopreservation Biotechnology in Biomedical and Biological Sciences, Chapter 4. IntechOpen, Dec. 7, 2018, pp. 47-70.
Booth et al., "Lyophilized human platelets are superior to apheresis or fresh-drawn platelets in their ability to accelerate thrombin production", Research and Practice in Thrombosis and Haemostasisc, 2022, ISTH2022 Congress Jul. 2022, 1 page, Poster PB0154.
Booth et al., "Lyophilized human platelets are superior to apheresis or fresh-drawn platelets in their ability to accelerate thrombin production", Research and Practice in Thrombosis and Haemostasis, 2022, 1 page, ISTH 2022 Congress, Abstract PB0154, https://abstracts.isth.org/abstract/lyophilized-human-platelets-are-superior-to-apheresis-or-fresh-drawn-platelets-in-their-ability-to-accelerate-thrombin-production/.
Bullok, et al., "Permeation Peptide Conjugates for In Vivo Molecular Imaging Applications", Molecular Imaging, Jan.-Mar. 2006, vol. 5, Issue 1, pp. 1-15.
Bynum et al., "Evaluation of a lyophilized platelet-derived hemostatic product," Transfusion, 2019, 49:1490-1498.
Cap, et. al., "Trauma Induced Coagulopathy", Chapter 22: Platelet Transfusion, Springer International Publishing, 2016, pp. 347-376.
Cellphire, Inc. "A Prospective, Multicenter, Randomized, Open-Label Phase 2, Parallel, Dose Ranging Multidose Study of Thrombosomes® vs Liquid Stored Platelets (LSP) in Bleeding Thrombocytopeniatients" Cellphire, Inc, IND 017156, Informed Consent Form and HIPAA Authorization, Protocol Version 1, Jan. 31, 2020, ICF Version 2.0, pp. 1-17.
Charkhkar et al., "Amyloid beta modulation of neuronal network activity in vitro", Brain Research, vol. 1629, Dec. 2015, pp. 1-9, doi: 10.1016/j.brainres.2015.09.036.
Chassot et al., "Perioperative Antiplatelet Therapy", American Family Physician, vol. 82, No. 12, Dec. 15, 2010, pp. 1484-1489.
Chelliah et. al., "p. selectin antagonism reduces thrombus formation in humans", Journal of Thrombosis and Haemostasis, vol. 7, No. 11, Nov. 2009, pp. 1915-1919. doi: 10.1111/j.1538-7836.2009.03587.x.
Chen et al., "Expanding the Potential of Doxorubicin-Loaded Cryopreserved Platelets for Targeted Cancer Drug Delivery", Cellphire, Inc., 21st International Drug Delivery and Nanomedicines Symposium, Sep. 15-17, 2023, 1 page, poster.
Chen et al., "Modifying murine von Willebrand factor AI domain for in vivo assessment of human platelet therapies," Nature biotechnology, Jan. 2008, 26(1):114-119.
Chen et al., "Stabilized Platelets: A Drug Delivery System for Potential Human Hepatocellular Carcinoma Therapy", Research and Practice in Thrombosis and Haemostasis, 2023, ISTH 2023, Montréal, Jun. 24-28, 2023, 1 page, Poster PB0731.
Chen, et al., "Advance of molecular imaging technology and targeted imaging agent in imaging and therapy," Biomed. Res. Int., 2014, 819324, 12 pages.

Chen, et al., "Stabilizaton of peptides against proteolysis through disulfide-bridged conjugation with synthetic aromatics," Org. Biomol. Chem., 2017, 15(8):1921-1929.
Christenson et al., "Autologous fibrin glue reinforced by platelets in surgery of ascending aorta", Thorac. Cardiovasc. Surg., vol. 52, p. 225-229, 2004.
Christopher, et al., "MicroRNA therapeutics: discovering novel targets and developing specific therapy," Perspect. Clin. Res., 2016, 7(2):68-74.
Clemmons et al., "Acquisition and aggregation of canine blood platelets: basic mechanisms of function and differences because of breed origin," Americanjournal of veterinary research, Jan. 1, 1984, 45(1):137-144.
Cogswell et al., "Amyloid-Related Imaging Abnormalities with Emerging Alzheimer Disease Therapeutics: Detection and Reporting Recommendations for Clinical Practice", American Journal of Neuroradiology, vol. 43, Issue 9, Sep. 2022, pp. E19-E35, doi: 10.3174/ajnr.A7586.
Colman, "Are hemostasis and thrombosis two sides of the same coin?", Journal of Experimental Medicine, Mar. 20, 2006, vol. 203, No. 3, pp. 493-495, doi: 10.1084/jem.20060217.
Cowles, "Anticoagulant effect of aspirin goes beyond platelet aggregation", Hematology/Oncology, May 1, 2007, 3 pages.
Cox, et al., "Platelets and the innate immune system: mechanisms of bacterial-induced platelet activation," Journal of Thrombosis and Haemostasis, 2011, 9:1097-1107.
Crowe et al., "Freeze-dried platelets: Moving towards clinical use", Cryobiology, vol. 66, Issue 3, Jun. 2013, p. 348, Abstract, doi.org/10.1016/j.cryobiol.2013.02.028.
Crowe et. al., "Stabilization of Dry Mammalian Cells: Lessons from Nature", Integrative and Comparative Biology, vol. 45, Issue 5, Nov. 2005, pp. 810-820, https://doi.org/10.1093/icb/45.5.810.
Crowe, et. al., "Stabilization of membranes in human platelets freeze-dried with trehalose", Chemistry and Physics of Lipids, vol. 122, Issues 1-2, Jan. 2003, pp. 41-52, https://doi.org/10.1016/S0009-3084(02)00177-9.
Daidone, "Usefulness of the Total Thrombus-formation Analysis System (T-TAS) in the diagnosis and characterization ofvon Willebrand disease," Haemophillia, 2016, 22:949-956.
Daly et al., "Hemostatic regulators of tumor angiogenesis: a source of antiangiogenic agents for cancer treatment?" Journal of the National Cancer Institute, 2003, 95(22):1660-1673.
Dee et al., "Trehalose Stabilized Freeze Dried Human Platelets, Thrombosomes, Express Surface Markers, Thromboelastogram (TEG) Values and Size Distribution Similar to Two to Three Day Old Stored Platelets", International Society of Blood Transfusion Vox Sanguinis, vol. 99, Suppl. 1, P-0453, 2010, p. 262, Abstract.
Dee et al., "Trehalose Stabilized Freeze Dried Human Platelets, Thrombosomes, Express Surface Markers, Thromboelastogram (TEG) Values and Size Distribution Similar to Two to Three Day Old Stored Platelets", Cellphire, Inc., P-0453, 2019, 1 page, Poster.
Orser et al., "Loading Platelets with Biological Agents for Enhanced Local Delivery", Cellphire, Inc., May 8, 2019, 14 pages, retrieved from https://www.bodevet.com/wp-content/uploads/2019/07/Loading-Platelets-with-Biological-Agents.pdf.
Pan, et al., "Wound healing monitoring using near infrared fluorescent fibrinogen", Biomedical Optics Express, Jul. 27, 2010, vol. 1, Issue 1, pp. 285-294, doi: 10.1364/boe.1.000285.
Pati et al., "Targeting the Endotheliopathy of Trauma in Hemorrhagic Shock and Traumatic Brain Injury with Freeze-Dried Platelets", Defense Technical Information Center, U.S. Army Medical Research and Development Command, Medicine and Medical Research; Biology, Sep. 1, 2020, 22 pages, https://apps.dtic.mil/sti/pdfs/AD1112058.pdf.
Pati et al., "Targeting the Endotheliopathy of Trauma in Hemorrhagic Shock and Traumatic Brain Injury with Freeze-Dried Platelets", Defense Technical Information Center, Sep. 1, 2020, 2 pages, Abstract.
Pemmaraju et al., "Bleeding Risk in Thrombocytopenia Cancer Patients with Venous Thromboembolism (VTE) Receiving Anticoagulation", Blood, vol. 120, Issue 21, Abstract 3408, Nov. 16, 2012, 3 pages, doi.org/10.1182/blood.V120.21.3408.3408.

(56) References Cited

OTHER PUBLICATIONS

Pierce, et al., "Platelet-derived growth factor and transforming growth factor-beta enhance tissue repair activities by unique mechanisms", J. Cell Biol., 1989, 109:429-440.
Pietramaggiori et al., "Freeze-dried platelet-rich plasma shows beneficial healing properties in chronic wounds", Wound Repair and Regeneration, vol. 14, Issue 5, Sep. 29, 2006, pp. 573-580, doi.org/10.1111/j.1743-6109.2006.00164.x.
Pietramaggiori, et. al., "Trehalose Lyophilized Platelets for Wound Healing", Wound Repair and Regeneration : Official Publication of the Wound Healing Society [and] the European Tissue Repair Society, vol. 15 (2), Mar. 9, 2007, pp. 213-220. doi:10.1111/j.1524-475X.2007.00207.x.
Powner, et. al., "Counteracting the Effects of Anticoagulants and Antiplatelet Agents During Neurosurgical Emergencies", Neurosurgery, vol. 57, No. 5, Nov. 2005 pp. 823-831.
Prior, et al., "A Sprayable Hemostat Containing Fibrillar Collagen, Bovine Thrombin, and Autologous Plasma", Ann. Thorac. Surg., 1999, 68:479-485.
Read, et. al., "Preservation of hemostatic and structural properties of rehydrated lyophilized platelets: potential for long-term storage of dried platelets for transfusion", Proceedings of the National Academy of Sciences of the USA, vol. 92, Jan. 1995, pp. 397-401, DOI: 10.1073/pnas.92.2.397.
Reddoch et al., "Extended Storage of Refrigerated Platelets in Isoplate and Intersol PAS: An Evaluation of Two FDA-Approved Methods of Collection", Blood, vol. 128, Issue 22, Dec. 2, 2016, 3 pages, doi.org/10.1182/blood.V128.22.2631.2631.
Reuss et al., "Intracellular delivery of carbohydrates into mammalian cells through swelling-activated pathways", The Journal of Membrane Biology, vol. 200, Issue 2, Jul. 15, 2004, pp. 67-81, doi: 10.1007/s00232-004-0694-7.
Robson, et. al., "Coronavirus RNA Proofreading: Molecular Basis and Therapeutic Targeting", Molecular Cell, vol. 79, No. 5, Sep. 3, 2020, pp. 710-727, DOI:10.1016/j.molcel.2020.07.027, XP055785471.
Rosing et al., "Impaired factor X and prothrombin activation associated with decreased phospholipid exposure in platelets from a patient with a bleeding disorder", Blood, 1985, 65:1557-1561.
Rowley, et. al., "Platelet mRNA: the meaning behind the message," Curr. Opin. Hematol., 2012, 19(5):385-391.
Roytman et al., "Amyloid-Related Imaging Abnormalities: An Update", American Journal of Roentgenol, Issue 220, Issue 4, Nov. 2, 2022, pp. 562-574, doi: 10.2214/AJR.22.28461.
Samanbar et al., "Evaluation of the Hemostatic Ability of the New Device 'Total Thrombus Formation Analysis System' (T-TAS) for Thrombocytopenic Patients. Invitro effect of lyophilized human platelets", Research adn Preactice in Thrombosis and Haemostasis, Jul. 2022, 1 page, Poster.
Samanbar et al., "Evaluation of the hemostatic ability of the new device Total Thrombus Formation Analysis System (T-TAS) for thrombocytopenia patients. In vitro effect of Thrombosomes®", Research and Practice in Thrombosis and Haemostasis, 2022, 2 pages, ISTH 2022 Congress, Abstract PB0854, https://abstracts.isth.org/abstract/evaluation-of-the-hemostatic-ability-of-the-new-device-total-thrombus-formation-analysis-system-t-tas-for-thrombocytopeniatients-in-vitro-effect-of-thrombosomes/.
Samanbar et al., "Hemostatic Ability of Thrombosomes® in Blood from Thrombocytopenia Patients Using the Total Thrombus Formation Analysis System (T-TAS) and Confocal Microscopy in Microfluidic Chambers", Blood, Nov. 15, 2022, 140 (Supplement 1), pp. 11242-11243, doi.org/10.1182/blood-2022-169346.
Sane, et. al., "Bleeding During Thrombolytic Therapy for Acute Myocardial Infarction: Mechanisms and Management", Annals of Internal Medicine, vol. 111, No. 12, Dec. 15, 1989, pp. 1010-1022.
Scheinkönig et al., "Adoption of long-term cultures to evaluate the cryoprotective potential of trehalose for freezing hematopoietic stem cells", Bone Marrow Transplantation, September, vol. 34, Issue 6, Sep. 2004, pp. 531-536, doi: 10.1038/sj.bmt.1704631.
Schoug, et.al., "Differential effects of polymers PVP90 and Ficoll400 on storage stability and viability of Lactobacillus coryniformis Si3 freeze-dried in sucrose", Journal of Applied Microbiology, vol. 108, No. 3, pp. 1032-1040, Feb. 8, 2010.
Serebruany, et al., "Crossreactivity of Human versus Swine Platelet Surface Antigens Is Similar for Glycoproteins Ib and IIIa, but Not for the Glycoprotein IIb/IIIa Complex," Journal of Thrombosis and Thrombolysis, vol. 5, Issue 1, 1998, pp. 37-41, doi: 10.1023/a:1008867930862.
Sheik et al., "Stably Loading Human Platelets with Gadolinium Conjugates to Enhance Magnetic Resonance Imaging", Cellphire, Inc., 2020,1 page.
Sheik et al., "Stably Loading Human Platelets with Gadolinium Conjugates to Enhance Magnetic Resonance Imaging", Cellphire, Inc., 2020, 3 pages, poster.
Shi et al., "Impact of Anti-amyloid-β Monoclonal Antibodies on the Pathology and Clinical Profile of Alzheimer's Disease: A Focus on Aducanumab and Lecanemab", Frontiers in Aging Nuroscience, vol. 14, Article 870517, Apr. 12, 2022, 11 pages, doi: 10.3389/fnagi.2022.870517.
Sibbing, et. al., "Antiplatelet effects of clopidogrel and bleeding in patients undergoing coronary stent placement", Journal of Thrombosis and Haemostasis, vol. 8, Issue 2, pp. 250-256, DOI: 10.1111/j.1538-7836.2009.03709.x.
Sims et al., "Complement Proteins C5b-9 Cause Release of Membrane Vesicles from the Platelet Surface That Are Emiched in the Membrane Receptor for Coagulation Factor Va and Express Prothrombinase Activiy", J. Biol Chem., 1988, 263:18205-18212.
Sims et al., "Regulatory control of complement on blood platelets. Modulation of platelet procoagulant responses by a membrane inhibitor of the C5b-9 complex", J Biol. Chem., 1989, 264:19228-19235.
Srivastava, et. al., "The rebirth of the contact pathway: a new therapeutic target", Current Opinion in Hematology, vol. 27, No. 5, Sep. 2020, pp. 311-319, doi: 10.1097/MOH.0000000000000603.
Steed, "The role of growth factors in wound healing," Surg. Clin. North Am., 1997, 77:575-586.
Strober, "Trypan blue exclusion test of cell viability," Current Protocols in Immunology, 1997, A.3B. 1-A.3B.2.
Strong, ed., "Indications for Platelet Transfusion Therapy," Transfusion Medicine Bulletin, Vo. 2, No. 2, Jul. 1999, http://www.scbinfo.org/publications/bulletin_v2_n2.htm, pp. 1-6.
Sum et al., "Wound-healing properties of trehalose-stabilized freeze-dried outdated platelets", Transfusion, vol. 47, Issue 4, Apr. 2007, pp. 672-679, doi: 10.1111/j.1537-2995.2007.01170.x.
Swami, et.al., "von Willebrand Disease: A Concise Review and Update for the Practicing Physician", Clinical and Applied Thrombosis/Hemostasis, vol. 23 (8), Nov. 2017, pp. 900-910, DOI: 10.1177/1076029616675969.
Szekely and Lex, "Antifibrinolytics," Heart, Lung and Vessels, 2014, 6(1):5-7.
Tacar et al., "Doxorubicin: an update on anticancer molecular action, toxicity and novel drug delivery systems," The Journal of Pharmacy and Pharmacolo11:v, 2013, 65(2):157-170.
Tang, et. al., "Targeted repair of heart injury by stem cells fused with platelet nanovesicles", Nature Biomedical Engineering, vol. 2, No. 1, May 30, 2018, pp. 17-26, DOI:10.1038/s41551-017-0182-x.
Tans et al., "Comparison of anticoagulant and procoagulant activities of stimulated platelets and platelet-derived microparticles", Blood, 1991, 77:2641-2648.
Taune, et al., "Whole blood coagulation assays ROTEM and T-TAS to monitor dabigatran t dabigatran treatment," Thrombosis Research, 2017, 153(30):76-82.
thrombinoscope.com [online], "Thrombin Calibrator," retrieved on Feb. 18, 2021, retrieved from URL , 2 pages.
Török et al., "Preservation of Trehalose-Loaded Red Blood Cells by Lyophilization", Cell Preservation Technology, vol. 3, No. 2, Jul. 11, 2005, pp. 96-11, doi.org/10.1089/cpt.2005.3.96.
Trivedi, et. al., "Freeze-Dried Platelets Promote Clot Formation, Attenuate Endothelial Cell Permeability, and Decrease Pulmonary Vascular Leak in a Murine Model of Hemorrhagic Shock", The Journal of Trauma and Acute Care Surgery, vol. 90, Issue 2, Feb. 1, 2021, pp. 203-214, doi: 10.1097/TA.0000000000002984.
Tsai etal, "Increased risk of bleeding in patients on clopidogrel therapy after drug-eluting stents implantation: insights from the

(56) References Cited

OTHER PUBLICATIONS

HMO Research Network-Stent Registry (HMORN-stent)", Circulation Cardiovascular Interventions, vol. 3, Issue 3, Jun. 1, 2010, pp. 230-235, DOI: 10.1161/CIRCINTERVENTIONS.109.919001.
Tsegaye et al., "Platelet activation suppresses HIV-1 infection of T cells," Retrovirology, 2013, 10:48:00.
T-TAS.info [online], Publications, 2019, retrieved on Aug. 28, 2019, retrieved from URL, 8 pages.
Ullah et al., "A Review on Malarial Parasite", World Journal of Zoology, vol. 10, No. 4, 2015, pp. 285-290, DOI:10.5829/idosi.wjz.2015.10.4.95268, XP055785474.
Undas et al., "Antithrombotic properties of aspirin and resistance to aspirin: beyond strictly antiplatelet actions", Blood, vol. 109, No. 6, Mar. 15, 2007, pp. 2285-2292, DOI: 10.1182/blood-2006-01-010645.
Valentini et al., "Use of CD9 and CD61 for the characterization of AML-M7 by flow cytometry in a dog," Veterinary Comparative Oncology, Aug. 31, 2011, vol. 10, No. 4, pp. 312-318, DOI: 10.1111/j.1476-5829.2011.00290.x.
International Search Report and Written Opinion in International Appln. No. PCT/US2020/031172, mailed Aug. 12, 2020, 8 pages.
International Search Report and Written Opinion in International Appln. No. PCT/US2020/042492, mailed Nov. 24, 2020, 9 pages.
International Search Report and Written Opinion in International Appln. No. PCT/US2020/046522, mailed Nov. 10, 2020, 10 Pages.
International Search Report and Written Opinion in International Appln. No. PCT/US2020/046525, mail date Nov. 10, 2020, 11 Pages.
International Search Report and Written Opinion in International Appln. No. PCT/US2020/049489, mail date Feb. 16, 2021, 7 Pages.
International Search Report and Written Opinion in International Appln. No. PCT/US2020/062214, mail date Mar. 17, 2021, 8 pages.
International Search Report and Written Opinion in International Appln. No. PCT/US2020/062216, mailed Feb. 9, 2021, 9 pages.
International Search Report and Written Opinion in International Appln. No. PCT/US2021/016360, mailed May 21, 2021, 13 pages.
International Search Report and Written Opinion in International Appln. No. PCT/US2021/016363, mailed May 18, 2021, 15 pages.
International Search Report and Written Opinion in International Appln. No. PCT/US2021/016389, mailed May 18, 2021, 15 pages.
International Search Report and Written Opinion in International Appln. No. PCT/US2021/016390, mailed May 18, 2021, 13 pages.
International Search Report and Written Opinion in International Appln. No. PCT/US2021/032783, mailed Aug. 24, 2021, 13 pages.
International Search Report and Written Opinion in International Appln. No. PCT/US2021/058814, mailed Mar. 17, 2022, 14 pages.
International Search Report and Written Opinion in International Appln. No. PCT/US2022/016866, mailed Jul. 4, 2022, 18 pages.
International Search Report and Written Opinion in International Appln. No. PCT/US2022/016883, mailed May 11, 2022.
International Search Report and Written Opinion in International Appln. No. PCT/US2023/066904, mailed Sep. 12, 2023, 12 pages.
International Search Report and Written Opinion in International Appln. No. PCT/US2023/066965, mailed Aug. 4, 2023, 10 pages.
International Search Report and Written Opinion in International Appln. No. PCT/US2024/031785, mailed Sep. 24, 2024, 12 pages.
International Search Report and Written Opinion in International Appln.No. PCT/US2024/019800, mailed Jul. 17, 2024.
Invitation to Pay Additional Fees in PCT Appln. No. PCT/US2020/022705, mailed May 18, 2020, 2 pages.
Ishler et al., "Lyophilized Human Platelets Interact with Fresh Platelets to Promote Hemostasis Under Shear In Vitro", Cellphire, Inc., 2021, 2 page, Abstract.
Ishler et al., "Lyophilized Human Platelets Interact with Fresh Platelets to Promote Hemostasis Under Shear In Vitro", Cellphire, Inc., PB0990, Jul. 2021, 1 page, Poster.
Ishler et al., "Lyophilized Human Platelets Show Hemostatic Function Independent of von Willebrand Factor", Research and Practice in Thrombosis and Haemostasis, 2020; 4 (Suppl 1), 2 pages, ISth 2020 Virtual Congress Presentation, Jul. 2020, Abstract PB1533, https://abstracts.isth.org/abstract/lyophilized-human-platelets-show-hemostatic-function-independent-of-von-willebrand-factor/.
Ishler et al., "Lyophilized Platelets Show Hemostatic Function Independent of von Willebrand Factor", Cellphire, Inc., Department of Discovery and Research, ISth 2020 Virtual Congress, PB1533, Jul. 2020, 1 page, Poster.
Ishler et al., "StablePlate RX Canine Promotes in vitro Thromblin Generation and Thrombus Formation Under High Shear," Journal of Veterinary Internal Medicine, 2019 ACVIM Forum Research Abstract Program, p. 2483, Abstract.
Ishler et al., "StablePlate RX® Canine Promotes In Vitro Thrombin Generation and Thrombus Formation Under High Shear", Cellphire, Inc., 2019, 1 page, Poster1.
Ishler et al., "StablePlate RX® Canine Promotes In Vitro Thrombin Generation and Thrombus Formation Under High Shear", Cellphire, Inc., 2019, 1 page, Poster2.
Ito et al., "Total Thrombus-formation Analysis System (T-TAS) can predict periprocedural bleeding events in patients undergoing catheter ablation for atrial fibrillation," Journal of American Heart Association, 2015, 5(1):e002744, 12 pages.
Jennings et al., "Antiplatelet and anticoagulant agents: Key differences in mechanisms of action, clinical application, and therapeutic benefit in patients with non-ST-segment-elevation acute coronary syndromes", Current Opinion in Cardiology vol. 23, No. 4, Jul. 2008, pp. 302-308, DOI: 10.1097/HCO.0b013e3283021ad9.
Jennings et al., "The pharmacodynamics of parenteral glycoprotein IIb/IIIa inhibitors", Journal of Interventional Cardiology, vol. 15, No. 1, Feb. 2002, pp. 45-60, DOI: 10.1111/j.1540-8183.2002.tb01034.x.
Johnson et al., "Platelet microparticles in cryopreserved platelets: Potential mediators of hemostasis", Transfusion and Apheresis Science, vol. 53, Issue 2, Oct. 2015, pp. 146-152, doi.org/10.1016/j.transci.2015.10.011.
Joshi et al., "Lyophilised Reconstituted Human Platelets Increase Thrombus Formation in a Clinical Ex Vivo Model of Deep Arterial Injury", Thrombosis and Haemostasis, vol. 108, No. 1, 2012, pp. 176-182, DOI: 10.1160/TH12-02-0059.
Joshi et al., "Thrombosomes Show Dose-Dependent Increase in Thrombus Formation in a Model of Deep Arterial Injury", Blood, vol. 118, Issue 21, Nov. 18, 2011, Abstract 2319, 8 pages, doi.org/10.1182/blood.V118.21.2319.2319.
Kariko et al., "Phosphate-enhanced transfection of cationic lipid-complexed mRNA and plasmid DNA," Biochim. Biophys. Acta, 1998, 1369(2):320-334.
Kerrigan, "Platelet interactions with bacteria," The non-thrombotic role of platelets in health and disease; Chapter 4, 2015, 65-84.
Kerrigan, et al., "Molecular basis for *Staphylococcus aureus* mediated platelet aggregate formation under arterial shear in vitro," Arteriosclerosis Thrombosis and Vascular Biology, 2008, 28(2):334-340.
Kessler, "Bleeding after treatment with rivaroxaban or apixaban", Clinical Advances in Hemotology and Oncology, vol. 17, No. 9, Supplement 15, Sep. 2019, pp. 3-19.
Kirby et al., "Preparation of liposomes containing Factor VIII for oral treatment of haemophilia," 1984, J. Microencapsul. 1(1): 33-45.
Kirkley et al., "Use of single donor platelets", Blood Reviews, vol. 8, Issue 3, Sep. 1994, pp. 142-147, doi.org/10.1016/0268-960X(94)90074-R.
Kishbaugh et al., "Intervening with Platelet Therapies", National Elephant Herpesvirus Laboratory at the National Zoo, vol. 4, No. 2, 2017, 4 pages.
Kreuger et al., "HLA-matched platelet transfusions are effective only in refractory patients with positive HLA antibody screening", Transfusion, The Journal of American Association of Blood Banks, vol. 59, No. 11, Oct. 11, 2019, pp. 3303-3307, doi.org/10.1111/trf.15530.
Kuhn et al., "Assessing Circulation Persistence of Human Platelet Products in a NOD-SCID Mouse Model", Research and Practice in Thrombosis and Haemostasis, 2022, ISTH 2022 Congress Jul. 2022, 1 page, Poster PB0874.
Kuhn et al., "Assessing Circulation Persistence of Human Platelet Products in a NOD-SCID Mouse Model", Research and Practice in

(56) References Cited

OTHER PUBLICATIONS

Thrombosis and Haemostasis, 2022, 2 pages, ISTH 2022 Congress, Abstract PB0874, https://abstracts.isth.org/abstract/assessing-circulation-persistence-of-human-platelet-products-in-a-nod-scid-mouse-model/.

Kuhn et al., "Mechanism of Action of a Freeze-dried Platelet-derived Hemostatic Product", Cellphire, Inc. Cellular Therapeutics in Trauma and Critical Care, May 8-11, 2023, 1 page, poster.

Kuhn et al., "Mechanisms of action of an investigational new freeze-dried platelet-derived hemostatic product", Journal of Thrombosis and Haemostasis, Dec. 9, 2023, 4 pages, doi.org/10.1016/j.jtha.2023.11.022.

Lam, et al., "siRNA versus miRNA as therapeutics for gene silencing," Molecular Therapy—Nucleic Acids, 2015, 4:e252.

Lannan, et. al., "Breaking the Mold: Transcription Factors in the Anuceleate Platelet and Platelet-Derived Microparticles," Front Imunnol., 2015, 6:48, 17 pages.

Lassila et. al., "Dynamic Monitoring of Platelet Deposition on Severely Damaged Vessel Wall in Flowing Blood. Effects of Different Stenoses on Thrombus Growth", Arteriosclerosis, vol. 10, No. 2, Mar.-Apr. 1990, pp. 306-315, doi: 10.1161/01.atv.10.2.306.

Lee et al., "High Efficiency Transfection and Preservation of Platelets with Tumor Suppressing Short RNA", Research and Practice in Thrombosis and Haemostasis, Jul. 2020, 1 page, Poster PB1724, ISTH 2020 Congress.

Lee et al., "High Efficiency Transfection and Preservation of Platelets with Tumor Suppressing Short RNA", Research and Practice in Thrombosis and Haemostasis, 2020; 4 (Suppl 1). 2 pages, Abstract PB1724, ISTH 2020 Congress, https://abstracts.isth.org/abstract/high-efficiency-transfection-and-preservation-of-platelets-with-tumor-suppressing-short-rna/.

Human Translation of Chinese patent No. CN103907595 A Published Jul. 9, 2014, Trehalose-containing platelet low temperature preservation solution and application thereof, First Inventor Zhao Shuming.

Machine Language Translation of Chinese Patent No. CN108715834 A Titled [EN], "A Kind of Platelet Lysates Liquid and Preparation Method There of Rich in CD41+, CD81+ Micro-Capsule", Oct. 30, 2018, 10 pages.

Machine Language Translation of Chinese Patent No. CN109942687 A, Shen et at., Titled [EN], "68Ga Marks EACA Modification c-Met Molecular Imaging Probe and Preparation and Application", Jun. 28, 2019, 10 pages.

Machine Language Translation of Japanese Patent JP2012143554 A2 Titled "[EN] Polysulfone-Based Hollow Fiber Membrane, Hollow Fiber Membrane Module for Cleaning Platelet Suspension, and Cleaning Method of Platelet Suspension.", Aug. 2, 2012, 33 pages.

Machine Language Translation of WO2018084228A1: Nagamura et al., Titled [EN], "Solution for Cryopreservation of Animal Cells or Animal Tissues, Cryopreserved Product, and Cryopreservation Method", May 11, 2018, 16 pages.

Machine Language Translation of Yamamoto, "Appropriate use of platelet preparations", Journal of Thrombosis and Hemostasis, vol. 29, No. 6, 2018, pp. 647-650.

Valeri et al., "Freezing human platelets with 6 percent dimethyl sulfoxide with removal of the supernatant solution before freezing and storage at–80° C. without post thaw processing" Transfusion, vol. 45 (12), Dec. 2005, pp. 1890-1898, DOI: 10.1111/j.1537-2995.2005.00647.x.

Valeri et al., "Survival of baboon biotin-X-N-hydroxysuccinimide and 11 IIn-oxine-labelled autologous fresh and lyophilized reconstituted platelets," Vox Sanguinis, 2005, 88:122-129.

Van Der Meer et al, Platelet preservation: Agitation and containers, Transfusion and Apheresis Science, vol. 44, Issue 3, Jun. 2011, pp. 297-304, //doi.org/10.1016/j.transci.2011.03.005.

Van Der Meijden et al., "Platelet- and erythrocyte-derived microparticles trigger thrombin generation via factor XIIa", Journal of Thrombosis and Haemostasis, vol. 10, Issue 7, Apr. 26, 2012, pp. 1355-1362, doi.org/10.1111/j.1538-7836.2012.04758.x.

Vibhudutta et al., "Trehalose Stabilized Freeze Dried Human Platelets, Thrombosomes, Reduce Blood Loss in Thrombocytopenic Rabbit Ear Bleed Model by as Much as 89.5%", Cellphire, Inc., www.bodevet.com, Mar. 2017, 1 page, Poster P-0454.

Vibhudutta et al., "Trehalose Stabilized Freeze Dried Human Platelets, Thrombosomes, Persist in Circulation 24 Hours After Infusion and Are Non-Immunogenic in New Zealand White Rabbits", International Society of Blood Transfusion Vox Sanguinis, vol. 99, Suppl. 1, 2010, p. 262, Abstract P-0454.

Vibhudutta et al., "Trehalose Stabilized Freeze Dried Human Platelets, Thrombosomes, Persist in Circulation 24 Hours After Infusion and Are Non-Immunogenic in New Zealand White Rabbits", Cellphire, Inc., 1 page, Poster P-0454.

Vibhudutta et al., "Trehalose Stabilized Freeze Dried Human Platelets, Thrombosomes, Reduce Blood Loss in Thrombocytopenia Rabbit Ear Bleed Model by as Much as 89.5%", International Society of Blood Transfusion Vox Sanguinis, vol. 99, Suppl. 1, 2010, p. 261, Abstract P-0452.

Viswanathan et al., "Clopidogrel Alters Thrombus Quantity and Quality in Patients With Type II Diabetes Mellitus and Stable Coronary Artery Disease", Journal of the American College of Cardiology, vol. 61, No. 10, Mar. 2013, E1154, 1 page.

Vlieghe et al., "Synthetic therapeutic peptides: science and market," Drug Discovery Today, 2010, 15:40-56.

Volz et al., "Inhibition of platelet GPVI induces intratumor hemorrhage and increases efficacy of chemotherapy in mice," Blood, 2019, 133(25):2696-2706.

Wajon et al., "Intraoperative Plateletpheresis and Autologous Platelet Gel Do Not Reduce Chest Tube Drainage or Allogeneic Blood Transfusion After Reoperative Coronary Artery Bypass Graft", Anesth. Analg;., 2001, 93:536-542.

Wang et al., "Commonly used dietary supplements on coagulation function during surgery," Medicines, 2015, 2:157-185.

Wang et al., "Solubility and Molecular Interactions of Trimetazidine Hydrochloride in 12 Monosolvents and Solvent Mixtures of Methanol + (Ethanol, N,N-Dimethylformamide or Ethyl Acetate)", Journal of Chemical Engineering Data, Folume 63, Sep. 6, 2018, pp. 3704-3714, doi.org/10.1021/acs.jced.8b00235.

Wei et al., "ICAM-5/Telencephalin Is a Functional Entry Receptor for Enterovirus D68", Cell Host Microbe, vol. 20, Issue 5, Nov. 9, 2016, pp. 631-641, doi: 10.1016/j.chom.2016.09.013.

Whitman et al., "Design of the CRYPTICS Trail: A Randomized Controlled Trial Comparing Cryopreserved to Liquid Stored Platelets in Patients Undergoing Cardiac Surgery", Journal of Thoracic and Cardiovascular Surgery, 2022, doi.org/10.1016/j.xjon.2022.11.003.

Whitney et al. "Ratiometric Activatable Cell-Penetrating Peptides Provide Rapid In Vivo Readout of Thrombin Activation", Angewandte Chemie International Edition, vol. 52, Jan. 2, 2013, Issue 1, pp. 325-330, doi: 10.1002/anie.201205721.

Wickramasinghe, "Washing Cryopreserved Blood Products Using Hollow Fibres", Food and Bioproducts Processing, vol. 77, Issue 4, Dec. 1999, pp. 287-292, DOI:org/10.1205/096030899532574.

Wikström et al., "Viability of freeze dried microencapsulated human retinal pigment epithelial cells", European Journal of Pharmaceutical Sciences, vol. 47, Issue 2, Sep. 29, 2012, pp. 520-526, doi: 10.1016/j.ejps.2012.06.014.

Wilkerson et al., "Platelet size, platelet surface-associated IgG, and reticulated platelets in dogs with immune-mediated thrombocytopenia," Veterinary Clinical Pathology, 2001, 30(3):141-149.

Wilson et al., "A simple rapid method for layering blood on Ficoll-Isopaque gradients," Journal of Immunological Methods, 1975, 9(1): 67-68.

Wolkers et al., "Human Platelets Loaded with Trehalose Survive Freeze-Drying", Cryobiology, vol. 42, 2001, pp. 79-87.

WPI Database No. AN 2014-E98028 / CN103524613, Jan. 22, 2014: 2 pages.

Wright et al., "Doxorubicin delivery via novel lyophilized/reconstituted platelet-product has anti-cancer activity", Hematology & Transfusion International Journal, vol. 9, Issue 3, 2021, pp. 41-51.

Xu et al., "Doxorubicin-loaded platelets as a smart drug delivery system: An improved therapy for lymphoma", Scientific Reports vol. 7, Article No. 42632, Feb. 15, 2017, 15 pages.

(56) References Cited

OTHER PUBLICATIONS

Xu et al., "EACA Loaded Platelets Sustain Clots More Efficiently Than Free EACA", Cellphire, Inc., Jul. 2021, 1 page, Poster.
Xu et al., "EACA Loaded Platelets Sustain Clots More Efficiently Then Free EACA", Cellphire, Inc., 2021. 2 page.
Xu et al., "Human Platelet Derived Lyophilized Hemostatic Retains Hemostatic Properties Heparin Complexation with Protamine", Cellphire, Inc. Jul. 2022, 1 page, Poster.
Xu et al., "Thrombosomes as a Treatment Option for Low-Dose Heparin Reversal", Cellphire Therapeutics, Inc., Rockville, MD, 2020 Annual Meeting, 3 pages.
Yamamoto, "Appropriate use of platelet preparations", Journal of Thrombosis and Hemostasis, vol. 29, No. 6, 2018, pp. 647-650.
Yarovoi et al., "Factor VIII ectopically expressed in platelets: efficacy in hemophilia A treatment", Blood 102(12):4006-4013, 2003.
Zafar et. al., "Badimon Perfusion Chamber: An Ex Vivo Model of Thrombosis", Methods Molecular Biology, vol. 1816, 2018, pp. 161-171, doi: 10.1007/978-1-4939-8597-5_12.
Zhang et al., "Coupling of liquid chromatography with mass spectrometry by desorption electrospray ionization (DESI)", Chemical Communications, Issue 14, Feb. 28, 2011, pp. 4171-4173, doi.org/10.1039/C0CC05736C.
Zhou et al., "Freeze-drying of human platelets: influence of saccharide, freezing rate and cell concentration", Cryoletters, vol. 28, No. 3, May/Jun. 2007, pp. 187-196.
Zhou et al., "Hemostatic and Thrombogenic Properties of Lyophilized Human Platelets", CellPhire, Inc. Jul. 2021, 1 page, Poster.
Zhou et al., "Loading Trehalose into Red Blood Cells by Improved Hypotonic Method," Cell Preservation Technology, 2008, 6(2):119-122.
Zhou et al., "Lyophilized Human Platelets Promote Coagulation in Humanized Mouse VWF Transgenic Models of Hemostasis and Thrombosis", Cellphire, Inc., 2021, 1 page.

\* cited by examiner

METHODS USING FREEZE-DRIED PLATELET DERIVATIVE COMPOSITIONS FOR RESTORING HEMOSTASIS IN A SUBJECT

CROSS-REFERENCE TO RELATED APPLICATIONS

This application is a continuation of U.S. patent application Ser. No. 17/674,770, filed on Feb. 17, 2022. U.S. patent application Ser. No. 17/674,770 claims priority to U.S. Provisional Application Ser. No. 63/150,338, filed on Feb. 17, 2021, U.S. Provisional Application Ser. No. 63/275,937, filed on Nov. 4, 2021, U.S. Provisional Application Ser. No. 63/276,420, filed on Nov. 5, 2021, and U.S. Provisional Application Ser. No. 63/264,227, filed on Nov. 17, 2021. Each of the aforementioned applications is incorporated herein by reference in its entirety.

FIELD OF THE INVENTION

This disclosure relates to the use of platelet derivatives as a treatment for anti-thrombotic agent-induced coagulopathy. The use of antiplatelet agents can result in increased bleeding potential.

BACKGROUND

Antiplatelet drugs (also herein called antiplatelet agents) are common in the U.S. adult population and employ multiple mechanisms of inhibiting platelet action. Antiplatelet drugs are used to treat and/or prevent a number of cerebrovascular and cardiovascular diseases Antiplatelet drugs, however, are responsible for many adverse drug-related events (ADEs). Overdose and adverse events related to these drugs carry the risk of serious bleeding and related complications in the patient population. In addition, subjects treated with antiplatelet drugs face additional complications for surgery, as a subject may need to be tapered off the drugs before surgery, though cessation of therapy could put the subject at an increased risk for heart attack, stroke, or death.

There is therefore a need in the art for the treatment of coagulopathy, such as antiplatelet agent-induced coagulopathy, as well as a need for a solution for preparing subjects taking an anti-platelet drug for surgery.

SUMMARY OF THE INVENTION

Accordingly, the use of anti-thrombotic agents (i.e. anti-platelet agents and/or anti-coagulants) can result in increased bleeding potential of a subject. Here we demonstrate that platelet derivatives can circumvent or overcome this inhibition to restore hemostasis. Accordingly, provided herein are platelet derivatives, in illustrative embodiment freeze-dried platelet derivative (FDPD) and compositions comprising the same, that can reduce this increased bleeding potential of a subject, and in certain illustrative embodiments, circumvent or overcome this inhibition of platelets by such anti-thrombotic agents, to restore hemostasis.

Provided herein are methods and compositions for treating a coagulopathy in a subject. Such methods can include administering to the subject in need thereof, for example because they have been administered an anticoagulant agent, an effective amount of a composition including platelets, or in illustrative embodiments platelet derivatives, and in further illustrative embodiments FDPDs. Various properties of exemplary embodiments of such FDPDs and methods, as well as numerous additional aspects and embodiments are provided herein.

Further details regarding aspects and embodiments of the present disclosure are provided throughout this patent application. The preceding paragraphs in this Summary section are not an exhaustive list of aspects and embodiments disclosed herein. Sections and section headers are for ease of reading and are not intended to limit combinations of disclosure, such as methods, compositions, and kits or functional elements therein across sections.

DETAILED DESCRIPTION

Figure 1:
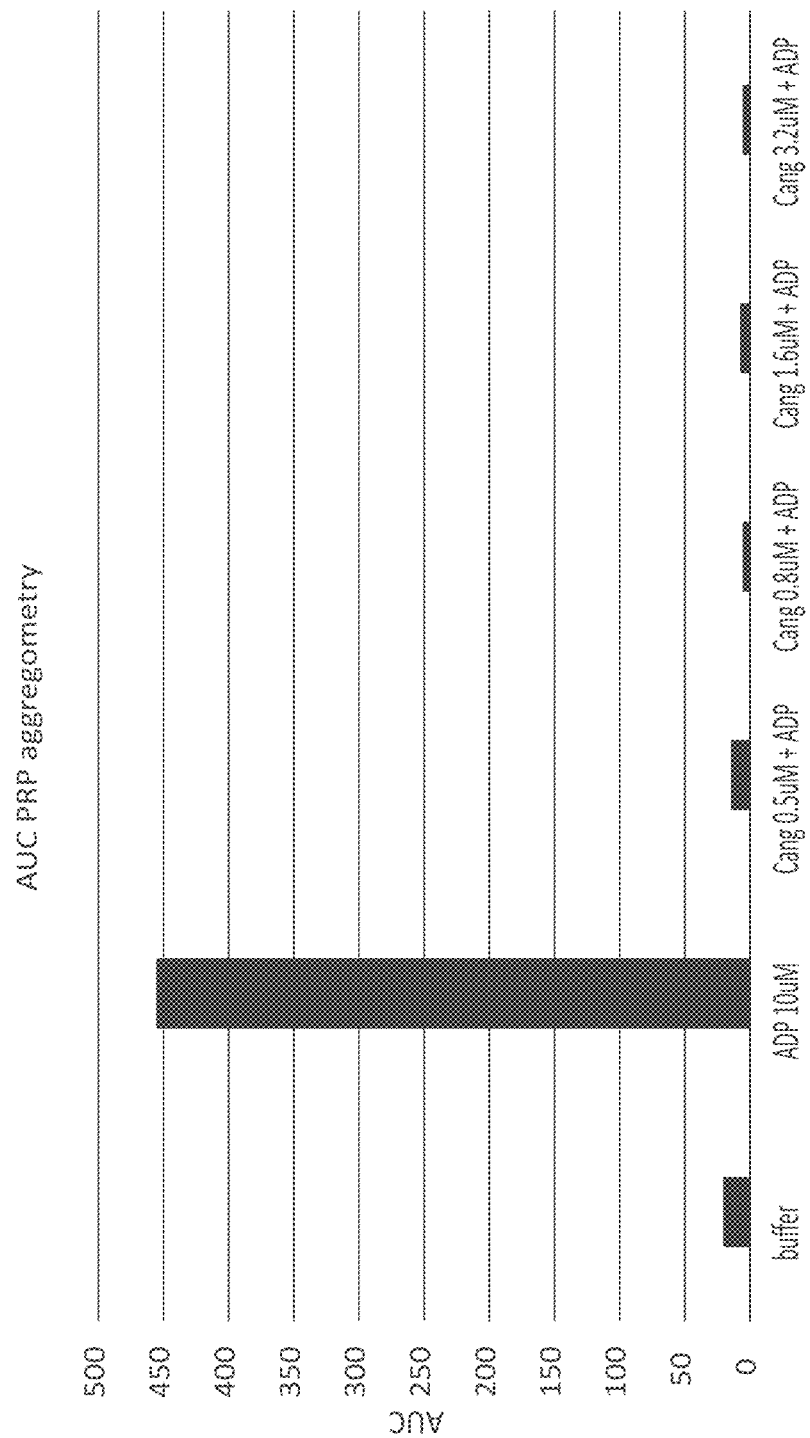
FIG. 1 shows transmission light aggregometry of cangrelor ("Cang") in platelet rich plasma, expressed as the integrated aggregation curve, induced by 10 µM adenosine diphosphate (ADP) activation with and without increasing concentrations of cangrelor.

Before embodiments of the present invention are described in detail, it is to be understood that the terminology used herein is for the purpose of describing particular embodiments only, and is not intended to be limiting. Unless defined otherwise, all technical and scientific terms used herein have the same meaning as commonly understood by one of ordinary skill in the art to which the term belongs. Although any methods and materials similar or equivalent to those described herein can be used in the practice of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein, the singular forms "a", "an", and "the" include plural referents unless the context clearly dictates otherwise. Thus, for example, reference to "a saccharide" includes reference to one or more saccharides, and equivalents thereof known to those skilled in the art. Furthermore, the use of terms that can be described using equivalent terms include the use of those equivalent terms. Thus, for example, the use of the term "subject" is to be understood to include the terms "patient", "person", "animal", "human", and other terms used in the art to indicate one who is subject to a medical treatment. The use of multiple terms to encompass a single concept is not to be construed as limiting the concept to only those terms used.

It is to be understood that the terminology used herein is for the purpose of describing particular embodiments only, and is not intended to be limiting. Further, where a range of values is disclosed, the skilled artisan will understand that all other specific values within the disclosed range are inherently disclosed by these values and the ranges they represent without the need to disclose each specific value or range herein. For example, a disclosed range of 1-10 includes 1-9, 1-5, 2-10, 3.1-6, 1, 2, 3, 4, 5, and so forth. In addition, each disclosed range includes up to 5% lower for the lower value of the range and up to 5% higher for the higher value of the range. For example, a disclosed range of 4-10 includes 3.8-10.5. This concept is captured in this document by the term "about".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

As used herein, the term "coagulopathy" means any derangement of hemostasis resulting in either excessive bleeding or clotting. Coagulopathies caused by administration of an anti-platelet or anti-coagulant to a subject typically includes an increased bleeding potential. Thus, methods herein for treating a coagulopathy in illustrative embodiments, are methods for decreasing the bleeding potential of a subject.

As used herein, the term "platelet" can include whole platelets, fragmented platelets, platelet derivatives, or FDPDs. "Platelets" within the above definition may include, for example, platelets in whole blood, platelets in plasma, platelets in buffer optionally supplemented with select plasma proteins, cold stored platelets, dried platelets, cryopreserved platelets, thawed cryopreserved platelets, rehydrated dried platelets, rehydrated cryopreserved platelets, lyopreserved platelets, thawed lyopreserved platelets, or rehydrated lyopreserved platelets. "Platelets" may be "platelets" of mammals, such as of humans, or such as of non-human mammals. As used herein, "preparation agent" can include any appropriate components. In some embodiments, the preparation agent may comprise a liquid medium. In some embodiments the preparation agent may comprise one or more salts selected from phosphate salts, sodium salts, potassium salts, calcium salts, magnesium salts, and any other salt that can be found in blood or blood products, or that is known to be useful in drying platelets, or any combination of two or more of these. In some embodiments, the preparation agent comprises one or more salts, such as phosphate salts, sodium salts, potassium salts, calcium salts, magnesium salts, and any other salt that can be found in blood or blood products. Exemplary salts include sodium chloride (NaCl), potassium chloride (KCl), and combinations thereof. In some embodiments, the preparation agent includes from about 0.5 mM to about 100 mM of the one or more salts. In some embodiments, the preparation agent includes from about 0.5 mM to about 100 mM (e.g., about 0.5 to about 2 mM, about 2 mM to about 90 mM, about 2 mM to about 6 mM, about 50 mM to about 100 mM, about 60 mM to about 90 mM, about 70 to about 85 mM) of the one or more salts. In some embodiments, the preparation agent includes about 5 mM, about 75 mM, or about 80 mM of the one or more salts. In some embodiments, the preparation agent comprises one or more salts selected from calcium salts, magnesium salts, and a combination of the two, in a concentration of about 0.5 mM to about 2 mM.

As used herein, "thrombosomes" (sometimes also herein called "Tsomes" or "Ts", particularly in the Examples and Figures) are platelet derivatives that have been treated with an incubating agent (e.g., any of the incubating agents described herein) and lyopreserved (i.e. freeze-dried). Thus, thrombosomes are freeze-dried platelet derivatives (FDPDs). In some cases, FDPDs can be prepared from pooled platelets. FDPDs can have a shelf life of 2-3 years in dry form at ambient temperature and can be rehydrated with sterile water within minutes for immediate infusion. One example of FDPDs are THROMBOSOMES®, which are in clinical trials for the treatment of acute hemorrhage in thrombocytopenic patients and are a product of Cellphire, Inc. In non-limiting illustrative embodiments, FDPD compositions, or illustrative freeze-dried platelet-derivative (i.e. "FDPD") compositions herein, such as those prepared according to Example 15 herein, are compositions that include a population of platelet derivatives having a reduced propensity to aggregate such that no more than 10% of the platelet derivatives in the population aggregate under aggregation conditions comprising an agonist but no platelets, and wherein the platelet derivatives have a potency of at least 1.5 thrombin generation potency units (TGPU) per $10^6$ platelet derivatives. In non-limiting illustrative embodiments, FDPD compositions, or illustrative FDPD compositions herein, such as those prepared according to Example 15 herein, are compositions that include platelet derivatives, wherein at least 50% of the platelet derivatives are CD 41-positive platelet derivatives, wherein less than 15%, 10%, or in further, non-limiting illustrative embodiments less than 5% of the CD 41-positive platelet derivatives are microparticles having a diameter of less than 0.5 μm, and wherein the platelet derivatives have a potency of at least 0.5, 1.0 and in further, non-limiting illustrative embodiments 1.5 thrombin generation potency units (TGPU) per $10^6$ platelet derivatives. In certain illustrative embodiments, including non-limiting examples of the illustrative embodiment in the preceding sentence, the platelet derivatives are between 0.5 and 2.5 um in diameter.

As used herein, an "anticoagulant" is an antithrombotic that does not include antiplatelet agents. Typically, agents that inhibit Factor IIa, VIIa, IX, Xa, XI, Tissue Factor, or vitamin K-dependent synthesis of clotting factors (e.g., Factor II, VII, IX, or X) or that activate antithrombin (e.g., antithrombin III) are considered to be anticoagulants. Other mechanisms of anticoagulants are known. Anticoagulants include dabigatran, argatroban, hirudin, rivaroxaban, apixaban, edoxaban, fondaparinux, warfarin, heparin, and low molecular weight heparins.

As used herein, an "antiplatelet agent" is an antithrombotic and does not include anticoagulants. Typically, agents that inhibit P2Y receptors (e.g., P2Y12), glycoprotein IIb/IIIa (I.e. CD41), or that antagonize thromboxane synthase or thromboxane receptors, are considered to be antiplatelet agents. Other mechanisms of antiplatelet agents are known. As used herein, aspirin is considered to be an antiplatelet agent but not an anticoagulant. Examples of antiplatelet agents include aspirin (also called acetylsalicylic acid or ASA), cangrelor (e.g., KENGREAL®), ticagrelor (e.g., BRILINTA®), clopidogrel (e.g., PLAVIX®), prasugrel (e.g., EFFIENT®), eptifibatide (e.g., INTEGRILIN®), tirofiban (e.g., AGGRASTAT®), and abciximab (e.g., REOPRO®). For the purpose of this disclosure, antiplatelet agents include agents that inhibit P2Y receptors (e.g., $P2Y_{12}$), glycoprotein IIb/IIIa, or that antagonize thromboxane synthase or thromboxane receptors. Non-limiting examples of thromboxane $A_2$ antagonists are aspirin, terutroban, and picotamide. Non-limiting examples of P2Y receptor antagonists include cangrelor, ticagrelor, elinogrel, clopidogrel, prasugrel, and ticlopidine. Non-limiting examples of glycoprotein IIb/IIIa include abciximab, eptifibatide, and tirofiban. NSAIDS (e.g., ibuprofen) are also considered to be antiplatelet agents for the purposes of this disclosure. Other mechanisms of anti-platelet agents are known. Antiplatelet agents also include PAR1 antagonists, PAR4 antagonists GPVI antagonists and alpha2beta1 collagen receptor antagonists. Non-limiting examples of PAR-1 antagonists include vorapaxar and atopaxar. As used herein, aspirin is considered to be an antiplatelet agent but not an anticoagulant. Additional non-limiting examples of antiplatelet agents include cilostazol, prostaglandin E1, epoprostenol, dipyridamole, treprostinil sodium, and sarpogrelate.

In some embodiments, an antiplatelet agent can be selected from the group consisting of aspirin, cangrelor, ticagrelor, clopidogrel, prasugrel, eptifibatide, tirofiban, abciximab, and combinations thereof. In some embodiments, an antiplatelet agent can be selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, and combinations thereof. In some embodiments, an antiplatelet agent can be selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, sarpogrelate and combinations thereof. In some embodiments, the antiplatelet agent can include multiple antiplatelet agents, such as 2 (or more) of any of the antiplatelet agents described herein. In some embodiments, the antiplatelet agent can be aspirin and clopidogrel.

Cangrelor like clopidogrel, ticagrelor, and prasugrel, blocks the $P2Y_{12}$ (ADP) receptor on platelets. Cangrelor can in some cases be used as a representative of this class of drug. Cangrelor, unlike clopidogrel and prasugrel, does not need hepatic metabolism to become biologically active.

Eptifibatide is a peptide therapeutic that blocks the fibrin binding role of GPIIb-IIIa receptor on platelets. The drug is typically administered via IV as a 180 μg/kg bolus followed by 2 μg/kg/min continuous infusion. The blood concentration of eptifibatide is typically about 1-2 μM. Bleeding times generally return to normal within about 1 hour of drug stoppage.

Aspirin is an irreversible cyclooxygenase (COX) inhibitor. The COX enzyme in platelets is responsible for synthesis of thromboxane A2, prostaglandin E2 and prostacyclin (PGI2). Aspirin permanently inactivates the COX enzyme within platelets, and since platelets do not have the nuclear material to synthesize new enzyme, new platelets must be produced to overcome the aspirin effect. Without thromboxane A2, prostaglandin E2, and prostacyclin (PGI2) platelets are limited in their pro-aggregation activity. Many people are maintained on a low dose of aspirin to prevent unwanted clotting events. Aspirin bioavailability largely varies with administration route, with a single 500 mg dose IV at peaks of 500 μM and the same dose orally at 44 μM.

The antiplatelet class of drugs is widely used to prevent unwanted clotting episodes that lead to heart failure, stroke, and the like. In many cases, an antiplatelet drug may need to be reversed or stopped, or bleeding potential needs to be reduced in some other manner in a subject who has an antiplatelet drug in their blood stream, such that a bleeding potential of the subject is increased. In the case of advanced notice, as in a pre-planned surgery situation, the antiplatelet drug dose can sometimes be stopped before the surgery, preventing unwanted bleeding during surgery. In the case where an antiplatelet agent needs reversing quickly, reversal agents are typically not readily available, are expensive, or carry significant risk to the patient. In the case of need for rapid antiplatelet reversal, a platelet transfusion is typically administered, though the response to this is often only partial reversal. The caveat of this course of reversal is that the newly-infused platelets themselves are susceptible to circulating drug antiplatelet activity whereas, in some embodiments, compositions as described herein (e.g., including FDPDs) are not. In some embodiments, compositions as described herein (e.g., including FDPDs) are an active reversal agent. In some embodiments, the hemostatic activity of compositions as described herein (e.g., including FDPDs) does not succumb to antiplatelet drugs.

Some exemplary antiplatelet agents and potential methods of reversal are described below.

Acetylsalicylic acid (ASA; aspirin)—aspirin acts as a COX-1 blocker in platelets, which renders the platelet inactive by irreversibly inhibiting platelet-derived thromboxane formation. Clinically, aspirin is sometimes reversed by a platelet transfusion in emergency situations or by stopping treatment where surgery is scheduled in the future.

Clopidogrel (e.g., PLAVIX®)—clopidogrel acts as to prevent ADP from binding to its receptor on platelets. ADP binding leads to platelet shape change and aggregation. Clopidogrel is non-reversible. Clinically, clopidogrel is sometimes reversed by a platelet transfusion in emergency situations or by stopping treatment where surgery is scheduled in the future.

Cangrelor (e.g., KENGREAL®)—cangrelor acts to prevent ADP from binding to its receptor on platelets. ADP binding leads to platelet shape change and aggregation. Clopidogrel is reversible and platelet function is returned approximately 1 hour after stopping infusion. Clinically it is generally preferred when reversal is needed after a procedure.

Ticagrelor (e.g., BRILINTA®)—ticagrelor acts to prevent ADP from binding to its receptor and acts as an inverse agonist. Ticagrelor is reversible and platelet function can return after approximately 72 hours of the last dosage. Reversal of action of ticagrelor can be affected by the time after the last dose. If the last dose was longer than 24 hours previous, then platelet transfusion can sometimes be therapeutic to reverse the results.

Effient (e.g., PRASUGREL®)—Effient acts to prevent ADP from binding to its receptor and acts as a non-reversable antagonist. It being a non-reversible antagonist, new platelets must be formed to overcoming its effect.

Clinically Effient is reversed by a platelet transfusion in emergency situations or by stopping treatment where surgery is scheduled in the future.

Eptifibatide (Integrilin)—Eptifibatide acts to block the GpIIb/IIIa and acts as a reversible antagonist. Clinically, Integrilin is reversed by a platelet transfusion in emergency situations or by stopping treatment where surgery is scheduled in the future.

Platelets infusions are currently used as a treatment method for antiplatelet drugs, but platelet transfusions only act to dilute out the effect of these drugs. In some embodiments, FDPDs are not reactive to these drugs and maintain their ability to aid in clotting. This makes treatment via FDPDs entirely unique and introduces a new application for the product.

Platelet-derived products are not currently used as a treatment method to counteract the activity of an anti-thrombotic agent(s) (i.e. anticoagulant or antiplatelet drugs), when such effects can have detrimental consequences to a subject or pose an unacceptable risk to a subject, for example during a surgical procedure or as the results of a traumatic event. There are no currently approved reversal agents for antiplatelet agents or agents that otherwise reduce the bleeding potential of a subject, or restore hemostasis after treatment with an anti-coagulant and/or antiplatelet agent. As such, emergency treatments (pre-op, trauma, and the like) are typically require blanket precautions to avoid or mitigate hemorrhage. Non-limiting examples include infusion of plasma, red blood cells, and anti-fibrinolytics. Platelet derivatives, in illustrative embodiments freeze-dried platelet derivatives (FDPDs) provided herein, overcome this long-standing need, and are an effective alternative or supplement to these general treatments or risk-mitigation strategies.

The results provided in numerous Examples in the Examples section herein demonstrate the impact of a composition comprising FDPDs product in an in vitro model of a subject taking antiplatelet drugs. FDPD compositions and other lyophilized platelet products are designed for infusion into a subject's bloodstream following diagnosis of trauma or hemostatic failure. These anti-platelet drugs utilize multiple forms of platelet inhibition mechanisms which inhibit platelet response to adenosine diphosphate (ADP), arachidonic acid, fibrinogen and von Willebrand factor binding to name a few. These include drugs like aspirin, clopidogrel, ticagrelor, effient, cangrelor and eptifibatide. Regardless of the mechanism, FDPDs provided herein are able to decrease the bleeding potential of a subject taking such anti-platelet agents, and in some embodiments, restore normal hemostasis to the subject.

Without being bound by any particular theory, it is believed that certain platelet derivatives, in illustrative embodiments FDPDs provided herein, can work at least in part by providing a procoagulant negatively charged surface to augment thrombin generation above and beyond that suppressed by the anti-coagulants. Similarly, without being bound by any particular theory, it is believed that certain platelet derivatives, in illustrative embodiments FDPDs provided herein, can work at least in part by binding to and co-aggregating with circulating platelets. Thus, such FDPDs provide the surprising property of being able to reduce bleeding potential of a subject taking an anti-thrombotic agent (i.e. anti-coagulant or anti-platelet agent) despite having a reduced ability to aggregate and despite retaining at least some if not all of the surface markers that are targeted by at least some, if not all anti-platelet agents.

Products and methods are described herein for controlling bleeding and improving healing. The compositions, products and methods described herein can also be used to counteract the activity of any of the antiplatelet agents disclosed herein (e.g., as non-limiting examples, aspirin (also called acetylsalicylic acid or ASA), cangrelor (e.g., KENGREAL®), ticagrelor (e.g., BRILINTA®), clopidogrel (e.g., PLAVIX®), prasugrel (e.g., EFFIENT®), eptifibatide (e.g., INTEGRILIN®), tirofiban (e.g., AGGRASTAT®), or abciximab (e.g., REOPRO®)). The products and methods disclosed herein in certain embodiments, are directed toward embodiments that can aid in the closure and healing of wounds.

In certain aspects, provided herein, a composition comprising platelets, or in illustrative embodiments a composition comprising platelet derivatives, which in further illustrative embodiments are FDPDs, may be delivered to a wound on the surface of or in the interior of a patient. In various embodiments, a composition comprising platelets, or in illustrative embodiments a composition comprising platelet derivatives, which in further illustrative embodiments are FDPDs, or in illustrative embodiments a composition comprising platelet derivatives, which in further illustrative embodiments are FDPDs can be applied in selected forms including, but not limited to, adhesive bandages, compression bandages, liquid solutions, aerosols, matrix compositions, and coated sutures or other medical closures. In embodiments, a composition comprising platelets, or in illustrative embodiments a composition comprising platelet derivatives, which in further illustrative embodiments are FDPDs may be administered to all or only a portion of an affected area on the surface of a patient. In other embodiments, a composition comprising platelets, or in illustrative embodiments a composition comprising platelet derivatives, which in further illustrative embodiments are FDPDs may be administered systemically, for example via the blood stream. In embodiments, an application of the platelet derivative can produce hemostatic effects for 2 or 3 days, preferably 5 to 10 days, or most preferably for up to 14 days.

Some aspects provide a method of treating a coagulopathy in a subject, the method comprising administering to the subject in need thereof an effective amount of a composition comprising platelets, or in illustrative embodiments a composition comprising platelet derivatives, which in further illustrative embodiments are FDPDs. In some embodiments, the composition comprising FDPDs further comprises additional components, such as components that were present when such FDPDs were freeze-dried. Such additional components can include components of an incubating agent comprising one or more salts, a buffer, and in certain embodiments a cryoprotectant (also called a lyophilizing agent) and/or an organic solvent. For example, such compositions can comprise one or more saccharides, as provided further herein, which in illustrative embodiments include trehalose and in further illustrative embodiments include polysucrose.

Some aspects provide a method of treating a coagulopathy in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some embodiments of any of the methods described herein, the coagulopathy is the result of the presence of an antiplatelet agent in the blood of a subject.

Some aspects provide a method of treating coagulopathy in a subject, wherein the subject has been treated or is being treated with an antiplatelet agent, the method comprising administering to the subject in need thereof an effective amount of a composition comprising platelets, or in illustrative embodiments a composition comprising platelet derivatives, which in further illustrative embodiments are FDPDs and an incubating agent comprising one or more salts, a buffer, optionally a cryoprotectant, and optionally an organic solvent.

Some aspects provide a method of treating coagulopathy in a subject, wherein the subject has been treated or is being treated with an antiplatelet agent, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some aspects provide a method of restoring normal hemostasis in a subject, the method comprising administering to the subject in need thereof an effective amount of a composition comprising platelets, or in illustrative embodiments a composition comprising platelet derivatives, which in further illustrative embodiments are FDPDs. In some embodiments, the composition comprising FDPDs further comprises additional components, such as components that were present when such FDPDs were freeze-dried. Such additional components can include components of an incubating agent comprising one or more salts, a buffer, and in certain embodiments a cryoprotectant (also called a lyophilizing agent) and/or an organic solvent. For example, such compositions can comprise one or more saccharides, as provided further herein, which in illustrative embodiments include trehalose and in further illustrative embodiments include polysucrose.

Some aspects provide a method of restoring normal hemostasis in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some aspects provide a method of restoring normal hemostasis in a subject, wherein the subject has been treated or is being treated with an antiplatelet agent, the method comprising administering to the subject in need thereof an effective amount of a composition comprising platelets, or in illustrative embodiments a composition comprising platelet derivatives, which in further illustrative embodiments are FDPDs. In some embodiments, the composition comprising FDPDs further comprises additional components, such as components that were present when such FDPDs were freeze-dried. Such additional components can include components of an incubating agent comprising one or more salts, a buffer, and in certain embodiments a cryoprotectant (also called a lyophilizing agent) and/or an organic solvent. For example, such compositions can comprise one or more saccharides, as provided further herein, which in illustrative embodiments include trehalose and in further illustrative embodiments include polysucrose.

Some embodiments provide a method of restoring normal hemostasis in a subject, wherein the subject has been treated or is being treated with an antiplatelet agent, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Compositions as described herein can also be administered to prepare a subject for surgery, in some cases. For some patients taking an antiplatelet agent, it may be difficult or impossible to reduce the dosage of the antiplatelet agent before surgery (e.g., in the case of trauma or other emergency surgery). For some patients taking an antiplatelet agent, it may be inadvisable to reduce the dosage of the antiplatelet agent before surgery (e.g., if the patient would be at risk of a thrombotic event (e.g., deep vein thrombosis, pulmonary embolism, or stroke) if the dosage of the antiplatelet agent were reduced over time.

Accordingly, some embodiments provide a method of preparing a subject for surgery, the method comprising administering to the subject in need thereof an effective amount of a composition comprising platelets, or in illustrative embodiments a composition comprising platelet derivatives, which in further illustrative embodiments are FDPDs. In some embodiments, the composition comprising FDPDs further comprises additional components, such as components that were present when such FDPDs were freeze-dried. Such additional components can include components of an incubating agent comprising one or more salts, a buffer, and in certain embodiments a cryoprotectant (also called a lyophilizing agent) and/or an organic solvent. For example, such compositions can comprise one or more saccharides, as provided further herein, which in illustrative embodiments include trehalose and in further illustrative embodiments include polysucrose.

Some embodiments provide a method of preparing a subject for surgery, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some embodiments provide a method of preparing a subject for surgery, wherein the subject has been treated or is being treated with an antiplatelet agent, the method comprising administering to the subject in need thereof an effective amount of a composition comprising platelets, or in illustrative embodiments a composition comprising platelet derivatives, which in further illustrative embodiments are FDPDs. In some embodiments, the composition comprising FDPDs further comprises additional components, such as components that were present when such FDPDs were freeze-dried. Such additional components can include components of an incubating agent comprising one or more salts, a buffer, and in certain embodiments a cryoprotectant (also called a lyophilizing agent) and/or an organic solvent. For example, such compositions can comprise one or more saccharides, as provided further herein, which in illustrative embodiments include trehalose and in further illustrative embodiments include polysucrose.

Some embodiments provide a method of preparing a subject for surgery, wherein the subject has been treated or is being treated with an antiplatelet agent, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some embodiments, a surgery can be an emergency surgery (e.g., in the case of trauma) or a scheduled surgery.

In some embodiments, treatment with an anticoagulant can be stopped (e.g., in preparation for surgery) in illustrative embodiments before the composition comprising platelet derivatives is administered to the subject. In some embodiments, treatment with an anticoagulant can continue in illustrative embodiments for a time period after the composition comprising platelet derivatives is administered to the subject. Such a time period can include 1, 2, 3, 4, 5, 6, or 7 days, or 1, 2, 3, or 4 weeks, or 1, 2, or 3 months or longer.

Some embodiments provide a method of ameliorating the effects of an antiplatelet agent in a subject, the method comprising administering to the subject in need thereof an effective amount of a composition comprising platelets, or in illustrative embodiments a composition comprising platelet derivatives, which in further illustrative embodiments are FDPDs and an incubating agent comprising one or more salts, a buffer, optionally a cryoprotectant, and optionally an organic solvent.

Some aspects provide a method of ameliorating the effects of an antiplatelet agent in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some embodiments, the effects of an antiplatelet agent may need to be ameliorated due to an incorrect dosage of an antiplatelet agent. For example, in some embodiments, the effects of an antiplatelet agent can be ameliorated following an overdose of the antiplatelet agent. In some embodiments, the effects of an antiplatelet agent may need to be ameliorated due to a potential for interaction with another drug (e.g., a second antiplatelet agent). For example, in some embodiments, the effects of an antiplatelet agent can be ameliorated following an erroneous dosing of two or more drugs, at least one of which is an antiplatelet agent.

In some embodiments of any of the methods described herein, the composition can further comprise an active agent, such as an anti-fibrinolytic agent. Non-limiting examples of anti-fibrinolytic agents include ε-aminocaproic acid (EACA), tranexamic acid, aprotinin, aminomethylbenzoic acid, and fibrinogen. In some embodiments, platelets or platelet derivatives can be loaded with an active agent, such as an anti-fibrinolytic agent.

Compositions comprising FDPDs herein, in certain embodiments have the surprising property that they can reduce bleeding potential and in illustrative embodiments, restore hemostasis in a subject whose blood has an elevated bleeding potential, independent of whether a laboratory test for bleeding potential of the subject is negative or positive after administration of the FDPDs. Such elevated bleeding potential in illustrative embodiments is typically because an effective amount of anti-platelet agent was delivered to the subject and is in the blood of the subject. Accordingly, in any of the aspects herein, in some embodiments, the composition comprising FDPDs has the property that it is capable of reducing the bleeding potential of the subject, independent of whether a post-administering evaluation of bleeding potential, if performed, yields a normal or abnormal result. In some embodiments such post-administering evaluation comprises an in vitro laboratory test performed on a sample taken or drawn at a time period, for example, between 1 and 4, or 1 and 3, or 1 and 2 hours after administering the composition comprising FDPDs to the subject. In other embodiments of any of the aspects herein, wherein the composition comprising FDPDs has the property that it is capable of reducing the bleeding potential of a subject such that normal hemostasis is restored in a subject having an increased bleeding potential, independent of whether a post-administering evaluation of bleeding potential yields a normal or abnormal result. In some embodiments, such post-administering evaluation if performed, comprises an in vitro laboratory test performed on a sample taken or drawn at a time period, for example, between 1 and 4, or 1 and 3, or 1 and 2 hours after administering the composition comprising FDPDs to the subject. The time period, can be for example, within 0 minutes and 72 hours, or between 10 minutes and 72 hours, or between 10 minutes and 48 hours, or between 10 minutes 24 hours, or between 10 minutes and 4 hours, or between 10 minutes and 1 hour, or between 10 minutes and 30 minutes, or between 30 minutes and 24 hours, or between 30 minutes and 4 hours, or between 30 minutes and 1 hour after administering the composition comprising the platelet derivatives (e.g. FDPDs) to the subject. The lab test in certain embodiments, is one or more, or two or more, or three or more of the bleeding parameters disclosed herein.

In any of the aspects herein, in some embodiments the composition comprising platelet derivatives (e.g. FDPDs) has the property that it is capable of reducing the bleeding potential of a subject having an elevated bleeding potential. Furthermore, the composition comprising FDPDs typically has the additional and surprising property, that after being administered to the subject in an effective amount, for example for reducing the bleeding potential of the subject, the subject may have an abnormal value for one or more in vitro lab tests, for example of one or more clotting parameters in a post-administering evaluation performed using an, or the in vitro laboratory test performed on a blood sample taken between 15 minutes and 4 hours, 30 minutes and 4 hours, 1 hour and 4 hours, or taken between 15 minutes and 2 hours, 30 minutes and 2 hours, or 1 hour and 2 hours, or taken between 15 minutes and 1 hour or 30 minutes and 1 hour, after administering the composition comprising FDPDs. In some subembodiments of this embodiment, the composition comprising FDPDs has the property that it is capable of reducing the bleeding potential of a subject to about or at a normal hemostasis or about or at the hemostasis level of the subject when not taking the antiplatelet agent. Yet, in these embodiments, the composition comprising FDPDs retains the additional and surprising property, that after being administered to the subject in the effective amount, such a property is independent of a post-administering lab test for bleeding potential. Thus, in some embodiments, the subject would have an abnormal value for the one or more clotting parameters in a post-administering evaluation performed using an, or the in vitro laboratory test performed on a blood sample taken between 1 and 4 hours, or any of the time ranges recited immediately above, after administering the composition comprising FDPDs. It will be understood that in methods that include compositions comprising FDPDs with such properties, or any properties that include an evaluation or test, no testing actually needs to be performed to practice such methods unless such testing step is actually recited as a step of the method.

Platelet derivatives, and especially FDPDs provided herein, for example produced using methods provided herein, in certain embodiments have a number of identified properties as disclosed herein. For example, in some embodiments the FDPDs comprise (detectable amounts of) the biomolecule (e.g. receptor) targeted by an anti-platelet reversal agent. For example, the FDPDs can comprise one or more biomolecules that are targeted by one or more anti-platelet reversal agents that are administered or are being administered to the same subject to which a composition comprising the FDPDs is administered. In some embodiments the receptor present on the FDPDs is selected from a P2Y receptor (e.g., the P2Y12 receptor), glycoprotein IIb (i.e. CD41)/IIIa (i.e. CD61), thromboxane synthase or thromboxane receptors, PAR1, PAR4, VPVI, or collagen receptor (e.g. alpha2beta1 collagen receptor). In certain embodiments, at least 55%, 60%, 70%, 75%, 80%, 85%, 90%, or 95% of the platelet derivatives, in illustrative embodiments FDPDs, are positive for (i.e. have detectable levels of) a biomolecule targeted by the anti-platelet agent administered to the subject and/or detectable in the blood of the subject. As a few noteworthy non-limiting examples, the biomarker present on FDPDs can be CD41 or it can be the CD41/CD61 complex. In some embodiments, the CD41/CD61 complex on FDPDs is bound by fibrinogen (Factor 1).

In certain embodiments the composition comprising FDPDs comprises a population of FDPDs having a reduced propensity to aggregate such that no more than 2%, 3%, 4%, 5%, 7.5%, 10%, 12.5%, 15%, 17.5%, 20%, 22.5%, or 25% of the FDPDs in the population aggregate under aggregation conditions comprising an agonist but no platelets. In certain embodiments the FDPDs have a potency of at least 1.2 (e.g., at least 1.3, 1.4, 1.5, 1.6, 1.7, 1.8, 1.9, 2.0, 2.1, 2.2, 2.3, 2.4, or 2.5) thrombin generation potency units (TGPU) per $10^6$ particles.

In certain embodiments the FDPDs have one or more characteristics of super-activated platelets. Such characteristics can include one or more of the following:

A) the presence of thrombospondin (TSP) on their surface at a level that is greater than on the surface of resting platelets;
B) the presence of von Willebrand factor (vWF) on their surface at a level that is greater than on the surface of resting platelets; and
C) an inability to increase expression of a platelet activation marker in the presence of an agonist as compared to the expression of the platelet activation marker in the absence of an agonist.

In some embodiments less than 5% of a population of FDPDs, and in illustrative embodiments CD 41-positive FDPDs are microparticles having a diameter of less than 0.5 µm. Platelet derivatives herein have been observed to have numerous surprising properties, as disclosed in further detail herein. It will be understood, as illustrated in the Examples provided herein, that although platelet derivatives in some aspects and embodiments are in a solid, such as a powder form, the properties of such platelet derivatives can be identified, confirmed, and/or measured when a composition comprising such platelet derivatives is in liquid form.

In some embodiments, the platelets or platelet derivatives (e.g., FDPDs) have a particle size (e.g., diameter, max dimension) of at least about 0.5 µm (e.g., at least about at least about 0.6 µm, at least about 0.7 µm, at least about 0.8 µm, at least about 0.9 µm, at least about 1.0 µm, at least about 1.2 µm, at least about 1.5 µm, at least about 2.0 µm, at least about 2.5 µm, or at least about 5.0 µm). In some embodiments, the particle size is less than about 5.0 µm (e.g., less than about 2.5 µm, less than about 2.0 µm, less than about 1.5 µm, less than about 1.0 µm, less than about 0.9 µm, less than about 0.8 µm, less than about 0.7 µm, less than about 0.6 µm, less than about 0.5 µm, less than about 0.4 µm, or less than about 0.3 µm). In some embodiments, the particle size is from about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets or platelet derivatives (e.g., FDPDs), have a particle size in the range of about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, at most 99% (e.g., at most about 95%, at most about 80%, at most about 75%, at most about 70%, at most about 65%, at most about 60%, at most about 55%, or at most about 50%) of the platelets or platelet derivatives (e.g., FDPDs), are in the range of about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, about 50% to about 99% (e.g., about 55% to about 95%, about 60% to about 90%, about 65% to about 85, about 70% to about 80%) of the platelets or platelet derivatives (e.g., FDPDs) are in the range of about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

Platelets or platelet derivatives (e.g., FDPDs) as described herein can have cell surface markers. The presence of cell surface markers can be determined using any appropriate method. In some embodiments, the presence of cell surface markers can be determined using binding proteins (e.g., antibodies) specific for one or more cell surface markers and flow cytometry (e.g., as a percent positivity, e.g., using approximately $2.7 \times 10^5$ FDPDs/µL; and about 4.8 µL of an anti-CD41 antibody, about 3.3 µL of an anti-CD42 antibody, about 1.3 µL of annexin V, or about 2.4 µL of an anti-CD62 antibody). Non-limiting examples of cell-surface markers include CD41 (also called glycoprotein IIb or GPIIb, which can be assayed using e.g., an anti-CD41 antibody), CD42 (which can be assayed using, e.g., an anti-CD42 antibody), CD62 (also called CD62P or P-selectin, which can be assayed using, e.g., an anti-CD62 antibody), phosphatidylserine (which can be assayed using, e.g., annexin V (AV)), and CD47 (which is used in self-recognition; absence of this marker, in some cases, can lead to phagocytosis). The percent positivity of any cell surface marker can be any appropriate percent positivity. For example, populations of platelet derivatives (e.g., FDPDs), such as those prepared by methods described herein and included in compositions herein, can have an average CD41 percent positivity of at least 55% (e.g., at least 60%, at least 65%, at least 67%, at least 70%, at least 75%, at least 80%, at least 85%, at least 90%, or at least 95%). In some embodiments, at least 90%, 91%, 92%, 93%, 94%, 95%, 96%, 97%, 98%, 99% platelet derivatives that are positive for CD 41 have a size in the range of 0.5-2.5 µm. In some embodiments, at least 90%, 91%, 92%, 93%, 94%, 95%, 96%, 97%, 98%, or 99% platelet derivatives that are positive for CD 41 have a size in the range of 0.4-2.8 µm. In some embodiments, at least 90%, 91%, 92%, 93%, 94%, 95%, 96%, 97%, 98%, or 99% platelet derivatives that are positive for CD 41 have a size in the range of 0.3-3 µm.

As another example, platelets or platelet derivatives (e.g., FDPDs), such as those described herein, can have an average CD42 percent positivity of at least 65% (e.g., at least 67%, at least 70%, at least 75%, at least 80%, at least 85%, at least 90%, or at least 95%). In some embodiments, at least 90%, 91%, 92%, 93%, 94%, 95%, 96%, 97%, 98%, or 99% platelet derivatives that are positive for CD 42 have a size in the range of 0.5-2.5 µm. In some embodiments, at least 90%, 91%, 92%, 93%, 94%, 95%, 96%, 97%, 98%, or 99% platelet derivatives that are positive for CD 42 have a size in the range of 0.4-2.8 µm. In some embodiments, at least 90%, 91%, 92%, 93%, 94%, 95%, 96%, 97%, 98%, or 99% platelet derivatives that are positive for CD 42 have a size in the range of 0.3-3 µm.

As another example, platelets or platelet derivatives (e.g., FDPDs), such as those prepared by methods described herein, can have an average CD62 percent positivity of at least 10% (e.g., at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 83%, at least 84%, at least 85%, at least 90%, or at least 95%). In some embodiments, at least 70%, 75%, 80%, 85%, 90%, 91%, 92%, 93%, 94%, 95%, 96%, 97%, 98%, or 99% platelet derivatives that are positive for CD 62 have a size in the range of 0.5-2.5 µm. In some embodiments, at least 70%, 75%, 80%, 85%, 90%, 91%, 92%, 93%, 94%, 95%, 96%, 97%, 98%, or 99% platelet derivatives that are positive for CD 62 have a size in the range of 0.4-2.8 µm. In some embodiments, at least 70%, 75%, 80%, 85%, 90%, 91%, 92%, 93%, 94%, 95%, 96%, 97%, 98%, or 99% platelet derivatives that are positive for CD 62 have a size in the range of 0.3-3 µm.

As yet another example, platelets or platelet derivatives (e.g., FDPDs), such as those prepared by methods described herein, can have an average annexin V positivity of at least 25% (e.g., at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, or at least 99%). In some embodiments, at least 90%, 91%, 92%, 93%, 94%, 95%, 96%, 97%, 98%, 99% platelet derivatives that are positive for annexin V have a size in the range of 0.5-2.5 µm. In some embodiments, at least 90%, 91%, 92%, 93%, 94%, 95%, 96%, 97%, 98%, or 99% platelet derivatives that are positive for annexin V have a size in the range of 0.4-2.8 µm. In some embodiments, at least 90%, 91%, 92%, 93%, 94%, 95%, 96%, 97%, 98%, or 99% platelet derivatives that are positive for annexin V have a size in the range of 0.3-3 µm.

As another example, platelets or platelet derivatives (e.g., FDPDs), such as those prepared by methods described herein, can have an average CD47 percent positivity of at least about 8% (e.g., at least about 10%, 15%, 20%, 25%, 30%, 35%, 40%, 45%, 50%, or 55%).

Platelets or platelet derivatives (e.g., FDPDs) as described herein can be capable of generating thrombin, for example, when in the presence of a reagent containing tissue factor and phospholipids. For example, in some cases, platelets or platelet derivatives (e.g., FDPDs) (e.g., at a concentration of about $4.8 \times 10^3$ particles/µL) as described herein can generate a thrombin peak height (TPH) of at least 25 nM (e.g., at least 30 nM, 35 nM, 40 nM, 45 nM, 50 nM, 52 nM, 54 nM, 55 nM, 56 nM, 58 nM, 60 nM, 65 nM, 70 nM, 75 nM, or 80 nM) when in the presence of a reagent containing tissue factor (e.g., at 0.25 pM, 0.5 pM, 1 pM, 2 pM, 5 pM or 10 pM) and optionally phospholipids. For example, in some cases, platelets or platelet derivatives (e.g., FDPDs) (e.g., at a concentration of about $4.8 \times 10^3$ particles/µL) as described herein can generate a TPH of about 25 nM to about 100 nM (e.g., about 25 nM to about 50 nM, about 25 to about 75 nM, about 50 to about 100 nM, about 75 to about 100 nM, about 35 nM to about 95 nM, about 45 to about 85 nM, about 55 to about 75 nM, or about 60 to about 70 nM) when in the presence of a reagent containing tissue factor and (e.g., at 0.25 pM, 0.5 pM, 1 pM, 2 pM, 5 pM or 10 pM) and optionally phospholipids. In some cases, platelets or platelet derivatives (e.g., FDPDs) (e.g., at a concentration of about $4.8 \times 10^3$ particles/µL) as described herein can generate a TPH of at least 25 nM (e.g., at least 30 nM, 35 nM, 40 nM, 45 nM, 50 nM, 52 nM, 54 nM, 55 nM, 56 nM, 58 nM, 60 nM, 65 nM, 70 nM, 75 nM, or 80 nM) when in the presence of PRP Reagent (cat #TS30.00 from Thrombinoscope), for example, using conditions comprising 20 µL of PRP Reagent and 80 µL of a composition comprising about $4.8 \times 10^3$ particles/µL of platelets or platelet derivatives (e.g., FDPDs). In some cases, platelets or platelet derivatives (e.g., FDPDs) (e.g., at a concentration of about $4.8 \times 10^3$ particles/µL) as described herein can generate a TPH of about 25 nM to about 100 nM (e.g., about 25 nM to about 50 nM, about 25 to about 75 nM, about 50 to about 100 nM, about 75 to about 100 nM, about 35 nM to about 95 nM, about 45 to about 85 nM, about 55 to about 75 nM, or about 60 to about 70 nM) when in the presence of PRP Reagent (cat #TS30.00 from Thrombinoscope), for example, using conditions comprising 20 µL of PRP Reagent and 80 µL of a composition comprising about $4.8 \times 10^3$ particles/µL of platelets or platelet derivatives (e.g., FDPDs).

Platelets or Platelet derivatives (e.g., FDPDs) as described herein can be capable of generating thrombin, for example, when in the presence of a reagent containing tissue factor and phospholipids. For example, in some cases, platelets or platelet derivatives (e.g., FDPDs) can have a potency of at least 1.2 (e.g., at least 1.3, 1.4, 1.5, 1.6, 1.7, 1.8, 1.9, 2.0, 2.1, 2.2, 2.3, 2.4, or 2.5) thrombin generation potency units (TGPU) per $10^6$ particles. For example, in some cases, platelets or platelet derivatives (e.g., FDPDs) can have a potency of between 1.2 and 2.5 TPGU per $10^6$ particles (e.g., between 1.2 and 2.0, between 1.3 and 1.5, between 1.5 and 2.25, between 1.5 and 2.0, between 1.5 and 1.75, between 1.75 and 2.5, between 2.0 and 2.5, or between 2.25 and 2.5 TPGU per $10^6$ particles). TPGU can be calculated as follows: TGPU/million particles=[TPH in nM]*[Potency Coefficient in IU/(nM)]/[0.576 million particles in the well]. Similarly, the Potency Coefficient for a sample of thrombin can be calculated as follows: Potency Coefficient=Calculated Calibrator Activity (IU)/Effective Calibrator Activity (nM). In some cases, the calibrator activity can be based on a WHO international thrombin standard.

Platelets or platelet derivatives (e.g., FDPDs) as described herein can be capable of clotting, as determined, for example, by using a total thrombus-formation analysis system (T-TAS®)). In some cases, platelets or platelet derivatives as described herein, when at a concentration of at least $70 \times 10^3$ particles/µL (e.g., at least $73 \times 10^3$, $100 \times 10^3$, $150 \times 10^3$, $173 \times 10^3$, $200 \times 10^3$, $250 \times 10^3$, or $255 \times 10^3$ particles/µL) can result in a T-TAS occlusion time (e.g., time to reach kPa of 80) of less than 14 minutes (e.g., less than 13.5, 13, 12.5, 12, 11.5, or 11 minutes), for example, in platelet-reduced citrated whole blood. In some cases, platelets or platelet derivatives as described herein, when at a concentration of at least $70 \times 10^3$ particles/µL (e.g., at least $73 \times 10^3$, $100 \times 10^3$, $150 \times 10^3$, $173 \times 10^3$, $200 \times 10^3$, $250 \times 10^3$, or $255 \times 10^3$ particles/µL) can result in an area under the curve (AUC) of at least 1300 (e.g., at least 1380, 1400, 1500, 1600, or 1700), for example, in platelet-reduced citrated whole blood.

Platelets or platelet derivatives (e.g., FDPDs) as described herein can be capable of thrombin-induced trapping in the presence of thrombin. In some cases, platelets or platelet derivatives (e.g., FDPDs) as described herein can have a percent thrombin-induced trapping of at least 5% (e.g., at least 10%, 15%, 20%, 25%, 30%, 35%, 40%, 45%, 50%, 55%, 60%, 65%, 67%, 70%, 75%, 85%, 90%, or 99%) in the presence of thrombin. In some cases, platelets or platelet derivatives (e.g., FDPDs) as described herein can have a percent thrombin-induced trapping of about 25% to about 100% (e.g., about 25% to about 50%, about 25% to about 75%, about 50% to about 100%, about 75% to about 100%, about 40% to about 95%, about 55% to about 80%, or about 65% to about 75%) in the presence of thrombin. Thrombin-induced trapping can be determined by any appropriate method, for example, light transmission aggregometry. Without being bound by any particular theory, it is believed that the thrombin-induced trapping is a result of the interaction of fibrinogen present on the surface of the platelet derivatives with thrombin.

Platelets For platelet derivatives (e.g., FDPDs) as described herein can be capable of co-aggregating, for example, in the presence of an aggregation agonist, and fresh platelets. Non-limiting examples of aggregation agonists include, collagen, epinephrine, ristocetin, arachidonic acid, adenosine di-phosphate, and thrombin receptor associated protein (TRAP). In some cases, platelets or platelet derivatives (e.g., FDPDs) as described herein can have a percent co-aggregation of at least 5% (e.g., at least 10%, 15%, 20%, 25%, 30%, 35%, 40%, 45%, 50%, 55%, 60%, 65%, 67%, 70%, 75%, 85%, 90%, or 99%) in the presence of an aggregation agonist, and fresh platelets. In some cases, platelets or platelet derivatives (e.g., FDPDs) as described herein can have a percent co-aggregation of about 25% to about 100% (e.g., about 25% to about 50%, about 25% to about 75%, about 50% to about 100%, about 75% to about 100%, about 40% to about 95%, about 55% to about 80%, or about 65% to about 75%) in the presence of an aggregation agonist. Percent co-aggregation can be determined by any appropriate method, for example, light transmission aggregometry.

Platelet derivative compositions, which in certain illustrative embodiments herein are FDPD compositions, comprise a population of platelet derivatives (e.g. FDPDs) having a reduced propensity to aggregate under aggregation conditions comprising an agonist but no fresh platelets, compared to the propensity of fresh platelets and/or activated to aggregate under these conditions. Platelet derivatives (e.g., FDPDs) as described herein in illustrative embodiments, display a reduced propensity to aggregate under aggregation conditions comprising an agonist but no fresh platelets, compared to the propensity of fresh platelets and/or activated platelets to aggregate under these conditions. Surprisingly, such FDPDs have the ability to increase clotting and aggregation of platelets in in vitro and in vivo assays, in the presence of anti-thrombotic agents such as anti-coagulants and anti-platelet agents, under conditions where such anti-thrombotic agents reduce clotting and/or aggregation, including in the presence of two of such agents. It is noteworthy that aggregation of platelet derivatives is different from co-aggregation in that aggregation conditions typically do not include fresh platelets, whereas co-aggregation conditions include fresh platelets. Exemplary aggregation and co-aggregation conditions are provided in the Examples herein. Thus, in some embodiments, the platelet derivatives as described herein have a higher propensity to co-aggregate in the presence of fresh platelets and an agonist, while having a reduced propensity to aggregate in the absence of fresh platelets and an agonist, compared to the propensity of fresh platelets to aggregate under these conditions. In some embodiments, a platelet derivative composition comprises a population of platelet derivatives having a reduced propensity to aggregate, wherein no more than 2%, 3%, 4%, 5%, 7.5%, 10%, 12.5%, 15%, 17.5%, 20%, 22.5%, or 25% of the platelet derivatives in the population aggregate under aggregation conditions comprising an agonist but no platelets, in illustrative embodiments no fresh platelets. In some embodiments, the population of platelet derivatives aggregate in the range of 2-30%, 5-25%, 10-30%, 10-25%, or 12.5-25% of the platelet derivatives under aggregation conditions comprising an agonist but no platelets, in illustrative embodiments no fresh platelets.

As provided in Examples herein, exemplary aggregation conditions and related methods include treating FDPD sample preparations at room temperature with an agonist at a final agonist concentration of 20 μM ADP, 0.5 mg/mL arachidonic acid, 10 μg/mL collagen, 200 μM epinephrine, 1 mg/mL ristocetin, and 10 μM TRAP-6 and measured by LTA, for example, 5 minutes after agonist addition to the FDPD sample, which can be compared to LTA measurements of the sample prior to agonist addition.

In some embodiments, the platelet derivatives as described herein are activated to a maximum extent such that in the presence of an agonist, the platelet derivatives are not able to show an increase in the platelet activation markers on them as compared to the level of the platelet activation markers which were present prior to the exposure with the agonist. In some embodiments, the platelet derivatives as described herein show an inability to increase expression of a platelet activation marker in the presence of an agonist as compared to the expression of the platelet activation marker in the absence of an agonist. In some embodiments, the agonist is selected from the group consisting of collagen, epinephrine, ristocetin, arachidonic acid, adenosine di-phosphate, and thrombin receptor associated protein (TRAP). In some embodiments, the platelet activation marker is selected from the group consisting of Annexin V, and CD 62. In some embodiments, the platelet derivatives as described herein show an inability to increase expression of Annexin V in the presence of TRAP. An increased amount of the platelet activation markers on the platelets indicates the state of activeness of the platelets. However, in some embodiments, the platelet derivatives as described herein are not able to increase the amount of the platelet activation markers on them even in the presence of an agonist. This property indicates that the platelet derivatives as described herein are activated to a maximum extent. In some embodiments, the property can be beneficial where maximum activation of platelets is required, because the platelet derivatives as described herein is able to show a state of maximum activation in the absence of an agonist.

Thrombospondin is a glycoprotein secreted from the α-granules of platelets upon activation. In the presence of divalent cations, the secreted protein binds to the surface of the activated platelets and is responsible for the endogenous lectin-like activity associated with activated platelets. In some embodiments, the platelet derivatives have the presence of thrombospondin (TSP-1) on their surface at a level that is greater than that presence on the surface of resting platelets, activated platelets, or lyophilized fixed platelets. In some embodiments, the platelet derivatives have the presence of thrombospondin (TSP-1) on their surface at a level that is at least 10%, 20%, 25%, 30%, 50%, 60%, 70%, 80%, 90%, or 100% higher than on the surface of resting platelets, or lyophilized fixed platelets. In some embodiments, the platelet derivatives have the presence of thrombospondin (TSP-1) on their surface at a level that is more than 100% higher than on the surface of resting platelets, or lyophilized fixed platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, 40 folds, 50 folds, 60 folds, 70 folds, 80 folds, 90 folds, or 100 folds higher mean fluorescent intensity (MFI) in the absence of an agonist as compared to the MFI of binding of anti-TSP antibody to the resting platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, or 40 folds higher mean fluorescent intensity (MFI) in the absence of an agonist as compared to the MFI of binding of anti-TSP antibody to the lyophilized fixed platelets. In some embodiments, the platelet derivatives when analyzed for the binding of anti-thrombospondin (TSP) antibody to the platelet derivatives using flow cytometry exhibit 10-800 folds, 20-800 folds, 100-700 folds, 150-700 folds, 200-700 folds, or 250-500 folds higher mean fluorescent intensity (MFI) in the absence of an agonist as compared to the MFI of binding of anti-TSP antibody to the resting platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, or 40 folds higher mean fluorescent intensity (MFI) in the absence of an agonist as compared to the MFI of binding of anti-TSP antibody to the active platelets. In some embodiments, the platelet derivatives when analyzed for the binding of anti-thrombospondin (TSP) antibody to the platelet derivatives using flow cytometry exhibit 2-40 folds, 5-40 folds, 5-35 folds, 10-35 folds, or 10-30 folds higher mean fluorescent intensity (MFI) in the absence of an agonist as compared to the MFI of binding of anti-TSP antibody to the active platelets.

Von Willebrand factor (vWF)P is a multimeric glycoprotein that plays a major role in blood coagulation. vWF serves as a bridging molecule that promotes platelet binding to sub-endothelium and other platelets, thereby promoting platelet adherence and aggregation. vWF also binds to collagens to facilitate clot formation at sites of injury. In some embodiments, the platelet derivatives as described herein have the presence of von Willebrand factor (vWF) on their surface at a level that is greater than that on the surface of resting platelets, activated platelets, or lyophilized fixed platelets. In some embodiments, the platelet derivatives have the presence of von Willebrand factor (vWF) on their surface at a level that is at least 10%, 20%, 25%, 30%, 50%, 60%, 70%, 80%, 90%, or 100% higher than on the surface of resting platelets, or lyophilized fixed platelets. In some embodiments, the platelet derivatives when analyzed for the binding of anti-von Willebrand factor (vWF) antibody to the platelet derivatives using flow cytometry exhibits at least 1.5 folds, 2 folds, or 3 folds, or 4 folds higher mean fluorescent intensity (MFI) in the absence of an agonist as compared to the MFI of binding of anti-vWF antibody to the resting platelets, or lyophilized fixed platelets. In some embodiments, the platelet derivatives when analyzed for the binding of anti-von Willebrand factor (vWF) antibody to the platelet derivatives using flow cytometry exhibits 2-4 folds, or 2.5-3.5 higher mean fluorescent intensity (MFI) in the absence of an agonist as compared to the MFI of binding of anti-vWF antibody to the resting platelets, or lyophilized fixed platelets.

Platelet derivatives, in illustrative embodiments FDPDs, in further illustrative aspects and embodiments herein are surrounded by a compromised plasma membrane. In these further illustrative aspects and embodiments, the platelet derivatives lack an integrated membrane around them. Instead, the membrane surrounding such platelet derivatives (e.g. FDPDs) comprises pores that are larger than pores observed on living cells. Not to be limited by theory, it is believed that in embodiments where platelet derivatives have a compromised membrane, such platelet derivatives have a reduced ability to, or are unable to transduce signals from the external environment into a response inside the particle that are typically transduced in living platelets. Furthermore, such platelet derivatives (e.g. FDPDs) are not believed to be capable of mitochondrial activation or glycolysis.

A compromised membrane can be identified through a platelet derivative's inability to retain more than 50% of lactate dehydrogenase (LDH) as compared to fresh platelets, or cold stored platelets, or cryopreserved platelets. In some embodiments, the platelet derivatives are incapable of retaining more than 35%, 40%, 45%, 50%, 55%, 60%, 65%, 70%, or 75% of lactate dehydrogenase as compared to lactate dehydrogenase retained in fresh platelets, or cold stored platelets, or cryopreserved platelets. In some embodiments, the platelet derivatives exhibit an increased permeability to antibodies. In some embodiments, the antibodies can be IgG antibodies. The increased permeability can be identified by targeting IgG antibodies against a stable intracellular antigen. One non-limiting type of stable intracellular antigen is β tubulin. The compromised membrane of the platelet derivatives can also be determined by flow cytometry studies.

Platelet or platelet derivatives (e.g., FDPDs) as described herein can retain some metabolic activity, for example, as evidenced by lactate dehydrogenase (LDH) activity. In some cases, platelets or platelet derivatives (e.g., FDPDs) as described herein can retain at least about 10% (e.g., at least about 12%, 15%, 20%, 25%, 30%, 35%, 40%, or 45%) of the LDH activity of donor apheresis platelets. Without being bound by any particular theory, it is believed that the addition of increasing amounts of polysucrose increases the amount of LDH activity remained (e.g., products of a preparation agent with 8% polysucrose have more retained LDH activity than products of a preparation agent with 4% polysucrose). Similarly unbound by any particular theory, it is believed that thermal treatment of a lyophilized composition comprising platelets or platelet derivatives (e.g., FDPDs) increases the amount of LDH activity retained. As another example, metabolic activity can be evidenced by retained esterase activity, such as the ability of the cells to cleave the acetate groups on carboxyfluorescein diacetate succinimidyl ester (CFDASE) to unmask a fluorophore.

Clotting parameters of blood (e.g., the subject's blood) can be assessed at any appropriate time during the methods described herein. For example, one or more clotting parameters of blood can be assessed before administration of a composition comprising platelets, or in illustrative embodiments a composition comprising platelet derivatives, which in further illustrative embodiments are FDPDs as described herein, e.g., in order to determine the need for administration of a composition comprising platelets or platelet derivatives as described herein. For example, such clotting parameters can be assessed using a pre-administration evaluation or test, such as an in vitro lab test. Such test can be performed on a liquid sample, for example a blood sample, taken within 7, 5, 3, 2, or 1 day, or within 12, 8, 6, 4, 2, or 1 hour before administering a composition comprising platelet derivatives to the subject. As another example, one or more clotting parameters of blood can be assessed after administration of a composition comprising platelets or platelet derivatives as described herein, e.g., in order to determine the effectiveness of the administered composition, to determine whether additional administration of the composition is warranted, or to determine whether it is safe to perform a surgical procedure. Such post-administering evaluation or test can be performed on a liquid sample, for example a blood sample, taken within 7, 5, 3, 2, or 1 day, or within 12, 8, 6, 4, 2, or 1 hour after administering a composition comprising platelet derivatives to the subject.

Accordingly, any of the methods described herein can include steps of assessing one or more clotting parameters of blood before administration of a composition comprising platelets or platelet derivatives as described herein, assessing one or more clotting parameters of blood after administration of a composition comprising platelets or platelet derivatives as described herein, or both.

Any appropriate method can be used to assess (or evaluate) clotting parameters of blood. Non-limiting examples of methods include the World Health Organization (WHO) bleeding scale, prothrombin time (PT) assay, thrombin generation (TGA; which can be used to generate parameters such as, e.g., peak thrombin, endogenous thrombin potential (ETP), and lag time), thromboelastography (TEG), multiple electrode aggregometry, light transmission aggregometry (LTA), activated clotting time (ACT), P2Y12 Reaction Units (PRU) or Aspirin Reaction Units (ARU) tests, and partial thromboplastin time (PTT or aPTT).

The WHO bleeding scale was developed to help clinicians and researchers assess bleeding, particularly in the context of toxicity reporting in cancer treatment, but it is also used in other contexts.

Prothrombin time (PT) is a measure of how long it takes blood to clot, typically in the presence of Tissue Factor. In some cases, PT can be affected by laboratory reagents, so a normalized ratio (INR) is more frequently used.

The activated partial thromboplastin time (aPTT) is a measure of how long it takes blood to clot, typically in the presence of an activator such as silica, celite, kaolin, or ellagic acid. In some cases, aPTT can be affected by laboratory reagents, so INR is sometimes used instead of or in addition to aPTT.

The thrombin generation assay measured the production of thrombin after sample activation via a pro-coagulation agent resulting of thrombin enzymatic cleavage of a fluorescent peptide and release of fluorescent molecule. The peak thrombin is a measure of the maximum thrombin produced, lag time, the time to start of thrombin production, and ETP as the total thrombin potentially produced.

In some embodiments, a patient can have a peak thrombin of about 60 nM to about 170 nM, such as about 65 nM to about 170 nM, such as about 65 nM to about 120 nM, such as about 80 nM, before administration of a composition comprising platelets or platelet derivatives as described herein.

Thrombin clotting time (TCT) is a measure of how long it takes blood to clot, after an excess of thrombin has been added.

TEG assesses intrinsic hemostasis via plots of clot strength over time. Calcium chloride ($CaCl_2$) is typically used as the initiating reagent. A TEG waveform (see, e.g., FIG. 16) has multiple parameters that can provide information about clotting.

R-time=reaction time (s)—time of latency from start of test to initial fibrin formation.

K=kinetics (s)—speed of initial fibrin formation, time taken to achieve a certain level of clot strength (e.g., an amplitude of 20 mm)

alpha angle=slope of line between R and K—measures the rate of clot formation.

MA=maximum amplitude (mm)—represents the ultimate strength of the fibrin clot.

$A_{30}$=amplitude 30 minutes after maximum amplitude is reached—represents rate of lysis phase.

In hypercoagulable blood states, R-time increases and MA decreases. R-time typically provides a broader response range than MA.

Multiple electrode aggregometry (MEA) can also be used to evaluate clotting parameters of blood. MEA measures changes in electrical impedance when platelets aggregate on metal electrodes. Typically, aggregation agonists such as ADP, epinephrine, collagen, or ristocetin are used to initiate aggregation.

Light transmission aggregometry (LTA) is sometimes used to evaluate clotting parameters of blood; unaggregated blood allows little light to pass through, but aggregation (typically initiated by an agonist) results in an increase in aggregation.

In the Total Thrombus-formation Analysis System (T-TAS®, FUJIMORI KOGYO CO., LTD), the sample is forced through collagen-coated microchannels using mineral oil. Changes in pressure are used to assess thrombus formation. The Occlusion Start Time is time it takes to reach 10 kPa, and the Occlusion Time=time it takes to each Δ80 kPa using an AR chip (e.g., Zacros Item No, TC0101). According to the manufacturer, an AR chip can be used for analyzing the formation of a mixed white thrombus consisting chiefly of fibrin and activated platelets. It has a flow path (300 µm wide by 50 µm high) coated with collagen and tissue factors and can be used to analyze the clotting function and platelet function. In comparison, a PL chip can be used for analyzing the formation of a platelet thrombus consisting chiefly of activated platelets. A PL chip has a flow path coated with collagen only and can be used to analyze the platelet function.

The ACT assay is the most basic, but possibly most reliable, way to measure clotting time ($t_{ACT}$), determined by a magnet's resistance to gravity as a clot forms around it. Typical donor blood has a $t_{ACT}$~200-300 s using only $CaCl_2$.

VerifyNow measures platelet aggregation in PRU units (P2Y12 reaction units) in the presence of P2Y12 inhibitors (PRU)) or platelet dysfunction in ARU units (aspirin reaction units) in the presence of aspirin. The VerifyNow System is a turbidimetric based optical detection system utilising microbeads that measures platelet induced aggregation as an increase in light transmittance available from Werfren (https://www.werfen.com).

The VerifyNow-P2Y12 Assay/VerifyNow PRU Test is a rapid test that uses ADP to stimulate platelets in the presence of PGE1 [Prostaglandin E1] and which inhibits activation downstream of a second ADP receptor P2Y1—making the assay more sensitive and specific for the activity of the P2Y12 receptor and of drugs that bind to the P2Y12 receptor. The assay system reagent is designed to specifically measure P2Y12—mediated platelet aggregation.

VerifyNow Aspirin Assay methodology is very similar to the VerifyNow-P2Y12 Assay/VerifyNow PRU Test where Arachidonic Acid is incorporated to measure the response of the platelet to Aspirin. In an individual on Aspirin, Aspirin irreversibly inhibits the COX-1, the enzyme that converts Arachidonic acid to Thromboxane A [TxA2] and which ultimately activates the GPIIb/IIIa receptor involved in platelet aggregation. In the presence of Aspirin the aggregation does not occur.

Exemplary normal ranges for some of these clotting parameters are shown below in Table E1. Typically, a value outside of the ranges shown below is considered to be abnormal.

TABLE E1

| Evaluation | Exemplary Normal Range |
|---|---|
| Bleeding (WHO scale) | $0^{(4)}$ |
| LTA (percent aggregation) | |
| 5 µmol/L ADP | $70 \pm 10^{(1)}$ |
| 2 µg/mL collagen | $80 \pm 13^{(1)}$ |
| 1 mmol/L arachidonic acid | $77 \pm 10^{(1)}$ |
| 2 mmol/L arachidonic acid | $80 \pm 11^{(1)}$ |
| 5 mmol/L arachidonic acid | $78 \pm 5^{(1)}$ |
| TEG | |
| 1 mmol/L arachidonic acid (% aggregation) | $95 \pm 9^{(1)}$ |
| MA (mm) | $50\text{-}60^{(6)}$ |
| R-time (minutes) | $7.5\text{-}1^{(6)}$ |
| K (minutes) | $3\text{-}6^{(6)}$ |
| Alpha angle (degrees) | $45\text{-}45^{(6)}$ |
| PT (seconds) | $10\text{-}14^{(5)}$ |
| aPTT (seconds) | $22\text{-}35^{(2)}$ |
| TCT (seconds) | $20\text{-}30^{(2)}$ |
| $t_{ACT}$ (seconds) | 200-300 |
| MEA (Units) | |
| ADP-induced | $53\text{-}122^{(3)}$ |
| Arachidonic acid-induced | $76\text{-}136^{(3)}$ |
| VerifyNow | |
| PRU | $180\text{-}376^{(7)}$ |
| ARU | $550\text{-}700^{(7)}$ |

[1] DiChiara, et al. "The effect of aspirin dosing on platelet function in diabetic and nondiabetic patients: an analysis from the aspirin-induced platelet effect (ASPECT) study." Diabetes 56. 12 (2007): 3014-3019.
[2] Thrombosis Canada. Use And Interpretation Of Laboratory Coagulation Tests In Patients Who Are Receiving A New Oral Anticoagulant (Dabigatran, Rivaroxaban, Apixaban). 2013
[3] Beynon, et al. "Multiple electrode aggregometry in antiplatelet-related intracerebral haemorrhage." Journal of Clinical Neuroscience 20. 12 (2013): 1805-1806.
[4] Rodeghiero, Francesco, et al. "Standardization of bleeding assessment in immune thrombocytopenia: report from the International Working Group." Blood 121. 14 (2013): 2596-2606.
[5] Cleveland Clinic "Prothrombin Time (PT) test" https://my.clevelandclinic.org/health/diagnostics/17691-prothrombin-time-pt-test#results-and-follow-up. Accessed 15 Feb. 2021.
[6] Bose and Hravnak. "Thromboelastography: a practice summary for nurse practitioners treating hemorrhage." The Journal for Nurse Practitioners 11. 7 (2015): 702-709.
[7] Regional Medical Laboratory "VerifyNow PRU testing". https://www.rmlonline.com/site/sections/684. Accessed 15 Feb. 2021.

Some embodiments provide a method of increasing thrombin generation in a subject, the method comprising administering to the subject in need thereof an effective amount of a composition comprising platelets, or in illustrative embodiments a composition comprising platelet derivatives, which in further illustrative embodiments are FDPDs and an incubating agent comprising one or more salts, a buffer, optionally a cryoprotectant, and optionally an organic solvent.

Some embodiments, provide a method of increasing thrombin generation in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some embodiments provide a method of increasing peak thrombin in a subject, the method comprising administering to the subject in need thereof an effective amount of a composition comprising platelets, or in illustrative embodiments a composition comprising platelet derivatives, which in further illustrative embodiments are FDPDs and an incubating agent comprising one or more salts, a buffer, optionally a cryoprotectant, and optionally an organic solvent.

Some embodiments provide a method of increasing peak thrombin in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some embodiments, prior to the administering, the peak thrombin of the subject was below 66 nM (e.g., below 64 nM, 62 nM, 60 nM, 55 nM, 50 nM, 45 nM, 40 nM, 35 nM, 30 nM, 25 nM, 20 nM, 15 nM, 10 nM, or 5 nM). In some embodiments, after the administering, the peak thrombin of the subject is above 66 nM (e.g., above 68 nM, 70 nM, 75 nM, 80 nM, 85 nM, 90 nM, 95 nM, 100 nM, 110 nM, 120 nM, 130 nM, 140 nM, or 150 nM). In some embodiments, after the administering, the peak thrombin of the subject is between 66 and 166 nM. Peak thrombin can be measured by any appropriate method.

In some embodiments a composition as provided herein, or a composition produced by a method described herein can be administered to a subject because of an abnormal result in an evaluation of one or more clotting parameters, e.g., indicating that the subject is in a hypocoagulable state.

Some embodiments include a method of treating a coagulopathy in a subject that is being administered or has been administered an antiplatelet agent, the method including: (a) determining that the subject has an abnormal result for evaluation of one or more clotting parameters; and (b) after (a), administering to the subject in need thereof an effective amount of a composition including platelets or platelet derivatives and an incubating agent including one or more salts, a buffer, optionally a cryoprotectant, and optionally an organic solvent.

Some embodiments include a method of treating a coagulopathy in a subject that is being administered or has been administered an antiplatelet agent, the method including: (a) determining that the subject an abnormal result for evaluation of one or more clotting parameters; and (b) after (a), administering to the subject in need thereof an effective amount of a composition prepared by a process including incubating platelets with an incubating agent including one or more salts, a buffer, optionally a cryoprotectant, and optionally an organic solvent, to form the composition.

Some embodiments include a method of treating a coagulopathy in a subject that is being administered or has been administered an antiplatelet agent, the method including: administering to the subject in need thereof an effective amount of a composition including platelets or platelet derivatives and an incubating agent including one or more salts, a buffer, optionally a cryoprotectant, and optionally an organic solvent, wherein before the administering, for example at the moment before or immediately before the administering, the subject has been determined to have an abnormal result for evaluation of one or more clotting parameters.

Some embodiments include a method of treating a coagulopathy in a subject that is being administered or has been administered an antiplatelet agent, the method including: administering to the subject in need thereof an effective amount of a composition prepared by a process including incubating platelets with an incubating agent including one or more salts, a buffer, optionally a cryoprotectant, and optionally an organic solvent, to form the composition, wherein before the administering, for example at the moment before or immediately before the administering, the subject has been determined to have an abnormal result for evaluation of one or more clotting parameters.

In some embodiments of any of the methods herein, a subject has been administered an antiplatelet agent or is being administered an antiplatelet agent in any appropriate time frame. For example, in some cases, a subject has been administered an antiplatelet agent and/or a composition comprising platelet derivatives, in illustrative embodiments FDPDs, before the effect of a prior dose of the antiplatelet agent wears off. For example, in some cases, a subject is being administered an antiplatelet agent and the effect of the antiplatelet agent has not worn off. As another example, in some cases, a subject has been administered an antiplatelet agent (e.g., the most recent dose) within about 1 week, about 5 days, about 3 days, about 36 hours, about 24 hours, about 18 hours, about 12 hours, about 8 hours, about 6 hours, about 4 hours, about 2 hours, or about 1 hour. As another example, in some cases, a subject is being administered an antiplatelet agent and the last dose (e.g., the most recent dose as prescribed by a medical professional or self-administered by the subject) was within about 1 week, about 5 days, about 3 days, about 36 hours, about 24 hours, about 18 hours, about 12 hours, about 8 hours, about 6 hours, about 4 hours, about 2 hours, or about 1 hour.

In some embodiments of any of the methods herein, determination of an abnormal result for the evaluation of one or more clotting parameters can be at any appropriate time. For example, determination of an abnormal result for the evaluation of one or more clotting parameters can be before the abnormal result returns to a normal result. As another example, determination of an abnormal result for the evaluation of one or more clotting parameters can be within about 1 week, about 5 days, about 3 days, about 36 hours, about 24 hours, about 18 hours, about 12 hours, about 8 hours, about 6 hours, about 4 hours, about 2 hours, or about 1 hour of the administering.

In some embodiments, the method can further include determining the result of the evaluation one or more clotting parameters following the administering. For example, in some embodiments, the evaluation of the one or more clotting parameters following the administering shows a normal result for at least one of the one or more clotting parameters. In some embodiments, the result of the evaluation of the one or more clotting parameters following the administering is improved from the result of the evaluation of the one or more parameters prior to the administering.

In some cases, a subject might be administered an antiplatelet agent, but they were not supposed to be, for example, if a subject is confused, or if a medical error occurs. In some such cases, a subject can be administered any of the compositions provided herein, or a composition produced by any of the methods described herein.

Some embodiments include a method of treating a coagulopathy in a subject, the method including: (a) determining that the subject, contrary to medical instruction, was administered an antiplatelet agent; and (b) administering to the subject in need thereof an effective amount of a composition including platelets or platelet derivatives and an incubating agent including one or more salts, a buffer, optionally a cryoprotectant, and optionally an organic solvent.

Some embodiments include a method of treating a coagulopathy in a subject, the method including: (a) determining that the subject, contrary to medical instruction, was administered an antiplatelet agent; and (b) administering to the subject in need thereof an effective amount of a composition prepared by a process including incubating platelets with an incubating agent including one or more salts, a buffer, optionally a cryoprotectant, and optionally an organic solvent, to form the composition.

Some embodiments include a method of treating a coagulopathy in a subject, the method including: administering to the subject in need thereof an effective amount of a composition including platelets or platelet derivatives and an incubating agent including one or more salts, a buffer, optionally a cryoprotectant, and optionally an organic solvent, wherein the subject is determined to have been administered an antiplatelet agent contrary to medical instruction.

Some embodiments include a method of treating a coagulopathy in a subject, the method including: administering to the subject in need thereof an effective amount of a composition prepared by a process including incubating platelets with an incubating agent including one or more salts, a buffer, optionally a cryoprotectant, and optionally an organic solvent, to form the composition, wherein the subject is determined to have been administered an antiplatelet agent contrary to medical instruction.

Some embodiments include a method of restoring normal hemostasis in a subject, the method including: (a) determining that the subject, contrary to medical instruction, was administered an antiplatelet agent; and (b) administering to the subject in need thereof an effective amount of a composition including platelets or platelet derivatives and an incubating agent including one or more salts, a buffer, optionally a cryoprotectant, and optionally an organic solvent.

Some embodiments include a method of restoring normal hemostasis in a subject, the method including: (a) determining that the subject, contrary to medical instruction, was administered an antiplatelet agent; and (b) administering to the subject in need thereof an effective amount of a composition prepared by a process including incubating platelets with an incubating agent including one or more salts, a buffer, optionally a cryoprotectant, and optionally an organic solvent, to form the composition.

Some embodiments include a method of restoring normal hemostasis in a subject, the method including: administering to the subject in need thereof an effective amount of a composition including platelets or platelet derivatives and an incubating agent including one or more salts, a buffer, optionally a cryoprotectant, and optionally an organic solvent, wherein the subject is determined to have been administered an antiplatelet agent contrary to medical instruction.

Some embodiments include a method of restoring normal hemostasis in a subject, the method including: administering to the subject in need thereof an effective amount of a composition prepared by a process including incubating platelets with an incubating agent including one or more salts, a buffer, optionally a cryoprotectant, and optionally an organic solvent, to form the composition, wherein the subject is determined to have been administered an antiplatelet agent contrary to medical instruction.

In some embodiments of any of the methods herein, determining that the subject has been administered an antiplatelet agent contrary to medical instruction can be at any appropriate time. For example, determining that the subject has been administered an antiplatelet agent contrary to medical instruction can be before the antiplatelet agent wears off. As another example, determining that the subject has been administered an antiplatelet agent contrary to medical instruction can be within about 1 week, about 5 days, about 3 days, about 36 hours, about 24 hours, about 18 hours, about 12 hours, about 8 hours, about 6 hours, about 4 hours, about 2 hours, or about 1 hour of the administering a composition provided herein or a composition produced by a method described herein.

Administration of the antiplatelet agent can include any appropriate method, including self-administering by the subject or administering by a medical professional.

Medical instruction can be any appropriate method, including verbal instruction, written instruction, or both verbal and written instruction.

In some cases, a subject may have been administered or is being administered a second agent that affects (e.g., decreases) platelet function. For example, such an administration can put the subject into a hypercoagulable state.

Some embodiments include a method of treating a coagulopathy in a subject, the method including: (a) determining that the subject was administered an antiplatelet agent and a second agent that decreases platelet function; and (b) administering to the subject in need thereof an effective amount of a composition including platelets or platelet derivatives and an incubating agent including one or more salts, a buffer, optionally a cryoprotectant, and optionally an organic solvent.

Some embodiments include a method of treating a coagulopathy in a subject, the method including: (a) determining that the subject was administered an antiplatelet agent and a second agent that decreases platelet function; and (b) administering to the subject in need thereof an effective amount of a composition prepared by a process including incubating platelets with an incubating agent including one or more salts, a buffer, optionally a cryoprotectant, and optionally an organic solvent, to form the composition.

Some embodiments include a method of treating a coagulopathy in a subject, the method including: administering to the subject in need thereof an effective amount of a composition including platelets or platelet derivatives and an incubating agent including one or more salts, a buffer, optionally a cryoprotectant, and optionally an organic solvent, wherein the subject is determined to have been administered an antiplatelet agent and a second agent that decreases platelet function.

Some embodiments include a method of treating a coagulopathy in a subject, the method including: administering to the subject in need thereof an effective amount of a composition prepared by a process including incubating platelets with an incubating agent including one or more salts, a buffer, optionally a cryoprotectant, and optionally an organic solvent, to form the composition, wherein the subject is determined to have been administered an antiplatelet agent and a second agent that decreases platelet function.

Some embodiments include a method of restoring normal hemostasis in a subject, the method including: (a) determining that the subject was administered an antiplatelet agent and a second agent that decreases platelet function; and (b) administering to the subject in need thereof an effective amount of a composition including platelets or platelet derivatives and an incubating agent including one or more salts, a buffer, optionally a cryoprotectant, and optionally an organic solvent.

Some embodiments include a method of restoring normal hemostasis in a subject, the method including: (a) determining that the subject was administered an antiplatelet agent and a second agent that decreases platelet function; and (b) administering to the subject in need thereof an effective amount of a composition prepared by a process including incubating platelets with an incubating agent including one or more salts, a buffer, optionally a cryoprotectant, and optionally an organic solvent, to form the composition.

Some embodiments include a method of restoring normal hemostasis in a subject, the method including: administering to the subject in need thereof an effective amount of a composition including platelets or platelet derivatives and an incubating agent including one or more salts, a buffer, optionally a cryoprotectant, and optionally an organic solvent, wherein the subject is identified as having been administered an antiplatelet agent and a second agent that decreases platelet function.

Some embodiments include a method of restoring normal hemostasis in a subject, the method including: administering to the subject in need thereof an effective amount of a composition prepared by a process including incubating platelets with an incubating agent including one or more salts, a buffer, optionally a cryoprotectant, and optionally an organic solvent, to form the composition, wherein the subject is identified as having been administered an antiplatelet agent and a second agent that decreases platelet function.

In some embodiments, administration of the second agent is stopped (for example, if the benefits of stopping the second agent outweigh the costs of stopping the second agent). In some embodiments, administration of the second agent is continued (for example, if removal of the second agent would be detrimental to the subject, as can be the case with certain medications, such as antidepressants).

The second agent can be any appropriate second agent that affects (e.g., decreases) platelet function. For example, a second agent can include (or be selected from the group consisting of) an antihypertensive, a proton pump inhibitor, or a combination thereof. As another example, a second agent can include (or be selected from the group consisting of) a chemotherapeutic agent, an antibiotic, a cardiovascular agent, a H2 antagonist, a neuropsychiatric agent, or a combination thereof. In some embodiments, the second agent can include (or be) an antidepressant (e.g., a selective serotonin reuptake inhibitor (SSRI), a serotonin antagonist and reuptake inhibitor (SARI), a serotonin and norepinephrine reuptake inhibitor (SNRI), or a combination thereof). In some embodiments, the second agent is not an anticoagulant.

In some embodiments of any of the methods provided herein, administration of the antiplatelet agent is stopped. In some embodiments of any of the methods provided herein, administration of the antiplatelet agent is continued.

In cases, such as certain emergency situations, it can be impossible to timely determine whether a subject is being administered an antiplatelet agent. In some such cases, a composition provided herein or a composition produced by a method provided herein can be administered to a subject to prevent a coagulopathy. In some embodiments, a composition provided herein or a composition produced by a method provided herein can be administered to a subject to mitigate the potential for a coagulopathy in the subject.

Some embodiments include a method of preventing or mitigating the potential for a coagulopathy in a subject, the method including: (a) determining that information regarding whether the subject was administered an antiplatelet agent is unavailable; and (b) administering to the subject an effective amount of a composition including platelets or platelet derivatives and an incubating agent including one or more salts, a buffer, optionally a cryoprotectant, and optionally an organic solvent.

Some embodiments include a method of preventing or mitigating the potential for a coagulopathy in a subject, the method including: (a) determining that information regarding whether the subject was administered an antiplatelet agent is unavailable; and (b) administering to the subject an effective amount of a composition prepared by a process including incubating platelets with an incubating agent including one or more salts, a buffer, optionally a cryoprotectant, and optionally an organic solvent, to form the composition.

Some embodiments include method of preventing or mitigating the potential for a coagulopathy in a subject, the method including: administering to the subject in need thereof an effective amount of a composition including platelets or platelet derivatives and an incubating agent including one or more salts, a buffer, optionally a cryoprotectant, and optionally an organic solvent, wherein the subject has been determined to be a subject for which information regarding whether the subject was administered an antiplatelet agent is unavailable.

Some embodiments include a method of preventing or mitigating the potential for a coagulopathy in a subject, the method including: administering to the subject in need thereof an effective amount of a composition prepared by a process including incubating platelets with an incubating agent including one or more salts, a buffer, optionally a cryoprotectant, and optionally an organic solvent, to form the composition, wherein the subject has been determined to be a subject for which information regarding whether the subject was administered an antiplatelet agent is unavailable.

In some embodiments of any of the methods herein, determining that information regarding whether the subject was administered an antiplatelet agent is unavailable can be at any appropriate time. For example, determining that information regarding whether the subject was administered an antiplatelet agent is unavailable can be within about 1 week, about 5 days, about 3 days, about 36 hours, about 24 hours, about 18 hours, about 12 hours, about 8 hours, about 6 hours, about 4 hours, about 2 hours, or about 1 hour of the administering a composition provided herein or a composition produced by a method described herein.

There are several reasons that information regarding whether the subjected was administered an antiplatelet agent is unavailable. For example, a reason can include that the subject cannot be identified, that the medical history of the subject is unavailable, that the subject is in need of emergency treatment, that the subject is in need of emergency surgery, that the subject is having emergency surgery, or a combination thereof.

In some embodiments of any of the methods provided herein, the method can further include determining that the subject has an abnormal result for one or more evaluations of clotting parameters. In some embodiments of any of the methods provided herein the subject has been determined to have an abnormal result for one or more evaluations of clotting parameters.

In some cases, before an abnormal result was determined, the subject was previously identified as having a normal result for at least one of the one or more clotting parameters.

In some embodiments of any of the methods provided herein, the method can further include determining the result of the evaluation one or more clotting parameters following the administering of a composition provided herein or a composition produced by a method provided herein. In some such cases, the evaluation of the one or more clotting parameters following the administering shows a normal result, such as defined in Table E1 for at least one of the one or more clotting parameters. In some embodiments, the result of the evaluation of the one or more clotting parameters following the administering is improved from the result of the evaluation of the one or more parameters prior to the administering.

In some embodiments, the subject is identified as having an abnormal result for one or more evaluations of clotting parameters during surgery (e.g., emergency surgery or scheduled surgery)

An evaluation of one or more clotting parameters can be any appropriate evaluation of clotting parameters, such as any of the evaluations of clotting parameters provided herein. In some embodiments, an evaluation of clotting parameters can be selected from the group consisting of the World Health Organization (WHO) bleeding scale, prothrombin time (PT) assay, international normalized ratio (INR), thrombin generation (TGA), thromboelastography (TEG), multiple electrode aggregometry (MEA), light transmission aggregometry (LTA), activated clotting time (ACT), VerifyNow, and partial thromboplastin time (e.g., PTT or aPTT), subparameters thereof, and a combination of any thereof.

In some embodiments, the one or more clotting parameters includes an evaluation of bleeding (e.g., performed based on the World Health Organization (WHO) bleeding scale). In some embodiments, before the administering, the subject has bleeding of grade 2, 3, or 4 based on the WHO bleeding scale. In some embodiments, after the administering, the subject has bleeding of grade 0 or 1 based on the WHO bleeding scale. In some embodiments, after the administering, the subject has bleeding of one grade less, based on the WHO bleeding scale, than before the administering. In some embodiments, after the administering, the subject has bleeding of two grades less, based on the WHO bleeding scale, than before the administering. In some embodiments, after the administering, the subject has bleeding of three grades less, based on the WHO bleeding scale, than before the administering.

In some embodiments, the one or more clotting parameters includes an evaluation of prothrombin time (PT). In some embodiments the abnormal results for PT comprises a PT of greater than about 14 seconds (e.g., greater than about 15 seconds, 18 seconds, 20 seconds, 25 seconds, or more). In some embodiments, after the administering, the subject has a decrease in PT of at least 1 second (e.g., at least 2, 3, 4, 5, 6, 7, 8, 9, 10, or more, seconds). In some embodiments, after the administering, the subject has a normal PT, such as defined in Table E1.

In some embodiments, the one or more clotting parameters includes an evaluation of activated partial thromboplastin time (aPTT). In some embodiments, the abnormal result for aPTT comprises an aPTT of greater than about 40 seconds (e.g., greater than about 43 seconds, 45 seconds, 50 seconds, 55 seconds, 60 seconds, 65 seconds, 70 seconds, or more). In some embodiments, after the administering, the subject has a decrease in aPTT of at least 5 seconds (e.g., at least 10, 15, 20, 25, 30, or more, seconds). In some embodiments, after the administering, the subject has a normal aPTT, such as defined in Table E1.

In some embodiments, the one or more clotting parameters includes an evaluation of thrombin clot time (TCT). In some embodiments, the abnormal result for TCT comprises a TCT of greater than about 35 seconds (e.g., greater than about 38 seconds, 40 seconds, 45 seconds, 50 seconds, 55 seconds, 60 seconds, or more). In some embodiments, after the administering, the subject has a decrease in TCT of at least 5 seconds (e.g., at least 10, 15, 20, 25, 30, or more, seconds). In some embodiments, after the administering, the subject has a normal TCT, such as defined in Table E1.

In some embodiments, the evaluation of the one or more clotting parameters includes thromboelastography (TEG). In some embodiments, the abnormal result for TEG comprises a maximum amplitude (MA) of less than about 50 mm (e.g., less than about 48 mm, 45 mm, 40 mm, 35 mm, or less). In some embodiments, after the administering, the subject has an increase in MA of at least 5 mm (e.g., at least 10, 15, 20, 25, 30, or more, mm). In some embodiments, after the administering, the subject has a normal MA, such as defined in Table E1. In some embodiments, the abnormal result for TEG comprises a percent aggregation (in the presence of 1 mmol/L arachidonic acid) of less than about 85% (e.g., less than about 83%, 80%, 75%, 70%, or less). In some embodiments, after the administering, the subject has an increase in percent aggregation (in the presence of 1 mmol/L arachidonic acid) of at least 2 percentage points (e.g., at least, 3, 5, 8, 10, 12, 15, 18, 20, or more, percentage points). In some embodiments, after the administering, the subject has a normal percent aggregation (in the presence of 1 mmol/L arachidonic acid), such as defined in Table E1. In some embodiments, the TEG is used to evaluate adenosine diphosphate-induced platelet-fibrin clot strength. In some embodiments, the TEG is used to evaluate arachidonic acid-induced platelet-fibrin clot strength.

In some embodiments, the evaluation of one or more clotting parameters includes VerifyNow. In some embodiments, abnormal result for VerifyNow comprises a P2Y12 reaction unit (PRU) of less than about 195 (e.g., less than about 190, 185, 180, 170, 165, 160, 155, or less), In some embodiments, after the administering, the subject has an increase in PRU of at least 25 (e.g., at least 30, 35, 40, 45, 50, 75, 100, or more). In some embodiments, after the administering, the subject has a normal PRU, such as defined in Table E1. In some embodiments, the abnormal result for VerifyNow comprises an Aspirin Reaction Unit (ARU) of less than about 550 (e.g., less than about 540, 530, 520, 510, 500, 490, 480, 470, or less). In some embodiments, after the administering, the subject has an increase in ARU of at least 25 (e.g., at least 30, 35, 40, 45, 50, 75, 100, or more). In some embodiments, after the administering, the subject has a normal ARU, such as defined in Table E1.

In some embodiments, the evaluation of one or more clotting parameters includes multiple electrode aggregometry (MEA). In some embodiments the abnormal result for MEA comprises an abnormal result for ADP-induced platelet activity. In some embodiments the abnormal result for MEA comprises a result of less than about 50 units (U) (e.g., less than about 48, 45, 40, 35, or less, U) for ADP-induced platelet activity. In some embodiments, after the administering, the subject has an increase in ADP-induced platelet activity by at least 5 U (e.g., at least 8, 10, 15, 20, or more U). In some embodiments, after the administering, the subject has a normal value for ADP-induced platelet activity, such as defined in Table E1. In some embodiments, the abnormal result for MEA comprises an abnormal result for arachidonic acid-induced platelet activity. In some embodiments, the abnormal result for MEA comprises a result of less than about 70 units (U) (e.g., less than about 68, 65, 60, 55, 50, 45, or less, U) for arachidonic acid-induced platelet activity. In some embodiments, after the administering, the subject has an increase in arachidonic acid-induced platelet activity by at least 5 (e.g., at least 8, 10, 15, 20, or more, units). In some embodiments, after the administering, the subject has a normal value for arachidonic acid-induced platelet activity, such as defined in Table E1.

In some embodiments, the evaluation of one or more clotting parameters includes light transmission aggregometry (LTA). In some embodiments, the abnormal result for LTA includes, in the presence of 5 μmol/L adenosine diphosphate, a percent aggregation of less than about 60% (e.g., less than about 58%, 55%, 50%, 45%, or less). In some embodiments, the abnormal result for LTA includes, in the presence of 2 μg/mL collagen, a percent aggregation of less than about 65% (e.g., less than about 63%, 60%, 55%, 50%, 45%, or less). In some embodiments, the abnormal result for LTA includes, in the presence of 1 mmol/L arachidonic acid, a percent aggregation of less than about 65% (e.g., less than about 63%, 60%, 55%, 50%, 45%, or less). In some embodiments, the abnormal result for LTA includes, in the presence of 2 mmol/L arachidonic acid, a percent aggregation of less than about 69% (e.g., less than about 67%, 65%, 60%, 55%, 50%, 45%, or less). In some embodiments, the abnormal result for LTA includes, in the presence of 5 mmol/L arachidonic acid, a percent aggregation of less than about 73% (e.g., less than about 70%, 65%, 60%, 55%, 50%, or less). In some embodiments, after the administering, the subject has an increase in percent aggregation (in the presence of 5 μmol/L adenosine diphosphate) of at least 2 percentage points (e.g., at least 3, 5, 8, 10, 12, or more, percentage points). In some embodiments, after the administering, the subject has a normal percent aggregation (in the presence of 5 μmol/L adenosine diphosphate), such as defined in Table EL. In some embodiments, after the administering, the subject has an increase in percent aggregation (in the presence of 2 μg/mL collagen) of at least 2 percentage points (e.g., at least 3, 5, 8, 10, 12, or more, percentage points). In some embodiments, after the administering, the subject has a normal percent aggregation (in the presence of 2 μg/mL collagen), such as defined in Table E1. In some embodiments, after the administering, the subject has an increase in percent aggregation (in the presence of 1 mmol/L arachidonic acid) of at least 2 percentage points (e.g., at least 3, 5, 8, 10, 12, or more, percentage points). In some embodiments after the administering, the subject has a normal percent aggregation (in the presence of 1 mmol/L arachidonic acid), such as defined in Table E1. In some embodiments, after the administering, the subject has an increase in percent aggregation (in the presence of 2 mmol/L arachidonic acid) of at least 2 percentage points (e.g., at least 3, 5, 8, 10, 12, or more, percentage points). In some embodiments, after the administering, the subject has a normal percent aggregation (in the presence of 2 mmol/L arachidonic acid), such as defined in Table E1. In some embodiments, after the administering, the subject has an increase in percent aggregation (in the presence of 5 mmol/L arachidonic acid) of at least 2 percentage points (e.g., at least, 3, 5, 8, 10, 12, or more, percentage points). In some embodiments, after the administering, the subject has a normal percent aggregation (in the presence of 5 mmol/L arachidonic acid), such as defined in Table E1.

In some embodiments, an additional antiplatelet agent reversal agent can be administered to a subject in addition to a composition provided herein or a composition produced by a method described herein. The additional antiplatelet agent reversal agent can be administered in any order with the composition provided herein or the composition produced by a method provided herein. In some embodiments, the administering of the composition occurs concurrently with administering of the additional antiplatelet agent reversal agent. In some embodiments, the administering of the composition occurs after administering of the additional antiplatelet agent reversal agent. In some embodiments, the administering of the composition occurs before administering of the additional antiplatelet agent reversal agent.

In one aspect of any of the embodiments herein, the subject does not have cancer.

An "effective amount" as used herein is an amount of the composition that comprises an amount of platelets, typically platelet derivatives, which in illustrative embodiments are FDPDs, effective in treating the subject. Such treating, for example with respect to methods for treating a coagulopathy or methods for counteracting the effect of an anti-thrombotic agent (i.e. an anti-platelet agent or an anti-coagulant) of a subject herein reduces the bleeding potential of the subject. In some embodiments, the bleeding potential can be reduced to such an extent that normal hemostasis is restored for the subject, such as to a level for that subject without any anti-platelet agent in their body, at least for a period of time. Thus, in some embodiments, an effective amount of a composition comprising platelet derivatives, for example FDPDs, is an amount that results in reduced bleeding potential of a subject, which in some embodiments results in normal hemostasis, for any period of time. In some embodiments, the bleeding potential is reduced for at least 10, 20, 30, 40, 50 or 60 minutes after being administered a dose of an effective amount of the platelet derivatives, for example the FDPDs, or a second, third, fourth. Fifth, or sixth dose of composition comprising platelet derivatives that each, or two or more, or all, cumulatively add up to an effective dose.

Such an amount of platelets or typically platelet derivatives (e.g., FDPDs) includes any appropriate dosage of a composition comprising the platelet derivatives as described herein that can be administered to the subject, in illustrative embodiments that results in reduced bleeding potential of a subject. For example, in some embodiments, a dose of a composition comprising platelets or platelet derivatives (e.g., FDPDs) can include between about or exactly $1.0 \times 10^7$ to $1.0 \times 10^{11}$ particles (e.g. FDPDs)/kg of a subject, $1.0 \times 10^7$ to $1.0 \times 10^{10}$ particles (e.g. FDPDs)/kg of a subject, $1.6 \times 10^7$ to $1.0 \times 10^{10}$ particles (e.g. FDPDs)/kg of subject, $1.6 \times 10^7$ to $5.1 \times 10^9$ particles (e.g. FDPDs/kg of a subject, $1.6 \times 10^7$ to $3.0 \times 10^9$ particles (e.g. FDPDs)/kg of a subject, $1.6 \times 10^7$ to $1.0 \times 10^9$ particles (e.g. FDPDs)/kg of a subject, $1.6 \times 10^7$ to $5.0 \times 10^8$ particles (e.g. FDPDs)/kg of a subject, $1.6 \times 10^7$ to $1.0 \times 10^8$ particles (e.g. FDPDs)/kg of a subject, $1.6 \times 10^7$ to $5.0 \times 10^7$ particles (e.g. FDPDs)/kg of a subject, $5.0 \times 10^7$ to $1.0 \times 10^8$ particles (e.g. FDPDs)/kg of a subject, $1.0 \times 10^8$ to $5.0 \times 10^8$ particles (e.g. FDPDs)/kg of a subject, $5.0 \times 10^8$ to $1.0 \times 10^9$ particles (e.g. FDPDs)/kg of a subject, $1.0 \times 10^9$ to $5.0 \times 10^9$ particles (e.g. FDPDs)/kg of a subject, or $5.0 \times 10^9$ to $1.0 \times 10^{10}$ particles (e.g. FDPDs)/kg of a subject). In some embodiments an effective amount of a composition comprising FDPDs is an activity-based amount that has a potency between 250 and 5000 TGPU per kg of a subject. Such activity-based amount can be combined with any of the particle number ranges/kg in this paragraph.

In certain embodiments, any of the dose ranges provided above, and in illustrative embodiments those that include less than $1 \times 10^{11}$ particles/kg, can be administered more than 1 time to a subject. For example, a dose range of between $1.0 \times 10^7$ particles to about $1.0 \times 10^{10}$ particles, can be administered between 2 and 10 times, or between 2 and 8 times, or between 2 and 6 times, or between 3 and 8 times, or between 3 and 6 times, or between 4 and 6 times in a timeframe between within 1, 2, 3, 4, 5, or 7 days from the first dose.

In some embodiments of the methods herein, the composition is administered topically. In some embodiments, topical administration can include administration via a solution, cream, gel, suspension, putty, particulates, or powder. In some embodiments, topical administration can include administration via a bandage (e.g. an adhesive bandage or a compression bandage) or medical closure (e.g., sutures, staples)); for example the platelet derivatives (e.g., lyopreserved platelets (e.g., FDPDs)) can be embedded therein or coated thereupon), as described in PCT Publication No. WO2017/040238 (e.g., paragraphs [013]-[069]), corresponding to U.S. patent application Ser. No. 15/776,255, the entirety of which is herein incorporated by reference.

In some embodiments of the methods herein, the composition is administered parenterally. In some illustrative embodiments of the methods herein, the composition is administered intravenously. In some embodiments of the methods herein, the composition is administered intramuscularly. In some embodiments of the methods herein, the composition is administered intrathecally. In some embodiments of the methods herein, the composition is administered subcutaneously. In some embodiments of the methods herein, the composition is administered intraperitoneally.

In some embodiments of the methods herein, the composition is dried prior to the administration step. In illustrative embodiments of the methods herein, the composition is freeze-dried prior to the administration step. Such FDPD composition in illustrative embodiments, is prepared according to methods provided in the Examples herein. In illustrative embodiments of the methods herein, the composition is rehydrated following the drying or freeze-drying step, for example within 24, 12, 8, 6, 4, 3, 2, or 1 hour, or within 30, 20. 15, 10, or 5 minutes before being administered to a subject.

In some embodiments, the antiplatelet agent is selected from the group consisting of aspirin (also called acetylsalicylic acid or ASA); a P2Y12 inhibitor such as cangrelor (e.g., KENGREAL®), ticagrelor (e.g., BRILINTA®), clopidogrel (e.g., PLAVIX®), or prasugrel (e.g., EFFIENT®); a glycoprotein IIb/IIIa inhibitor such as eptifibatide (e.g., INTEGRILIN®), tirofiban (e.g., AGGRASTAT®), or abciximab (e.g., REOPRO®)); supplements such as herbal supplements; or a combination of any thereof. Examples of supplements include ginger, *ginseng, ginkgo*, green tea, kava, saw palmetto, boldo (*Peumus boldus*), Danshen (*Salvia miltiorrhiza*), Dong quai (*Angelica sinensis*) papaya (*Carica papaya*), fish oil, and vitamin E. Examples of herbal supplements include ginger, *ginseng*, and *ginkgo*.

The prescribing information for each of the FDA-approved anticoagulants provided herein is incorporated by reference in its entirety. Such prescribing information includes, for example:

HIGHLIGHTS OF PRESCRIBING INFORMATION for DURLAZA® (aspirin), Revised December 2019.

HIGHLIGHTS OF PRESCRIBING INFORMATION for KENGREAL® (cangrelor), Revised: June 2015.

HIGHLIGHTS OF PRESCRIBING INFORMATION for BRILINTA® (ticagrelor), Revised: September 2016.

HIGHLIGHTS OF PRESCRIBING INFORMATION for PLAVIX® (clopidogrel bisulfate), Revised: August 2010.

HIGHLIGHTS OF PRESCRIBING INFORMATION for EFFIENT® (prasugrel), Revised September 2011.

HIGHLIGHTS OF PRESCRIBING INFORMATION for INTEGRILIN® (eptifibatide), Revised March 2013.

HIGHLIGHTS OF PRESCRIBING INFORMATION for AGGRASTAT® (tirofiban), Revised August 2016.

PRESCRIBING INFORMATION for REOPRO® (abciximab), Revision Date: November 1997.

APPROVAL PACKAGE for TICLID® (ticlopidine hydrochloride), Revised March 2001.

DESCRIPTION—MOTRIN® (ibuprofen), Effective Date January 2007.
HIGHLIGHTS OF PRESCRIBING INFORMATION for ZONTIVITY™ (vorapaxar), Revised May 2014.
HIGHLIGHTS OF PRESCRIBING INFORMATION for PLETAL® (cilostazol), Revised May 2017.
HIGHLIGHTS OF PRESCRIBING INFORMATION for VELETRI® (epoprostenol), Revised June 2012.
PRESCRIBING INFORMATION for PERSANTINE® (dipyridamole), Revised December 2019.
HIGHLIGHTS OF PRESCRIBING INFORMATION for REMODULIN® (acenocoumarol), December 2014.

In some embodiments, the antiplatelet agent is aspirin. In some embodiments, the antiplatelet agent is cangrelor (e.g., KENGREAL®). In some embodiments, the antiplatelet agent is ticagrelor (e.g., BRILINTA®). In some embodiments, the antiplatelet agent is clopidogrel (e.g., PLAVIX®). In some embodiments, the antiplatelet agent is prasugrel (e.g., EFFIENT®). In some embodiments, the antiplatelet agent is eptifibatide (e.g., INTEGRILIN®). In some embodiments, the antiplatelet agent is tirofiban (e.g., AGGRASTAT®). In some embodiments, the antiplatelet agent is abciximab (e.g., REOPRO®). In some embodiments, the antiplatelet agent is terutroban. In some embodiments, the antiplatelet agent is picotamide. In some embodiments, the antiplatelet agent is elinogrel. In some embodiments, the antiplatelet agent is ticlopidine. In some embodiments, the antiplatelet agent is ibuprofen. In some embodiments, the antiplatelet agent is vorapaxar. In some embodiments, the antiplatelet agent is atopaxar. In some embodiments, the antiplatelet agent is cilostazol. In some embodiments, the antiplatelet agent is prostaglandin E1. In some embodiments, the antiplatelet agent is epoprostenol. In some embodiments, the antiplatelet agent is dipyridamole. In some embodiments, the antiplatelet agent is treprostinil sodium. In some embodiments, the antiplatelet agent is sarpogrelate. In some embodiments, the antiplatelet agent is a supplement. In some embodiments, the antiplatelet agent is an herbal supplement.

In some embodiments, the antiplatelet agent was last administered at a dosage and timepoint relative to the time that the composition comprising platelet derivatives is administered to a subject, such that the blood of the subject comprises the antiplatelet agent, in illustrative embodiments, a detectable quantity of the antiplatelet agent. Typically, such agent is present in the blood of the subject at the time the subject is administered a dose of the composition comprising the composition comprising platelet derivatives, and is present in the blood of the subject in an amount that is sufficient to increase the bleeding potential of the subject. For example, the anti-platelet agent is present at a concentration that is sufficient to yield an abnormal value for one or more clotting parameters, for example in an in vitro test. In some embodiments, the antiplatelet agent is present in the subject at the time the composition comprising the FDPDs is administered at a level that increases the bleeding potential of the subject. In some embodiments, the antiplatelet agent is present at a Cmax within 15, 30 or 45 minutes, or within 1, 2, 3, 4, 6, or 8 hours of the time the composition comprising the FDPDs is administered or the time the first or last dose of the composition comprising the FDPDs is administered.

In some embodiments, antiplatelet agent comprises aspirin at a dosage of about 80 mg to about 700 mg (e.g., 80 mg, 100 mg, 150 mg, 200 mg, 250 mg, 300 mg, 400 mg, 500 mg, 600 mg, or 700 mg), once, twice, three times, or four times a day. In some embodiments, the antiplatelet agent comprises aspirin, and the subject achieved a $C_{max}$ of about 3 to about 25 mg/L (e.g., about 3 to about 5 mg/L for a dose of about 100 mg, about 10 to about 15 mg/L for a dose of about 300 mg, or about 20 to about 25 mg/L for a dose of about 500 mg). See also, e.g., Nagelschmitz, J et al. "Pharmacokinetics and pharmacodynamics of acetylsalicylic acid after intravenous and oral administration to healthy volunteers." *Clinical Pharmacology: Advances and Applications* vol. 6 51-9. 19 Mar. 2014, doi:10.2147/CPAA.S47895. In some embodiments, the antiplatelet agent comprises aspirin, and before the administering of a composition provided herein or a composition produced by a method described herein, the subject had a ARU of about 350 to about 549 ARU (e.g., about 400 to about 500 ARU). In some embodiments, the antiplatelet agent comprises aspirin, and after the administering of a composition provided herein or a composition produced by a method described herein, the subject had a ARU of about 550 to about 700 ARU (e.g., about 600 to about 700 ARU). In some embodiments, the antiplatelet agent comprises aspirin, and before the administering of a composition provided herein or a composition produced by a method described herein, the subject had a high on-treatment platelet reactivity (HPR) using MEA of greater than about 30 units (e.g., greater than about 33, 35, 40, 45, 50, or more units). See, e.g., Krüger, Jan-Christopher, et al. "Monitoring ASA and P2Y12-specific platelet inhibition-comparison of conventional (single) and multiple electrode aggregometry." *Scandinavian journal of clinical and laboratory investigation* 74.7 (2014): 568-574.

In some embodiments, the antiplatelet agent comprises cangrelor at an initial dosage of about 25 to about 35 µg/kg body weight of the subject (e.g., about 30 µg/kg body weight of the subject) or a following dosage of about 3 to about 5 µg/kg/min body weight of the subject (e.g., about 4 µg/kg/min body weight of the subject). In some embodiments, the antiplatelet agent comprises cangrelor, and the subject achieved a $C_{max}$ of about 400 to about 500 ng/mL. See, e.g., the manufacturer's fact sheet for KENGREAL® found at https://resources.chiesiusa.com/Kengreal/KENGREAL_Dosing_and_Administration_Fact_Sheet.pdf. In some embodiments, the antiplatelet agent comprises cangrelor, and before the administering of a composition provided herein or a composition produced by a method described herein, the subject had a maximum amplitude (TEG-ADP) of less than about 50 mm (e.g., less than about 48 mm, 45 mm, 40 mm, or less). In some embodiments, the antiplatelet agent comprises cangrelor, and after the administering of a composition provided herein or a composition produced by a method described herein, the subject had a maximum amplitude (TEG-ADP) of at least about 50 mm (e.g., at least 53 mm, 55 mm, 50 mm, 60 mm, 65 mm, 70 mm, or more). See, e.g., Corliss B M, Polifka A J, Harris N S, Hoh B L, Fox W C. Laboratory assessments of therapeutic platelet inhibition in endovascular neurosurgery: comparing results of the VerifyNow P2Y12 assay to thromboelastography with platelet mapping. *J Neurosurg*. 2018 Nov. 1; 129(5):1160-1165. doi: 10.3171/2017.6.JNS17535. PMID: 29271717.

In some embodiments, the antiplatelet agent comprises ticagrelor at an initial dosage of about 170 to about 190 mg (e.g., about 180 mg), or a following dosage in a first year of treatment of about 80 to about 100 mg (e.g., about 90 mg) twice daily, or a following dosage in a second year of treatment of about 50 to about 70 mg twice daily (e.g., about 60 mg), optionally in combination with aspirin. In some embodiments, the antiplatelet agent comprises ticagrelor, and the subject achieved a $C_{max}$ of about 550 to about 650 ng/mL (e.g., about 600 mg/L). See, e.g., Teng R, Muldowney S, Zhao Y, Berg J K, Lu J, Khan N D. Pharmacokinetics and pharmacodynamics of ticagrelor in subjects on hemodialysis and subjects with normal renal function. *Eur J Clin Pharmacol.* 2018 September; 74(9):1141-1148. doi: 10.1007/s00228-018-2484-7. Epub 2018 May 30. PMID: 29850937; PMCID: PMC6096709. In some embodiments, the antiplatelet agent comprises ticagrelor, and before the administering of a composition provided herein or a composition produced by a method described herein, the subject had a PRU of less than about 180 (e.g., less than about 175, 170, 165, 160, 155, 150, or less). In some embodiments, the antiplatelet agent comprises ticagrelor, and after the administering of a composition provided herein or a composition produced by a method described herein, the subject had a PRU of at least 180 (e.g., at least 180, 185, 190, 195, 200, 225, 250, 275, 300, 350, or more). In some embodiments, the antiplatelet agent comprises ticagrelor, and after the administering of a composition provided herein or a composition produced by a method described herein, the subject had a PRU of about 180 to about 376 PRU (e.g., about 200 to about 300 PRU). In some embodiments, the antiplatelet agent comprises ticagrelor, and before the administering of a composition provided herein or a composition produced by a method described herein, the subject had a maximum amplitude (TEG-ADP) of less than about 50 mm (e.g., less than about 48 mm, 45 mm, 40 mm, or less). In some embodiments, the antiplatelet agent comprises ticagrelor, and after the administering of a composition provided herein or a composition produced by a method described herein, the subject had a maximum amplitude (TEG-ADP) of at least about 50 mm (e.g., at least 53 mm, 55 mm, 50 mm, 60 mm, 65 mm, 70 mm, or more). See, e.g., Corliss B M, Polifka A J, Harris N S, Hoh B L, Fox W C. Laboratory assessments of therapeutic platelet inhibition in endovascular neurosurgery: comparing results of the VerifyNow P2Y12 assay to thromboelastography with platelet mapping. *J Neurosurg.* 2018 Nov. 1; 129(5):1160-1165. doi: 10.3171/2017.6.JNS17535. PMID: 29271717.

In some embodiments, the antiplatelet agent comprises clopidogrel at an initial dosage of about 275 to about 325 mg (e.g., about 300 mg), or a following dosage of about 70 to about 80 mg (e.g., about 75 mg) once daily, optionally in combination with aspirin. In some embodiments, the antiplatelet agent comprises clopidogrel, and the subject achieved a $C_{max}$ of about 1 to about 40 mg/L (e.g., about 1 to about 15 ng/mL for a dosage of about 75 mg, or about 1 to about 40 ng/mL for a dosage of about 300 mg). See, e.g., Karaźniewicz-Lada, Marta et al. "Clinical pharmacokinetics of clopidogrel and its metabolites in patients with cardiovascular diseases." *Clinical Pharmacokinetics* vol. 53,2 (2014): 155-64. doi:10.1007/s40262-013-0105-2. In some embodiments, the antiplatelet agent comprises clopidogrel, and before the administering of a composition provided herein or a composition produced by a method described herein, the subject had a PRU of less than about 180 (e.g., less than about 175, 170, 165, 160, 155, 150, or less). In some embodiments, the antiplatelet agent comprises clopidogrel, and after the administering of a composition provided herein or a composition produced by a method described herein, the subject had a PRU of at least 180 (e.g., at least 180, 185, 190, 195, 200, 225, 250, 275, 300, 350, or more). In some embodiments, the antiplatelet agent comprises clopidogrel, and after the administering of a composition provided herein or a composition produced by a method described herein, the subject had a PRU of about 180 to about 376 PRU (e.g., about 200 to about 300 PRU). In some embodiments, the antiplatelet agent comprises clopidogrel, and before the administering of a composition provided herein or a composition produced by a method described herein, the subject had a high on-treatment platelet reactivity (HPR) using MEA of greater than about 47 units (e.g., greater than about 48, 50, 55, or more units). See, e.g., Krüger, Jan-Christopher, et al. "Monitoring ASA and P2Y12-specific platelet inhibition-comparison of conventional (single) and multiple electrode aggregometry." *Scandinavian journal of clinical and laboratory investigation* 74.7 (2014): 568-574. In some embodiments, the antiplatelet agent comprises clopidogrel, and before the administering of a composition provided herein or a composition produced by a method described herein, the subject had a maximum amplitude (TEG-ADP) of less than about 50 mm (e.g., less than about 48 mm, 45 mm, 40 mm, or less). In some embodiments, the antiplatelet agent comprises clopidogrel, and after the administering of a composition provided herein or a composition produced by a method described herein, the subject had a maximum amplitude (TEG-ADP) of at least about 50 mm (e.g., at least 53 mm, 55 mm, 50 mm, 60 mm, 65 mm, 70 mm, or more). See, e.g., Corliss B M, Polifka A J, Harris N S, Hoh B L, Fox W C. Laboratory assessments of therapeutic platelet inhibition in endovascular neurosurgery: comparing results of the VerifyNow P2Y12 assay to thromboelastography with platelet mapping. *J Neurosurg.* 2018 Nov. 1; 129(5):1160-1165. doi: 10.3171/2017.6.JNS17535. PMID: 29271717.

In some embodiments, the antiplatelet agent comprises prasugrel at an initial dosage of about 50 to about 70 mg (e.g., about 60 mg), or a following dosage of about 3 to about 12 mg (e.g., about 5 mg or about 10 mg) once daily, optionally in combination with aspirin. In some embodiments, the antiplatelet agent comprises prasugrel, and the subject achieved a $C_{max}$ of about 200 to about 525 ng/mL (e.g., about 330 to about 350 ng/mL for a dose of about 20 mg). See, e.g., Umemura, Kazuo, and Takayuki Iwaki. "The Pharmacokinetics and Pharmacodynamics of Prasugrel and Clopidogrel in Healthy Japanese Volunteers." *Clinical Pharmacology in Drug Development* vol. 5,6 (2016): 480-487. doi:10.1002/cpdd.259. In some embodiments, the antiplatelet agent comprises prasugrel, and before the administering of a composition provided herein or a composition produced by a method described herein, the subject had a PRU of less than about 180 (e.g., less than about 175, 170, 165, 160, 155, 150, or less). In some embodiments, the antiplatelet agent comprises prasugrel, and after the administering of a composition provided herein or a composition produced by a method described herein, the subject had a PRU of at least 180 (e.g., at least 180, 185, 190, 195, 200, 225, 250, 275, 300, 350, or more). In some embodiments, the antiplatelet agent comprises prasugrel, and after the administering of a composition provided herein or a composition produced by a method described herein, the subject had a PRU of about 180 to about 376 PRU (e.g., about 200 to about 300 PRU). In some embodiments, the antiplatelet agent comprises prasugrel, and before the administering of a composition provided herein or a composition produced by a method described herein, the subject had a maximum amplitude (TEG-ADP) of less than about 50 mm (e.g., less than about 48 mm, 45 mm, 40 mm, or less). In some embodiments, the antiplatelet agent comprises prasugrel, and after the administering of a composition provided herein or a composition produced by a method described herein, the subject had a maximum amplitude (TEG-ADP) of at least about 50 mm (e.g., at least 53 mm, 55 mm, 50 mm, 60 mm, 65 mm, 70 mm, or more). See, e.g., Corliss B M, Polifka A J, Harris N S, Hoh B L, Fox W C. Laboratory assessments of therapeutic platelet inhibition in endovascular neurosurgery: comparing results of the VerifyNow P2Y12 assay to thromboelastography with platelet mapping. *J Neurosurg.* 2018 Nov. 1; 129(5):1160-1165. doi: 10.3171/2017.6.JNS17535. PMID: 29271717. In some embodiments, the antiplatelet agent comprises prasugrel, and before the administering of a composition provided herein or a composition produced by a method described herein, the subject had a high on-treatment platelet reactivity (HPR) using MEA of greater than about 47 units (e.g., greater than about 48, 50, 55, or more units). See, e.g., Krüger, Jan-Christopher, et al. "Monitoring ASA and P2Y12-specific platelet inhibition-comparison of conventional (single) and multiple electrode aggregometry." *Scandinavian journal of clinical and laboratory investigation* 74.7 (2014): 568-574.

In some embodiments, antiplatelet agent comprises eptifibatide at an initial dosage of about 170 to about 190 mcg/kg body weight of the subject (e.g., about 180 mcg/kg body weight of the subject), optionally a second initial dosage of about 170 to about 190 mcg/kg body weight of the subject (e.g., about 180 mcg/kg body weight of the subject), or a following dose of about 1 to about 2 mcg/kg body weight of the subject/min (e.g., about 1.5 mcg/kg body weight of the subject/min.

In some embodiments the antiplatelet agent comprises tirofiban at an initial dosage of about 0.3 to about 0.5 µg/kg body weight of the subject/min (e.g., about 0.5 µg/kg body weight of the subject/min) for about 30 minutes, or a following dosage of about 0.1 µg/kg body weight of the subject/min.

In some embodiments, the antiplatelet agent comprises abciximab at an initial dosage of about 0.2 to about 0.3 mg/kg body weight of the subject (e.g., about 0.25 mg/kg body weight of the subject), or a following dosage of about 0.10 to about 0.15 µg/kg body weight of the subject/min (e.g., about 0.125 µg/kg body weight of the subject/min). In some embodiments, the antiplatelet agent comprises abciximab at an initial dosage of about 0.2 to about 0.3 mg/kg body weight of the subject (e.g., about 0.25 mg/kg body weight of the subject), or a following dosage of about 8 to about 10 µg/min (e.g., about 9 µg/min).

In some embodiments, the antiplatelet agent comprises ticlopidine at a dosage of about 240 to about 260 mg (e.g., about 250 mg) twice per day.

In some embodiments, the antiplatelet agent comprises ibuprofen at a dosage of about 100 to about 600 mg (e.g., about 100 mg, 200 mg, 250 mg, 300 mg, 400 mg, 500 mg, or 600 mg) once, twice, three times, or four times per day.

In some embodiments, the antiplatelet agent comprises vorapaxar at a dosage of about 2 to about 3 mg (e.g., about 2.5 mg) once per day, optionally with aspirin or clopidogrel.

In some embodiments, the antiplatelet agent comprises cilostazol at a dosage of about 40 to about 110 mg (e.g., about 50 mg, 75 mg, or 100 mg) twice daily.

In some embodiments, the antiplatelet agent comprises epoprostenol at an initial dosage of about 2 ng/kg body weight of the subject/min, or a following dosage of about 4, 6, 8, 10, 12, 14, 16, 18, or 20 ng/kg body weight of the subject/min.

In some embodiments, the antiplatelet agent comprises dipyridamole at a dosage of about 60 to about 110 mg (e.g., about 75 mg or 100 mg) four times daily.

In some embodiments, the antiplatelet agent comprises treprostinil sodium at a dosage of about 0.5 to about 3.0 ng/kg body weight of the subject/min (e.g., about 0.625 ng/kg body weight of the subject/min about 1.25 ng/kg body weight of the subject/min or about 2.5 ng/kg body weight of the subject per min).

In some embodiments, rehydrating the composition comprising platelet derivatives comprises adding to the platelet derivatives (e.g. FDPDs) an aqueous liquid. In some embodiments, the aqueous liquid is water. In some embodiments, the aqueous liquid is an aqueous solution (e.g., a buffer). In some embodiments, the aqueous liquid is a saline solution. In some embodiments, the aqueous liquid is a suspension.

In some embodiments, the rehydrated platelet derivatives (e.g., FDPDs) have coagulation factor levels showing all individual factors (e.g., Factors VII, VIII and IX) associated with blood clotting at 40 international units (IU) or greater.

In some embodiments, the platelet derivatives (e.g., FDPDs) have less than about 100%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelet derivatives (e.g., FDPDs), have less than about 10%, such as less than about 8%, such as less than about 6%, such as less than about 4%, such as less than about 2%, such as less than about 0.5% crosslinking of platelet membranes via proteins and/or lipids present on the membranes.

In some embodiments, the platelets, typically platelet derivatives, and in illustrative embodiments FDPDs, have a particle size (e.g., diameter, max dimension) of at least about 0.2 µm (e.g., at least about 0.3 µm, at least about 0.4 µm, at least about 0.5 µm, at least about 0.6 µm, at least about 0.7 µm, at least about 0.8 µm, at least about 0.9 µm, at least about 1.0 µm, at least about 1.2 µm, at least about 1.5 µm, at least about 2.0 µm, at least about 2.5 µm, or at least about 5.0 µm). In some embodiments, the particle size is less than about 5.0 µm (e.g., less than about 2.5 µm, less than about 2.0 µm, less than about 1.5 µm, less than about 1.0 µm, less than about 0.9 µm, less than about 0.8 µm, less than about 0.7 µm, less than about 0.6 µm, less than about 0.5 µm, less than about 0.4 µm, or less than about 0.3 µm). In some embodiments, the particle size is from about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets, or in illustrative embodiments platelet derivatives (e.g., FDPDs), have a particle size in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, at most 99% (e.g., at most about 95%, at most about 80%, at most about 75%, at most about 70%, at most about 65%, at most about 60%, at most about 55%, or at most about 50%) of the platelets, or in illustrative embodiments platelet derivatives (e.g., FDPDs), are in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, about 50% to about 99% (e.g., about 55% to about 95%, about 60% to about 90%, about 65% to about 85, about 70% to about 80%) of the platelets, or in illustrative embodiments platelet derivatives (e.g., FDPDs) are in the range of about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm).

In some illustrative embodiments, a microparticle can be a particle having a particle size (e.g., diameter, max dimension) of less than about 0.5 μm (less than about 0.45 μm or 0.4 μm) In some cases, a microparticle can be a particle having a particle size of about 0.01 μm to about 0.5 μm (e.g., about 0.02 μm to about 0.5 μm).

Compositions comprising platelets or platelet derivatives (e.g., FDPDs), such as those prepared according to methods described herein, can have a microparticle content that contributes to less than about 5.0% (e.g., less than about 4.5%, 4.0%, 3.5%, 3.0%, 2.5%, 2.0%, 1.5%, 1.0%, or 0.5%) of the total scattering intensity of all particles from about 1 nm to about 60,000 nm in radius in the composition. In some embodiments, the platelet derivative composition comprises a population of platelet derivatives comprising CD41-positive platelet derivatives, wherein less than 15%, 10%, 7.5%, 5%, 4.5%, 4%, 3.5%, 3%, 2.5%, 2%, 1.5%, 1%, 0.5%, or 0.1% of the CD41-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm, which in certain illustrative embodiments are less than 0.5 μm. In some embodiments, the platelet derivative composition comprises a population of platelet derivatives comprising CD42-positive platelet derivatives, wherein less than 15%, 10%, 7.5%, 5%, 4.5%, 4%, 3.5%, 3%, 2.5%, 2%, 1.5%, 1%, 0.5%, or 0.1% of the CD42-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm, which in certain illustrative embodiments are less than 0.5 μm. In some embodiments, the platelet derivative composition comprises a population of platelet derivatives comprising CD61-positive platelet derivatives, wherein less than 15%, 10%, 7.5, 5%, 4.5%, 4%, 3.5%, 3%, 2.5%, 2%, 1.5%, 1%, 0.5%, or 0.1% of the CD61-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm, which in certain illustrative embodiments are less than 0.5 μm. In some illustrative embodiments, the microparticles have a diameter of less than 0.5 μm. In some embodiments of any of the aspects and embodiments herein that include a platelet derivative composition in a powdered form, the diameter of the microparticles is determined after rehydrating the platelet derivative composition with an appropriate solution. In some embodiments, the amount of solution for rehydrating the platelet derivative composition is equal to the amount of buffer or preparation agent present at the step of freeze-drying. As used herein, a content of microparticles "by scattering intensity" refers to the microparticle content based on the scattering intensity of all particles from about 1 nm to about 60,000 nm in radius in the composition. The microparticle content can be measured by any appropriate method, for example, by dynamic light scattering (DLS). In some cases, the viscosity of a sample used for DLS can be at about 1.060 cP (or adjusted to be so), as this is the approximate viscosity of plasma. In some embodiments, the platelet derivative composition as per any aspects, or embodiments comprises a population of platelet derivatives, and microparticles, wherein the numerical ratio of platelet derivatives to the microparticles is at least 90:1, 91:1, 92:1, 93:1, 94:1, 95:1, 96:1, 97:1, 98:1, or 99:1. In some embodiments, the platelet derivatives have a diameter in the range of 0.5-2.5 μm, and the microparticles have a diameter less than 0.5 μm.

In some embodiments, platelets are isolated, for example in a liquid medium, for example prior to processing to form platelet derivatives, or prior to directly administering to a subject.

In some embodiments, platelets are donor-derived platelets. In some embodiments, platelets are obtained by a process that comprises an apheresis step. In some embodiments, platelets are pooled platelets.

In some embodiments, platelets are pooled from a plurality of donors. Such platelets pooled from a plurality of donors may be also referred herein to as pooled platelets. In some embodiments, the donors are more than 5, such as more than 10, such as more than 20, such as more than 50, such as up to about 100 donors. In some embodiments, the donors are from about 5 to about 100, such as from about 10 to about 50, such as from about 20 to about 40, such as from about 25 to about 35. Pooled platelets can be used to make any of the compositions described herein.

In some embodiments, platelets are derived in vitro. In some embodiments, platelets are derived or prepared in a culture. In some embodiments, preparing the platelets comprises deriving or growing the platelets from a culture of megakaryocytes. In some embodiments, preparing the platelets comprises deriving or growing the platelets (or megakaryocytes) from a culture of human pluripotent stem cells (PCSs), including embryonic stem cells (ESCs) and/or induced pluripotent stem cells (iPSCs).

Accordingly, in some embodiments, platelets are prepared prior to treating a subject as described herein. In some embodiments, the platelets are lyophilized. In some embodiments, the platelets are cryopreserved.

In some embodiments, the platelets or pooled platelets may be acidified to a pH of about 6.0 to about 7.4 prior to the incubation with the incubating agent. In some embodiments, the method comprises acidifying the platelets to a pH of about 6.5 to about 6.9. In some embodiments, the method comprises acidifying the platelets to a pH of about 6.6 to about 6.8. In some embodiments, the acidifying comprises adding to the pooled platelets a solution comprising Acid Citrate Dextrose (ACD).

In some embodiments, tangential flow filtration (TFF) is used to process platelets for making platelet derivatives, in illustrative embodiments FDPDs, for use in aspects here. For example, TFF can be used for concentration and/or buffer or other solution exchange, such that platelets are suspended at an appropriate concentration range in an appropriate medium, for example an incubating agent and/or a lyophilizing agent, or an incubating agent which is or comprises a lyophilizing agent, for example before the composition is dried to form platelet derivatives, or in illustrative embodiments, before the platelet composition is freeze-dried to form FDPDs.

In some embodiments, the method can include an initial dilution step, for example, a starting material (e.g., an unprocessed blood product (e.g., donor apheresis material (e.g., pooled donor apheresis material)) can be diluted with a preparation agent (e.g., any of the preparation agents described herein) to form a diluted starting material. In some cases, the initial dilution step can include dilution with a preparation agent with a mass of preparation agent equal to at least about 10% of the mass of the starting material (e.g., at least about 15%, 25%, 50%, 75%, 100%, 150%, or 200% of the mass of the starting material. In some embodiments, an initial dilution step can be carried out using the TFF apparatus.

In some embodiments, the method can include concentrating (e.g., concentrating platelets) (e.g., concentrating a starting material or a diluted starting material) to form a concentrated platelet composition. For example, concentrated can include concentrating to a about $1000 \times 10^3$ to about $4000 \times 10^3$ platelets/µL (e.g., about $1000 \times 10^3$ to about $2000 \times 10^3$, about $2000 \times 10^3$ to about $3000 \times 10^3$, or about $4000 \times 10^3$ platelets/µL). In some embodiments, a concentration step can be carried out using the TFF apparatus.

The concentration of platelets or platelet derivatives (e.g., FDPDs) can be determined by any appropriate method. For example, a counter can be used to quantitate concentration of blood cells in suspension using impedance (e.g., a Beckman Coulter AcT 10 or an AcT diff 2).

In some embodiments, TFF can include diafiltering (sometimes called "washing") of a starting material, a diluted starting material, a concentrated platelet composition, or a combination thereof. In some embodiments, diafiltering can include washing with at least 2 (e.g., at least 3, 4, 5, 6, 7, 8, 9, 10, or more) diavolumes. In some embodiments, TFF can include buffer exchange. In some embodiments, a buffer can be used in TFF. A buffer can be any appropriate buffer. In some embodiments, the buffer can be a preparation agent (e.g., any of the preparation agents described herein). In some embodiments, the buffer can be the same preparation agent as was used for dilution. In some embodiments, the buffer can be a different preparation than was used for dilution. In some embodiments, a buffer can include a lyophilizing agent, including a buffering agent, a base, a loading agent, optionally a salt, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof. A buffering agent can be any appropriate buffering agent. In some embodiments, a buffering agent can be HEPES ((4-(2-hydroxyethyl)-1-piperazineethanesulfonic acid). A base can be any appropriate base. In some embodiments, a base can be sodium bicarbonate. In some embodiments, a saccharide can be a monosaccharide. In some embodiments, a loading agent can be a saccharide. In some embodiments, a saccharide can include sucrose, maltose, trehalose, glucose (e.g., dextrose), mannose, or xylose. In some embodiments, a monosaccharide can be trehalose. In some embodiments, the loading agent can include polysucrose. A salt can be any appropriate salt. In some embodiments, a salt can be selected from the group consisting of sodium chloride (NaCl), potassium chloride (KCl), or a combination thereof.

In some embodiments, a membrane with a pore size of about 0.1 µm to about 1 µm (e.g., about 0.1 µm to about 1 µm, about 0.1 µm to about 0.5 µm, about 0.2 to about 0.45 µm, about 0.45 to about 1 µm, about 0.1 µm, about 0.2 µm, about 0.45 µm, about 0.65 µm, or about 1 µm) can be used in TFF. A membrane can be made from any appropriate material. In some cases, a membrane can be a hydrophilic membrane. In some embodiments, a membrane can be a hydrophobic membrane. In some embodiments, a membrane with a nominal molecular weight cutoff (NMWCO) of at least about 100 kDa (e.g., at least about 200, 300 kDa, 500 kDa, or 1000 kDa) can be used in TFF. The TFF can be performed with any appropriate pore size within the range of 0.1 µm to 1.0 µm with the aim of reducing the microparticles content in the composition and increasing the content of platelet derivatives in the composition. A skilled artisan can appreciate the required optimization of the pore size in order to retain the platelet derivatives and allow the microparticles to pass through the membrane. The pore size in illustrative embodiments, is such that the microparticles pass through the membrane allowing the TFF-treated composition to have less than 5% microparticles. The pore size in illustrative embodiments is such that a maximum of platelet derivatives gets retained in the process allowing the TFF-treated composition to have a concentration of the platelet derivatives in the range of $100 \times 10^3$ to $20,000 \times 10^3$. The pore size during the TFF process can be exploited to obtain a higher concentration of platelet derivatives in the platelet derivative composition such that a person administering the platelet derivatives to a subject in need has to rehydrate/reconstitute fewer vials, therefore, being efficient with respect to time and effort during the process of preparing such platelet derivatives for a downstream procedure, for example a method of treating provided herein. TFF can be performed at any appropriate temperature. In some embodiments, TFF can be performed at a temperature of about 20° C. to about 37° C. (e.g., about 20° C. to about 25° C., about 20° C. to about 30° C., about 25° C. to about 30° C., about 30° C. to about 35° C., about 30° C. to about 37° C., about 25° C. to about 35° C., or about 25° C. to about 37° C.). In some embodiments, TFF can be carried out at a flow rate (e.g., a circulating flow rate) of about 100 ml/min to about 800 ml/min (e.g., about 100 to about 200 ml/min, about 100 to about 400 ml/min, about 100 to about 600 ml/min, about 200 to about 400 ml/min, about 200 to about 600 ml/min, about 200 to about 800 ml/min, about 400 to about 600 ml/min, about 400 to about 800 ml/min, about 600 to about 800 ml/min, about 100 ml/min, about 200 ml/min, about 300 ml/min, about 400 ml/min, about 500 ml/min, about 600 ml/min, about 700 ml/min, or about 800 ml/min).

In some embodiments, TFF can be performed until a particular endpoint is reached, forming a TFF-treated composition. An endpoint can be any appropriate endpoint. In some embodiments, an endpoint can be a percentage of residual plasma (e.g., less than or equal to about 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of residual plasma). In some embodiments, an endpoint can be a relative absorbance at 280 nm (A280). For example, an endpoint can be an A280 (e.g., using a path length of 0.5 cm) that is less than or equal to about 50% (e.g., less than or equal to about 40%, 30%, 20%, 15%, 10%, 9%, 8%, 7%, 6%, 5%, 40%, 3%, 2%, 1%, 0.9%, 0.8%, 0.7%, 0.6%, 0.5%, 0.4%, 0.3%, 0.2%, or 0.1%) of the A280 (e.g., using a path length of 0.5 cm) prior to TFF (e.g., of a starting material or of a diluted starting material). In some embodiments, an A280 can be relative to a system that measures 7.5% plasma=1.66 AU. In some embodiments, an instrument to measure A280 can be configured as follows: a 0.5 cm gap flow cell can be attached to the filtrate line of the TFF system. The flow cell can be connected to a photometer with fiber optics cables attached to each side of the flow cell (light source cable and light detector cable). The flow cell can be made with a silica glass lens on each side of the fiber optic cables. Apart from the relative protein concentration of proteins in the aqueous medium, the protein concentration in the aqueous medium can also be measured in absolute terms. In some embodiments, the protein concentration in the aqueous medium is less than or equal to 15%, or 14%, or 13%, or 12%, or 11%, or 10%, or 9%, or 8%, or 7%, or 6%, or 5%, or 4%, or 3%, or 2%, or 1%, or 0.1/%, or 0.01%. In some exemplary embodiments, the protein concentration is less than 3% or 4%. In some embodiments, the protein concentration is in the range of 0.01-15%, or 0.1-15%, or 1-15%, or 1-10%, or 0.01-10%, or 3-12%, or 5-10% in the TFF-treated composition. In some embodiments, an endpoint can be an absolute A280 (e.g., using a path length of 0.5 cm). For example, an endpoint can be an A280 that is less than or equal to 2.50 AU, 2.40 AU, 2.30 AU, 2.20 AU, 2.10 AU, 2.0 AU, 1.90 AU, 1.80 AU, or 1.70 AU (e.g., less than or equal to 1.66, 1.6, 1.5, 1.4, 1.3, 1.2, 1.1, 1.0, 0.9, 0.8, 0.7, 0.6, 0.5, 0.4, 0.3, 0.2, or 0.1 AU) (e.g., using a path length of 0.5 cm). In some embodiments, a percentage of residual plasma, a relative A280, or an A280 can be determined based on the aqueous medium of a composition comprising platelets and an aqueous medium. In some embodiments, a percentage of residual plasma can be determined based on a known correlation to an A280. In some embodiments, an endpoint can be a platelet concentration, as TFF can include concentration or dilution of a sample (e.g., using a preparation agent). For example, an endpoint can be a platelet concentration of at least about $2000 \times 10^3$ platelets/μL (e.g., at least about $2050 \times 10^3$, $2100 \times 10^3$, $2150 \times 10^3$, $2200 \times 10^3$, $2250 \times 10^3$, $2300 \times 10^3$, $2350 \times 10^3$, $2400 \times 10^3$, $2450 \times 10^3$, or $2500 \times 10^3$ platelets/μL). As another example, an endpoint can be a platelet concentration of about $1000 \times 10^3$ to about 2500 platelets/μL (e.g., about $1000 \times 10^3$ to about $2000 \times 10^3$, about $1500 \times 10^3$ to about $2300 \times 10^3$, or about $1700 \times 10^3$ to about $2300 \times 10^3$ platelets/μL). In some embodiments, an endpoint can be a concentration of platelets in the TFF-treated composition are at least $100 \times 10^3$ platelets/μL, $200 \times 10^3$ platelets/μL, $400 \times 10^3$ platelets/μL, $1000 \times 10^3$ platelets/μL, $1250 \times 10^3$ platelets/μL, $1500 \times 10^3$ platelets/μL, $1750 \times 10^3$ platelets/μL, $2000 \times 10^3$ platelets/μL, $2250 \times 10^3$ platelets/μL, $2500 \times 10^3$ platelets/μL, $2750 \times 10^3$ platelets/μL, $3000 \times 10^3$ platelets/μL, $3250 \times 10^3$ platelets/μL, $3500 \times 10^3$ platelets/μL, $3750 \times 10^3$ platelets/μL, $4000 \times 10^3$ platelets/μL, $4250 \times 10^3$ platelets/μL, $4500 \times 10^3$ platelets/μL, $4750 \times 10^3$ platelets/μL, $5000 \times 10^3$ platelets/μL, $5250 \times 10^3$ platelets/μL, $5500 \times 10^3$ platelets/μL, $5750 \times 10^3$ platelets/μL, $6000 \times 10^3$ platelets/μL, $7000 \times 10^3$ platelets/μL, $8000 \times 10^3$ platelets/μL, $9000 \times 10^3$ platelets/μL, $10,000 \times 10^3$ platelets/μL, $11,000 \times 10^3$ platelets/μL, $12,000 \times 10^3$ platelets/μL, $13,000 \times 10^3$ platelets/μL, $14,000 \times 10^3$ platelets/μL, $15,000 \times 10^3$ platelets/μL, $16,000 \times 10^3$ platelets/μL, $17,000 \times 10^3$ platelets/μL, $18,000 \times 10^3$ platelets/μL, $19,000 \times 10^3$ platelets/μL, $20,000 \times 10^3$ platelets/μL. In some embodiments, the platelets or platelet derivatives in the TFF-treated composition is in the range of $100 \times 10^3$-$20,000 \times 10^3$ platelets/μL, or $1000 \times 10^3$-$20,000 \times 10^3$ platelets/μL, or $1000 \times 10^3$-$10,000 \times 10^3$ platelets/μL, or $500 \times 10^3$-$5,000 \times 10^3$ platelets/μL, or $1000 \times 10^3$-$5,000 \times 10^3$ platelets/μL, or $2000 \times 10^3$-$8,000 \times 10^3$ platelets/μL, or $10,000 \times 10^3$-$20,000 \times 10^3$ platelets/μL, or $15,000 \times 10^3$-$20,000 \times 10^3$ platelets/μL.

In some embodiments, an endpoint can include more than one criterion (e.g., a percentage of residual plasma and a platelet concentration, a relative A280 and a platelet concentration, or an absolute A280 and a platelet concentration).

Typically, a TFF-treated composition is subsequently lyophilized, optionally with a thermal treatment step, to form a final blood product (e.g., platelets, cryopreserved platelets, FDPDs. However, in some cases, a TFF-treated composition can be considered to be a final blood product.

In some embodiments, a blood product can be prepared using centrifugation of a blood product (e.g., an unprocessed blood product (e.g., donor apheresis material (e.g., pooled donor apheresis material)), or a partially processed blood product (e.g., a blood product that has undergone TFF)). In some embodiments, a blood product can be prepared without centrifugation of a blood product (e.g., an unprocessed blood product (e.g., donor apheresis material), or a partially processed blood product (e.g., a blood product that has undergone TFF)). Centrifugation can include any appropriate steps. In some embodiments, centrifugation can include a slow acceleration, a slow deceleration, or a combination thereof. In some embodiments, centrifugation can include centrifugation at about 1400×g to about 1550×g (e.g., about 1400 to about 1450×g, about 1450 to about 1500×g, or 1500 to about 1550×g, about 1400×g, about 1410×g, about 1430×g, about 1450×g, about 1470×g, about 1490×g, about 1500×g, about 1510×g, about 1530×g, or about 1550×g). In some embodiments, the duration of centrifugation can be about 10 min to about 30 min (e.g., about 10 to about 20 min, about 20 to about 30 min, about 10 min, about 20 min, or about 30 min).

In some embodiments, a final blood product can be prepared using both TFF and centrifugation (e.g., TFF followed by centrifugation or centrifugation followed by TFF).

Also provided herein are compositions prepared by any of the methods described herein.

In some embodiments, a composition as described herein can be analyzed at multiple points during processing. In some embodiments, a starting material (e.g., donor apheresis material (e.g., pooled donor apheresis material)) can be analyzed for antibody content (e.g., HLA or HNA antibody content). In some embodiments, a starting material (e.g., donor apheresis material (e.g., pooled donor apheresis material)) can be analyzed for protein concentration (e.g., by absorbance at 280 nm (e.g., using a path length of 0.5 cm)). In some embodiments, a composition in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of an unprocessed blood product) can be analyzed for antibody content (e.g., HLA or HNA antibody content). In some embodiments, the antibody content (e.g., HLA or HNA antibody content) of a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of the starting material. In some embodiments, a final blood product (e.g., (e.g., platelets, cryopreserved platelets, FDPDs can be analyzed for antibody content (e.g., HLA or HNA antibody content). In some embodiments described herein, a final blood product can be a composition that includes platelets and an aqueous medium. In some embodiments, the antibody content (e.g., HLA or HNA antibody content) of a final blood product (e.g., (e.g., platelets, cryopreserved platelets, FDPDs can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of the starting material. In some embodiments, a final blood product can have no detectable level of an antibody selected from the group consisting of HLA Class I antibodies, HLA Class II antibodies, and HNA antibodies. In some embodiments, the aqueous medium of a composition as described herein can be analyzed as described herein.

In some embodiments, the platelets are isolated prior to the incubation with the incubating agent and/or lyophilizing agent. In some embodiments, the incubating agent is or comprises a lyophilizing agent as disclosed in more detail herein. In some embodiments, the method further comprises isolating platelets by using centrifugation. In some embodiments, the centrifugation occurs at a relative centrifugal force (RCF) of about 1000×g to about 2000×g. In some embodiments, the centrifugation occurs at relative centrifugal force (RCF) of about 1300×g to about 1800×g. In some embodiments, the centrifugation occurs at relative centrifugal force (RCF) of about 1500×g. In some embodiments, the centrifugation occurs for about 1 minute to about 60 minutes. In some embodiments, the centrifugation occurs for about 10 minutes to about 30 minutes. In some embodiments, the centrifugation occurs for about 30 minutes.

An incubating agent can include any appropriate components. In some embodiments, the incubating agent may comprise a liquid medium. In some embodiments the incubating agent may comprise one or more salts selected from phosphate salts, sodium salts, potassium salts, calcium salts, magnesium salts, and any other salt that can be found in blood or blood products, or that is known to be useful in drying platelets, or any combination of two or more of these.

In some embodiments, the incubating agent comprises one or more salts, such as phosphate salts, sodium salts, potassium salts, calcium salts, magnesium salts, and any other salt that can be found in blood or blood products. Exemplary salts include sodium chloride (NaCl), potassium chloride (KCl), and combinations thereof. In some embodiments, the incubating agent includes from about 0.5 mM to about 100 mM of the one or more salts. In some embodiments, the incubating agent includes from about 0.5 mM to about 100 mM (e.g., about 0.5 to about 2 mM, about 2 mM to about 90 mM, about 2 mM to about 6 mM, about 50 mM to about 100 mM, about 60 mM to about 90 mM, about 70 to about 85 mM) about of the one or more salts. In some embodiments, the incubating agent includes about 5 mM, about 60 mM, about 65 mM, about 70 mM, about 75 mM, or about 80 mM of the one or more salts. In some embodiments, the incubating agent comprises one or more salts selected from calcium salts, magnesium slats, and a combination of the two, in a concentration of about 0.5 mM to about 2 mM.

Preferably, these salts are present in the composition comprising platelets or platelet derivatives, such as freeze-dried platelets, at an amount that is about the same as is found in whole blood.

In some embodiments, the incubating agent further comprises a carrier protein. In some embodiments, the carrier protein comprises human serum albumin, bovine serum albumin, or a combination thereof. In some embodiments, the carrier protein is present in an amount of about 0.05% to about 1.0% (w/v).

The incubating agent may be any buffer that is non-toxic to the platelets and provides adequate buffering capacity to the solution at the temperatures at which the solution will be exposed during the process provided herein. Thus, the buffer may comprise any of the known biologically compatible buffers available commercially for example phosphate buffers such as phosphate buffered saline (PBS), bicarbonate/carbonic acid buffers such as sodium-bicarbonate buffer, N-2-hydroxyethylpiperazine-N'-2-ethanesulfonic acid (HEPES), and tris-based buffers such as tris-buffered saline (TBS). Likewise, it may comprise one or more of the following buffers: propane-1,2,3-tricarboxylic (tricarballylic); benzenepentacarboxylic; maleic; 2,2-dimethylsuccinic; EDTA; 3,3-dimethylglutaric; bis(2-hydroxyethyl)imino-tris (hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); piperazine-1,4-bis-(2-ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl) trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propane-sulfonic acid (MOPS); phosphoric; and N-tris(hydroxymethyl)methyl-2-amminoethane sulfonic acid (TES). In some embodiments, the incubating agent includes one or more buffers, e.g., N-2-hydroxyethylpiperazine-N'-2-ethanesulfonic acid (HEPES), or sodium-bicarbonate (NaHCO$_3$). In some embodiments, the incubating agent includes from about 5 to about 100 mM of the one or more buffers. In some embodiments, the incubating agent includes from about 5 to about 50 mM (e.g., from about 5 mM to about 40 mM, from about 8 mM to about 30 mM, about 10 mM to about 25 mM) about of the one or more buffers. In some embodiments, the incubating agent includes about 10 mM, about 20 mM, about 25 mM, or about 30 mM of the one or more buffers.

In some embodiments, the incubating agent includes one or more saccharides, such as monosaccharides and disaccharides, including sucrose, maltose, trehalose, glucose, mannose, dextrose, and xylose. In some embodiments, the saccharide is a monosaccharide. In some embodiments, the saccharide is a disaccharide. In some embodiments, the saccharide comprises a monosaccharide, a disaccharide, or a combination thereof. In some embodiments, the saccharide is a non-reducing disaccharide. In some embodiments, the saccharide comprises sucrose, maltose, trehalose, glucose (e.g., dextrose), mannose, or xylose. In some embodiments, the saccharide comprises trehalose. In some embodiments, the incubating agent comprises a starch. In some embodiments, the incubating agent includes polysucrose, a polymer of sucrose and epichlorohydrin. In some embodiments, the incubating agent includes from about 10 mM to about 1,000 mM of the one or more saccharides. In some embodiments, the incubating agent includes from about 50 to about 500 mM of the one or more saccharides. In embodiments, one or more saccharides is present in an amount of from 10 mM 10 to 500 mM. In some embodiments, one or more saccharides is present in an amount of from 50 mM to 200 mM. In embodiments, one or more saccharides is present in an amount from 100 mM to 150 mM. In some embodiments, the one or more saccharides is the lyophilizing agent; for example, in some embodiments, the lyophilizing agent comprises trehalose, polysucrose, or a combination thereof.

In some embodiments the composition comprising platelets or platelet derivatives, (e.g., FDPDs), may comprise one or more of water or a saline solution. In some embodiments the composition comprising platelets or platelet derivatives, such as freeze-dried platelets, may comprise DMSO.

In some embodiments, the incubating agent comprises an organic solvent, such as an alcohol (e.g., ethanol). In such an incubating agent, the amount of solvent can range from 0.1% to 5.0% (v/v). In some embodiments, the organic solvent can range from about 0.1% (v/v) to about 5.0% (v/v), such as from about 0.3% (v/v) to about 3.0% (v/v), or from about 0.5% (v/v) to about 2% (v/v).

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof. In some embodiments the organic solvent is selected from the group consisting of ethanol, acetic acid, acetone, acetonitrile, dimethylformamide, dimethyl sulfoxide (DMSO), dioxane, methanol, n-propanol, isopropanol, tetrahydrofuran (THF), N-methyl pyrrolidone, dimethylacetamide (DMAC), or combinations thereof. In some embodiments, the organic solvent comprises ethanol, DMSO, or a combination thereof. The presence of organic solvents, such as ethanol, can be beneficial in the processing of platelets, platelet derivatives, or FDPDs (e.g., freeze-dried platelet derivatives).

In some embodiments the incubating agent is incubated into the platelets in the presence of an aqueous medium. In some embodiments the incubating agent is incubated in the presence of a medium comprising DMSO.

In some embodiments, one or more other components may be incubated in the platelets. Exemplary components may include Prostaglandin E1 or Prostacyclin and or EDTA/EGTA to prevent platelet aggregation and activation during the incubating process.

Non-limiting examples of incubating agent compositions that may be used are shown in Tables 1-5.

TABLE 1

Buffer

| Component | Concentration (mM unless otherwise specified) |
|---|---|
| NaCl | 75.0 |
| KCl | 4.8 |
| HEPES | 9.5 |
| NaHCO$_3$ | 12.0 |
| Dextrose | 3 |
| Trehalose | 100 |
| Ethanol (optional) | 1% (v/v) |

TABLE 2

Buffer A

| Component | Concentration (mM unless specified otherwise) |
|---|---|
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |
| pH | 6.5 |

TABLE 3

Buffer B

| Component | Concentration (mM unless otherwise specified) |
|---|---|
| Buffer and Salts | Table 4 (below) |
| BSA | 0.35% |
| Dextrose | 5 |
| pH | 7.4 |

Table 3. Buffer B can used when incubating platelets, e.g., for flow cytometry. Such an incubation can be done at room temperature in the dark. Albumin is an optional component of Buffer B.

TABLE 4

Concentration of HEPES and of Salts in Buffer B

| Component | Concentration (mM unless otherwise specified) |
|---|---|
| HEPES | 25 |
| NaCl | 119 |
| KCl | 5 |
| CaCl$_2$ | 2 |
| MgCl$_2$ | 2 |
| glucose | 6 g/l |

Table 4 is another exemplary incubating agent. The pH can be adjusted to 7.4 with NaOH. Albumin is an optional component of Buffer B.

TABLE 5

Tyrode's HEPES Buffer (plus PGE1)

| Component | Concentration (mM) |
|---|---|
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |
| pH | 6.5 |
| Prostaglandin E1 (PGE1) | 1 µg/ml |

Table 5 is another exemplary incubating agent.

In some embodiments, platelets (e.g., apheresis platelets, platelets isolated from whole blood, pooled platelets, or a combination thereof) are incubated with the incubating agent for different durations at or at different temperatures from 15-45° C., or about 37° C.

In some embodiments, platelets (e.g., apheresis platelets, platelets isolated from whole blood, pooled platelets, or a combination thereof) form a suspension in an incubating agent and/or a lyophilizing agent, or an incubating agent that is or comprises a lyophilizing agent, comprising a liquid medium at a concentration from 10,000 platelets/µL to 10,000,000 platelets/µL, such as 50,000 platelets/µL to 2,000,000 platelets/µL, such as 100,000 platelets/µL to 500,000 platelets/µL, such as 150,000 platelets/µL to 300,000 platelets/µL, such as 200,000 platelets/µL.

The platelets (e.g., apheresis platelets, platelets isolated from whole blood, pooled platelets, or a combination thereof) may be incubated with the incubating agent, for example that is or comprises a lyophilizing agent, for different durations, such as, for example, for at least about 5 minutes (mins) (e.g., at least about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, about 42 hrs, about 48 hrs, or at least about 48 hrs. In some embodiments, the platelets may be incubated with the incubating agent for no more than about 48 hrs (e.g., no more than about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, or no more than about 42 hrs). In some embodiments, the platelets may be incubated with the incubating agent for from about 10 mins to about 48 hours (e.g., from about 20 mins to about 36 hrs, from about 30 mins to about 24 hrs, from about 1 hr to about 20 hrs, from about 2 hrs to about 16 hours, from about 10 mins to about 24 hours, from about 20 mins to about 12 hours, from about 30 mins to about 10 hrs, or from about 1 hr to about 6 hrs. In some embodiments, the platelets, the platelet derivatives, or the FDPDs are incubated with the incubating agent for a period of time of 5 minutes to 48 hours, such as 10 minutes to 24 hours, such as 20 minutes to 12 hours, such as 30 minutes to 6 hours, such as 1 hour minutes to 3 hours, such as about 2 hours.

In some embodiments, the platelets (e.g., apheresis platelets, platelets isolated from whole blood, pooled platelets, or a combination thereof) are incubated with the incubating agents at different temperatures. In embodiments, incubation is conducted at 37° C. In certain embodiments, incubation is performed at 4° C. to 45° C., such as 15° C. to 42° C. For example, in embodiments, incubation is performed at 35° C. to 40° C. (e.g., 37° C.) for 110 to 130 (e.g., 120) minutes and for as long as 24-48 hours. In some embodiments, the platelets are incubated with the incubating agent for different durations as disclosed herein, and at temperatures from 15-45° C., or about 37° C.

In some embodiments, platelets (e.g., apheresis platelets, platelets isolated from whole blood, pooled platelets, or a combination thereof) are loaded with one or more active agents. In some embodiments, the platelets can be loaded with an anti-fibrinolytic agent. Non-limiting examples of anti-fibrinolytic agents include ε-aminocaproic acid (EACA), tranexamic acid, aprotinin, aminomethylbenzoic acid, and fibrinogen.

Loading platelets (e.g., apheresis platelets, platelets isolated from whole blood, pooled platelets, or a combination thereof) with an active agent (e.g., an anti-fibrinolytic agent) can be performed by any appropriate method. See, for example, PCT Publication Nos. WO2020113090A1, WO2020113101A1, WO2020113035A1, and WO2020112963A1. Generally, the loading includes contacting the platelets with the anti-fibrinolytic agent. In some embodiments, the loading can be performed by combining the active agent with the incubating agent. In some embodiments, the loading can be performed in a separate step from the incubating step. For example, the loading can be performed in a step prior to the incubation step. In some such embodiments, the active agent can be supplied to the platelets as a solution or suspension in any of the incubation agents described herein, which may or may not be the same as the incubating agent used in the incubating step. In some embodiments, the loading step can be performed during the incubation step. In some such embodiments, the active agent can be added to the incubation agent (e.g., as a solid or in a solution or suspension) during the incubation). In some embodiments, the loading step can be performed in a step following the incubation step. In some such embodiments, be supplied to the platelets as a solution or suspension in any of the incubation agents described herein, which may or may not be the same as the incubating agent used in the incubating step.

An active agent can be applied to the platelets in any appropriate concentration. In some embodiments, an active agent can be applied to the platelets (e.g., as part of the incubating agent or another solution or suspension) in a concentration of about 1 µM to about 100 mM (e.g., about 1 µM to about 10 µm, about 1 µM to about 50 µM, about 1 µM to about 100 µM, about 1 µM to about 500 µM, about 1 µM to about 1 mM, about 1 µM to about 10 mM, about 1 µM to about 25 mM, about 1 µM to about 50 mM, about 1 µM to about 75 mM, about 10 µM to about 100 mM, about 50 µM to about 100 mM, about 100 µM to about 100 mM, about 500 µM to about 100 mM, about 1 mM to about 100 mM, about 10 mM to about 100 mM, about 25 mM to about 100 mM, about 50 mM to about 100 mM, about 75 mM to about 100 mM, about 10 µM to about 100 mM, about 200 µM to about 1 mM, about 800 µM to about 900 µM, about 400 µM to about 800 µM, about 500 µM to about 700 µM, about 600 µM, about 5 mM to about 85 mM, about 20 mM to about 90 mM, about 25 mM to about 75 mM, about 30 mM to about 90 mM, about 35 mM to about 65 mM, about 40 mM to about 60 mM, about 50 mM to about 60 mM, about 40 mM to about 70 mM, about 45 mM to about 55 mM, or about 50 mM).

In some embodiments, the method further comprises drying the platelets. In some embodiments, the drying step comprises lyophilizing the platelets. In some embodiments, the drying step comprises freeze-drying the platelets. In some embodiments, the method further comprises rehydrating the platelets obtained from the drying step.

In some embodiments, the platelets are cold stored, cryopreserved, or lyophilized (e.g., to produce FDPDs) prior to use in therapy or in functional assays.

Any known technique for drying platelets can be used in accordance with the present disclosure, as long as the technique can achieve a final residual moisture content of less than 5%. Preferably, the technique achieves a final residual moisture content of less than 2%, such as 1%, 0.5%, or 0.1%. Non-limiting examples of suitable techniques are freeze-drying (lyophilization) and spray-drying. A suitable lyophilization method is presented in Table A. Additional exemplary lyophilization methods can be found in U.S. Pat. Nos. 7,811,558, 8,486,617, and 8,097,403. An exemplary spray-drying method includes: combining nitrogen, as a drying gas, with a incubating agent according to the present disclosure, then introducing the mixture into GEA Mobile Minor spray dryer from GEA Processing Engineering, Inc. (Columbia MD, USA), which has a Two-Fluid Nozzle configuration, spray drying the mixture at an inlet temperature in the range of 150° C. to 190° C., an outlet temperature in the range of 65° C. to 100° C., an atomic rate in the range of 0.5 to 2.0 bars, an atomic rate in the range of 5 to 13 kg/hr, a nitrogen use in the range of 60 to 100 kg/hr, and a run time of 10 to 35 minutes. The final step in spray drying is preferentially collecting the dried mixture. The dried composition in some embodiments is stable for at least six months at temperatures that range from −20° C. or lower to 90° C. or higher.

TABLE A

Exemplary Lyophilization Protocol

|  | Step | Temp. Set | Type | Duration | Pressure Set |
|---|---|---|---|---|---|
| Freezing Step | F1 | −50° C. | Ramp | Var | N/A |
|  | F2 | −50° C. | Hold | 3 Hrs | N/A |
| Vacuum Pulldown | F3 | −50° | Hold | Var | N/A |
| Primary Dry | P1 | −40° | Hold | 1.5 Hrs | 0 mT |
|  | P2 | −35° | Ramp | 2 Hrs | 0 mT |
|  | P3 | −25° | Ramp | 2 Hrs | 0 mT |
|  | P4 | −17° C. | Ramp | 2 Hrs | 0 mT |
|  | P5 | 0° C. | Ramp | 1.5 Hrs | 0 mT |
|  | P6 | 27° C. | Ramp | 1.5 Hrs | 0 mT |
|  | P7 | 27° C. | Hold | 16 Hrs | 0 mT |
| Secondary Dry | S1 | 27° C. | Hold | >8 Hrs | 0 mT |

In some embodiments, the step of drying the platelets that are obtained as disclosed herein, to produce platelet derivatives for use in any of the aspects or embodiments herein, such as the step of freeze-drying the platelets that are obtained as disclosed herein, to produce FDPDs for use in any of the aspects or embodiments herein comprises incubating the platelets with a lyophilizing agent (e.g., a non-reducing disaccharide). Accordingly, in some embodiments, the methods for preparing platelets further comprise incubating the platelets with a lyophilizing agent. In some embodiments the lyophilizing agent is a saccharide. In some embodiments the saccharide is a disaccharide, such as a non-reducing disaccharide.

In some embodiments, the platelets are incubated with a lyophilizing agent for a sufficient amount of time and at a suitable temperature to incubate the platelets with the lyophilizing agent. In some embodiments, the incubating agent is the lyophilizing agent. Non-limiting examples of suitable lyophilizing agents are saccharides, such as monosaccharides and disaccharides, including sucrose, maltose, trehalose, glucose (e.g., dextrose), mannose, and xylose. In some embodiments, non-limiting examples of lyophilizing agent include serum albumin, dextran, polyvinyl pyrrolidone (PVP), starch, and hydroxyethyl starch (HES). In some embodiments, exemplary lyophilizing agents can include a high molecular weight polymer. By "high molecular weight" it is meant a polymer having an average molecular weight of about or above 70 kDa and up to 1,000,000 kDa. Non-limiting examples are polymers of sucrose and epichlorohydrin (e.g., polysucrose). In some embodiments, the lyophilizing agent is polysucrose. Although any amount of high molecular weight polymer can be used as a lyophilizing agent, it is preferred that an amount be used that achieves a final concentration of about 3% to 10% (w/v), such as 3% to 7%₀, for example 6%.

An exemplary saccharide for use in the compositions disclosed herein is trehalose. Regardless of the identity of the saccharide, it can be present in the composition that is dried to form platelet derivatives, or freeze-dried to form, FDPDs, and in rehydrated compositions of such dried platelet derivatives and FDPDs, in any suitable amount. For example, it can be present in an amount of 1 mM to 1 M. In embodiments, it is present in an amount of from 10 mM to 500 mM. In some embodiments, it is present in an amount of from 20 mM to 200 mM. In embodiments, it is present in an amount from 40 mM to 100 mM. In various embodiments, the saccharide is present in different specific concentrations within the ranges recited above, and one of skill in the art can immediately understand the various concentrations without the need to specifically recite each herein. Where more than one saccharide is present in the composition, each saccharide can be present in an amount according to the ranges and particular concentrations recited above.

Within the process provided herein for making the compositions provided herein, addition of the lyophilizing agent can be the last step prior to drying. However, in some embodiments, the lyophilizing agent is added at the same time or before other components of the composition, such as a salt, a buffer, optionally a cryoprotectant, or other components. In some embodiments, the lyophilizing agent is added to the incubating agent, thoroughly mixed to form a drying solution, dispensed into a drying vessel (e.g., a glass or plastic serum vial, a lyophilization bag), and subjected to conditions that allow for drying of the solution to form a dried composition.

The step of incubating the platelets with a cryoprotectant can include incubating the platelets for a time suitable for loading, as long as the time, taken in conjunction with the temperature, is sufficient for the cryoprotectant to come into contact with the platelets and, preferably, be incorporated, at least to some extent, into the platelets. In embodiments, incubation is carried out for about 1 minute to about 180 minutes or longer.

The step of incubating the platelets with a cryoprotectant can include incubating the platelets and the cryoprotectant at a temperature that, when selected in conjunction with the amount of time allotted, is suitable for incubating. In general, the composition is incubated at a temperature above freezing for at least a sufficient time for the cryoprotectant to come into contact with the platelets. In embodiments, incubation is conducted at 37° C. In certain embodiments, incubation is performed at 20° C. to 42° C. For example, in embodiments, incubation is performed at 35° C. to 40° C. (e.g., 37° C.) for 110 to 130 (e.g., 120) minutes.

In various embodiments, the lyophilization bag is a gas-permeable bag configured to allow gases to pass through at least a portion or all portions of the bag during the processing. The gas-permeable bag can allow for the exchange of gas within the interior of the bag with atmospheric gas present in the surrounding environment. The gas-permeable bag can be permeable to gases, such as oxygen, nitrogen, water, air, hydrogen, and carbon dioxide, allowing gas exchange to occur in the compositions provided herein. In some embodiments, the gas-permeable bag allows for the removal of some of the carbon dioxide present within an interior of the bag by allowing the carbon dioxide to permeate through its wall. In some embodiments, the release of carbon dioxide from the bag can be advantageous to maintaining a desired pH level of the composition contained within the bag.

In some embodiments, the container of the process herein is a gas-permeable container that is closed or sealed. In some embodiments, the container is a container that is closed or sealed and a portion of which is gas-permeable. In some embodiments, the surface area of a gas-permeable portion of a closed or sealed container (e.g., bag) relative to the volume of the product being contained in the container (hereinafter referred to as the "SAN ratio") can be adjusted to improve pH maintenance of the compositions provided herein. For example, in some embodiments, the SAN ratio of the container can be at least about 2.0 $cm^2/mL$ (e.g., at least about 2.1 $cm^2/mL$, at least about 2.2 $cm^2/mL$, at least about 2.3 $cm^2/mL$, at least about 2.4 $cm^2/mL$, at least about 2.5 $cm^2/mL$, at least about 2.6 $cm^2/mL$, at least about 2.7 $cm^2/mL$, at least about 2.8 $cm^2/mL$, at least about 2.9 $cm^2/mL$, at least about 3.0 $cm^2/mL$, at least about 3.1 $cm^2/mL$, at least about 3.2 $cm^2/mL$, at least about 3.3 cm²/mL, at least about 3.4 cm²/mL, at least about 3.5 cm²/mL, at least about 3.6 cm²/mL, at least about 3.7 cm²/mL, at least about 3.8 cm²/mL, at least about 3.9 cm²/mL, at least about 4.0 cm²/mL, at least about 4.1 cm²/mL, at least about 4.2 cm²/mL, at least about 4.3 cm²/mL, at least about 4.4 cm²/mL, at least about 4.5 cm²/mL, at least about 4.6 cm²/mL, at least about 4.7 cm²/mL, at least about 4.8 cm²/mL, at least about 4.9 cm²/mL, or at least about 5.0 cm²/mL. In some embodiments, the SAN ratio of the container can be at most about 10.0 cm²/mL (e.g., at most about 9.9 cm²/mL, at most about 9.8 cm²/mL, at most about 9.7 cm²/mL, at most about 9.6 cm²/mL, at most about 9.5 cm²/mL, at most about 9.4 cm²/mL, at most about 9.3 cm²/mL, at most about 9.2 cm²/mL, at most about 9.1 cm²/mL, at most about 9.0 cm²/mL, at most about 8.9 cm²/mL, at most about 8.8 cm²/mL, at most about 8.7 cm²/mL, at most about 8.6, cm²/mL at most about 8.5 cm²/mL, at most about 8.4 cm²/mL, at most about 8.3 cm²/mL, at most about 8.2 cm²/mL, at most about 8.1 cm²/mL, at most about 8.0 cm²/mL, at most about 7.9 cm²/mL, at most about 7.8 cm²/mL, at most about 7.7 cm²/mL, at most about 7.6 cm²/mL, at most about 7.5 cm²/mL, at most about 7.4 cm²/mL, at most about 7.3 cm²/mL, at most about 7.2 cm²/mL, at most about 7.1 cm²/mL, at most about 6.9 cm²/mL, at most about 6.8 cm²/mL, at most about 6.7 cm²/mL, at most about 6.6 cm²/mL, at most about 6.5 cm²/mL, at most about 6.4 cm²/mL, at most about 6.3 cm²/mL, at most about 6.2 cm²/mL, at most about 6.1 cm²/mL, at most about 6.0 cm²/mL, at most about 5.9 cm²/mL, at most about 5.8 cm²/mL, at most about 5.7 cm²/mL, at most about 5.6 cm²/mL, at most about 5.5 cm²/mL, at most about 5.4 cm²/mL, at most about 5.3 cm²/mL, at most about 5.2 cm²/mL, at most about 5.1 cm²/mL, at most about 5.0 cm²/mL, at most about 4.9 cm²/mL, at most about 4.8 cm²/mL, at most about 4.7 cm²/mL, at most about 4.6 cm²/mL, at most about 4.5 cm²/mL, at most about 4.4 cm²/mL, at most about 4.3 cm²/mL, at most about 4.2 cm²/mL, at most about 4.1 cm²/mL, or at most about 4.0 cm²/mL. In some embodiments, the SAN ratio of the container can range from about 2.0 to about 10.0 cm²/mL (e.g., from about 2.1 cm²/mL to about 9.9 cm²/mL, from about 2.2 cm²/mL to about 9.8 cm²/mL, from about 2.3 cm²/mL to about 9.7 cm²/mL, from about 2.4 cm²/mL to about 9.6 cm²/mL, from about 2.5 cm²/mL to about 9.5 cm²/mL, from about 2.6 cm²/mL to about 9.4 cm²/mL, from about 2.7 cm²/mL to about 9.3 cm²/mL, from about 2.8 cm²/mL to about 9.2 cm²/mL, from about 2.9 cm²/mL to about 9.1 cm²/mL, from about 3.0 cm²/mL to about 9.0 cm²/mL, from about 3.1 cm²/mL to about 8.9 cm²/mL, from about 3.2 cm²/mL to about 8.8 cm²/mL, from about 3.3 cm²/mL to about 8.7 cm²/mL, from about 3.4 cm²/mL to about 8.6 cm²/mL, from about 3.5 cm²/mL to about 8.5 cm²/mL, from about 3.6 cm²/mL to about 8.4 cm²/mL, from about 3.7 cm²/mL to about 8.3 cm²/mL, from about 3.8 cm²/mL to about 8.2 cm²/mL, from about 3.9 cm²/mL to about 8.1 cm²/mL, from about 4.0 cm²/mL to about 8.0 cm²/mL, from about 4.1 cm²/mL to about 7.9 cm²/mL, from about 4.2 cm²/mL to about 7.8 cm²/mL, from about 4.3 cm²/mL to about 7.7 cm²/mL, from about 4.4 cm²/mL to about 7.6 cm²/mL, from about 4.5 cm²/mL to about 7.5 cm²/mL, from about 4.6 cm²/mL to about 7.4 cm²/mL, from about 4.7 cm²/mL to about 7.3 cm²/mL, from about 4.8 cm²/mL to about 7.2 cm²/mL, from about 4.9 cm²/mL to about 7.1 cm²/mL, from about 5.0 cm²/mL to about 6.9 cm²/mL, from about 5.1 cm²/mL to about 6.8 cm²/mL, from about 5.2 cm²/mL to about 6.7 cm²/mL, from about 5.3 cm²/mL to about 6.6 cm²/mL, from about 5.4 cm²/mL to about 6.5 cm²/mL, from about 5.5 cm²/mL to about 6.4 cm²/mL, from about 5.6 cm²/mL to about 6.3 cm²/mL, from about 5.7 cm²/mL to about 6.2 cm²/mL, or from about 5.8 cm²/mL to about 6.1 cm²/mL.

Gas-permeable closed containers (e.g., bags) or portions thereof can be made of one or more various gas-permeable materials. In some embodiments, the gas-permeable bag can be made of one or more polymers including fluoropolymers (such as polytetrafluoroethylene (PTFE) and perfluoroalkoxy (PFA) polymers), polyolefins (such as low-density polyethylene (LDPE), high-density polyethylene (HDPE)), fluorinated ethylene propylene (FEP), polystyrene, polyvinylchloride (PVC), silicone, and any combinations thereof.

In some embodiments, dried platelets or platelet derivatives (e.g., FDPDs) can undergo heat treatment. Heating can be performed at a temperature above about 25° C. (e.g., greater than about 40° C., 50° C., 60° C., 70° C., 80° C. or higher). In some embodiments, heating is conducted between about 70° C. and about 85° C. (e.g., between about 75° C. and about 85° C., or at about 75° C. or 80° C.). The temperature for heating can be selected in conjunction with the length of time that heating is to be performed. Although any suitable time can be used, typically, the lyophilized platelets are heated for at least 1 hour, but not more than 36 hours. Thus, in embodiments, heating is performed for at least 2 hours, at least 6 hours, at least 12 hours, at least 18 hours, at least 20 hours, at least 24 hours, or at least 30 hours. For example, the lyophilized platelets can be heated for 18 hours, 19 hours, 20 hours, 21 hours, 22 hours, 23 hours, 24 hours, 25 hours, 26 hours, 27 hours, 28 hours, 29 hours, or 30 hours. Non-limiting exemplary combinations include: heating the dried platelets or platelet derivatives (e.g., FDPDs) for at least 30 minutes at a temperature higher than 30° C.; heating the dried platelets or platelet derivatives (e.g., FDPDs) for at least 10 hours at a temperature higher than 50° C.; heating the dried platelets or platelet derivatives (e.g., FDPDs) for at least 18 hours at a temperature higher than 75° C.; and heating the dried platelets or platelet derivatives (e.g., FDPDs) for 24 hours at 80° C. In some embodiments, heating can be performed in sealed container, such as a capped vial. In some embodiments, a sealed container be subjected to a vacuum prior to heating. The heat treatment step, particularly in the presence of a cryoprotectant such as albumin or polysucrose, has been found to improve the stability and shelf-life of the freeze-dried platelets. Indeed, advantageous results have been obtained with the particular combination of serum albumin or polysucrose and a post-lyophilization heat treatment step, as compared to those cryoprotectants without a heat treatment step. A cryoprotectant (e.g., sucrose) can be present in any appropriate amount (e.g. about 3% to about 10% by mass or by volume of the platelets or platelet derivatives (e.g., FDPDs).

In some embodiments, the platelets or platelet derivatives (e.g., FDPDs) prepared as disclosed herein by a process comprising incubation with an incubating agent have a storage stability that is at least about equal to that of the platelets prior to the incubation.

In some embodiments, the method further comprises cryopreserving the platelets or platelet derivatives prior to administering the platelets or platelet derivatives (e.g., with an incubating agent, e.g., an incubating agent described herein).

In some embodiments, the method further comprises drying a composition comprising platelets or platelet derivatives, (e.g., with an incubating agent e.g., an incubating agent described herein) prior to administering the platelets or platelet derivatives (e.g., FDPDs). In some embodiments, the method may further comprise heating the composition following the drying step. In some embodiments, the method may further comprise rehydrating the composition following the freeze-drying step or the heating step.

In some embodiments, the method further comprises freeze-drying a composition comprising platelets or platelet derivatives (e.g., with an incubating agent e.g., an incubating agent described herein) prior to administering the platelets or platelet derivatives (e.g., FDPDs) In some embodiments, the method may further comprise heating the composition following the freeze-drying step. In some embodiments, the method may further comprise rehydrating the composition following the freeze-drying step or the heating step.

In some embodiments, the method further comprises cold storing the platelets, platelet derivatives, or the FDPDs prior to administering the platelets, platelet derivatives, or FDPDs (e.g., with an incubating agent, e.g., an incubating agent described herein).

Storing conditions include, for example, standard room temperature storing (e.g., storing at a temperature ranging from about 20 to about 30° C.) or cold storing (e.g., storing at a temperature ranging from about 1 to about 10° C.). In some embodiments, the method further comprises cryopreserving, freeze-drying, thawing, rehydrating, and combinations thereof, a composition comprising platelets or platelet derivatives (e.g., FDPDs) (e.g., with an incubating agent e.g., an incubating agent described herein) prior to administering the platelets or platelet derivatives (e.g., FDPDs). For example, in some embodiments, the method further comprises drying (e.g., freeze-drying) a composition comprising platelets or platelet derivatives (e.g., with an incubating agent e.g., an incubating agent described herein) (e.g., to form FDPDs) prior to administering the platelets or platelet derivatives (e.g., FDPDs). In some embodiments, the method may further comprise rehydrating the composition obtained from the drying step.

In some embodiments, provided herein is a composition comprising platelets or platelet derivatives (e.g., FDPDs), polysucrose and trehalose made by the process of obtaining fresh platelets, optionally incubating the platelets in DMSO, isolating the platelets by centrifugation, resuspending the platelets in an incubating agent which comprises trehalose and ethanol thereby forming a first mixture, incubating the first mixture, mixing polysucrose with the first mixture, thereby forming a second mixture, and lyophilizing the second mixture to form a freeze dried composition comprising platelets or platelet derivatives (e.g., FDPDs), polysucrose and trehalose.

In some embodiments, provided herein is a method of making a freeze-dried platelet composition comprising platelets or platelet derivatives (e.g., FDPDs), polysucrose and trehalose comprising obtaining fresh platelets, optionally incubating the platelets in DMSO, isolating the platelets by centrifugation, resuspending the platelets in a incubating agent which comprises trehalose and ethanol thereby forming a first mixture, incubating the first mixture, mixing polysucrose with the first mixture, thereby forming a second mixture, and lyophilizing the second mixture to form a freeze-dried composition comprising platelets or platelet derivatives (e.g., FDPDs), polysucrose and trehalose.

In some embodiments, provided herein is a process for making freeze-dried platelets, the process comprising incubating isolated platelets in the presence of at least one saccharide under the following conditions: a temperature of from 20° C. to 42° C. for about 10 minutes to about 180 minutes, adding to the platelets at least one cryoprotectant, and lyophilizing the platelets, wherein the process optionally does not include isolating the platelets between the incubating and adding steps, and optionally wherein the process does not include exposing the platelets to a platelet activation inhibitor. The cryoprotectant can be a polysugar (e.g., polysucrose). The process can further include heating the lyophilized platelets at a temperature of 70° C. to 80° C. for 8 to 24 hours. The step of adding to the platelets at least one cryoprotectant can further include exposing the platelets to ethanol. The step of incubating isolated platelets in the presence of at least one saccharide can include incubating in the presence of at least one saccharide. The step of incubating isolated platelets in the presence of at least one saccharide can include incubating in the presence of at least one saccharide. The conditions for incubating can include incubating for about 100 minutes to about 150 minutes. The conditions for incubating can include incubating for about 110 minutes to about 130 minutes. The conditions for incubating can include incubating for about 120 minutes. The conditions for incubating can include incubating at 35° C. to 40° C. The conditions for incubating can include incubating at 37° C. The conditions for incubating can include incubating at 35° C. to 40° C. for 110 minutes to 130 minutes. The conditions for incubating can include incubating at 37° C. for 120 minutes. The at least one saccharide can be trehalose, sucrose, or both trehalose and sucrose. The at least one saccharide can be trehalose. The at least one saccharide can be sucrose.

In some embodiments, provided herein is a method of preparing freeze-dried platelets, the method including providing platelets, suspending the platelets in a salt buffer that includes about 100 mM trehalose and about 1% (v/v) ethanol to make a first composition, incubating the first composition at about 37° C. for about 2 hours, adding polysucrose (e.g., polysucrose 400) to a final concentration of about 6% (w/v) to make a second composition, lyophilizing the second composition to make freeze-dried platelets, and heating the freeze-dried platelets at 80° C. for 24 hours.

Specific embodiments disclosed herein may be further limited in the claims using "consisting of" or "consisting essentially of" language.

The platelet derivative composition as described herein can be contained in containers/vials, which further can be packed into a plurality of containers for shipping to a customer, which can be part of a commercialization process to fulfill an order for such platelet derivative composition. The containers, in certain embodiments, are 5 ml vials, 10 ml vials, 20 ml vials, 25 ml vs, 30 ml vials, 40 ml vials, 50 ml vials, 60 ml vials, 75 ml vials, 100 ml vials, 125 ml vials, 150 ml vials, 200 ml vials, or 250 ml vials. The vial(s) can be a cryovial, or a cryotube especially in illustrative embodiments where the TFF-treated composition that includes platelets is lyophilized to obtain the platelet derivative composition in the form of a powder, which further can be baked or not baked after it is lyophilized. In some embodiments, the volume of the containers in a plurality of containers (e.g. vials or tubes), which for example can be all from one lot, or from more than one lot (e.g. 2, 3, 4, 5, 6, 7, 8, 9 or 10 lots), can vary from one or more than one size between 10-100 ml. Typically, the volume of the vial/container in embodiments where the platelet derivative is a freeze-dried solid/powder, is 1× the volume of, or 1.10, 1.25, 1.5, 2, 2.5, 3, 4 or 5 times the volume of a composition that was filled in the vial before lyophilization, and/or the volume in which the powder in the vials will be rehydrated, which is an illustrative embodiment. Thus, the maximum volume of such vials can be the same or more than the volume of the composition that was filled inside prior to lyophilization or the volume in which the platelet derivative composition in the form of a powder can be rehydrated. For example, in one non-limiting embodiment, a vial with a maximum capacity of 100 ml, can be used to fill 10 ml of a TFF-treated composition that includes platelets for lyophilization. In certain embodiments, the capacity of a vial in which a TFF-treated composition that includes platelets is lyophilized, is 1-2.5 times and in other embodiments, 1-2 times, 1-3 times, 1-4 times, 1-5 times, and in certain illustrative embodiments, 1.1 to 2 times or 1.25 to 2 times the volume of a TFF-treated composition that is lyophilized therein.

The TFF-treated platelet composition before lyophilization, or in some embodiments, the platelet derivative composition obtained after the lyophilization step, with or without post-lyophilization heat treatment (baking), can be filled into a plurality of vessels or other powder and liquid-holding containers, such as vials, in a sterile manner. In some embodiments, the containers can vary in volume from 5-100 ml, 10-90 ml, 25-75 ml, or 5-40 ml. In some embodiments, the volume of containers can be 5 ml, 10 ml, 15 ml, 20 ml, 25 ml, 30 ml, 35 ml, 40 ml, 45 ml, 50 ml, 55 ml, 60 ml, 65 ml, 70 ml, 75 ml, 80 ml, 85 ml, 90 ml, 95 ml, or 100 ml. In some embodiments, the volume of containers can be above 100 ml, for example, 125 ml, 150 ml, 175 ml, or 200 ml. The platelet derivative composition as described herein can be filled in vials of different volumes as per the commercialization requirements. A plurality (or collection) of containers having the platelet derivative composition as per any of the embodiments herein, obtained by lyophilizing the composition that includes platelets during one process (e.g. TFF or other process) for preparing a platelet derivative, can be referred to as a "batch" or a "lot". In some embodiments, a batch/lot can have 10-500 vials, 25-450 vials, 50-350 vials, 100-300 vials, or 150-250 vials. In some embodiments, a batch/lot can have 10, 20, 30, 40, 50, 60, 70, 80, 90, 100, 110, 120, 130, 140, 150, 160, 170, 180, 190, 200, 250, 300, 350, 400, 450, or 500 vials. In some embodiments, the number of vials per batch/lot can be increased to more than 500 as per the requirements, for example, 600, 700, 800, 900, or 1000 vials. In some embodiments, the number of vials can be 10-1000, 50-1000, 100-900, 200-800, 100-500, 100-400, 150-700, or 150-500 vials. The containers in a batch/lot can have a volume in the range of 5-100 ml, for example, such that a lot has several containers with the same volume or containers with different volumes. For example, 200 vials/containers in a batch/lot can have a volume of 10 ml each, 100 vials/containers in the same or a separate batch/lot can have a volume of 20 ml each, 100 vials/containers in the same or another batch/lot can have a volume of 30 ml each, or 300 vials/containers in the same or a different batch/lot can have a volume of 10 ml each. The number of containers (e.g. vials) in which a platelet derivative composition as per one of the embodiments or aspects described herein can be packed in a batch/lot can vary with manufacturing requirements, the requirements of downstream processes, for example clinical processes, and the amount of starting material comprising platelet composition.

The quantity of platelet derivatives that is present in a batch/lot can vary based on the units of starting material comprising platelets that is used to produce the platelet derivatives. Certain methods provided herein, such as the TFF methods provided herein, allow more platelet units to be used to make platelet derivatives with the characteristics provided herein than prior methods. This is the result, for example, of the ability to reduce the level of certain components in a platelet composition starting material, such as HLA antibodies, HNA antibodies, and/or microparticles, to very low levels, as provided herein. Accordingly, the starting material comprising platelets, the corresponding composition (e.g. TFF-treated composition) that is lyophilized in illustrative embodiments, and the resulting platelet derivative composition powder, can vary, such that for example, in some embodiments, the starting material, the TFF-treated composition, and/or the resulting platelet derivative composition powder can include 10-500 units of platelets or platelet derivatives (e.g. 0.5 to 2.5 µm in diameter), with one unit being $3 \times 10^{11}$ platelets or platelet derivatives. In some embodiments, the starting platelet material, the composition to be lyophilized, and/or the platelet derivative (e.g. 0.5 to 2.5 µm in diameter) composition can include, for example, 20-500 units, 30-400 units, 40-350 units, or 50-200 units of platelets or platelet derivatives, respectively. In some embodiments, the platelet units in the starting platelet composition can be a pooled platelet product from multiple donors as described herein, or multiple batches of processed platelet compositions, such as TFF-treated compositions comprising platelets, can be pooled before lyophilization. In some embodiments, there can be $1 \times 10^9$ to $1 \times 10^{16}$ platelets in a starting platelet composition for processing, in a platelet composition that is lyophilized, and/or of platelet derivatives in a platelet derivative composition that is produced after lyophilization, per batch/lot. In some embodiments, the platelet-containing starting composition, the platelet composition that is lyophilized, and/or the platelet derivatives that are produced, typically after lyophilization per batch/lot can vary from $1 \times 10^{10}$ to $1 \times 10^{15}$, $1 \times 10^{11}$ to $1 \times 10^{15}$, $1 \times 10^{12}$ to $1 \times 10^{16}$, $1 \times 10^{13}$ to $1 \times 10^{15}$ or $1 \times 10^{13}$ to $1 \times 10^{14}$.

In certain illustrative embodiments, platelet derivative compositions that are present in a liquid, or in illustrative embodiments, a solid form such as a dried powder in the plurality of containers (e.g. vials), in illustrative embodiments of a 1 or more lots, are compositions that include platelet derivatives, wherein at least 50% of the platelet derivatives are CD 41-positive platelet derivatives, wherein less than 15%, 10%, or in further, non-limiting illustrative embodiments less than 5% of the CD 41-positive platelet derivatives are microparticles having a diameter of less than 0.5 µm, and wherein the platelet derivatives have a potency of at least 0.5, 1.0 and in further, non-limiting illustrative embodiments 1.5 thrombin generation potency units (TGPU) per $10^6$ platelet derivatives. In certain illustrative embodiments, including non-limiting examples of the illustrative embodiment in the preceding sentence, the platelet derivatives are 0.5 to 2.5 um in diameter. Such platelet derivatives and platelet derivative compositions comprising the same, can have additional characteristics disclosed herein for such derivatives and compositions.

Processes provided herein for producing platelet derivative compositions, provide better lot to lot consistency than prior processes. For example, TFF methods provided herein provide improved lot to lot variability with respect to the components of compositions that include platelet derivatives prepared therein, in illustrative embodiments, compositions that include freeze-dried platelet derivates. Such freeze-dried platelet derivatives can be one of, or the main active ingredient(s). In some embodiments, a plurality of containers provided herein comprise the platelet derivative composition from at least 2 different lots in separate containers. In some embodiments, the amount of plasma protein in the powder of any two containers chosen from different lots, differs by less than 50%, 40%, 30%, 25%, or 20%, and in illustrative embodiments less than 10%, 5%, 2%, 1%, or 0.5%. The TFF process is highly controllable and can be stopped at a certain A280 for example, from 2.0 AU to 0.01 AU, or when it reaches 15% to 0.01% protein concentration in the composition that is to be lyophilized (e.g. TFF-treated composition), therefore, the plasma protein content can be very consistent not only within the containers/vials of a lot, but even between lots as well. Since different lots of platelet derivative compositions provided herein are typically prepared from platelets from different subjects or different combinations of subjects (e.g. pooled platelets from 2, 3, 4, 5, 6, 7, 8, 9, 10, 15, 20, 25, 30, 40, 50, 60, 70, 75, 80, or 100 subjects), different lots in illustrative embodiments differ in amino acid sequence of at least one (e.g., 1, 2, 3, 4, 5, 6, 7, 8, 9, 10, 1-100, or 1-10) of the proteins in, on, and/or associated with platelet derivatives of the compositions therein between the lots. In illustrative embodiments, these one or more amino acid differences occur at one or more (e.g., 1, 2, 3, 4, 5, 6, 7, 8, 9, 10, 1-100, or 1-10) of the site(s) of non-synonymous SNPs. In certain embodiments, such non-synonymous SNPs have a minor allele frequency of less than or equal to 5%. In some embodiments, such pooled platelets are provided by processes provided herein, for example because HLA or HNA antibody levels can be reduced to very low or non-existent levels. Thus, not only can platelets be pooled from more subjects, before processing to form platelet derivatives, but those subjects can be males or females. As a result, in certain embodiments, within a lot, greater than 10%, 20%, 25%, 30%, or 40%, and in illustrative embodiments greater than 50%, 60%, 70%, 75%, 80%, 90%, or 95% of non-synonymous SNPs in one or more proteins that are bound to or otherwise associated with or part of a platelet derivative, are present for SNPs with a minor allele frequency of greater than 5%, in certain embodiments including SNPs on a mammalian X and Y chromosome.

In some embodiments, the amount of microparticles that are less than 0.5 μm in the powder of any two containers chosen from different lots, differs in amount by less than 10%, 5%, 2%, or 1%. Since, for example, a TFF process disclosed herein is very controllable, the concentration of microparticles to be obtained in the platelet derivative composition can be optimized, for example, by performing scattering intensity studies at different time points. Once the desired level is achieved, the TFF-treated composition can be lyophilized and packed in the vials with or without the baking step.

In some embodiments, the percentage by weight of platelet derivative in the powder of any two containers chosen from different lots, differs by less than 10%, 5%, 2%, or 1%. The TFF process can be optimized to achieve a pre-determined level of platelet derivatives in the TFF-treated composition. Such a TFF-treated composition when lyophilized gives a platelet composition in the form of a powder having a certain weight percentage of platelet derivatives. Since, the TFF process is controllable, in some embodiments, there can be a minimum or a negligible variation in the weight percentages of the platelet derivatives in any two containers chosen from different lots.

In some embodiments, at least one container comprises a first lot of platelet derivatives and the one or more other containers comprise a second lot of platelet derivatives. In some embodiments, plurality of containers comprises the platelet derivative composition from at least 2, 3, 4, 5, 6, 7, 8, 9, or 10 different lots, wherein the platelet derivative composition in at least 2 of the lots have a different amino acid sequences for at least one protein of a collection of protein gene products from a corresponding collection of encoding genes. In illustrative embodiments all of the lots have a different amino acid sequences for at least one protein of a collection of protein gene products from a corresponding collection of encoding genes. In some embodiments, the amino acid difference(s) is at one or more residues corresponding to amino acid residues encoded by a non-synonymous single nucleotide polymorphism (SNP).

As per one of the embodiments, a platelet derivative composition as described herein can be prepared from multiple donors of a single species, for example, mammals, such as for example canine, equine, porcine and in illustrative embodiments humans that are genetically different, in order to obtain a platelet derivative composition to prepare allogenic platelet derivatives, an allogenic platelet derivative product, and/or a composition comprising allogenic platelet derivatives. Such a platelet derivative composition can be filled in vials and a plurality of such vials can be packaged in containers, for example boxes for commercialization as described herein, to obtain a commercial product that is a composition comprising allogeneic platelet derivatives. The allogenic platelet derivatives as described herein, in some embodiments, can be a U.S. FDA-approved product comprising an allogenic platelet derivative composition. In some embodiments, a platelet derivative composition as described herein can be a European EMA-approved product comprising an allogenic platelet derivative composition. In some other embodiments, a platelet derivative composition as described herein can be a China FDA-approved product comprising an allogenic platelet derivative composition.

In some embodiments, platelets are pooled from a plurality of donors before they are used as starting material for a process for producing a platelet derivative as provided herein. Such platelets pooled from a plurality of donors can be also referred herein to as pooled platelets. In some embodiments, the donors are more than 5, such as more than 10, such as more than 20, such as more than 50, such as up to about 100 donors. In some embodiments, the donors are from 5 to 100, such as from 10 to 50, such as from 20 to 40, such as from 25 to 35. Pooled platelets can be used to make any of the platelet derivative compositions as described herein. The platelets can be pooled wherein the platelets are donated by mammalian (e.g. bovine, feline, porcine, canine, and in illustrative embodiments, human) subjects. In some embodiments, the gender of the subjects can be male or female. In some embodiments, the donor can vary from any number of male to any number of female subjects, for example, from a total of 100 donors, any number can be female donors, ranging from 0-100, 5-95, 10-90, 20-80, 30-70, or 40-60, and the rest can be male donors. In some other embodiments, the donor can be a non-human animal. In some embodiments, the donor can be a canine, equine, porcine, bovine, or feline subject.

In some embodiments of any of the aspects and embodiments herein that include a composition, or in some compositions used in or formed by a process that includes a plurality of containers each filled with a platelet derivative composition in the form of a powder, each of the plurality of containers are purged with at least one inert gas. In some embodiments, the inert gas can be argon, or nitrogen.

Platelet derivatives in certain illustrative aspects and embodiments herein are surrounded by a compromised plasma membrane. In these illustrative aspects and embodiments, the platelet derivatives lack an integrated membrane around them. Instead, the membrane has pores on them that are larger than pores observed on living cells. Not to be limited by theory, it is believed that in embodiments where platelet derivatives have a compromised membrane, such platelet derivatives have a reduced ability to, or are unable to transduce signals from the external environment into a response inside the particle that are typically transduced in living platelets. A compromised membrane can be identified through a platelet derivative's inability to retain more than 50% of lactate dehydrogenase (LDH) as compared to fresh platelets, or cold stored platelets, or cryopreserved platelets. In some embodiments, the platelet derivatives are incapable of retaining more than 35%, 40%, 45%, 50%, 55%, 60%, 65%, 70%, or 75% of lactate dehydrogenase as compared to lactate dehydrogenase retained in fresh platelets, or cold stored platelets, or cryopreserved platelets. In some embodiments, the platelet derivatives exhibit an increased permeability to antibodies. In some embodiments, the antibodies can be IgG antibodies. The compromised membrane of the platelet derivatives can also be determined by flow cytometry studies.

Platelet or platelet derivatives (e.g., thrombosomes) as described herein can retain some metabolic activity, for example, as evidenced by lactate dehydrogenase (LDH) activity. In some cases, platelets or platelet derivatives (e.g., thrombosomes) as described herein can retain at least about 10% (e.g., at least about 12%, 15%, 20%, 25%, 30%, 35%, 40%, or 45%) of the LDH activity of donor apheresis platelets. Without being bound by any particular theory, it is believed that the addition of increasing amounts of polysucrose increases the amount of LDH activity remained (e.g., products of a preparation agent with 8% polysucrose have more retained LDH activity than products of a preparation agent with 4% polysucrose). Similarly unbound by any particular theory, it is believed that thermal treatment of a lyophilized composition comprising platelets or platelet derivatives (e.g., thrombosomes) increases the amount of LDH activity retained. As another example, metabolic activity can be evidenced by retained esterase activity, such as the ability of the cells to cleave the acetate groups on carboxyfluorescein diacetate succinimidyl ester (CFDASE) to unmask a fluorophore.

Platelet derivatives as described herein can have several applications in terms of treating a subject suffering with a disorder selected from the group consisting of alopecia areata, Von Willebrand Disease, hemophilia, thrombasthenia, thrombocytopenia, thrombocytopenic purpura, trauma, or a combination thereof. In some embodiments, the platelet derivatives can be used to treat clotting-related disorders. The platelet derivatives as described herein can be used both as a topical application and systemic administration. In some embodiments, there is provided a method for treating a clotting-related disorder in a subject, said method comprising administering to the subject a therapeutically effective amount of the platelet derivative composition of any of the aspects or embodiments herein, or the platelet derivative composition prepared by any of the process described in the aspects or embodiments herein. In some embodiments, the clotting-related disorder is selected from the group consisting of Von Willebrand Disease, hemophilia, thrombasthenia, thrombocytopenia, thrombocytopenic purpura, trauma, or a combination thereof. In some embodiments, a platelet derivative composition is passed through a filter of 18 μm before administering to the subject. A skilled artisan would be able to appreciate that the platelet derivative composition in the form of a powder which would be commercialized in vials would be rehydrated with an appropriate amount of a solution before administering to a subject. In some embodiments, such a rehydrated platelet derivative composition is passed through a filter of 18 μm before administering to the subject.

In some embodiments, the platelet derivatives as described herein can be used for healing wounds in a subject. In some embodiments, there is provided a method for healing a wound in a subject, comprising administering a therapeutically effective amount of a platelet derivative composition of any of the aspects or embodiments herein, or the platelet derivative composition prepared by any of the process described in the aspects or embodiments herein, to the subject and/or a wound of the subject.

In some embodiments, the administering can include administering topically. Administering can include administering parenterally. Administering can include administering intravenously. Administering can include administering intramuscularly. Administering can include administering intrathecally. Administering can include administering subcutaneously. Administering can include administering intraperitoneally.

EXEMPLARY EMBODIMENTS

Provided in this Exemplary Embodiments section are non-limiting exemplary aspects and embodiments provided herein and further discussed throughout this specification. For the sake of brevity and convenience, all of the aspects and embodiments disclosed herein, and all of the possible combinations of the disclosed aspects and embodiments are not listed in this section. Additional embodiments and aspects are provided in other sections herein. Furthermore, it will be understood that embodiments are provided that are specific embodiments for many aspects and that can be combined with any other embodiment, for example as discussed in this entire disclosure. It is intended in view of the full disclosure herein, that any individual embodiment recited below or in this full disclosure can be combined with any aspect recited below or in this full disclosure where it is an additional element that can be added to an aspect or because it is a narrower element for an element already present in an aspect. Such combinations are sometimes provided as non-limiting exemplary combinations and/or are discussed more specifically in other sections of this detailed description.

Provided herein in one aspect is a method of treating a coagulopathy in a subject, the method including administering to the subject in need thereof an effective amount of a composition including platelets, or in illustrative embodiments platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of treating a coagulopathy in a subject, the method including administering to the subject in need thereof an effective amount of a composition prepared by a process including incubating platelets with an incubating agent including one or more salts, a buffer, optionally a cryoprotectant, and optionally an organic solvent, and in illustrative embodiments freeze-drying the incubated platelets, to form the composition, wherein the composition includes platelet derivatives, and in illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of restoring normal hemostasis in a subject, the method including administering to the subject in need thereof an effective amount of a composition including platelets, or in illustrative embodiments platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of restoring normal hemostasis in a subject, the method including administering to the subject in need thereof an effective amount of a composition prepared by a process including incubating platelets with an incubating agent including one or more salts, a buffer, optionally a cryoprotectant, and optionally an organic solvent, and in illustrative embodiments freeze-drying the incubated platelets, to form the composition, wherein the composition comprises platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of preparing a subject for surgery, the method including administering to the subject in need thereof an effective amount of a composition including platelets, or in illustrative embodiments platelet derivatives, and in further illustrative embodiments FDPDs. Various properties of exemplary embodiments of such FDPDs are provided herein, thereby treating the coagulopathy. In illustrative embodiments, the composition comprising the platelet derivatives is administered such that the bleeding potential of the subject is reduced, and in illustrative embodiments such that normal hemostasis is restored in the subject. Implementations can include one or more of the following features. The surgery can be an emergency surgery. The surgery can be a scheduled surgery.

In one aspect, provided herein is a method of preparing a subject for surgery, the method including administering to the subject in need thereof an effective amount of a composition prepared by a process including incubating platelets with an incubating agent including one or more salts, a buffer, optionally a cryoprotectant, and optionally an organic solvent, and in illustrative embodiments freeze-drying the incubated platelets, to form the composition, wherein the composition includes platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject. Various properties of exemplary embodiments of such FDPDs are provided herein. Implementations can include one or more of the following features. The surgery can be an emergency surgery. The surgery can be a scheduled surgery.

In one aspect, provided herein is a method of ameliorating the effects of an antiplatelet agent in a subject, the method including administering to the subject in need thereof an effective amount of a composition platelets, or in illustrative embodiments platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of ameliorating the effects of an antiplatelet agent in a subject, the method including administering to the subject in need thereof an effective amount of a composition prepared by a process including incubating platelets with an incubating agent including one or more salts, a buffer, optionally a cryoprotectant, and optionally an organic solvent, to form the composition, wherein the composition includes platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of treating a coagulopathy in a subject, or of restoring hemostasis in a subject, or of reducing bleeding potential of a subject that is being administered, or has been administered, an antiplatelet agent, the method comprising: administering to the subject in need thereof an effective amount of a composition comprising platelet derivatives, thereby treating the coagulopathy. In illustrative embodiments, the platelet derivatives are freeze-dried platelet derivatives (FDPDs). In further illustrative embodiments, the composition comprising the platelet derivatives is administered such that the bleeding potential of the subject is reduced, and in illustrative embodiments such that normal hemostasis is restored in the subject.

In another aspect, provided herein is a method of treating a coagulopathy in a subject, or of restoring hemostasis in a subject, or of reducing bleeding potential of a subject, wherein the subject is being administered, or has been administered, an antiplatelet agent, the method comprising administering to the subject in need thereof an effective amount of the composition comprising FDPDs, wherein the composition comprising FDPDs comprises a population of FDPDs having a reduced propensity to aggregate such that no more than 10% of the FDPDs in the population aggregate under aggregation conditions comprising an agonist but no platelets, thereby treating the coagulopathy. In further illustrative embodiments, the composition comprising the FDPDs is administered such that the bleeding potential of the subject is reduced, and in illustrative embodiments such that normal hemostasis is restored in the subject.

In another aspect, provided herein is a method of preventing or mitigating the potential for a coagulopathy in a subject, the method comprises: (a) determining that information regarding whether the subject was administered an antiplatelet agent is unavailable; and (b) administering to the subject an effective amount of a composition comprising freeze-dried platelet derivatives (FDPDs). In some embodiments of such a method, information regarding whether the subject was administered an antiplatelet agent is unavailable for a reason comprising that the subject cannot be identified. In some embodiments of the method, information regarding whether the subject was administered an antiplatelet agent is unavailable for a reason comprising that the medical history of the subject is unavailable. In further embodiments information regarding whether the subject was administered an antiplatelet agent is unavailable for a reason comprising that the subject is in need of emergency treatment.

In another aspect, provided herein is a method of treating a coagulopathy in a subject or of reducing the bleeding potential of a subject, or of restoring hemostasis in a subject, wherein the method comprises: administering to the subject in need thereof an effective amount of a composition comprising platelet derivatives, in illustrative embodiments, FDPDs, wherein the subject before the administering the composition comprising platelet derivatives, was administered an antiplatelet agent and a second agent that decreases platelet function, thereby treating the coagulopathy. In further illustrative embodiments, the composition comprising the platelet derivatives is administered such that the bleeding potential of the subject is reduced, and in illustrative embodiments such that normal hemostasis is restored in the subject. In illustrative embodiments, before the administering of the composition comprising FDPDs the subject was in need thereof because of an increased risk of bleeding due to, or as a result of being administered the anti-platelet agent and the second agent.

In another aspect, provided herein is a composition comprising freeze-dried platelet derivatives (FDPDs) for treating a coagulopathy in a subject, wherein the treating comprises: administering to the subject in need thereof, an effective amount of the composition comprising FDPDs such that the bleeding potential, or risk of bleeding of the subject is reduced,
    wherein the subject was administered an antiplatelet agent and a second agent that decreases platelet function, and
    wherein the subject is in need thereof because of an increased potential for, or risk of bleeding due to, or as a result of being administered the antiplatelet agent and the second agent,
    thereby treating the coagulopathy.

In another aspect, provided herein is a composition comprising freeze-dried platelet derivatives (FDPDs) for treating a coagulopathy in a subject having an increased potential for, or risk of bleeding as a result of being administered or having been administered an anticoagulant, wherein the treating comprises:
    administering to the subject having the increased potential for, or risk of bleeding, an effective amount of the composition comprising FDPDs such that the bleeding potential or risk of bleeding of the subject is reduced,
    wherein the composition comprising FDPDs comprises a population of FDPDs having a reduced propensity to aggregate such that no more than 10% of the FDPDs in the population aggregate under aggregation conditions comprising an agonist but no platelets,
    thereby treating the coagulopathy.

In one aspect, provided herein is a composition comprising platelets or platelet derivatives and an aqueous medium, wherein the aqueous medium has a protein concentration less than or equal to 50% of the protein concentration of donor apheresis plasma.

In one aspect, provided herein is a platelet derivative composition in the form of a powder, comprising a population of platelet derivatives having a reduced propensity to aggregate, such that no more than 25%, and in non-limiting illustrative embodiments, no more than 10%, of the platelet derivatives in the population aggregate under aggregation conditions comprising an agonist but no platelets, and wherein the platelet derivatives are capable of generating thrombin, and in certain embodiments have a potency of at least 0.5, 1.0, and in non-limiting illustrative embodiments 1.5 thrombin generation potency units (TGPU) per $10^6$ platelet derivatives.

In one aspect, provided herein is a platelet derivative composition in the form of a powder, comprising a population of platelet derivatives having a reduced propensity to aggregate, wherein no more than 25%, and in non-limiting illustrative embodiments, no more than 10%, of the platelet derivatives in the population aggregate under aggregation conditions comprising an agonist but no platelets; and having one or more, two or more, or all of the following characteristics of a super-activated platelet selected from: a. the presence of thrombospondin (TSP) on their surface at a level that is greater than on the surface of resting platelets; b. the presence of von Willebrand factor (vWF) on their surface at a level that is greater than on the surface of resting platelets; c. an inability to increase expression of a platelet activation marker in the presence of an agonist as compared to the expression of the platelet activation marker in the absence of an agonist.

In one aspect, provided herein is a platelet derivative composition in the form of a powder, comprising platelet derivatives, wherein less than 15%, and in certain non-limiting illustrative embodiments less than 5% of the CD 41-positive platelet derivatives are microparticles, in non-limiting illustrative embodiments having a diameter of less than 1 μm, and in certain non-limiting illustrative embodiments less than 0.5 μm, and wherein the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives.

In one aspect, provided herein is a platelet derivative composition in the form of a powder, comprising a population of platelet derivatives comprising CD 41-positive platelet derivatives, wherein the population comprises platelet derivatives having a reduced propensity to aggregate such that no more than 25%, and in non-limiting illustrative embodiments, no more than 10%, of the platelet derivatives in the population aggregate under aggregation conditions comprising an agonist but no platelets, wherein the platelet derivatives have an inability to increase expression of a platelet activation marker in the presence of an agonist as compared to the expression of the platelet activation marker in the absence of the agonist, wherein the platelet derivatives are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives; and wherein less than 15%, and in certain non-limiting illustrative embodiments less than 5% of the CD 41-positive platelet derivatives are microparticles having a diameter of less than 1 μm, and in certain non-limiting illustrative embodiments less than 0.5 μm.

In one aspect, provided herein is a platelet derivative composition in the form of a powder, comprising a population of platelet derivatives having a reduced propensity to aggregate, such that no more than 25%, and in non-limiting illustrative embodiments, no more than 10%, of the platelet derivatives in the population aggregate under aggregation conditions comprising an agonist but no platelets, and further having one or both of: the presence of thrombospondin (TSP) on their surface at a level that is greater than on the surface of resting platelets; and the presence of von Willebrand factor (vWF) on their surface at a level that is greater than on the surface of resting platelets.

In one aspect, provided herein is a platelet derivative composition in the form of a powder, comprising a population of platelet derivatives comprising CD41-positive platelet derivatives, wherein less than 15%, and in certain non-limiting illustrative embodiments less than 5% of the CD41-positive platelet derivatives are microparticles having a diameter of less than 1 μm, and in certain non-limiting illustrative embodiments less than 0.5 µm, and comprising platelet derivatives having one or more of, two or more of, three or more of, and in illustrative embodiments all of the following: a reduced propensity to aggregate, in certain embodiments such that no more than 25%, and in illustrative embodiments no more than 10% of the platelet derivatives in the population aggregate under aggregation conditions comprising an agonist but no platelets; an inability to increase expression of a platelet activation marker in the presence of an agonist as compared to the expression of the platelet activation marker in the absence of the agonist; the presence of thrombospondin (TSP) on their surface at a level that is greater than on the surface of resting platelets; the presence of von Willebrand factor (vWF) on their surface at a level that is greater than on the surface of resting platelets; and are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives.

In one aspect, provided herein is a platelet derivative composition in the form of a powder, comprising trehalose in the range of 20-35% by weight, polysucrose in the range of 45-60% by weight, and platelet derivatives in the range of 0.5-20% by weight, wherein the platelet derivatives to microparticles have a numerical ratio of at least 95:1 in the platelet derivative composition, and wherein the platelet derivatives are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives.

In one aspect, provided herein is a platelet derivative composition in the form of a powder, comprising trehalose in the range of 20-35% by weight, polysucrose in the range of 45-60% by weight, and platelet derivatives in the range of 0.5-20% by weight, wherein the platelet derivative composition comprises a population of platelet derivatives having a reduced propensity to aggregate such that no more than 250%, and in non-limiting illustrative embodiments, no more than 10%, of the platelet derivatives in the population aggregate under aggregation conditions comprising an agonist but no platelets, and further having one or both of: the presence of thrombospondin (TSP) on their surface at a level that is greater than on the surface of resting platelets; and the presence of von Willebrand factor (vWF) on their surface at a level that is greater than on the surface of resting platelets.

In one aspect, provided herein is a plurality of containers each containing a platelet derivative composition in the form of a powder, wherein the platelet derivative composition in each container comprises a population of platelet derivatives having a reduced propensity to aggregate such that no more than 25%, and in non-limiting illustrative embodiments, no more than 10% of the platelet derivatives in the population aggregate under aggregation conditions comprising an agonist but no platelets, wherein the platelet derivative compositions in each container are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives, wherein the platelet derivatives have an inability to increase expression of a platelet activation marker in the presence of an agonist as compared to the expression of the platelet activation marker in the absence of the agonist, wherein the plurality of containers comprise the platelet derivative composition from at least 2 different lots in separate containers, and wherein one or more of: the amount of plasma protein in the powder of any two containers chosen from different lots, differs by less than 10%, 5%, 2%, or 1%, and the amount of microparticles that are less than 1 µm, and in certain non-limiting illustrative embodiments less than 0.5 µm in the powder of any two containers chosen from different lots, differs by less than 10%, 5%, 2%, or 1%.

In one aspect, provided herein is a plurality of containers each filled with a platelet derivative composition in the form of a powder, wherein the platelet derivative composition comprises trehalose in the range of 20-35% by weight; polysucrose in the range of 45-60% by weight; and platelet derivatives in the range of 0.5-20% by weight, wherein the platelet derivatives are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives, and a population of platelet derivatives comprising CD41-positive platelet derivatives, wherein less than 15%, and in certain non-limiting illustrative embodiments less than 5% of the CD41-positive platelet derivatives are microparticles having a diameter of less than 1 µm, and in certain non-limiting illustrative embodiments less than 0.5 µm.

To reiterate, any embodiments herein in this section and in this specification and associated claims, can be combined and/or used in any of the aspects herein and in combination with any of the other embodiments herein. Furthermore, a "powder" recited in any aspect or embodiment can alternatively be a solid, or a composition comprising less than 1% water content in such aspect or embodiment.

In certain illustrative embodiments of a composition, or in some compositions used in or formed by a process, the platelet derivatives in a composition, as a non-limited example a powder, and/or formed by a process disclosed herein, are surrounded by a compromised plasma membrane, are positive for CD 41, and/or are 0.5 to 2.5 µm in diameter. In some embodiments, the composition comprises platelet derivatives such that at least 95% platelet derivatives positive for CD 41 have a diameter in the range of 0.5 to 2.5 µm. Such diameter can be measured, for example by flow cytometry technique as known to a skilled artisan in the art.

In some embodiments of any of the aspects and embodiments herein that include platelet derivatives in a hydrated or rehydrated form, the protein concentration, or plasma protein concentration, is in the range of 0.01%-50%, 5%-50%, 5%-30%, 5-15%, 8%-10%, 7%-10%, or 3-7% of the protein concentration of donor apheresis plasma. In some embodiments of a composition or in some compositions used in or formed by a process herein, the protein concentration, or plasma protein concentration is less than or equal to 30%, 25%, 20%, 15%, 10%, 5%, 4%, 3%, 2%, or 1% of the protein concentration of donor apheresis plasma. In some embodiments of a composition or a process herein, the protein concentration, or plasma protein concentration is less than or equal to 15%, 14%, 13%, 12%, 11%, 10%, 9%, 8%, 7%, 6%, 5%, 4%, 3%, 2%, 1%, 0.1%, or 0.01%. In some exemplary embodiments, the protein concentration, or plasma protein concentration is less than 3% or 4%. In some embodiments, the protein concentration, or plasma protein concentration is between 0.01% and 20%, 0.01% and 15%, 0.01% and 10%, 0.01% and 5%, 0.1% and 20%, 0.1% and 15%, 0.1% and 10%, 0.1% and 5%, 1% and 20%, 1% and 15%, 1% and 10%, 1% and 5%, 2% and 10%, 2% and 5%, 2.5% and 5%, 2.5% and 7.5%, or between 3% and 5%. In some embodiments of a composition or a process herein, the protein concentration is in the range of 0.01-15%, 0.1-15%, 1-15%, 1-10%, 0.01-10%, 3-12%, or 5-10%. In some embodiments, the absorbance at 280 nm is less than or equal to 2.0 AU, or 1.90 AU, or 1.80 AU, or 1.7 AU, or 1.66 AU, or 1.6 AU when measured using a path length of 0.5 cm.

In some embodiments of any of the aspects and embodiments herein that include platelet derivatives in a powdered form, the protein concentration is in the range of 0.01-15%, 0.1-15%, 1-15%, 1-10%, 0.01-10%, 3-12%, or 5-10%. In some embodiments, the protein concentration is less than or equal to 25%, 20%, 15%, 10%, 7.5%, 5%, 2.5%, 1%, or 0.1%.

In some embodiments of any of the aspects and embodiments herein that include a composition, or in some compositions used in or formed by a process, a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 5%, 3%, or 1%. In some embodiments of the composition, a percentage of beads positive for HLA Class I antibodies, HLA Class II antibodies, and HNA antibodies, as determined for the composition by flow cytometry using beads coated with Class I HLAs, Class II HLAs, or HNAs, respectively, is less than 5%, 3%, or 1%. In some embodiments, the composition is negative for the antibodies selected from the group consisting of HLA Class I antibodies, HLA Class II antibodies, and HNA antibodies based on a regulatory agency approved test for the respective antibodies. In some embodiments, the composition is negative for HLA Class I antibodies, HLA Class II antibodies, and HNA antibodies based on a regulatory agency approved test for the respective antibodies.

In some embodiments of any of the aspects and embodiments herein that include a composition, or in some compositions used in or formed by a process that includes a population of platelet derivatives in a hydrated or rehydrated form, comprises trehalose in the range of 0.4-35%, or 1-35%, or 2-30%, or 1-10%, or 1-5%, or 0.5-5%. In an exemplary embodiment, the composition comprises 3.5% trehalose.

In some embodiments of any of the aspects and embodiments herein that include a composition, or in some compositions used in or formed by a process that includes a platelet composition in a powdered form, comprises trehalose having a weight percentage in the range of 10-60%, 15-55%, 20-60%, 20-50%, 25-60%, 25-50%, 10-50%, 20-40%, or 20-35%. In some embodiments, the weight percentage of trehalose can vary on the weight percentage of other components in the composition like, polysucrose, platelet derivatives, plasma protein, and buffering agents.

In some embodiments of any of the aspects and embodiments herein that include a composition, or in some compositions used in or formed by a process that includes a population of platelet derivatives in a hydrated or rehydrated form, comprises polysucrose in the range of 2-8%, 2.25-7.75%, 2.5-7.5%, or 2.5-6.5%. In an exemplary embodiment, the composition comprises 3% polysucrose. In another exemplary embodiment, the composition comprises 6% polysucrose.

In some embodiments of any of the aspects and embodiments herein that include a composition, or in some compositions used in or formed by a process that includes a platelet composition in a powdered form, comprises polysucrose having a weight percentage in the range of 20-80%, 25-75%, 30-70%, 35-65%, 30-80%, or 45-60%. In some embodiments, the weight percentage of trehalose can vary on the weight percentage of other components in the composition like, trehalose, platelet derivatives, plasma protein, and buffering agents.

In some embodiments of any of the aspects and embodiments herein that include a composition, or in some compositions used in or formed by a process that includes a platelet composition in a powdered form, comprises trehalose and polysucrose having a combined weight percentage in the range of 30-95%, 35-95%, 40-90%, 40-90%, 45-90%, or 60-95%.

In some embodiments of any of the aspects and embodiments herein that include a composition or in some compositions used in or formed by a process herein, comprises polysucrose, the polysucrose is a cationic form of polysucrose. In some embodiments, the cationic form of polysucrose is diethylaminoethyl (DEAE)-polysucrose. In some embodiments, the polysucrose is an anionic form of polysucrose. In some embodiments, the anionic form of polysucrose is carboxymethyl-polysucrose. In some embodiments of the composition, polysucrose has a molecular weight in the range of 70,000 MW to 400,000 MW, 100,000 MW to 400,000 MW, 200,00 MW to 400,000 MW, 80,000 MW to 350,000 MW, 100,000 MW to 300,00 MW, 100,000 MW to 200,000 MW, 120,000 MW to 200,000 MW. In some exemplary embodiments, polysucrose has a molecular weight of 150,000 MW, 160,000 MW, 170,000 MW, 180,000 MW, 190,000 MW, or 200,000 MW.

In some embodiments of any of the aspects and embodiments herein that include a composition or in some compositions used in or formed by a process herein, comprises platelet derivatives that are positive for at least one platelet activation marker selected from the group consisting of Annexin V, and CD 62. In some embodiments, the platelet derivatives are positive for at least one platelet marker selected from the group consisting of CD 41, CD 42, and CD 61. In some embodiments, the platelet derivatives are positive for CD 47. In some embodiments, the platelet derivatives are positive for Annexin V. In some embodiments, the platelet derivatives are positive for Annexin V. In some embodiments, at least 25%, 50%, or 75% of the platelet derivatives in the platelet derivative composition are Annexin V positive. In some embodiments, the platelet derivatives are positive for CD 41. In some embodiments, at least 30%, 35%, 40%, 45%, 50%, 55%, 60%, or 65% of the platelet derivatives in the platelet derivative composition are CD41 positive. In some embodiments, at least 90%, 91%, 92%, 93%, 94%, 95% 96%, 97%, 98%, or 99% platelet derivatives that are positive for CD 41 have a size in the range of 0.5-2.5 µm. In some exemplary embodiments, at least 95% platelet derivatives that are positive for CD 41 have a size in the range of 0.5-2.5 µm. In some embodiments, the platelet derivatives are positive for CD 42. In some embodiments, at least 65%, 80%, or 90% of the platelet derivatives in the platelet derivative composition are CD42 positive. In some embodiments, the platelet derivatives are positive for CD 47. In some embodiments, at least 8%, 10%, 15%, or 20% of the platelet derivatives in the platelet derivative composition are CD47 positive. In some embodiments, the platelet derivatives are positive for CD 62. In some embodiments, at least 10%, 50%, 80%, or 90% of the platelet derivatives in the platelet derivative composition are CD62 positive. In some embodiments, the platelet derivatives in the platelet derivative composition are positive for CD41, CD62, and Annexin V. In some embodiments, the platelet derivatives in the platelet derivative composition are at least 50% platelet derivatives are positive for CD41, at least 70% platelet derivatives are positive for CD62, and at least 70% platelet derivatives are positive for Annexin V.

In some embodiments of any of the aspects and embodiments herein that include a composition or in some compositions used in or formed by a process herein, the platelet derivatives have fibrinogen associated with their cell membrane. In some embodiments, the platelet derivatives have at least 25%, 30%, 35%, 40%, 45%, 50%, 55%, 60%, 65%, 70%, 75%, 80%, 85%, 90%, 95%, or 100% higher fibrinogen on their surface as compared to resting platelets, or activated platelets, or fixed platelets. In some embodiments, the platelet derivatives when analyzed for the binding of anti-fibrinogen antibody to the platelet derivatives using flow cytometry exhibit at least 10, 15, 20, 25, 30, 35, or 40 folds higher mean fluorescent intensity (MFI) in the absence of an agonist as compared to the MFI of binding of anti-fibrinogen antibody to the fixed platelets.

In some embodiments of any of the aspects and embodiments herein that include a composition or in some compositions used in or formed by a process herein that includes a population of platelet derivatives in a hydrated or rehydrated form, the platelet derivatives in the platelet derivative composition retain at least 10%, or 15%, or 20% of the lactate dehydrogenase activity of donor apheresis platelets. In some embodiments, the aqueous medium has a lactate concentration of less than 2.0 mmol/L, or 1.5 mmol/L. In some embodiments, the lactate concentration is in the range of 0.4 to 1.3 mmol/L, or 0.5 to 1.0 mmol/L.

In some embodiments of any of the aspects and embodiments herein that include a composition, or in some compositions used in or formed by a process that includes a population of platelet derivatives a powdered form, the platelet derivative composition comprises no more than 0.1%, 0.2%, 0.3%, 0.4%, 0.5%, 0.6%, 0.7%, 0.8%, 0.9%, 1%, 1.5%, 2%, 2.5%, 3%, 3.5%, 4.0%, 4.5%, or 4.9% residual moisture. In some embodiments, wherein the platelet derivative composition is in a powdered form, the platelet derivative composition comprises residual moisture in the range of 0.1-2%, 0.2-1.5%, 0.5-1.5%, 0.75-1.25%, 2-3%, 2.5-4.9%, 3-4.5%, 1.5-3%, or 1-2% residual moisture. In some illustrative embodiments, the platelet derivative composition comprises no more than 0.5% residual moisture.

In some embodiments of any of the aspects and embodiments herein that include a composition, or in some compositions used in or formed by a process that includes a plurality of containers each filled with a platelet derivative composition in the form of a powder, the platelet derivative composition in at least one of the plurality of containers comprises or is associated with a first protein from a first gene that has a different amino acid sequence than found in all the versions of the first protein from the first gene in the platelet derivative composition in one or more other containers of the plurality.

In some embodiments of any of the aspects and embodiments herein that include a composition, or in some compositions used in or formed by a process that includes a plurality of containers each filled with a platelet derivative composition in the form of a powder, the at least one container comprises a first lot of platelet derivatives and the one or more other containers comprise a second lot of platelet derivatives. In some embodiments, plurality of containers comprises the platelet derivative composition from at least 2, 3, 4, 5, 6, 7, 8, 9, or 10 different lots, wherein the platelet derivative composition in at least 2 of the lots have a different amino acid sequences for at least one protein of a collection of protein gene products from a corresponding collection of encoding genes. In illustrative embodiments all, of the lots have a different amino acid sequences for at least one protein of a collection of protein gene products from a corresponding collection of encoding genes. In some embodiments, the amino acid difference(s) is at one or more residues corresponding to amino acid residues encoded by a non-synonymous single nucleotide polymorphism (SNP).

In some embodiments of any of the aspects and embodiments herein that include a composition, or in some compositions used in or formed by a process that includes a plurality of containers each filled with a platelet derivative composition in the form of a powder, each of the plurality of containers are purged with at least one inert gas. In some embodiments, the inert gas can be argon, or nitrogen.

In some embodiments of any of the aspects and embodiments herein that include a composition, or in some compositions used in or formed by a process that includes a plurality of containers each filled with a platelet derivative composition in the form of a powder, the platelet derivative composition from the at least 2 lots have different amino acid sequences for at least one protein of a collection of protein gene products from a corresponding collection of encoding genes. In some embodiments, the different amino acid sequences differ at one or more residues corresponding to amino acid residues encoded by a non-synonymous single nucleotide polymorphism (SNP). In some embodiments, the platelet derivative composition is in a container, and wherein the container is filled with at least one inert gas.

In some embodiments of any of the aspects and embodiments herein that include a composition, or in some compositions used in or formed by a process that includes a plurality of containers each filled with a platelet derivative composition in the form of a powder, the amount of plasma protein in the powder of any two containers chosen from different lots, differs by less than 50%, 40%, 30%, 20%, 10%, 5%, 2%, 1%, or 0.5%.

In some embodiments of any of the aspects and embodiments herein that include a composition, or in some compositions used in or formed by a process that includes a plurality of containers each filled with a platelet derivative composition in the form of a powder, the amount of microparticles that are less than 0.5 µm in the powder of any two containers chosen from different lots, differs by less than 50%, 40%, 30%, 20%, 10%, 5%, 2%, 1%, or 0.5%.

In some embodiments of any of the aspects and embodiments herein that include a composition, or in some compositions used in or formed by a process that includes a plurality of containers each filled with a platelet derivative composition in the form of a powder, the platelet derivative composition from the at least 2 lots have different amino acid sequences for at least one, two, three, four, or five protein of a collection of protein gene products from a corresponding collection of encoding genes. In some embodiments, the different amino acid sequences differ at one or more residues corresponding to amino acid residues encoded by a non-synonymous single nucleotide polymorphism (SNP).

In some embodiments of any of the aspects and embodiments herein that includes a plurality of containers each filled with a platelet derivative composition in the form of a powder, the containers can vary in size from 5-100 ml, 10-90 ml, 25-75 ml, or 5-40 ml. In some illustrative embodiments, the size of vials is 30 ml. In some other illustrative embodiments, the size of vials is 10 ml. In some embodiments, enough of the starting material comprising platelet composition is processed for platelet derivative composition as described herein in order to pack around 200 vials of 10 ml each. The number of vials in which the end product of platelet derivative composition can vary with the manufacturing requirements and the amount of starting material.

In some embodiments of any of the aspects and embodiments herein that include a composition, or in some compositions used in or formed by a process that includes a plurality of containers each filled with a platelet derivative composition in the form of a powder.

In some embodiments of any of the aspects and embodiments herein that include a method for treating a clotting-related disorder in a subject, said method comprising administering to the subject a therapeutically effective amount of the platelet derivative composition of any of the aspects or embodiments herein, or the platelet derivative composition prepared by any of the process described in the aspects or embodiments herein. In some embodiments, the clotting-related disorder is selected from the group consisting of Von Willebrand Disease, hemophilia, thrombasthenia, thrombocytopenia, thrombocytopenic purpura, trauma, or a combination thereof. In some embodiments, the composition is passed through a filter of 18 µm before administering to the subject.

In some embodiments, the platelet derivative composition of any of the aspects or embodiments herein is provided for use in the treatment of a disorder selected from the group consisting of alopecia areata, Von Willebrand Disease, hemophilia, thrombasthenia, thrombocytopenia, thrombocytopenic purpura, trauma, or a combination thereof.

In some embodiments, the platelet derivatives as described herein can be used for healing wounds in a subject. In some embodiments, there is provided a method for healing a wound in a subject, comprising administering a therapeutically effective amount of a platelet derivative composition of any of the aspects or embodiments herein, or the platelet derivative composition prepared by any of the process described in the aspects or embodiments herein, to the subject. In some embodiments, the platelet derivative composition of any of the aspects or embodiments herein is provided for use in wound healing in a subject.

In some embodiments, for example of aspects wherein a subject was administered the antiplatelet agent and the second agent that decreases platelet function, such a method further comprises before the administering the composition comprising FDPDs, determining that the subject was administered the antiplatelet agent and the second agent that decreases platelet function. In some embodiments, the antiplatelet agent is a first antiplatelet agent and the second agent is a second antiplatelet agent. In some embodiments, the first antiplatelet agent and the second anti-platelet agent are each different antiplatelet agents selected from aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, and sarpogrelate. In some embodiments, the first antiplatelet agent and the second anti-platelet agent have different mechanisms of action. In some embodiments, the first antiplatelet agent and the second anti-platelet agent are each different anti-platelet agents selected from aspirin, cangrelor, ticagrelor, clopidogrel, prasugrel, eptifibatide, tirofiban, abciximab, terutroban, picotamide, elinogrel, ticlopidine, ibuprofen, vora- paxar, atopaxar, cilostazol, prostaglandin E1, epoprostenol, dipyridamole, treprostinil sodium, and sarpogrelate.

In some embodiments of any of the aspects herein, before, immediately before, at the moment before, at the moment of, and/or at an initial time of, the administering of the composition comprising platelet derivatives, for example FDPDs, the subject was or is at an increased risk of bleeding due to being administered or having been administered the anti-platelet agent. Furthermore, the subject can be at an increased risk of bleeding at 7, 6, 5, 4, 3, 2, or 1 day, 12 hours, 8 hours, 4 hours, 2 hours, 1 hour or 45, 30, 15, 10, 5, 4, 3, 2, or 1 minute before the administering of the composition comprising the platelet derivatives. In some optional embodiments, this is confirmed by laboratory testing. However, in some embodiments no laboratory testing of bleeding risk or any clotting parameter is performed 7, 6, 5, 4, 3, 2, or 1 day or sooner before and/or after the administering of the composition comprising the platelet derivatives. Bleeding risk is typically decreased after administration of an effective dose of the composition comprising platelet derivatives, in illustrative embodiments FDPDs. Furthermore, the subject may remain at an increased risk of bleeding even after the administering of the composition comprising platelet derivatives (e.g. FDPDs), for example for 1, 2, 3, 4, 5, 10, 15, 20, 30, or 45 minutes, or 1, 2, 3, 4, 5, or 8 hours, or longer after the administering, depending on how long it takes for the FDPDs to decrease the risk in the subject after they are administered. Furthermore, in some embodiments, the administration of the composition comprising the platelet derivatives (e.g. FDPDs) decreases but does not completely resolve the increased risk of bleeding in the subject.

In some embodiments, for example of aspects wherein a subject was administered the antiplatelet agent and the second agent that decreases platelet function, administration of the second agent is stopped, for example before administrating the composition comprising the platelet derivatives. In other embodiments of such aspects, administration of the second agent is continued, for example after administering the composition comprising the platelet derivatives.

In certain embodiments of any of the aspects provided herein, the method further comprises before administering the composition comprising platelet derivatives, determining in a pre-administering evaluation, that the subject has an abnormal value for one or more clotting parameters. The pre-administration evaluation, in illustrative embodiments, is an in vitro laboratory test.

In certain embodiments of any of the aspects provided herein, the antiplatelet agent is selected from aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, and sarpogrelate. In other embodiments, the anti-platelet agent is selected from cangrelor, ticagrelor, abciximab, terutroban, picotamide, elinogrel, ibuprofen, vorapaxar, atopaxar, cilostazol, prostaglandin E1, epoprostenol, dipyridamole, treprostinil sodium, and sarpogrelate.

In certain embodiments of any of the aspects provided herein, the FDPDs comprise (detectable amounts of) a biomolecule (e.g. receptor) targeted by the anti-platelet reversal agent that was administered or is being administered to the subject. In some embodiments the receptor is selected from a P2Y receptor (e.g., the P2Y12 receptor), glycoprotein IIb (i.e. CD41), glycoprotein IIIa (CD61), the glycoprotein IIb/IIIa complex, thromboxane synthase or thromboxane receptors, PAR1, PAR4, VPVI, or collagen receptor (e.g. alpha2beta1 collagen receptor). Provided in other sections herein are examples of anti-platelet agents that target these specific biomolecules. In certain embodiments, at least 55%, 60%, 70%, 75%, 80%, 85%, 90%, or 95% of the platelet derivatives, in illustrative embodiments FDPDs, are positive for (i.e. have detectable levels of) a biomolecule targeted by the anti-platelet agent administered to the subject and/or detectable in the blood of the subject. As noteworthy non-limiting examples, the anti-platelet agent inhibits the glycoprotein CDIIb/IIIa complex, and at least 55%, 60%, 70%, 75%, 80%, 85%, 90%, or 95% of the platelet derivatives, in illustrative embodiments FDPDs, are CD41 positive (i.e. comprise detectable CD41) and/or are positive for the CDIIb/IIIa complex.

In certain embodiments of any of the aspects provided herein, the composition comprising FDPDs comprises a population of FDPDs having a reduced propensity to aggregate such that no more than 2%, 3%, 4%, 5%, 7.5%, 10%, 12.5%, 15%, 17.5%, 20%, 22.5%, or 25% of the FDPDs in the population aggregate under aggregation conditions comprising an agonist but no platelets. In certain embodiments of any of the aspects provided herein, including for example, embodiments where the composition comprises FDPDs comprises a population of FDPDs having a reduced propensity to aggregate such that no more than 10% of the FDPDs in the population aggregate under aggregation conditions comprising an agonist but no platelets, the FDPDs have a potency of at least 1.2 (e.g., at least 1.3, 1.4, 1.5, 1.6, 1.7, 1.8, 1.9, 2.0, 2.1, 2.2, 2.3, 2.4, or 2.5) thrombin generation potency units (TGPU) per $10^6$ particles. For example, in some cases, platelets or platelet derivatives (e.g., FDPDs) can have a potency of between 1.2 and 2.5 TPGU per $10^6$ particles (e.g., between 1.2 and 2.0, between 1.3 and 1.5, between 1.5 and 2.25, between 1.5 and 2.0, between 1.5 and 1.75, between 1.75 and 2.5, between 2.0 and 2.5, or between 2.25 and 2.5 TPGU per $10^6$ particles).

In certain embodiments of any of the aspects provided herein, including for example, embodiments where the composition comprises FDPDs comprises a population of FDPDs having a reduced propensity to aggregate such that no more than 10% of the FDPDs in the population aggregate under aggregation conditions comprising an agonist but no platelets, the FDPDs have having one or more characteristics of a super-activated platelet selected from
A) the presence of thrombospondin (TSP) on their surface at a level that is greater than on the surface of resting platelets;
B) the presence of von Willebrand factor (vWF) on their surface at a level that is greater than on the surface of resting platelets; and
C) an inability to increase expression of a platelet activation marker in the presence of an agonist as compared to the expression of the platelet activation marker in the absence of an agonist.

In certain embodiments of any of the aspects provided herein wherein the composition comprising FDPDs comprises a population of FDPDs comprising CD 41-positive platelet derivatives, including non-limiting embodiments where the population comprises FDPDs have a reduced propensity to aggregate such that no more than 10% of the FDPDs in the population aggregate under aggregation conditions comprising an agonist but no platelets, the FDPDs have an inability to increase expression of a platelet activation marker in the presence of an agonist as compared to the expression of the platelet activation marker in the absence of the agonist. In some embodiments of such methods, the FDPDs have a potency of at least 1.5 thrombin generation potency units (TGPU) per $10^6$ platelet derivatives. In some embodiments of such methods, less than 5% of the CD 41-positive FDPDs are microparticles having a diameter of less than 0.5 µm.

In certain embodiments of any of the aspects provided herein, including non-limiting embodiments where the population comprises FDPDs have a reduced propensity to aggregate such that no more than 10% of the FDPDs in the population aggregate under aggregation conditions comprising an agonist but no platelets, the FDPDs further have one or both of: the presence of thrombospondin (TSP) on their surface at a level that is greater than on the surface of resting platelets; and the presence of von Willebrand factor (vWF) on their surface at a level that is greater than on the surface of resting platelets.

In certain embodiments of any of the aspects provided herein, the composition comprising FDPDs comprises a population of FDPDs comprising
  a population of platelet derivatives comprising CD 41-positive platelet derivatives, wherein less than 5% of the CD 41-positive platelet derivatives are microparticles having a diameter of less than 0.5 µm, and comprising platelet derivatives having one or more, or in illustrative embodiments all of the following characteristics:
  a reduced propensity to aggregate such that no more than 10% of the platelet derivatives in the population aggregate under aggregation conditions comprising an agonist but no platelets;
  an inability to increase expression of a platelet activation marker in the presence of an agonist as compared to the expression of the platelet activation marker in the absence of the agonist;
  the presence of thrombospondin (TSP) on their surface at a level that is greater than on the surface of resting platelets;
  the presence of von Willebrand factor (vWF) on their surface at a level that is greater than on the surface of resting platelets; and
  a potency of at least 1.5 thrombin generation potency units (TGPU) per $10^6$ platelet derivatives.

In some embodiments of any aspects herein, the platelet derivatives, and in illustrative embodiments FDPDs, are surrounded by a compromised plasma membrane. In such embodiments, the platelet derivatives lack an integrated membrane around them. In such embodiments, the platelet derivatives are not surrounded by an integrated membrane. Instead, the membrane comprises pores that are larger than pores observed on living cells. Thus, such platelet derivatives have a reduced ability to, or are unable to transduce signals from the external environment into a response inside the particle that are typically transduced in living platelets. Furthermore, such platelet derivatives (e.g. FDPDs) are not believed to be capable of mitochondrial activation or glycolysis.

In some embodiments of any aspects herein, the effective amount of the composition comprising FDPDs is between $1.0 \times 10^7$ to $1.0 \times 10^{11}$ particles or FDPDs/kg of the subject. In some embodiments of any of the aspects herein, the effective amount of the composition comprising FDPDs is between $1.6 \times 10^7$ to $5.1 \times 10^9$ particles or FDPDs/kg of the subject. In some embodiments of any of the aspects herein, which can be combined with either of the above embodiments with ranges of particles or FDPDs/kg, the effective amount of the composition comprising FDPDs is an amount that has a potency between 250 and 5000 TGPU per kg of the subject. Further examples of effective amounts are provided in a different section herein.

In one aspect, provided herein is a method of treating a coagulopathy in a subject, or of restoring hemostasis in a subject, or of reducing bleeding potential of a subject that is being administered, or has been administered, an antiplatelet agent, the method comprising: administering to the subject in need thereof an effective amount of a composition comprising platelet derivatives, thereby treating the coagulopathy, wherein the composition comprising FDPDs has the property that it is capable of reducing the bleeding potential of the subject, independent of whether a post-administering evaluation of bleeding potential, if performed, would yield a normal or abnormal result.

In any of the aspects herein, in some embodiments, the composition comprising FDPDs has the property that it is capable of reducing the bleeding potential of the subject, independent of whether a post-administering evaluation of bleeding potential, if performed, would yield a normal or abnormal result. In some optional embodiments, which in some embodiments is performed and in some embodiments is not performed, such post-administering evaluation comprises an in vitro laboratory test performed on a sample taken or drawn in a time period after administering the composition comprising FDPDs to the subject. In other embodiments of any of the aspects herein, wherein the composition comprising FDPDs has the property that it is capable of reducing the bleeding potential of a subject having an increased bleeding potential, and in some embodiments an abnormal value for one or more clotting parameters in an in vitro laboratory test, such that normal hemostasis is restored in the subject, independent of whether a post-administering evaluation of bleeding potential, if performed would yield a normal or abnormal result. In some embodiments, such post-administering evaluation comprises an in vitro laboratory test performed on a sample taken or drawn in a time period after administering the composition comprising FDPDs to the subject. The time period, can be for example, within 0 minutes and 72 hours, or between 10 minutes and 72 hours, or between 10 minutes and 48 hours, or between 10 minutes 24 hours, or between 10 minutes and 4 hours, or between 10 minutes and 1 hour, or between 10 minutes and 30 minutes, or between 30 minutes and 24 hours, or between 30 minutes and 4 hours, or between 30 minutes and 1 hour after administering the composition comprising the platelet derivatives (e.g. FDPDs) to the subject. For example, the time period in certain embodiments is between 1 and 4 hours after administering the composition comprising the platelet derivatives (e.g. FDPDs). In some embodiments of any of the aspects herein, a pre or post administration of the composition comprising platelet derivatives is not performed, for example during the recited time periods above.

In any of the aspects herein, in some embodiments the composition comprising platelet derivatives (e.g. FDPDs) has the property that it is capable of reducing the bleeding potential of a subject having an increased or elevated bleeding potential. In some embodiments, such increased or elevated bleeding potential can be determined by abnormal value for one or more clotting parameters in an in vitro laboratory test performed on a sample taken within 0 minutes and 72 hours, or between 10 minutes and 72 hours, or between 10 minutes and 48 hours, or between 10 minutes 24 hours, or between 10 minutes and 4 hours, or between 10 minutes and 1 hour, or between 10 minutes and 30 minutes, or between 30 minutes and 24 hours, or between 30 minutes and 4 hours, or between 30 minutes and 1 hour before administering the composition comprising the platelet derivatives (e.g. FDPDs). Furthermore, the composition comprising FDPDs typically has the additional and surprising property, that after being administered to the subject in an effective amount, for example for reducing the bleeding potential of the subject, the subject has an abnormal value for the one or more in vitro lab tests, for example of one or more clotting parameters in a post-administering evaluation performed using an, or the in vitro laboratory test performed on a blood sample taken between 15 minutes and 4 hours, 30 minutes and 4 hours, 1 hour and 4 hours, or taken between 15 minutes and 2 hours, 30 minutes and 2 hours, or 1 hour and 2 hours, or taken between 15 minutes and 1 hour or 30 minutes and 1 hour, after administering the composition comprising FDPDs. In some subembodiments of this embodiment, the composition comprising FDPDs has the property that it is capable of reducing the bleeding potential of a subject to about or at a normal hemostasis or about or at the hemostasis level of the subject when not taking the antiplatelet agent. Yet, in these embodiments, the composition comprising FDPDs retains the additional and surprising property, that after being administered to the subject in the effective amount, such a property is independent of a post-administering lab test for bleeding potential. Thus, in some embodiments, the subject would have an abnormal value for the one or more clotting parameters in a post-administering evaluation performed using an, or the in vitro laboratory test performed on a blood sample taken between 1 and 4 hours, or any of the time ranges recited immediately above, after administering the composition comprising FDPDs. It will be understood that in methods that include compositions comprising FDPDs with such properties, or any properties that include an evaluation or test, no testing actually needs to be performed to practice such methods unless such testing step is actually recited as a method step.

In any of the aspects herein, in illustrative embodiments the composition comprising platelet derivatives or FDPDs further comprises additional components, such as components that were present when such platelet derivatives were dried, or FDPDs were freeze-dried. Such additional components can include components of an incubating agent comprising one or more salts, a buffer, and in certain embodiments a cryoprotectant (also called a lyophilizing agent) and/or an organic solvent. For example, such compositions can comprise one or more saccharides, as provided further herein, which in illustrative embodiments include trehalose and in further illustrative embodiments include polysucrose.

In any of the aspects herein, in some embodiments the FDPDs are prepared using centrifugation. In some illustrative embodiments, the FDPDs are prepared using TFF, in further illustrative embodiments without isolating platelets by centrifugation during the process.

In some embodiments of any of the aspects herein, the method further includes determining the value of one or more clotting parameters in a post-administering evaluation, wherein the post-administering evaluation is performed following the administering. In some embodiments the post-administering evaluation of the one or more clotting parameters shows a normal value for at least one of the one or more clotting parameters. In further embodiments the method the result of the post-administering evaluation of the one or more clotting parameters is improved from the result of the evaluation of the one or more parameters prior to the administering.

In further embodiments of the method the administering of the antiplatelet agent contrary to medical instruction is self-administering by the subject, is administered by another, or is administering by a medical professional.

In some embodiments of any of the aspects or embodiments herein that include a second agent, typically a second agent that decreases platelet function, the second agent is selected from the group consisting of an antihypertensive, a proton pump inhibitor, and a combination thereof. In some embodiments the second agent is selected from the group consisting of a chemotherapeutic agent, an antibiotic, a cardiovascular agent, a H2 antagonist, a neuropsychiatric agent and a combination thereof. In some embodiments the second agent comprises an antidepressant. In further embodiments the antidepressant is selected from the group consisting of a selective serotonin reuptake inhibitor (SSRI), a serotonin antagonist and reuptake inhibitor (SARI), a serotonin and norepinephrine reuptake inhibitor (SNRI), and a combination thereof. In some embodiments the second agent is not an anticoagulant.

In any of the aspects herein, in some embodiments, administration of the antiplatelet agent is stopped before or when a composition comprising platelet derivatives (e.g. FDPDs) is administer to a subject. In some aspects of the method, administration of the antiplatelet agent is continued after a composition comprising platelet derivatives (e.g. FDPDs) is administer to a subject.

In any of the aspects herein, in some embodiments further comprise determining that the subject has an abnormal value for one or more clotting parameters in a pre-administering evaluation. In some aspects of the method, the method comprises determining the value of one or more clotting parameters in a post-administering evaluation. In some embodiments the post-administering evaluation of the one or more clotting parameters shows a normal result for at least one of the one or more clotting parameters. In some embodiments the result of the post-administering evaluation of the one or more clotting parameters is improved from the result of the evaluation of the one or more parameters prior to the administering.

In any of the aspects herein, in some embodiments, the subject is identified as having an abnormal result for one or more pre-administering evaluations of clotting parameters during surgery. In some embodiments the surgery is an emergency surgery. In some embodiments the surgery is a scheduled surgery.

In any of the aspects herein, in some embodiments, the clotting parameters includes an evaluation of bleeding. In some embodiments the evaluation of bleeding is performed based on the World Health Organization (WHO) bleeding scale. In some embodiments of the method, before administering, the subject has bleeding of grade 2, 3, or 4 based on the WHO bleeding scale; In some embodiments of the method, after administering, the subject has bleeding of grade 0 or 1 based on the WHO bleeding scale. In some embodiments, after the administering, the subject has bleeding of one grade less, based on the WHO bleeding scale, than before the administering. In some embodiments, after the administering, the subject has bleeding of two grades less, based on the WHO bleeding scale, than before the administering. In some embodiments, after the administering, the subject has bleeding of three grades less, based on the WHO bleeding scale, than before the administering.

In any of the aspects herein, in some embodiments, evaluation of the clotting parameters includes an evaluation of prothrombin time (PT). In some embodiments, abnormal results for PT comprises a PT of greater than about 14 seconds. In some embodiments, after the administering, the subject has a decrease in PT of at least 1, 2, 3, 4, 5, or more, seconds. In some embodiments, after the administering, the subject has a normal PT.

In any of the aspects herein, in some embodiments, the one or more clotting parameters includes an evaluation of activated partial thromboplastin time (aPTT). In some embodiments, the abnormal result for aPTT comprises an aPTT of greater than about 40 seconds. In some embodiments, after the administering, the subject has a decrease in aPTT of at least 5, 10, 15, 20, or more, seconds. In some embodiments, after the administering, the subject has a normal aPTT.

In any of the aspects herein, in some embodiments, the one or more clotting parameters includes an evaluation of thrombin clot time (TCT). In some embodiments, the abnormal result for TCT comprises a TCT of greater than about 35 seconds. In some embodiments, after the administering, the subject has a decrease in TCT of at least 5, 10, 15, 20, or more, seconds. In some embodiments, after the administering, the subject has a normal TCT.

In any of the aspects herein, in some embodiments, the evaluation of the one or more clotting parameters is measured using thromboelastography (TEG). In some embodiments, the abnormal result for TEG comprises a maximum amplitude (MA) of less than about 50 mm. In some embodiments, after the administering, the subject has an increase in MA of at least 5, 10, 15, 20, or more, mm. In some embodiments, after the administering, the subject has a normal MA.

In any of the aspects herein, in some embodiments, the abnormal result for TEG comprises a percent aggregation (in the presence of 1 mmol/L arachidonic acid) of less than about 85%. In some embodiments, after the administering, the subject has an increase in percent aggregation (in the presence of 1 mmol/L arachidonic acid) of at least 2, 3, 5, 8, 10, 12, or more, percentage points. In some embodiments, after the administering, the subject has a normal percent aggregation (in the presence of 1 mmol/L arachidonic acid). In some embodiments, the TEG is used to evaluate adenosine diphosphate-induced platelet-fibrin clot strength. In some aspects of the method, the TEG is used to evaluate arachidonic acid-induced platelet-fibrin clot strength.

In any of the aspects herein, in some embodiments, the evaluation of one or more clotting parameters is measured using an P2Y12 Reaction Units (PRU) or Aspirin Reaction Units (ARU) test method.

In any of the aspects herein, in some embodiments, the abnormal result of the P2Y12 reaction unit test method comprise a PRU of less than about 195, or less than about 180. In some embodiments, after the administering, the subject has an increase in PRU of at least 25, 50, 75, 100, or more. In some embodiments, after the administering, the subject has a normal PRU.

In any of the aspects herein, in some embodiments, the abnormal result of the Aspirin Reaction Unit test method comprise an ARU of less than about 550, or less than about 500. In some embodiments, after the administering, the subject has an increase in ARU of at least 25, 50, 75, 100, or more. In some embodiments, after the administering, the subject has a normal ARU.

In any of the aspects herein, in some embodiments, the one or more clotting parameters is measured using multiple electrode aggregometry (MEA). In some embodiments, the abnormal result using MEA comprises an abnormal result for ADP-induced platelet activity. In some embodiments, the abnormal result for MEA comprises a result of less than about 50 units (U) for ADP-induced platelet activity. In some embodiments, after the administering, the subject has an increase in ADP-induced platelet activity by 5, 10, 15, 20, or more units. In some embodiments, after the administering, the subject has a normal value for ADP-induced platelet activity. In some embodiments, the abnormal result for MEA comprises an abnormal result for arachidonic acid-induced platelet activity. In some embodiments, the abnormal result for MEA comprises a result of less than about 70 units (U) for arachidonic acid-induced platelet activity. In some embodiments, after the administering, the subject has an increase in arachidonic acid-induced platelet activity by 5, 10, 15, 20, or more units. In some embodiments, after the administering, the subject has a normal value for arachidonic acid-induced platelet activity.

In any of the aspects herein, in some embodiments, the one or more clotting parameters is measured using light transmission aggregometry (LTA).

In any of the aspects herein, in some embodiments, the abnormal result for LTA comprises one or more of the following: (a) in the presence of 5 µmol/L adenosine diphosphate, a percent aggregation of less than about 60%; (b) in the presence of 2 µg/mL collagen, a percent aggregation of less than about 65%; (c) in the presence of 1 mmol/L arachidonic acid, a percent aggregation of less than about 65%; (d) in the presence of 2 mmol/L arachidonic acid, a percent aggregation of less than about 69%; or (e) in the presence of 5 mmol/L arachidonic acid, a percent aggregation of less than about 73%.

In any of the aspects herein, in some embodiments, after the administering, the subject has an increase in percent aggregation (in the presence of 5 µmol/L adenosine diphosphate) of at least 2, 3, 5, 8, 10, 12, or more, percentage points. In some embodiments, after the administering, the subject has a normal percent aggregation (in the presence of 5 µmol/L adenosine diphosphate).

In any of the aspects herein, in some embodiments, after the administering, the subject has an increase in percent aggregation (in the presence of 2 µg/mL collagen) of at least 2, 3, 5, 8, 10, 12, or more, percentage points. In some embodiments, after the administering, the subject has a normal percent aggregation (in the presence of 2 µg/mL collagen).

In any of the aspects herein, in some embodiments, the administering, the subject has an increase in percent aggregation (in the presence of 1 mmol/L arachidonic acid) of at least 2, 3, 5, 8, 10, 12, or more, percentage points. In some embodiments, after the administering, the subject has a normal percent aggregation (in the presence of 1 mmol/L arachidonic acid). In some embodiments, after the administering, the subject has an increase in percent aggregation (in the presence of 2 mmol/L arachidonic acid) of at least 2, 3, 5, 8, 10, 12, or more, percentage points. In some embodiments, after the administering, the subject has a normal percent aggregation (in the presence of 2 mmol/L arachidonic acid). In some embodiments, after the administering, the subject has an increase in percent aggregation (in the presence of 5 mmol/L arachidonic acid) of at least 2, 3, 5, 8, 10, 12, or more, percentage points. In some embodiments, after the administering, the subject has a normal percent aggregation (in the presence of 5 mmol/L arachidonic acid).

In any of the aspects herein, in some embodiments, the method further comprises administering to the subject an additional antiplatelet agent reversal agent. In some embodiments, the administering of the composition occurs concurrently with administering of the additional antiplatelet agent reversal agent. In some embodiments, the administering of the composition occurs after administering of the additional antiplatelet agent reversal agent. In some embodiments, the administering of the composition occurs before administering of the additional antiplatelet agent reversal agent.

In any of the aspects herein, in some embodiments, the composition further comprises an anti-fibrinolytic agent. In some embodiments, the anti-fibrinolytic agent is selected from the group consisting of ε-aminocaproic acid (EACA), tranexamic acid, aprotinin, aminomethylbenzoic acid, fibrinogen, and a combination thereof. In some embodiments, the platelets or platelet derivatives are loaded with the anti-fibrinolytic agent.

In any of the aspects herein, in some embodiments, administering comprises administering topically, parenterally, intravenously, intramuscularly, intrathecally, subcutaneously, intraperitoneally, or a combination thereof.

In any of the aspects herein, in some embodiments, the composition is dried prior to the administration step. In some embodiments, the composition is rehydrated following the drying step.

In any of the aspects herein, in some embodiments, the composition is freeze-dried prior to the administration step. In some embodiments, the composition is rehydrated following the freeze-drying step.

In any of the aspects herein, in some embodiments, the incubating agent comprises one or more salts selected from phosphate salts, sodium salts, potassium salts, calcium salts, magnesium salts, and a combination of two or more thereof. In some embodiments, the incubating agent comprises a carrier protein. In some embodiments the incubating agent comprises a buffer that comprises HEPES, sodium bicarbonate ($NaHCO_3$), or a combination thereof.

In any of the aspects herein, in some embodiments, the composition comprises one or more saccharides. In some embodiments, the one or more saccharides comprise trehalose. In some embodiments, the one or more saccharides comprise polysucrose. In some embodiments, the one or more saccharides comprise dextrose.

In some aspects of the method, the composition comprises an organic solvent.

In some embodiments of any of the aspects herein, the antiplatelet agent is present in the subject at the time the composition comprising the FDPDs is administered at a level that increases the bleeding potential of the subject. In some embodiments, the antiplatelet agent is present at a Cmax within 15, 30 or 45 minutes, or within 1, 2, 3, 4, 6, or 8 hours of the time the composition comprising the FDPDs is administered or the time the first or last dose of the composition comprising the FDPDs is administered In any of the aspects herein, in some embodiments, the antiplatelet agent comprises aspirin that has been administered or is being administered at a dosage of about 80 mg to about 700 mg, once, twice, three times, or four times a day. In some embodiments, the antiplatelet agent comprises aspirin, that has been adminstered, or is being adminstered, to the subject such that the subject achieved a $C_{max}$ of about 3 to about 25 mg/L.

In any of the aspects herein, in some embodiments, the antiplatelet agent comprises cangrelor that has been administered, or is being administered, to the subject at an initial dosage of about 25 to about 30 µg/kg body weight of the subject or a following dosage of about 3 to about 5 µg/kg/min body weight of the subject. In some embodiments, the antiplatelet agent comprises cangrelor that has been administered, or is being administered, to the subject such that the subject achieved a $C_{max}$ of about 400 to about 500 ng/mL.

In any of the aspects herein, in some embodiments, the antiplatelet agent comprises ticagrelor that has been administered, or is being administered, to the subject at an initial dosage of about 170 to about 190 mg, or a following dosage in a first year of treatment of about 80 to about 100 mg twice daily, or a following dosage in a second year of treatment of about 50 to about 70 mg twice daily, optionally in combination with aspirin. In some embodiments the antiplatelet agent comprises ticagrelor, that has been administered, or is being administered, to the subject such that the subject achieved a $C_{max}$ of about 550 to about 650 ng/mL.

In any of the aspects herein, in some embodiments, the antiplatelet agent comprises clopidogrel that has been administered, or is being administered, to the subject at an initial dosage of about 275 to about 325 mg, or a following dosage of about 70 to about 80 mg once daily, optionally in combination with aspirin. In some embodiments, the antiplatelet agent comprises clopidogrel, that has been administered or is being administered to the subject such that the subject achieved a $C_{max}$ of about 6 to about 20 ng/mL.

In any of the aspects herein, in some embodiments, the antiplatelet agent comprises prasugrel that has been administered, or is being administered, to the subject at an initial dosage of about 50 to about 70 mg, or a following dosage of about 3 to about 12 once daily, optionally in combination with aspirin. In some embodiments, the antiplatelet agent comprises prasugrel that has been administered, or is being administered, to the subject such that the subject achieved a $C_{max}$ of about 200 to about 525 ng/mL.

In any of the aspects herein, in some embodiments, the antiplatelet agent comprises eptifibatide that has been administered, or is being administered, to the subject at an initial dosage of about 170 to about 190 mcg/kg body weight of the subject, optionally a second initial dosage of about 170 to about 190 mcg/kg body weight of the subject, or a following dose of about 1 to about 2 mcg/kg body weight of the subject/min.

In any of the aspects herein, in some embodiments, the antiplatelet agent comprises tirofiban that has been administered, or is being administered, to the subject at an initial dosage of about 0.3 to about 0.5 µg/kg body weight of the subject/min for about 30 minutes, or a following dosage of about 0.1 µg/kg body weight of the subject/min.

In any of the aspects herein, in some embodiments, antiplatelet agent comprises abciximab that has been administered, or is being administered, to the subject at an initial dosage of about 0.2 to about 0.3 mg/kg body weight of the subject, or a following dosage of about 0.10 to about 0.15 µg/kg body weight of the subject/min. In some embodiments, the antiplatelet agent comprises abciximab that has been administered, or is being administered, to the subject at an initial dosage of about 0.2 to about 0.3 mg/kg body weight of the subject, or a following dosage of about 8 to about 10 µg/min.

In any of the aspects herein, in some embodiments, the antiplatelet agent comprises ticlopidine that has been administered, or is being administered, to the subject at a dosage of about 240 to about 260 mg twice per day.

In any of the aspects herein, in some embodiments, the antiplatelet agent comprises ibuprofen that has been administered, or is being administered, to the subject at a dosage of about 100 to about 600 mg once, twice, three times, or four times per day.

In any of the aspects herein, in some embodiments, the antiplatelet agent comprises vorapaxar that has been administered, or is being administered, to the subject at a dosage of about 2 to about 3 mg once per day, optionally with aspirin or clopidogrel.

In any of the aspects herein, in some embodiments, the antiplatelet agent comprises cilostazol that has been administered, or is being administered, to the subject at a dosage of about 40 to about 110 mg twice daily.

In any of the aspects herein, in some embodiments, the antiplatelet agent comprises epoprostenol that has been administered, or is being administered, to the subject at an initial dosage of about 2 ng/kg body weight of the subject/min, or a following dosage of about 4, 6, 8, 10, 12, 14, 16, 18, or 20 ng/kg body weight of the subject/min.

In any of the aspects herein, in some embodiments, the antiplatelet agent comprises dipyridamole that has been administered, or is being administered, to the subject at a dosage of about 60 to about 110 mg four times daily.

In any of the aspects herein, in some embodiments, the antiplatelet agent comprises treprostinil sodium that has been administered, or is being administered, to the subject at a dosage of about 0.5 to about 1.3 ng/kg body weight of the subject/min.

In any of the aspects herein, in some embodiments, some aspects of the method, the subject does not have cancer.

Any of the method aspects herein, can be uses for a composition comprising platelet derivatives (e.g. FDPDs) provided herein, or uses for a kit comprising such composition, as set out in the following aspects that include such "use" language. It will be understood that where such aspects refer to FDPDs, they could refer to platelet derivatives instead. It will be further understood that such aspects can include any of the elements provided herein for method aspects, and any of the embodiments provided herein. For example, administering of an effective amount of composition comprising platelet derivatives (e.g. FDPDs) can be such that the bleeding potential of the subject is reduced, and in illustrative embodiments normal hemostasis is restored. Where such aspects refer to a disorder, the disorder in illustrative embodiments, is a bleeding disorder. Such disorder can be identified, for example, because a sample from a subject having such disorder yields an abnormal value for one or more clotting parameters.

In one aspect, provided herein is a use of a composition comprising platelet derivatives, in illustrative embodiments freeze-dried platelet derivatives (FDPDs), in the manufacture of a kit for treating a coagulopathy in a subject that is being administered or has been administered an antiplatelet agent, wherein the use of the kit comprises: (a) determining in a pre-administering evaluation, that the subject has an abnormal value for one or more clotting parameters; and (b) after (a), administering to the subject in need thereof an effective amount of a composition comprising freeze-dried platelet derivatives (FDPDs). In some embodiments, the use further comprises before the administering, determining that the subject was administered an anti-platelet agent. In some embodiments, the use further comprises before the administering, determining that information regarding whether the subject was administered an antiplatelet agent is unavailable. In some embodiments, the use further comprises determining that the subject has an abnormal value for one or more clotting parameters in a pre-administering evaluation before the administering of the composition comprising freeze-dried platelet derivatives. In some embodiments, the antiplatelet agent is a first antiplatelet agent and the second agent is a second antiplatelet agent.

In one aspect, provided herein is a use of a composition comprising platelet derivatives, in illustrative embodiments freeze-dried platelet derivatives (FDPDs), in the manufacture of a kit for treating a coagulopathy in a subject that is being administered or has been administered an antiplatelet agent, wherein the use of the kit comprises: administering to the subject in need thereof an effective amount of the FDPDs, wherein the composition comprising FDPDs comprises a population of FDPDs having a reduced propensity to aggregate such that no more than 10% of the FDPDs in the population aggregate under aggregation conditions comprising an agonist but no platelets.

In one aspect, provided herein is a use of a composition comprising platelet derivatives, in illustrative embodiments freeze-dried platelet derivatives (FDPDs), in the manufacture of a kit for treating a coagulopathy in a subject, wherein the use of the kit comprises: administering to the subject in need thereof an effective amount of a composition comprising freeze-dried platelet derivatives (FDPDs), wherein the subject was administered an antiplatelet agent and a second agent that decreases platelet function.

In one aspect, provided herein is a use of a composition comprising platelet derivatives, in illustrative embodiments freeze-dried platelet derivatives (FDPDs), of any aspect provided herein, in the manufacture of a kit for treating coagulopathy in a subject that is being administered or has been administered an antiplatelet agent.

In one aspect, provided herein is a use of a composition comprising platelet derivatives, in illustrative embodiments freeze-dried platelet derivatives (FDPDs), of any aspect provided herein, in the preparation of a medicament for use in treating coagulopathy in a subject that is being administered or has been administered an antiplatelet agent.

In one aspect, provided herein is a composition comprising platelet derivatives, in illustrative embodiments freeze-dried platelet derivatives (FDPDs), of any aspect provided herein, for use in the manufacture of a kit for treating coagulopathy in a subject that is being administered or has been administered an antiplatelet agent.

In one aspect, provided herein is a composition comprising platelet derivatives, in illustrative embodiments freeze-dried platelet derivatives (FDPDs), of any aspect provided herein, for use as a medicament for treating coagulopathy in a subject that is being administered or has been administered an antiplatelet agent.

In one aspect, provided herein is a composition comprising platelet derivatives, in illustrative embodiments freeze-dried platelet derivatives (FDPDs), of any aspect provided herein, for use in the treatment of coagulopathy in a subject that is being administered or has been administered an antiplatelet agent.

In one aspect, provided herein is a composition comprising platelet derivatives, in illustrative embodiments freeze-dried platelet derivatives (FDPDs), of any aspect provided herein, for use in the manufacture of a kit for treating a disorder in a subject that is being administered or has been administered an antiplatelet agent.

In one aspect, provided herein is a composition comprising platelet derivatives, in illustrative embodiments freeze-dried platelet derivatives (FDPDs), of any aspect provided herein, for use as a medicament for treating a disorder in a subject that is being administered or has been administered an antiplatelet agent.

In one aspect, provided herein is a composition comprising platelet derivatives, in illustrative embodiments freeze-dried platelet derivatives (FDPDs), of any aspect provided herein, for use in the treatment of a disorder in a subject that is being administered or has been administered an antiplatelet agent.

In any of the aspects provided herein that include a composition comprising platelet derivatives, in illustrative embodiments freeze-dried platelet derivatives (FDPDs), for use in the treatment of a disorder, or in the manufacture of a kit, or as a medicament, the disorder is selected from the group consisting of alopecia areata, Von Willebrand Disease, hemophilia, thrombasthenia, thrombocytopenia, thrombocytopenic purpura, trauma, or a combination thereof.

In any of the aspects provided herein that include a composition comprising platelet derivatives, in illustrative embodiments freeze-dried platelet derivatives (FDPDs), for use in the treatment of coagulopathy or a disorder, or in the manufacture of a kit, or as a medicament, the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, sarpogrelate, and a combination thereof.

In any of the aspects provided herein that include a composition comprising platelet derivatives, in illustrative embodiments freeze-dried platelet derivatives (FDPDs), for use in the treatment of coagulopathy or a disorder, or in the manufacture of a kit, or as a medicament, wherein the treatment, or the use of the kit, or the medicament comprises: administering to the subject in need thereof an effective amount of the FDPDs, wherein the composition comprising FDPDs comprises a population of FDPDs having a reduced propensity to aggregate such that no more than 10% of the FDPDs in the population aggregate under aggregation conditions comprising an agonist but no platelets. In some embodiments, the FDPDs have a potency of at least 1.5 thrombin generation potency units (TGPU) per $10^6$ platelet derivatives.

In any of the aspects provided herein that include a composition comprising platelet derivatives, in illustrative embodiments freeze-dried platelet derivatives (FDPDs), for use in the treatment of coagulopathy or a disorder, or in the manufacture of a kit, or as a medicament, wherein at least 50% of the FDPDs are CD 41-positive platelet derivatives, wherein less than 5% of the CD 41-positive FDPDs are microparticles having a diameter of less than 0.5 μm, and wherein the FDPDs have a potency of at least 1.5 thrombin generation potency units (TGPU) per $10^6$ platelet derivatives.

In any of the aspects provided herein that include a composition comprising platelet derivatives, in illustrative embodiments freeze-dried platelet derivatives (FDPDs), for use in the treatment of coagulopathy or a disorder, or in the manufacture of a kit, or as a medicament, wherein the FDPDs have one or more characteristics of a super-activated platelet selected from A) the presence of thrombospondin (TSP) on their surface at a level that is greater than on the surface of resting platelets; B) the presence of von Willebrand factor (vWF) on their surface at a level that is greater than on the surface of resting platelets; and C) an inability to increase expression of a platelet activation marker in the presence of an agonist as compared to the expression of the platelet activation marker in the absence of an agonist.

In any of the aspects provided herein that include a composition comprising platelet derivatives, in illustrative embodiments freeze-dried platelet derivatives (FDPDs), for use in the treatment of coagulopathy or a disorder, or in the manufacture of a kit, or as a medicament, wherein the effective amount of the composition comprising FDPDs is between $1.0 \times 10^7$ to $1.0 \times 10^{11}$/kg of the subject. In some embodiments, the effective amount of the composition comprising FDPDs is between $1.6 \times 10^7$ to $5.1 \times 10^9$/kg of the subject. In some embodiments, the effective amount of the composition comprising FDPDs is between an amount that has a potency between 250 and 5000 TGPU per kg of the subject. In some embodiments, the effective amount of the composition comprising FDPDs is between an amount that has a potency between 300 to 3800 TGPU per kg.

Further exemplary aspects and embodiments are provided as follows:

Provided herein in some embodiments is a method of treating a coagulopathy in a subject, the method including administering to the subject in need thereof an effective amount of a composition including platelets or platelet derivatives and an incubating agent including one or more salts, a buffer, optionally a cryoprotectant, and optionally an organic solvent.

In some embodiments, provided herein is a method of treating a coagulopathy in a subject, the method including administering to the subject in need thereof an effective amount of a composition prepared by a process including incubating platelets with an incubating agent including one or more salts, a buffer, optionally a cryoprotectant, and optionally an organic solvent, to form the composition.

In some embodiments, provided herein is a method of restoring normal hemostasis in a subject, the method including administering to the subject in need thereof an effective amount of a composition including platelets or platelet derivatives and an incubating agent including one or more salts, a buffer, optionally a cryoprotectant, and optionally an organic solvent.

In some embodiments, provided herein is a method of restoring normal hemostasis in a subject, the method including administering to the subject in need thereof an effective amount of a composition prepared by a process including incubating platelets with an incubating agent including one or more salts, a buffer, optionally a cryoprotectant, and optionally an organic solvent, to form the composition.

In some embodiments, provided herein is a method of preparing a subject for surgery, the method including administering to the subject in need thereof an effective amount of a composition including platelets or platelet derivatives and an incubating agent including one or more salts, a buffer, optionally a cryoprotectant, and optionally an organic solvent. Implementations can include one or more of the following features. The surgery can be an emergency surgery. The surgery can be a scheduled surgery.

In some embodiments, provided herein is a method of preparing a subject for surgery, the method including administering to the subject in need thereof an effective amount of a composition prepared by a process including incubating platelets with an incubating agent including one or more salts, a buffer, optionally a cryoprotectant, and optionally an organic solvent, to form the composition. Implementations can include one or more of the following features. The surgery can be an emergency surgery. The surgery can be a scheduled surgery.

In some embodiments of the above methods, the subject has been treated or is being treated with an antiplatelet agent. In some embodiments, treatment with the antiplatelet agent can be stopped. In some embodiments, treatment with the antiplatelet agent can be continued.

In some embodiments, provided herein is a method of ameliorating the effects of an antiplatelet agent in a subject, the method including administering to the subject in need thereof an effective amount of a composition including platelets or platelet derivatives and an incubating agent including one or more salts, a buffer, optionally a cryoprotectant, and optionally an organic solvent.

In some embodiments, provided herein is a method of ameliorating the effects of an antiplatelet agent in a subject, the method including administering to the subject in need thereof an effective amount of a composition prepared by a process including incubating platelets with an incubating agent including one or more salts, a buffer, optionally a cryoprotectant, and optionally an organic solvent, to form the composition.

In some embodiments, the effects of the antiplatelet agent can be the result of an overdose of the antiplatelet agent.

In some embodiments, the antiplatelet agent can be selected from the group consisting of aspirin, cangrelor, ticagrelor, clopidogrel, prasugrel, eptifibatide, tirofiban, abciximab, and a supplement.

Some embodiments of any of the methods herein can include one or more of the following features. Administering can include administering topically. Administering can include administering parenterally. Administering can include administering intravenously. Administering can include administering intramuscularly. Administering can include administering intrathecally. Administering can include administering subcutaneously. Administering can include administering intraperitoneally. The composition can be dried prior to the administration step. The composition can be rehydrated following the drying step. The composition can be freeze-dried prior to the administration step. The composition can be rehydrated following the freeze-drying step. The incubating agent can include one or more salts selected from sodium salts, potassium salts, calcium salts, magnesium salts, and a combination of two or more thereof. The incubating agent can include a carrier protein. The buffer can include HEPES, sodium bicarbonate ($NaHCO_3$), or a combination thereof. The composition can include one or more saccharides. The one or more saccharides can include trehalose. The one or more saccharides can include polysucrose. The one or more saccharides can include dextrose. The composition can include an organic solvent. The platelets or platelet derivatives can include FDPDs.

Further non-limiting example embodiments are provided in numbered form as follows:

Embodiment 1 is a method of treating a coagulopathy in a subject, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 2 is a method of treating a coagulopathy in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 3 is a method of restoring normal hemostasis in a subject, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 4 is a method of restoring normal hemostasis in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 5 is a method of preparing a subject for surgery, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 6 is a method of preparing a subject for surgery, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 7 is the method of any one of embodiments 5-6, wherein the surgery is an emergency surgery.

Embodiment 8 is the method of any one of embodiments 5-6, wherein the surgery is a scheduled surgery.

Embodiment 9 is the method of any one of embodiments 1-8, wherein the subject has been treated or is being treated with an antiplatelet agent.

Embodiment 10 is the method of embodiment 9, wherein treatment with the antiplatelet agent is stopped.

Embodiment 11 is the method of embodiment 9, wherein treatment with the antiplatelet agent is continued.

Embodiment 12 is a method of ameliorating the effects of an antiplatelet agent in a subject, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 13 is a method of ameliorating the effects of an antiplatelet agent in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 14 is the method of embodiment 12 or embodiment 13, wherein the effects of the antiplatelet agent are the result of an overdose of the antiplatelet agent.

Embodiment 15 is the method of any one of embodiments 1-14, wherein the composition further comprises an anti-fibrinolytic agent.

Embodiment 16 is the method of embodiment 15, wherein the anti-fibrinolytic agent is selected from the group consisting of ε-aminocaproic acid (EACA), tranexamic acid, aprotinin, aminomethylbenzoic acid, fibrinogen, and a combination thereof.

Embodiment 17 is the method of embodiment 15 or embodiment 16, wherein the platelets or platelet derivatives are loaded with the anti-fibrinolytic agent.

Embodiment 18 is the method of any one of embodiments 9-16, wherein the antiplatelet agent is selected from the group consisting of aspirin, cangrelor, ticagrelor, clopidogrel, prasugrel, eptifibatide, tirofiban, abciximab, a supplement, and a combination thereof.

Embodiment 19 is the method of any one of embodiments 9-16, wherein the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, and a combination thereof.

Embodiment 20 is the method of any one of embodiments 9-16, wherein the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, sarpogrelate, and a combination thereof.

Embodiment 21 is the method of any one of embodiments 1-20, wherein administering comprises administering topically.

Embodiment 22 is the method of any one of embodiments 1-20, wherein administering comprises administering parenterally.

Embodiment 23 is the method of any one of embodiments 1-20, wherein administering comprises administering intravenously.

Embodiment 24 is the method of any one of embodiments 1-20, wherein administering comprises administering intramuscularly.

Embodiment 25 is the method of any one of embodiments 1-20, wherein administering comprises administering intrathecally.

Embodiment 26 is the method of any one of embodiments 1-20, wherein administering comprises administering subcutaneously.

Embodiment 27 is the method of any one of embodiments 1-20, wherein administering comprises administering intraperitoneally.

Embodiment 28 is the method of any one of embodiments 1-27, wherein the composition is dried prior to the administration step.

Embodiment 29 is the method of embodiment 28, wherein the composition is rehydrated following the drying step.

Embodiment 30 is the method of any one of embodiments 1-28, wherein the composition is freeze-dried prior to the administration step.

Embodiment 31 is the method of embodiment 30, wherein the composition is rehydrated following the freeze-drying step.

Embodiment 32 is the method of any one of embodiments 1-31, wherein the incubating agent comprises one or more salts selected from phosphate salts, sodium salts, potassium salts, calcium salts, magnesium salts, and a combination of two or more thereof.

Embodiment 33 is the method of any one of embodiments 1-32, wherein the incubating agent comprises a carrier protein.

Embodiment 34 is the method of any one of embodiments 1-33, wherein the buffer comprises HEPES, sodium bicarbonate ($NaHCO_3$), or a combination thereof.

Embodiment 35 is the method of any one of embodiments 1-34, wherein the composition comprises one or more saccharides.

Embodiment 36 is the method of embodiment 35, wherein the one or more saccharides comprise trehalose.

Embodiment 37 is the method of embodiment 35 or embodiment 36, wherein the one or more saccharides comprise polysucrose.

Embodiment 38 is the method of any one of embodiments 35-37, wherein the one or more saccharides comprise dextrose.

Embodiment 39 is the method of any one of embodiments 1-38, wherein the composition comprises an organic solvent.

Embodiment 40 is the method of any of embodiments 1-39, wherein the platelets or platelet derivatives comprise FDPDs.

Embodiment 41 is a method of treating a coagulopathy in a subject that is being administered or has been administered an antiplatelet agent, the method comprising:
  (a) determining that the subject has an abnormal result for evaluation of one or more clotting parameters; and
  (b) after (a), administering to the subject in need thereof an effective amount of a composition comprising platelets or platelet derivatives and an incubating agent comprising one or more salts, a buffer, optionally a cryoprotectant, and optionally an organic solvent.

Embodiment 42 is a method of treating a coagulopathy in a subject that is being administered or has been administered an antiplatelet agent, the method comprising:
(a) determining that the subject an abnormal result for evaluation of one or more clotting parameters; and
(b) after (a), administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 43 is a method of treating a coagulopathy in a subject that is being administered or has been administered an antiplatelet agent, the method comprising:
administering to the subject in need thereof an effective amount of a composition comprising platelets or platelet derivatives and an incubating agent comprising one or more salts, a buffer, optionally a cryoprotectant, and optionally an organic solvent, wherein before the administering, the subject has been determined to have an abnormal result for evaluation of one or more clotting parameters.

Embodiment 44 is a method of treating a coagulopathy in a subject that is being administered or has been administered an antiplatelet agent, the method comprising:
administering to the subject in need thereof an effective amount of a composition prepared by a process comprising incubating platelets with an incubating agent comprising one or more salts, a buffer, optionally a cryoprotectant, and optionally an organic solvent, to form the composition, wherein before the administering, the subject has been determined to have an abnormal result for evaluation of one or more clotting parameters.

Embodiment 45 is the method of any one of embodiments 41-44, further comprising determining the result of the evaluation one or more clotting parameters following the administering.

Embodiment 46 is the method of embodiment 45, wherein the evaluation of the one or more clotting parameters following the administering shows a normal result for at least one of the one or more clotting parameters.

Embodiment 47 is the method of embodiment 45, wherein the result of the evaluation of the one or more clotting parameters following the administering is improved from the result of the evaluation of the one or more parameters prior to the administering.

Embodiment 48 is a method of treating a coagulopathy in a subject, the method comprising:
(a) determining that the subject, contrary to medical instruction, was administered an antiplatelet agent; and
(b) administering to the subject in need thereof an effective amount of a composition comprising platelets or platelet derivatives and an incubating agent comprising one or more salts, a buffer, optionally a cryoprotectant, and optionally an organic solvent.

Embodiment 49 is a method of treating a coagulopathy in a subject, the method comprising:
(a) determining that the subject, contrary to medical instruction, was administered an antiplatelet agent; and
(b) administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 50 is a method of treating a coagulopathy in a subject, the method comprising:
administering to the subject in need thereof an effective amount of a composition comprising platelets or platelet derivatives and an incubating agent comprising one or more salts, a buffer, optionally a cryoprotectant, and optionally an organic solvent, wherein the subject is determined to have been administered an antiplatelet agent contrary to medical instruction.

Embodiment 51 is a method of treating a coagulopathy in a subject, the method comprising:
administering to the subject in need thereof an effective amount of a composition prepared by a process comprising incubating platelets with an incubating agent comprising one or more salts, a buffer, optionally a cryoprotectant, and optionally an organic solvent, to form the composition, wherein the subject is determined to have been administered an antiplatelet agent contrary to medical instruction.

Embodiment 52 is a method of restoring normal hemostasis in a subject, the method comprising:
(a) determining that the subject, contrary to medical instruction, was administered an antiplatelet agent; and
(b) administering to the subject in need thereof an effective amount of a composition comprising platelets or platelet derivatives and an incubating agent comprising one or more salts, a buffer, optionally a cryoprotectant, and optionally an organic solvent.

Embodiment 53 is a method of restoring normal hemostasis in a subject, the method comprising:
(a) determining that the subject, contrary to medical instruction, was administered an antiplatelet agent; and
(b) administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 54 is a method of restoring normal hemostasis in a subject, the method comprising:
administering to the subject in need thereof an effective amount of a composition comprising platelets or platelet derivatives and an incubating agent comprising one or more salts, a buffer, optionally a cryoprotectant, and optionally an organic solvent, wherein the subject is determined to have been administered an antiplatelet agent contrary to medical instruction.

Embodiment 55 is a method of restoring normal hemostasis in a subject, the method comprising:
administering to the subject in need thereof an effective amount of a composition prepared by a process comprising incubating platelets with an incubating agent comprising one or more salts, a buffer, optionally a cryoprotectant, and optionally an organic solvent, to form the composition, wherein the subject is determined to have been administered an antiplatelet agent contrary to medical instruction.

Embodiment 56 is the method of any one of embodiments 48-55, wherein the administering of the antiplatelet agent contrary to medical instruction is self-administering by the subject.

Embodiment 57 is the method of any one of embodiments 48-55, wherein the administering of the antiplatelet agent contrary to medical instruction is administering by a medical professional.

Embodiment 58 is the method of any one of embodiments 48-57, wherein the medical instruction is verbal instruction by a medical professional.

Embodiment 59 is the method of any one of embodiments 48-57, wherein the medical instruction is written instruction.

Embodiment 60 is a method of treating a coagulopathy in a subject, the method comprising:
(a) determining that the subject was administered an antiplatelet agent and a second agent that decreases platelet function; and
(b) administering to the subject in need thereof an effective amount of a composition comprising platelets or platelet derivatives and an incubating agent comprising one or more salts, a buffer, optionally a cryoprotectant, and optionally an organic solvent.

Embodiment 61 is a method of treating a coagulopathy in a subject, the method comprising:
(a) determining that the subject was administered an antiplatelet agent and a second agent that decreases platelet function; and
(b) administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 62 is a method of treating a coagulopathy in a subject, the method comprising:
administering to the subject in need thereof an effective amount of a composition comprising platelets or platelet derivatives and an incubating agent comprising one or more salts, a buffer, optionally a cryoprotectant, and optionally an organic solvent, wherein the subject is determined to have been administered an antiplatelet agent and a second agent that decreases platelet function.

Embodiment 63 is a method of treating a coagulopathy in a subject, the method comprising:
administering to the subject in need thereof an effective amount of a composition prepared by a process comprising incubating platelets with an incubating agent comprising one or more salts, a buffer, optionally a cryoprotectant, and optionally an organic solvent, to form the composition, wherein the subject is determined to have been administered an antiplatelet agent and a second agent that decreases platelet function.

Embodiment 64 is a method of restoring normal hemostasis in a subject, the method comprising:
(a) determining that the subject was administered an antiplatelet agent and a second agent that decreases platelet function; and
(b) administering to the subject in need thereof an effective amount of a composition comprising platelets or platelet derivatives and an incubating agent comprising one or more salts, a buffer, optionally a cryoprotectant, and optionally an organic solvent.

Embodiment 65 is a method of restoring normal hemostasis in a subject, the method comprising:
(a) determining that the subject was administered an antiplatelet agent and a second agent that decreases platelet function; and
(b) administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 66 is a method of restoring normal hemostasis in a subject, the method comprising:
administering to the subject in need thereof an effective amount of a composition comprising platelets or platelet derivatives and an incubating agent comprising one or more salts, a buffer, optionally a cryoprotectant, and optionally an organic solvent, wherein the subject is identified as having been administered an antiplatelet agent and a second agent that decreases platelet function.

Embodiment 67 is a method of restoring normal hemostasis in a subject, the method comprising:
administering to the subject in need thereof an effective amount of a composition prepared by a process comprising incubating platelets with an incubating agent comprising one or more salts, a buffer, optionally a cryoprotectant, and optionally an organic solvent, to form the composition, wherein the subject is identified as having been administered an antiplatelet agent and a second agent that decreases platelet function.

Embodiment 68 is the method of any one of embodiments 60-67, wherein administration of the second agent is stopped.

Embodiment 69 is the method of any one of embodiments 60-67, wherein administration of the second agent is continued.

Embodiment 70 is the method of any one of embodiments 60-69, wherein the second agent is selected from the group consisting of an antihypertensive, a proton pump inhibitor, and a combination thereof.

Embodiment 71 is the method of any one of embodiments 60-69, wherein the second agent is selected from the group consisting of a chemotherapeutic agent, an antibiotic, a cardiovascular agent, a H2 antagonist, a neuropsychiatric agent and a combination thereof.

Embodiment 72 is the method of any one of embodiments 60-69, wherein the second agent comprises an antidepressant.

Embodiment 73 is the method of embodiment 72, wherein the antidepressant is selected from the group consisting of a selective serotonin reuptake inhibitor (SSRI), a serotonin antagonist and reuptake inhibitor (SARI), a serotonin and norepinephrine reuptake inhibitor (SNRI), and a combination thereof.

Embodiment 74 is the method of any one of embodiments 60-73, wherein the second agent is not an anticoagulant.

Embodiment 75 is the method of any one of embodiments 41-74, wherein administration of the antiplatelet agent is stopped.

Embodiment 76 is the method of any one of embodiments 41-74, wherein administration of the antiplatelet agent is continued.

Embodiment 77 is a method of preventing or mitigating the potential for a coagulopathy in a subject, the method comprising:
(a) determining that information regarding whether the subject was administered an antiplatelet agent is unavailable; and
(b) administering to the subject an effective amount of a composition comprising platelets or platelet derivatives and an incubating agent comprising one or more salts, a buffer, optionally a cryoprotectant, and optionally an organic solvent.

Embodiment 78 is a method of preventing or mitigating the potential for a coagulopathy in a subject, the method comprising:
  (a) determining that information regarding whether the subject was administered an antiplatelet agent is unavailable; and
  (b) administering to the subject an effective amount of a composition prepared by a process comprising incubating platelets with an incubating agent comprising one or more salts, a buffer, optionally a cryoprotectant, and optionally an organic solvent, to form the composition.

Embodiment 79 is a method of preventing or mitigating the potential for a coagulopathy in a subject, the method comprising:
  administering to the subject in need thereof an effective amount of a composition comprising platelets or platelet derivatives and an incubating agent comprising one or more salts, a buffer, optionally a cryoprotectant, and optionally an organic solvent, wherein the subject has been determined to be a subject for which information regarding whether the subject was administered an antiplatelet agent is unavailable.

Embodiment 80 is a method of preventing or mitigating the potential for a coagulopathy in a subject, the method comprising:
  administering to the subject in need thereof an effective amount of a composition prepared by a process comprising incubating platelets with an incubating agent comprising one or more salts, a buffer, optionally a cryoprotectant, and optionally an organic solvent, to form the composition, wherein the subject has been determined to be a subject for which information regarding whether the subject was administered an antiplatelet agent is unavailable.

Embodiment 81 is the method of any one of embodiments 77-80, wherein information regarding whether the subject was administered an antiplatelet agent is unavailable for a reason comprising that the subject cannot be identified.

Embodiment 82 is the method of any one of embodiments 77-81, wherein information regarding whether the subject was administered an antiplatelet agent is unavailable for a reason comprising that the medical history of the subject is unavailable.

Embodiment 83 is the method of any one of embodiments 77-82, wherein information regarding whether the subject was administered an antiplatelet agent is unavailable for a reason comprising that the subject is in need of emergency treatment.

Embodiment 84 is the method of any one of embodiments 77-83, wherein information regarding whether the subject was administered an antiplatelet agent is unavailable for a reason comprising that the subject is in need of emergency surgery.

Embodiment 85 is the method of any one of embodiments 77-84, wherein information regarding whether the subject was administered an antiplatelet agent is unavailable for a reason comprising that the subject is having emergency surgery.

Embodiment 86 is the method of any one of embodiments 48-85, wherein the method further comprises determining that the subject has an abnormal result for one or more evaluations of clotting parameters.

Embodiment 87 is the method of any one of embodiments 48-86, wherein the subject has been determined to have an abnormal result for one or more evaluations of clotting parameters.

Embodiment 88 is the method of any one of embodiments 84-87, wherein the subject was previously identified as having a normal result for at least one of the one or more clotting parameters.

Embodiment 89 is the method of any one of embodiments 84-88, further comprising determining the result of the evaluation one or more clotting parameters following the administering.

Embodiment 90 is the method of embodiment 89, wherein the evaluation of the one or more clotting parameters following the administering shows a normal result for at least one of the one or more clotting parameters.

Embodiment 91 is the method of embodiment 89, wherein the result of the evaluation of the one or more clotting parameters following the administering is improved from the result of the evaluation of the one or more parameters prior to the administering.

Embodiment 92 is the method of any one of embodiments 41-47 or 86-91, wherein the subject is identified as having an abnormal result for one or more evaluations of clotting parameters during surgery.

Embodiment 93 is the method of embodiment 92, wherein the surgery is an emergency surgery.

Embodiment 94 is the method of embodiment 92, wherein the surgery is a scheduled surgery.

Embodiment 95 is the method of any one of embodiments 41-47 or 86-94, wherein the one or more clotting parameters includes an evaluation of bleeding.

Embodiment 96 is the method of embodiment 95, wherein the evaluation of bleeding is performed based on the World Health Organization (WHO) bleeding scale.

Embodiment 97 is the method of embodiment 96, wherein before the administering, the subject has bleeding of grade 2, 3, or 4 based on the WHO bleeding scale.

Embodiment 98 is the method of embodiment 97, wherein after the administering, the subject has bleeding of grade 0 or 1 based on the WHO bleeding scale.

Embodiment 99 is the method of embodiment 96, wherein after the administering, the subject has bleeding of one grade less, based on the WHO bleeding scale, than before the administering.

Embodiment 100 is the method of embodiment 96, wherein after the administering, the subject has bleeding of two grades less, based on the WHO bleeding scale, than before the administering.

Embodiment 101 is the method of embodiment 96, wherein after the administering, the subject has bleeding of three grades less, based on the WHO bleeding scale, than before the administering.

Embodiment 102 is the method of any one of embodiments 41-47 or 86-101, wherein the one or more clotting parameters includes an evaluation of prothrombin time (PT).

Embodiment 103 is the method of embodiment 102, wherein the abnormal results for PT comprises a PT of greater than about 14 seconds.

Embodiment 104 is the method of embodiment 102 or embodiment 103, wherein after the administering, the subject has a decrease in PT of at least 1, 2, 3, 4, 5, or more, seconds.

Embodiment 105 is the method of any one of embodiments 102-104, wherein after the administering, the subject has a normal PT.

Embodiment 106 is the method of any one of embodiments 41-47 or 86-105, wherein the one or more clotting parameters includes an evaluation of activated partial thromboplastin time (aPTT).

Embodiment 107 is the method of embodiment 106, wherein the abnormal result for aPTT comprises an aPTT of greater than about 40 seconds.

Embodiment 108 is the method of embodiment 106 or embodiment 107, wherein after the administering, the subject has a decrease in aPTT of at least 5, 10, 15, 20, or more, seconds.

Embodiment 109 is the method of any one of embodiments 106-108, wherein after the administering, the subject has a normal aPTT.

Embodiment 110 is the method of any one of embodiments 41-47 or 86-109, wherein the one or more clotting parameters includes an evaluation of thrombin clot time (TCT).

Embodiment 111 is the method of embodiment 110, wherein the abnormal result for TCT comprises a TCT of greater than about 35 seconds.

Embodiment 112 is the method of embodiment 110 or embodiment 111, wherein after the administering, the subject has a decrease in TCT of at least 5, 10, 15, 20, or more, seconds.

Embodiment 113 is the method of any one of embodiments 110-111, wherein after the administering, the subject has a normal TCT.

Embodiment 114 is the method of any one of embodiments 41-47 or 86-113, wherein the evaluation of the one or more clotting parameters includes thromboelastography (TEG).

Embodiment 115 is the method of embodiment 114, wherein the abnormal result for TEG comprises a maximum amplitude (MA) of less than about 50 mm.

Embodiment 116 is the method of embodiment 114 or embodiment 115, wherein after the administering, the subject has an increase in MA of at least 5, 10, 15, 20, or more, mm.

Embodiment 117 is the method of any one of embodiments 114-116, wherein after the administering, the subject has a normal MA.

Embodiment 118 is the method of any one of embodiments 114-117, wherein the abnormal result for TEG comprises a percent aggregation (in the presence of 1 mmol/L arachidonic acid) of less than about 85%.

Embodiment 119 is the method of embodiment 118, wherein after the administering, the subject has an increase in percent aggregation (in the presence of 1 mmol/L arachidonic acid) of at least 2, 3, 5, 8, 10, 12, or more, percentage points.

Embodiment 120 is the method of embodiment 118 or embodiment 119, wherein after the administering, the subject has a normal percent aggregation (in the presence of 1 mmol/L arachidonic acid).

Embodiment 121 is the method of any one of embodiments 105-120 wherein the TEG is used to evaluate adenosine diphosphate-induced platelet-fibrin clot strength.

Embodiment 122 is the method of any one of embodiments 105-120, wherein the TEG is used to evaluate arachidonic acid-induced platelet-fibrin clot strength.

Embodiment 123 is the method of any one of embodiments 41-47 or 86-122, wherein the evaluation of one or more clotting parameters includes VerifyNow.

Embodiment 124 is the method of embodiment 123, wherein the abnormal result for VerifyNow comprises a P2Y12 reaction unit (PRU) of less than about 195, or less than about 180.

Embodiment 125 is the method of embodiment 123 or embodiment 124, wherein after the administering, the subject has an increase in PRU of at least 25, 50, 75, 100, or more.

Embodiment 126 is the method of any one of embodiments 123-125, wherein after the administering, the subject has a normal PRU.

Embodiment 127 is the method of any one of embodiments 123-126, wherein the abnormal result for VerifyNow comprises an Aspirin Reaction Unit (ARU) of less than about 550, or less than about 500.

Embodiment 128 is the method of embodiment 126 or embodiment 127, wherein after the administering, the subject has an increase in ARU of at least 25, 50, 75, 100, or more.

Embodiment 129 is the method of any one of embodiments 126-128, wherein after the administering, the subject has a normal ARU.

Embodiment 130 is the method of any one of embodiments 41-47 or 86-129, wherein the one or more clotting parameters includes multiple electrode aggregometry (MEA).

Embodiment 131 is the method of embodiment 130, wherein the abnormal result for MEA comprises an abnormal result for ADP-induced platelet activity.

Embodiment 132 is the method of embodiment 131, wherein the abnormal result for MEA comprises a result of less than about 50 units (U) for ADP-induced platelet activity.

Embodiment 133 is the method of embodiment 131 or embodiment 132, wherein after the administering, the subject has an increase in ADP-induced platelet activity by 5, 10, 15, 20, or more units.

Embodiment 134 is the method of any one of embodiments 131-133, wherein after the administering, the subject has a normal value for ADP-induced platelet activity.

Embodiment 135 is the method of any one of embodiments 131-134, wherein the abnormal result for MEA comprises an abnormal result for arachidonic acid-induced platelet activity.

Embodiment 136 is the method of embodiment 135, wherein the abnormal result for MEA comprises a result of less than about 70 units (U) for arachidonic acid-induced platelet activity.

Embodiment 137 is the method of embodiment 135 or embodiment 136, wherein after the administering, the subject has an increase in arachidonic acid-induced platelet activity by 5, 10, 15, 20, or more units.

Embodiment 138 is the method of any one of embodiments 135-137, wherein after the administering, the subject has a normal value for arachidonic acid-induced platelet activity.

Embodiment 139 is the method of any one of embodiments 41-47 or 86-138, wherein the one or more clotting parameters includes light transmission aggregometry (LTA).

Embodiment 140 is the method of embodiment 139, wherein the abnormal result for LTA comprises one or more of the following:
  (a) in the presence of 5 µmol/L adenosine diphosphate, a percent aggregation of less than about 60%;
  (b) in the presence of 2 g/mL collagen, a percent aggregation of less than about 65%;
  (c) in the presence of 1 mmol/L arachidonic acid, a percent aggregation of less than about 65%;
  (d) in the presence of 2 mmol/L arachidonic acid, a percent aggregation of less than about 69%; or (e) in the presence of 5 mmol/L arachidonic acid, a percent aggregation of less than about 73%.

Embodiment 141 is the method of embodiment 140, wherein after the administering, the subject has an increase in percent aggregation (in the presence of 5 μmol/L adenosine diphosphate) of at least 2, 3, 5, 8, 10, 12, or more, percentage points.

Embodiment 142 is the method of embodiment 140 or embodiment 141, wherein after the administering, the subject has a normal percent aggregation (in the presence of 5 μmol/L adenosine diphosphate).

Embodiment 143 is the method of embodiment 140, wherein after the administering, the subject has an increase in percent aggregation (in the presence of 2 μg/mL collagen) of at least 2, 3, 5, 8, 10, 12, or more, percentage points.

Embodiment 144 is the method of embodiment 140 or embodiment 143, wherein after the administering, the subject has a normal percent aggregation (in the presence of 2 g/mL collagen).

Embodiment 145 is the method of embodiment 140, wherein after the administering, the subject has an increase in percent aggregation (in the presence of 1 mmol/L arachidonic acid) of at least 2, 3, 5, 8, 10, 12, or more, percentage points.

Embodiment 146 is the method of embodiment 140 or embodiment 145, wherein after the administering, the subject has a normal percent aggregation (in the presence of 1 mmol/L arachidonic acid).

Embodiment 147 is the method of embodiment 140, wherein after the administering, the subject has an increase in percent aggregation (in the presence of 2 mmol/L arachidonic acid) of at least 2, 3, 5, 8, 10, 12, or more, percentage points.

Embodiment 148 is the method of embodiment 140 or embodiment 147, wherein after the administering, the subject has a normal percent aggregation (in the presence of 2 mmol/L arachidonic acid).

Embodiment 149 is the method of embodiment 140, wherein after the administering, the subject has an increase in percent aggregation (in the presence of 5 mmol/L arachidonic acid) of at least 2, 3, 5, 8, 10, 12, or more, percentage points.

Embodiment 150 is the method of embodiment 140 or embodiment 149, wherein after the administering, the subject has a normal percent aggregation (in the presence of 5 mmol/L arachidonic acid).

Embodiment 151 is the method of any one of embodiments 41-150, wherein the method further comprises administering to the subject an additional antiplatelet agent reversal agent.

Embodiment 152 is the method of embodiment 151, wherein the administering of the composition occurs concurrently with administering of the additional antiplatelet agent reversal agent.

Embodiment 153 is the method of embodiment 151, wherein the administering of the composition occurs after administering of the additional antiplatelet agent reversal agent.

Embodiment 154 is the method of embodiment 151, wherein the administering of the composition occurs before administering of the additional antiplatelet agent reversal agent.

Embodiment 155 is the method of any one of embodiments 41-154, wherein the composition further comprises an anti-fibrinolytic agent.

Embodiment 156 is the method of embodiment 155, wherein the anti-fibrinolytic agent is selected from the group consisting of ε-aminocaproic acid (EACA), tranexamic acid, aprotinin, aminomethylbenzoic acid, fibrinogen, and a combination thereof.

Embodiment 157 is the method of embodiment 155 or embodiment 156, wherein the platelets or platelet derivatives are loaded with the anti-fibrinolytic agent.

Embodiment 158 is the method of any one of embodiments 41-157, wherein the antiplatelet agent is selected from the group consisting of aspirin, cangrelor, ticagrelor, clopidogrel, prasugrel, eptifibatide, tirofiban, abciximab, a supplement, and a combination thereof.

Embodiment 159 is the method of any one of embodiments 41-157, wherein the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, and a combination thereof.

Embodiment 160 is the method of any one of embodiments 41-157, wherein the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, sarpogrelate, and a combination thereof.

Embodiment 161 is the method of any one of embodiments 41-160, wherein administering comprises administering topically, parenterally, intravenously, intramuscularly, intrathecally, subcutaneously, intraperitoneally, or a combination thereof.

Embodiment 162 is the method of any one of embodiments 41-161, wherein the composition is dried prior to the administration step.

Embodiment 163 is the method of embodiment 162, wherein the composition is rehydrated following the drying step.

Embodiment 164 is the method of any one of embodiments 41-161, wherein the composition is freeze-dried prior to the administration step.

Embodiment 165 is the method of embodiment 164, wherein the composition is rehydrated following the freeze-drying step.

Embodiment 166 is the method of any one of embodiments 41-165, wherein the incubating agent comprises one or more salts selected from phosphate salts, sodium salts, potassium salts, calcium salts, magnesium salts, and a combination of two or more thereof.

Embodiment 167 is the method of any one of embodiments 41-166, wherein the incubating agent comprises a carrier protein.

Embodiment 168 is the method of any one of embodiments 41-167, wherein the buffer comprises HEPES, sodium bicarbonate ($NaHCO_3$), or a combination thereof.

Embodiment 169 is the method of any one of embodiments 41-168, wherein the composition comprises one or more saccharides.

Embodiment 170 is the method of embodiment 169, wherein the one or more saccharides comprise trehalose.

Embodiment 171 is the method of embodiment 169 or embodiment 170, wherein the one or more saccharides comprise polysucrose.

Embodiment 172 is the method of any one of embodiments 169-171, wherein the one or more saccharides comprise dextrose.

Embodiment 173 is the method of any one of embodiments 41-172, wherein the composition comprises an organic solvent.

Embodiment 174 is the method of any one of embodiments 41-173, wherein the platelets or platelet derivatives comprise FDPDs.

Embodiment 175 is the method of any one of embodiments 41-174, wherein the antiplatelet agent comprises aspirin at a dosage of about 80 mg to about 700 mg, once, twice, three times, or four times a day.

Embodiment 176 is the method of any one of embodiments 41-175, wherein the antiplatelet agent comprises aspirin, and the subject achieved a Cmax of about 3 to about 25 mg/L.

Embodiment 137 is the method of any one of embodiments 41-176, wherein the antiplatelet agent comprises 177 at an initial dosage of about 25 to about 30 µg/kg body weight of the subject or a following dosage of about 3 to about 5 µg/kg/min body weight of the subject.

Embodiment 178 is the method of any one of embodiments 41-177, wherein the antiplatelet agent comprises cangrelor, and the subject achieved a Cmax of about 400 to about 500 ng/mL.

Embodiment 179 is the method of any one of embodiments 41-178, wherein the antiplatelet agent comprises ticagrelor at an initial dosage of about 170 to about 190 mg, or a following dosage in a first year of treatment of about 80 to about 100 mg twice daily, or a following dosage in a second year of treatment of about 50 to about 70 mg twice daily, optionally in combination with aspirin.

Embodiment 180 is the method of any one of embodiments 41-179, wherein the antiplatelet agent comprises ticagrelor, and the subject achieved a Cmax of about 550 to about 650 ng/mL.

Embodiment 181 is the method of any one of embodiments 41-180, wherein the antiplatelet agent comprises clopidogrel at an initial dosage of about 275 to about 325 mg, or a following dosage of about 70 to about 80 mg once daily, optionally in combination with aspirin.

Embodiment 182 is the method of any one of embodiments 41-181, wherein the antiplatelet agent comprises clopidogrel, and the subject achieved a Cmax of about 6 to about 20 ng/mL.

Embodiment 183 is the method of any one of embodiments 41-182, wherein the antiplatelet agent comprises prasugrel at an initial dosage of about 50 to about 70 mg, or a following dosage of about 3 to about 12 once daily, optionally in combination with aspirin.

Embodiment 184 is the method of any one of embodiments 41-183, wherein the antiplatelet agent comprises prasugrel, and the subject achieved a Cmax of about 200 to about 525 ng/mL.

Embodiment 185 is the method of any one of embodiments 41-184, wherein the antiplatelet agent comprises eptifibatide at an initial dosage of about 170 to about 190 mcg/kg body weight of the subject, optionally a second initial dosage of about 170 to about 190 mcg/kg body weight of the subject, or a following dose of about 1 to about 2 mcg/kg body weight of the subject/min.

Embodiment 186 is the method of any one of embodiments 41-185, wherein the antiplatelet agent comprises tirofiban at an initial dosage of about 0.3 to about 0.5 µg/kg body weight of the subject/min for about 30 minutes, or a following dosage of about 0.1 µg/kg body weight of the subject/min.

Embodiment 187 is the method of any one of embodiments 41-186, wherein the antiplatelet agent comprises abciximab at an initial dosage of about 0.2 to about 0.3 mg/kg body weight of the subject, or a following dosage of about 0.10 to about 0.15 µg/kg body weight of the subject/min.

Embodiment 188 is the method of any one of embodiments 41-187, wherein the antiplatelet agent comprises abciximab at an initial dosage of about 0.2 to about 0.3 mg/kg body weight of the subject, or a following dosage of about 8 to about 10 µg/min.

Embodiment 189 is the method of any one of embodiments 41-188, wherein the antiplatelet agent comprises ticlopidine at a dosage of about 240 to about 260 mg twice per day.

Embodiment 190 is the method of any one of embodiments 41-189, wherein the antiplatelet agent comprises ibuprofen at a dosage of about 100 to about 600 mg once, twice, three times, or four times per day.

Embodiment 191 is the method of any one of embodiments 41-190, wherein the antiplatelet agent comprises vorapaxar at a dosage of about 2 to about 3 mg once per day, optionally with aspirin or clopidogrel.

Embodiment 192 is the method of any one of embodiments 41-191, wherein the antiplatelet agent comprises cilostazol at a dosage of about 40 to about 110 mg twice daily.

Embodiment 193 is the method of any one of embodiments 41-192, wherein the antiplatelet agent comprises epoprostenol at an initial dosage of about 2 ng/kg body weight of the subject/min, or a following dosage of about 4, 6, 8, 10, 12, 14, 16, 18, or 20 ng/kg body weight of the subject/min.

Embodiment 194 is the method of any one of embodiments 41-193, wherein the antiplatelet agent comprises dipyridamole at a dosage of about 60 to about 110 mg four times daily.

Embodiment 195 is the method of any one of embodiments 41-194, wherein the antiplatelet agent comprises treprostinil sodium at a dosage of about 0.5 to about 1.3 ng/kg body weight of the subject/min.

Embodiment 196 is the method of any one of claims 1-195, wherein the subject does not have cancer.

EXAMPLES

Example 1—P2Y$_{12}$ Inhibitors

Cangrelor, like clopidogrel, ticagrelor, and prasugrel, blocks the P2Y$_{12}$ (ADP) receptor on platelets. Cangrelor is used here as a representative of this class of drug.

FDPDs were prepared consistent with the procedure in Example 4. Transmission light aggregometry and T-TAS® experiments were carried out according to Example 4.

The effect of cangrelor on the aggregation of platelets in platelet-rich plasma (PRP; taken from humans as whole blood and processed to isolate platelets in plasma without white blood cells (WBC) or red blood cells (rbc) was evaluated by transmission light aggregometry. Aggregation of platelets (platelet rich plasma) in response to agonist-induced activation showed complete inhibition of 10 µM adenosine diphosphate (ADP)-induced aggregation by cangrelor at therapeutic concentration of 0.5 µM-3.5 µM (FIG. 1). All doses of cangrelor investigated completely eliminated ADP-induced platelet aggregation in PRP.

Figure 2:
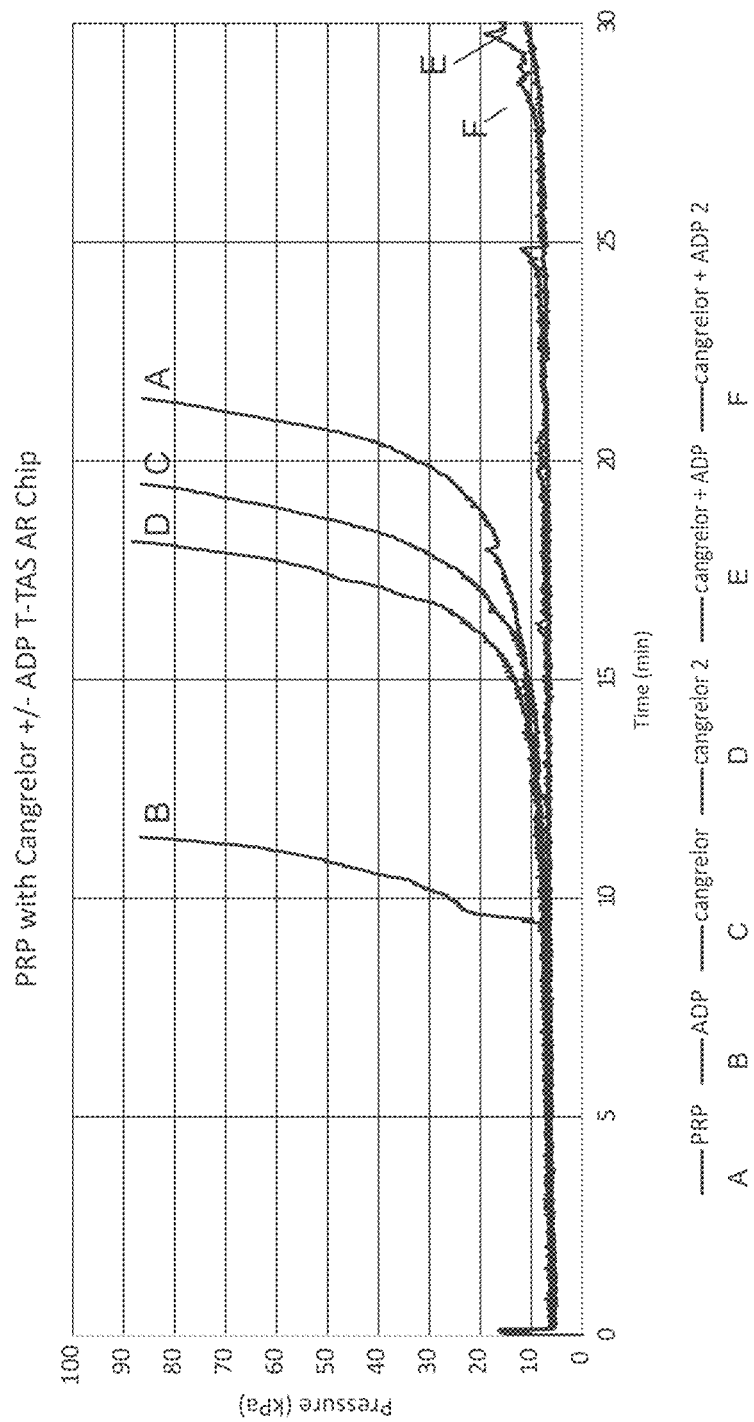
FIG. 2 shows the effect of cangrelor, ADP, or a combination thereof on platelet occlusion using T-TAS® technology.

The effect of cangrelor on platelet occlusion under shear was evaluated by T-TAS®. Fresh platelet rich plasma (platelet concentration 278,000/µL; PRP generally has a platelet concentration of about 200,000/µL to about 300,000/µL) stimulated in vitro with 10 µM ADP occluded earlier under high shear than unstimulated platelets (PRP) as determined by AR chip (collagen and tissue thromboplastin) using T-TAS® technology (FIG. 2). Cangrelor alone (1 µM) did not exhibit inhibition on occlusion, but when combined with ADP (10 µM), platelet adhesion and occlusion was essentially eliminated. These results are further illustrated in FIGS. 3 and 4. Without being bound by any particular theory, it is believed that this pattern is observed because platelets have other ADP receptors not blocked by cangrelor that respond to ADP and cause shape change and aggregation where the ADP receptor P2Y12 blocking inhibits collagen binding, and, accordingly, the platelets may bind each other due to ADP stimulation but may be prevented from binding collagen on the coated chip.

Figure 3:
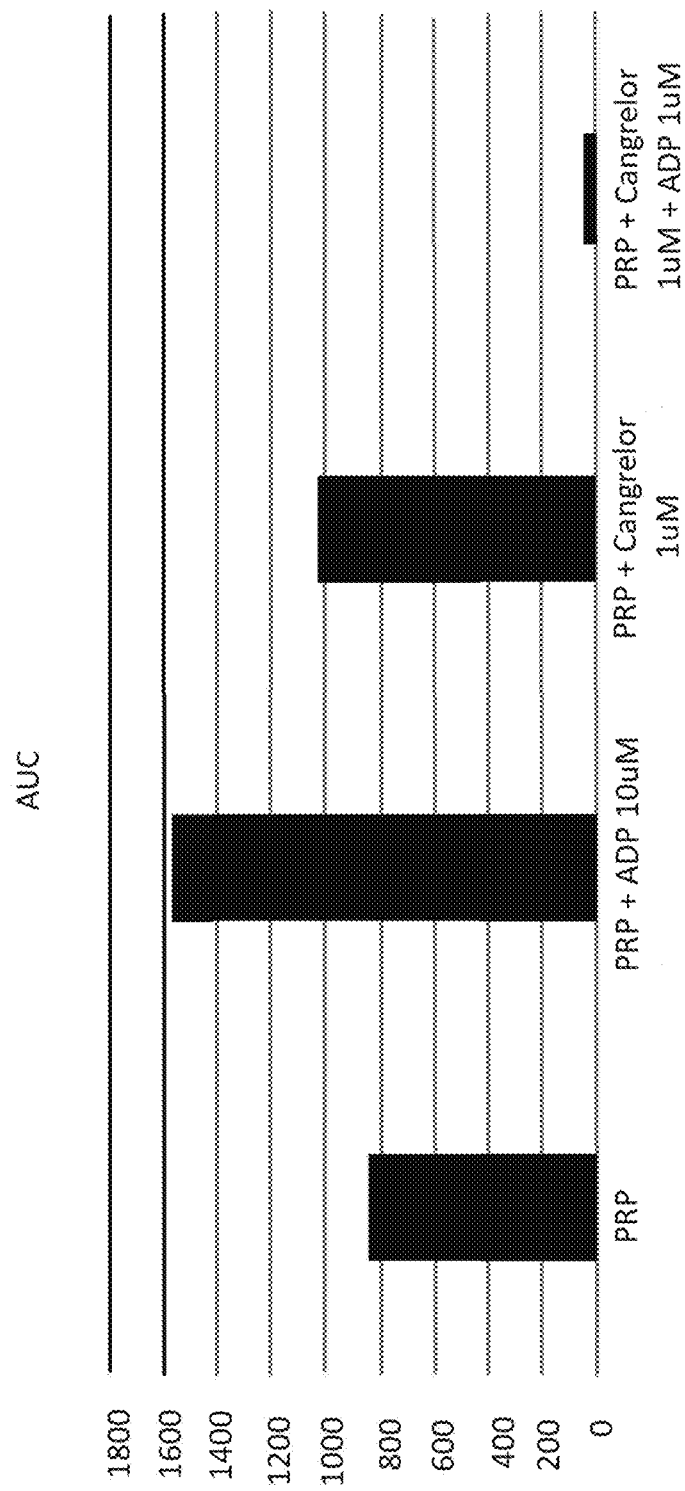
FIG. 3 is a bar plot of the area under the curve (AUC) for data sets from FIG. 2. Replicate data sets from FIG. 2 are presented as averages.

In FIG. 3, the area under the curve (AUC) values (derived from data in FIG. 2; replicates are averaged and plotted once) are indicative of a combined value of how quickly the thrombus happened in time and how substantial the thrombus is when it does happen. PRP AUC was increased with ADP stimulation. Cangrelor had little effect on AUC value, but when combined with ADP stimulation, the AUC dropped close to zero.

Figure 4:
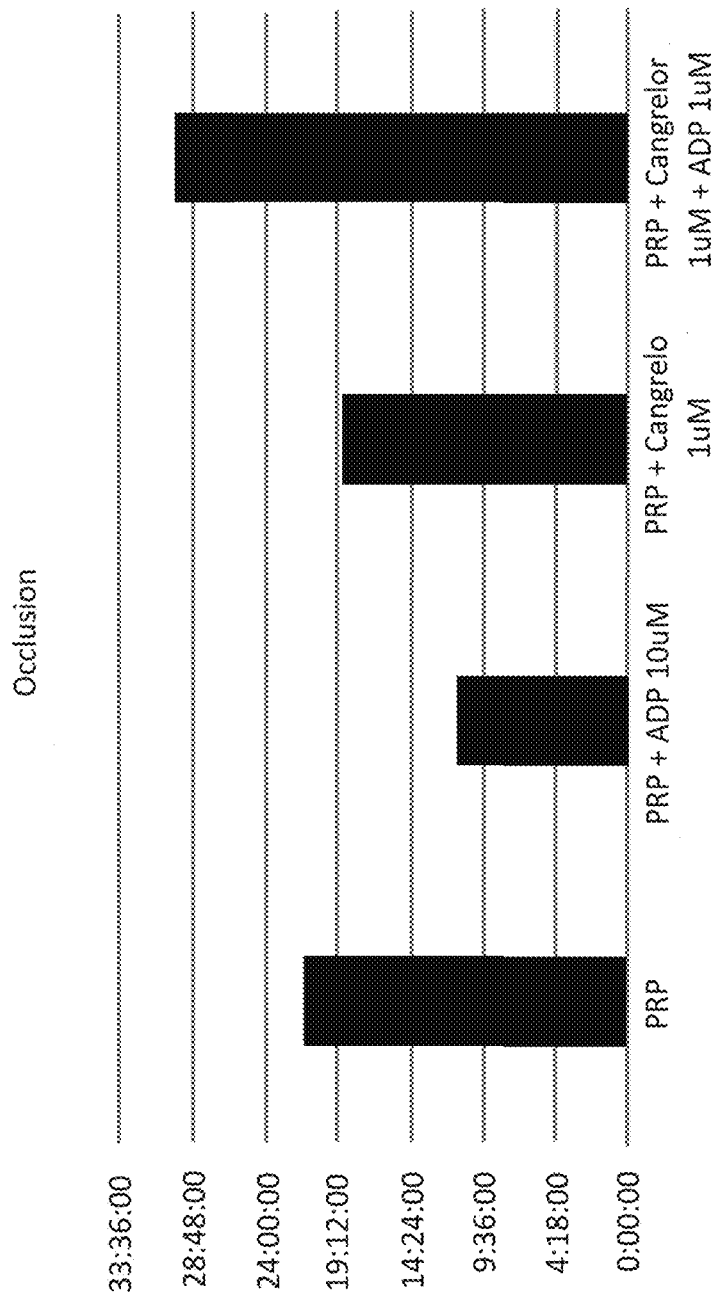
FIG. 4 is a bar plot of the occlusion time for data sets from FIG. 2. Replicate data sets from FIG. 2 are presented as averages.

In FIG. 4, the time to occlusion of the AR T-TAS® chip with drug treatment was evaluated. PRP occluded the chip channel at approximately 20 minutes, and stimulation of platelets with ADP decreased that time. Cangrelor had little effect on occlusion times, but addition of ADP stimulation to PRP sample inhibited occlusion essentially completely.

In the presence of cangrelor with ADP stimulation at the concentrations shown to be inhibitory of platelets, thrombosomes or FDPDs ("thromb" in FIGS. 5-7) were not inhibited, indicating that FDPDs can aid in a clot formation even in the presence of cangrelor at therapeutic levels.

Figure 5:
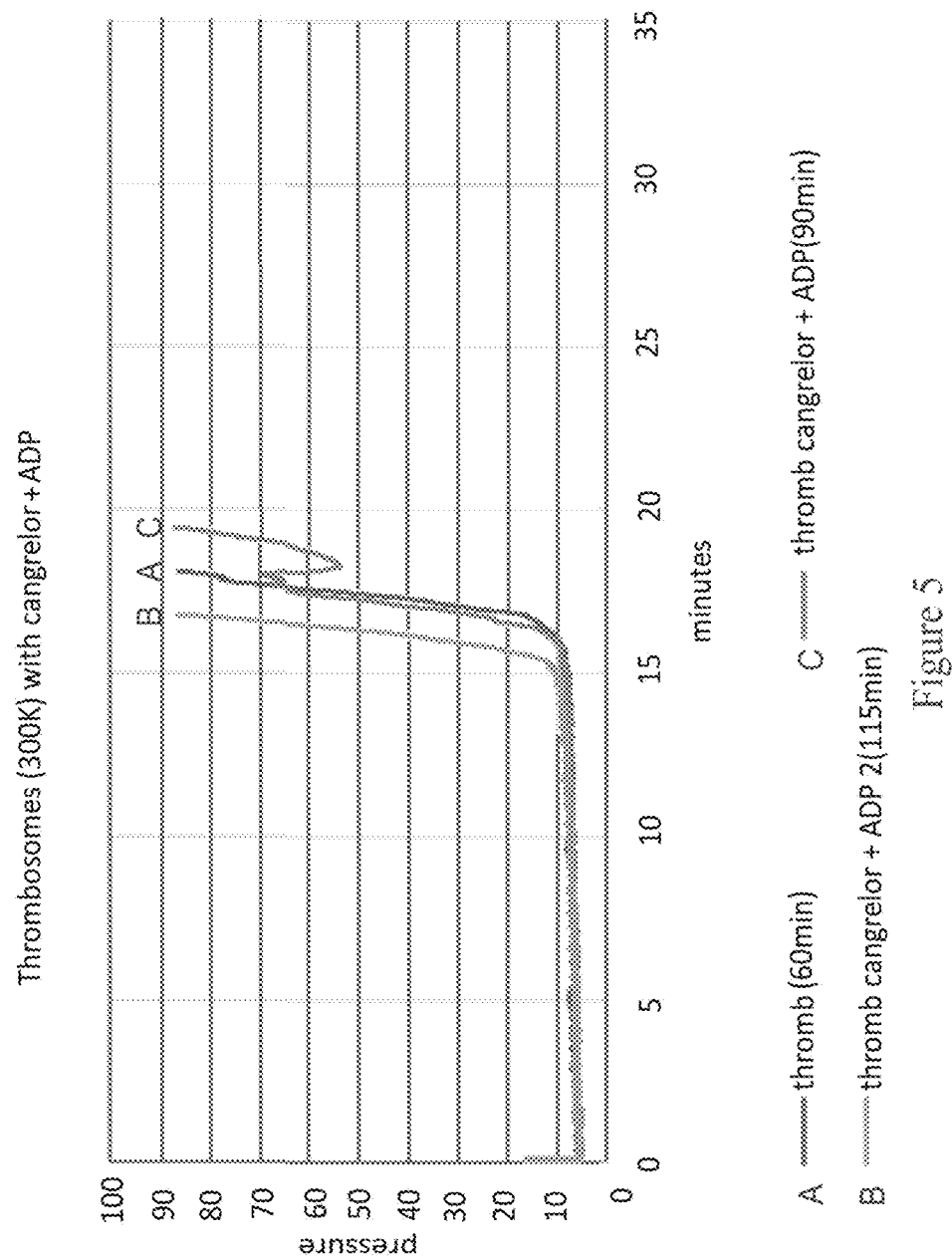
FIG. 5 shows the effect of FDPDs ("thromb"; 300,000/µL) supplemented to platelet rich plasma in the presence and absence of ADP and cangrelor, at 60, 90, or 115 minutes post-rehydration on platelet occlusion using T-TAS® technology.

The effect of cangrelor on FDPDs under shear was evaluated by T-TAS®. FIG. 5 shows that FDPDs (after 60, 90, or 115 minutes of rehydration, as indicated) retain hemostatic function in the absence or presence of cangrelor (1 µM), with ADP (10 µM) present. Unlike platelets, thrombosome occlusion of the T-TAS® AR Chip is unaffected by the antiplatelet effect of cangrelor+ADP. This suggests FDPDs will maintain expected function when infused into patients receiving cangrelor and similar agents. These results are further illustrated in FIGS. 6 and 7.

Figure 6:
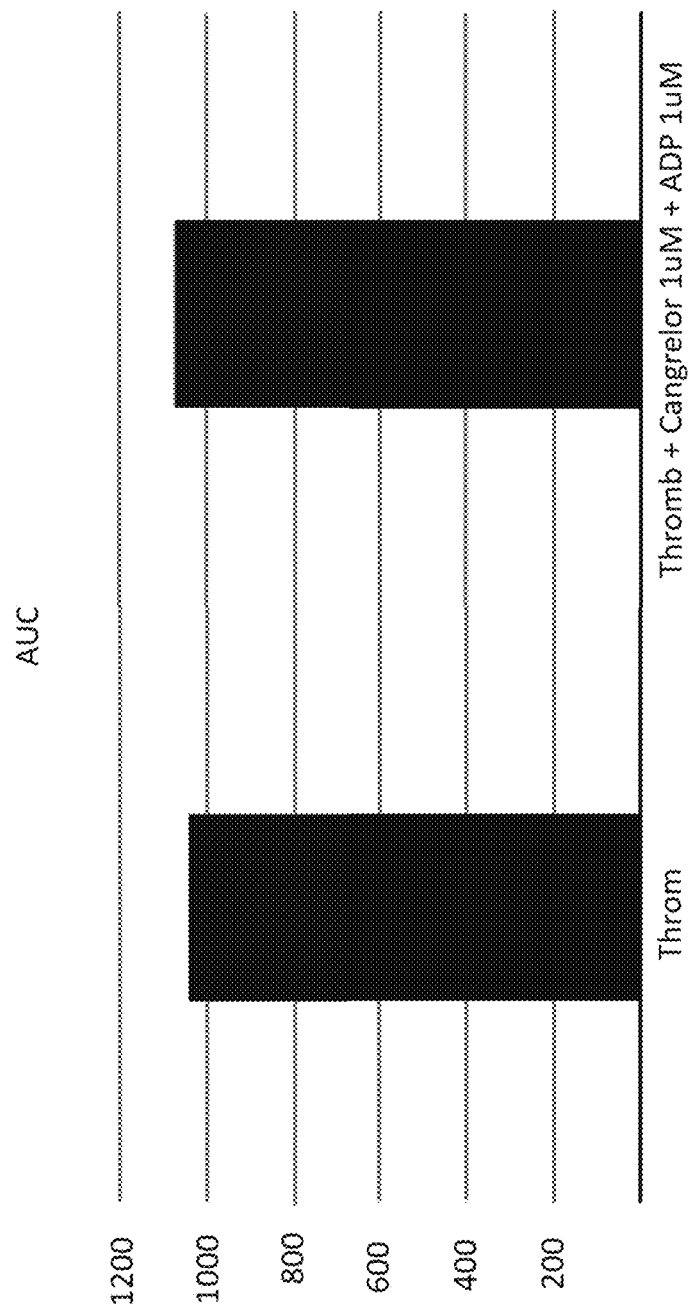
FIG. 6 is a bar plot of the AUC for data sets from FIG. 5. Replicate data sets from FIG. 5 are shown as averages.

In FIG. 6, the AUC values (derived from the data in FIG. 5) are indicative of thrombus formation. There was no effect of cangrelor+ADP on thrombosome adhesion and occlusion of the T-TAS® AR Chip in plasma; FDPDs caused a thrombus formation regardless of cangrelor and ADP. The same dose of cangrelor and ADP completely inhibited freshly harvested platelets.

Figure 7:
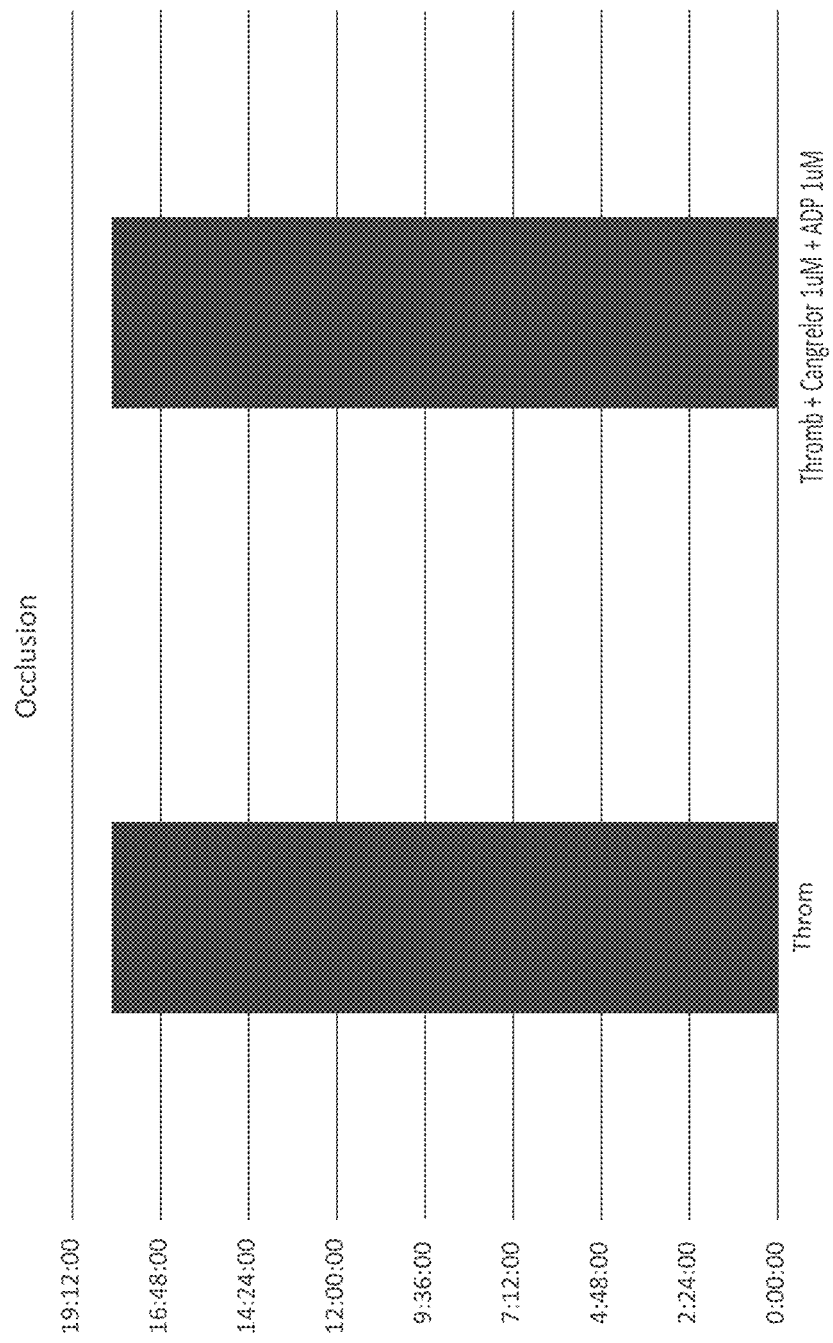
FIG. 7 is a bar plot of the occlusion time for data sets from FIG. 5. Replicate data sets from FIG. 5 are shown as averages.

In FIG. 7, the time to occlusion (derived from the data in FIG. 5) of the FDPDs on AR T-TAS® chip with drug treatment was evaluated. There was no effect from cangrelor+ADP on thrombosome time to occlusion using the T-TAS® AR Chip in plasma. The same dose of cangrelor and ADP completely inhibited freshly harvested platelets.

Example 2. GPIIb-IIIa Inhibitors

The results that follow demonstrate the impact of FDPDs in an in vitro model of a patient taking a GPIIb-IIIa inhibitor. Eptifibatide, a common antiplatelet drug, competitively inhibits the GPIIb-IIIa receptor on platelets which interact with fibrinogen and von Willebrand factor.

Eptifibatide is a peptide therapeutic that blocks the fibrin binding role of GPIIb-IIIa receptor on platelets. The drug is typically administered via IV as a 180 µg/kg bolus followed by 2 µg/kg/min continuous infusion. The blood concentration of eptifibatide is typically about 1-2 µM. Bleeding time generally returns to normal within about 1 hour of drug stoppage.

FDPDs were prepared consistent with the procedure in Example 4. Transmission light aggregometry and T-TAS® experiments were carried out according to Example 4.

Figure 8:
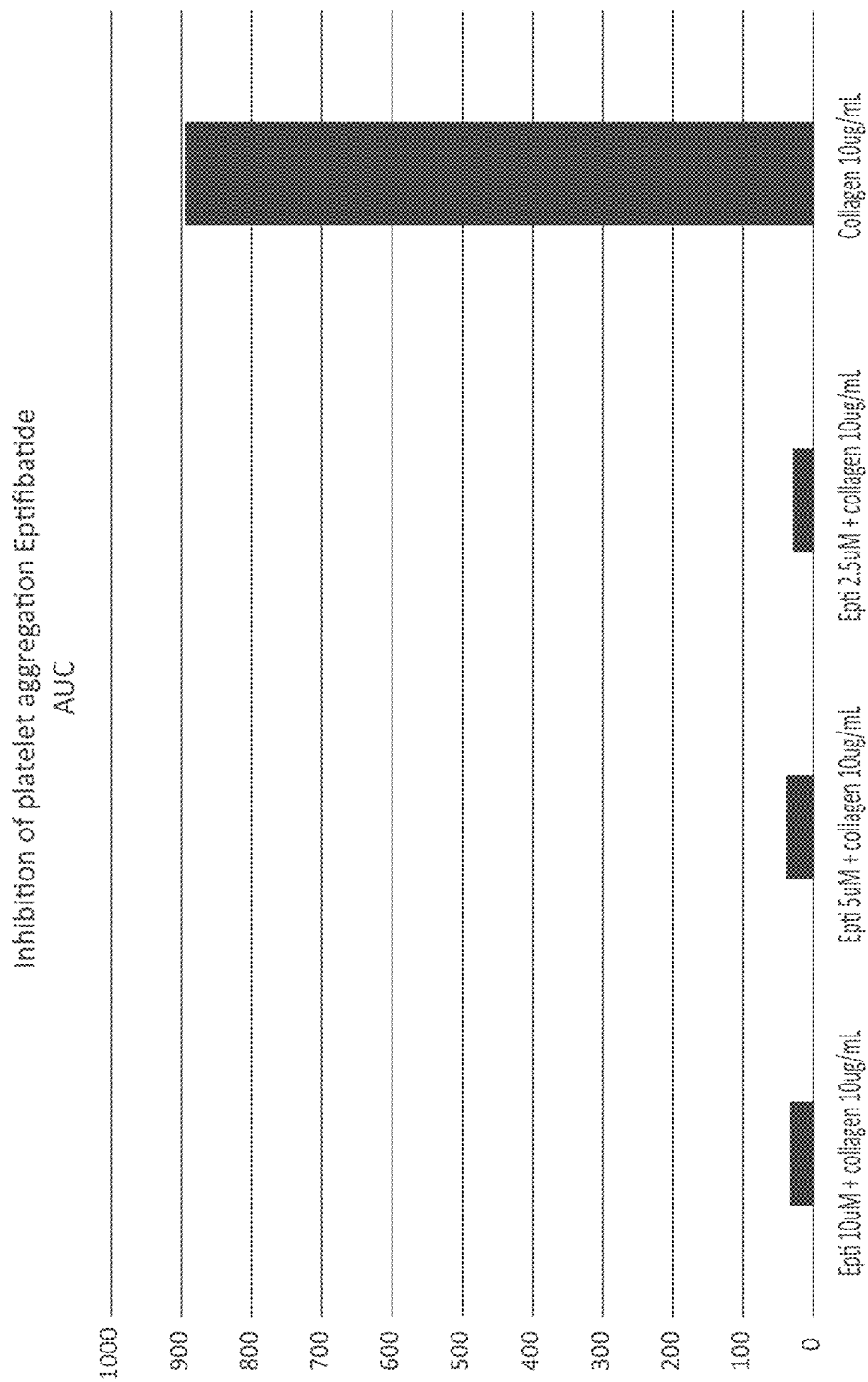
FIG. 8 is a bar plot of the AUC from aggregation experiments for platelets (at a concentration of 250,000 platelets per µL) treated with collagen (10 µg/mL) and various concentrations of eptifibatide ("Epti").

The aggregation of platelets (in platelet rich plasma) was evaluated using transmission light aggregometry. Eptifibatide completely inhibited collagen-induced (10 µg/mL) platelet aggregation in PRP at all concentrations tested, as detected by light transmission aggregometry in PRP. (FIG. 8).

Figure 9:
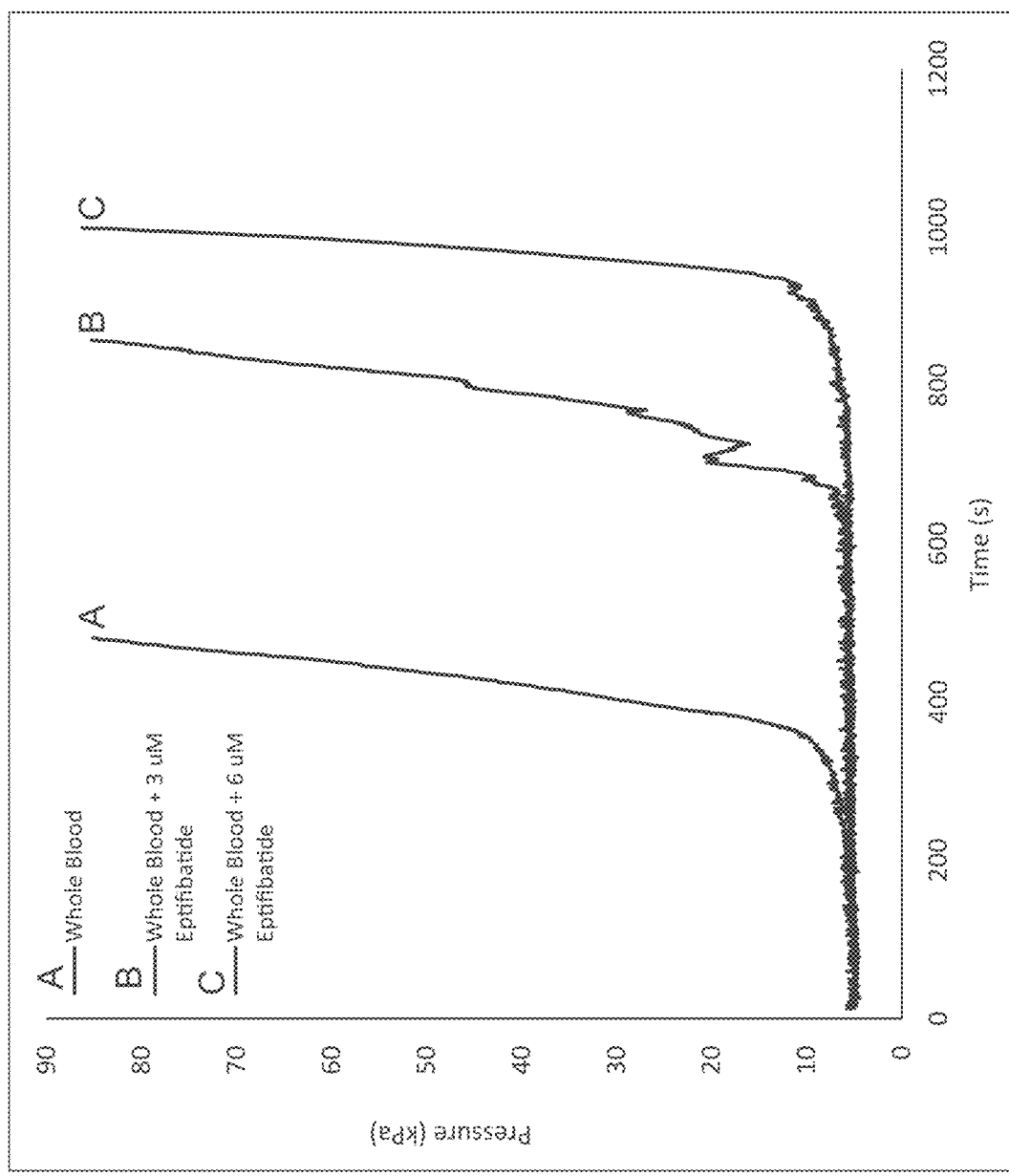
FIG. 9 shows the effect of eptifibatide at various concentrations on whole blood using T-TAS® technology.
Figure 10:
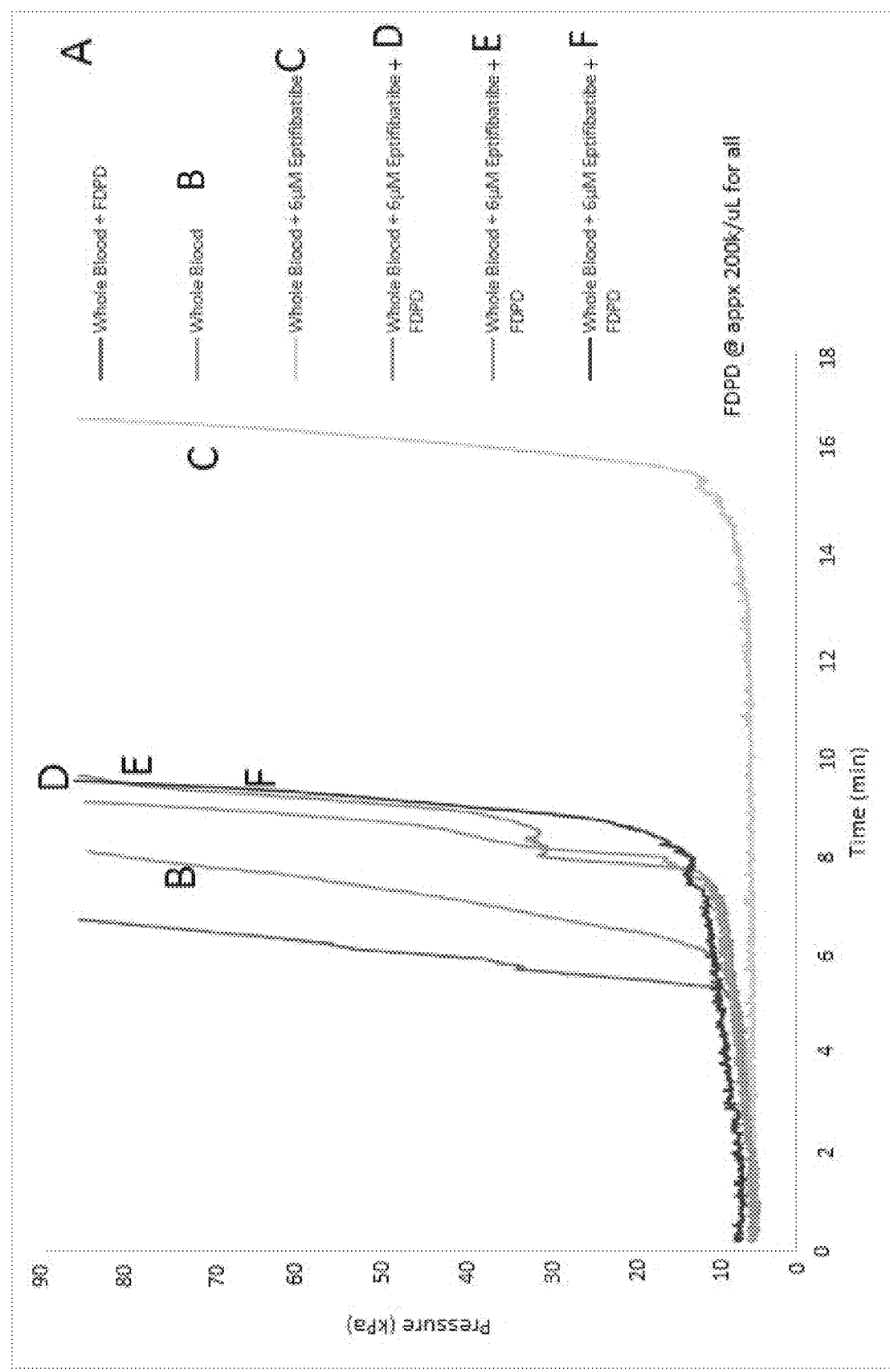
FIG. 10 shows the effect of FDPD ("Tsomes") supplementation (approximately 200,000/µL) on whole blood with and without various concentrations of eptifibatide using T-TAS® technology.

The effect of FDPDs on shortening clotting times while in the presence of eptifibatide was also studied. The ability of FDPDs to recover occlusion times was studied on the T-TAS® system. The T-TAS® system measures occlusion time under shear forces with collagen and thromboplastin stimulation. The whole blood profile of occlusion and AUC on the AR T-TAS® chip lengthened and decreased, respectively, with eptifibatide. Eptifibatide extended the occlusion time of whole blood on the T-TAS® AR Chip in a dose-dependent manner. In this experiment, whole blood occluded at 8 minutes, and the occlusion time was extended to 16 minutes with 6 µM eptifibatide (FIG. 9). FDPDs reversed the inhibitory effect of eptifibatide on thrombus formation. Eptifibatide inhibition of whole blood occlusion on the T-TAS® AR Chip was reversed by the addition of FDPDs at approximately 200,000/µL (N=3). When FDPDs (approximately 200 k/µL) were added to the sample of whole blood inhibited with eptifibatide, the time to occlusion decreased to 'normal' at 9 minutes (FIG. 10).

Figure 11:
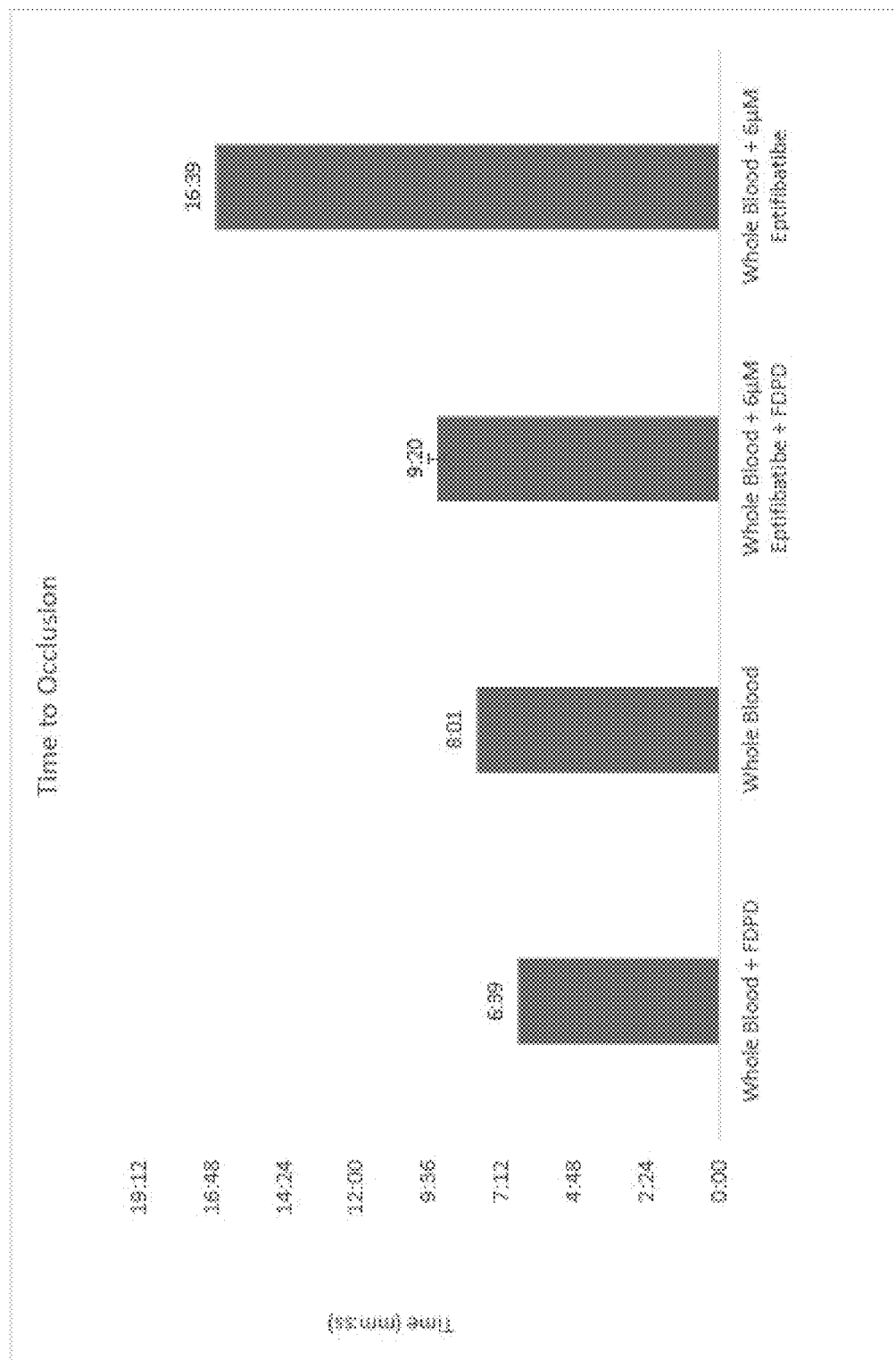
FIG. 11 is a bar plot of the occlusion time for the data sets from FIG. 10.
Figure 12:
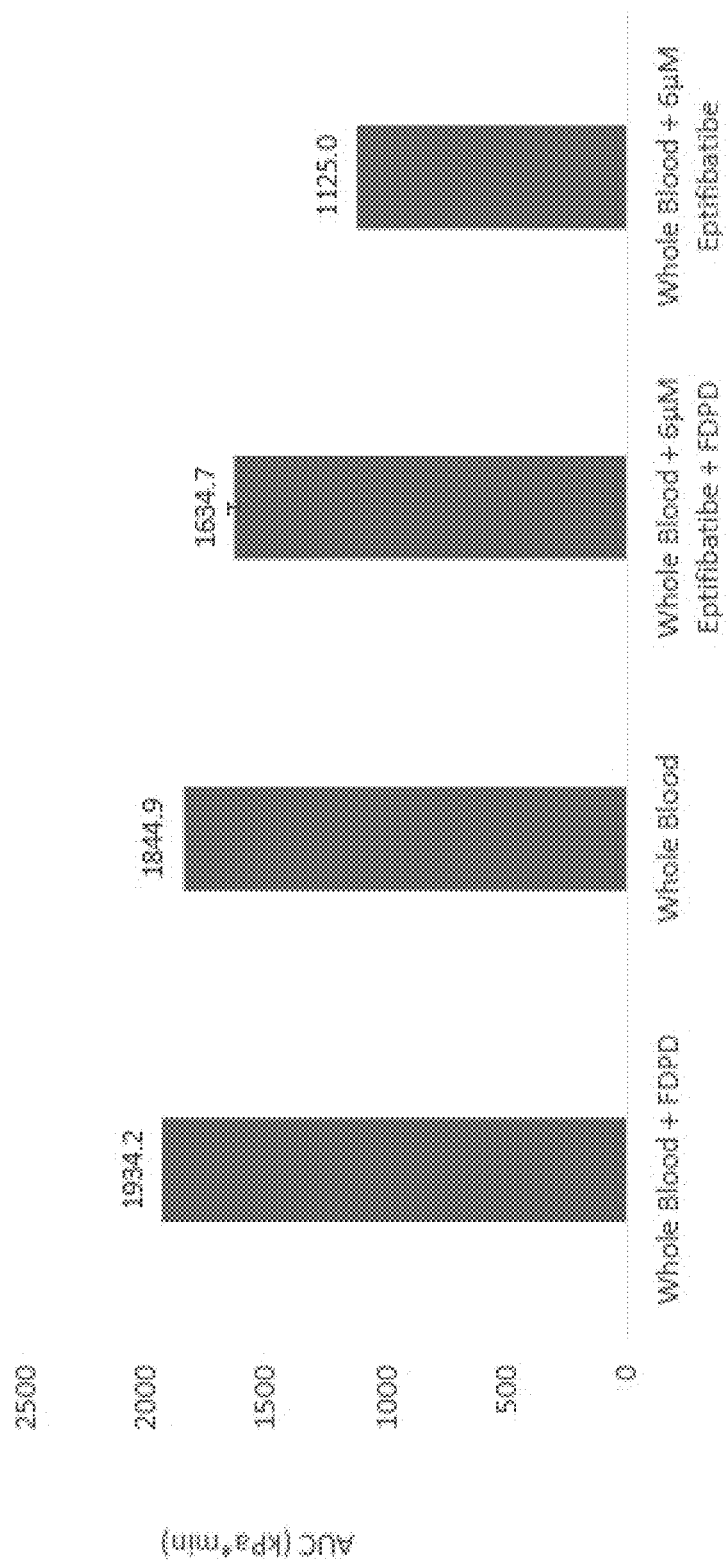
FIG. 12 is a bar plot of the AUC for the data sets from FIG. 10.

The area under the curve values with thrombosome treatment also increased with FDPDs compared to that of normal whole blood samples. FIG. 11 demonstrates the time to of occlusion of the FDPDs on AR T-TAS® chip with drug treatment; eptifibatide inhibition of T-TAS® AR Chip occlusion was nearly entirely reversed by the addition of FDPDs (200,000/µL; N=3). In FIG. 12, the area under the curve values were indicative of thrombus formation, where FDPDs returned inhibition by eptifibatide to normal levels; eptifibatide inhibition of platelet adhesion to and occlusion of the T-TAS® AR Chip is overcome by addition of FDPDs (200,000/µL; N=3).

Figure 13:
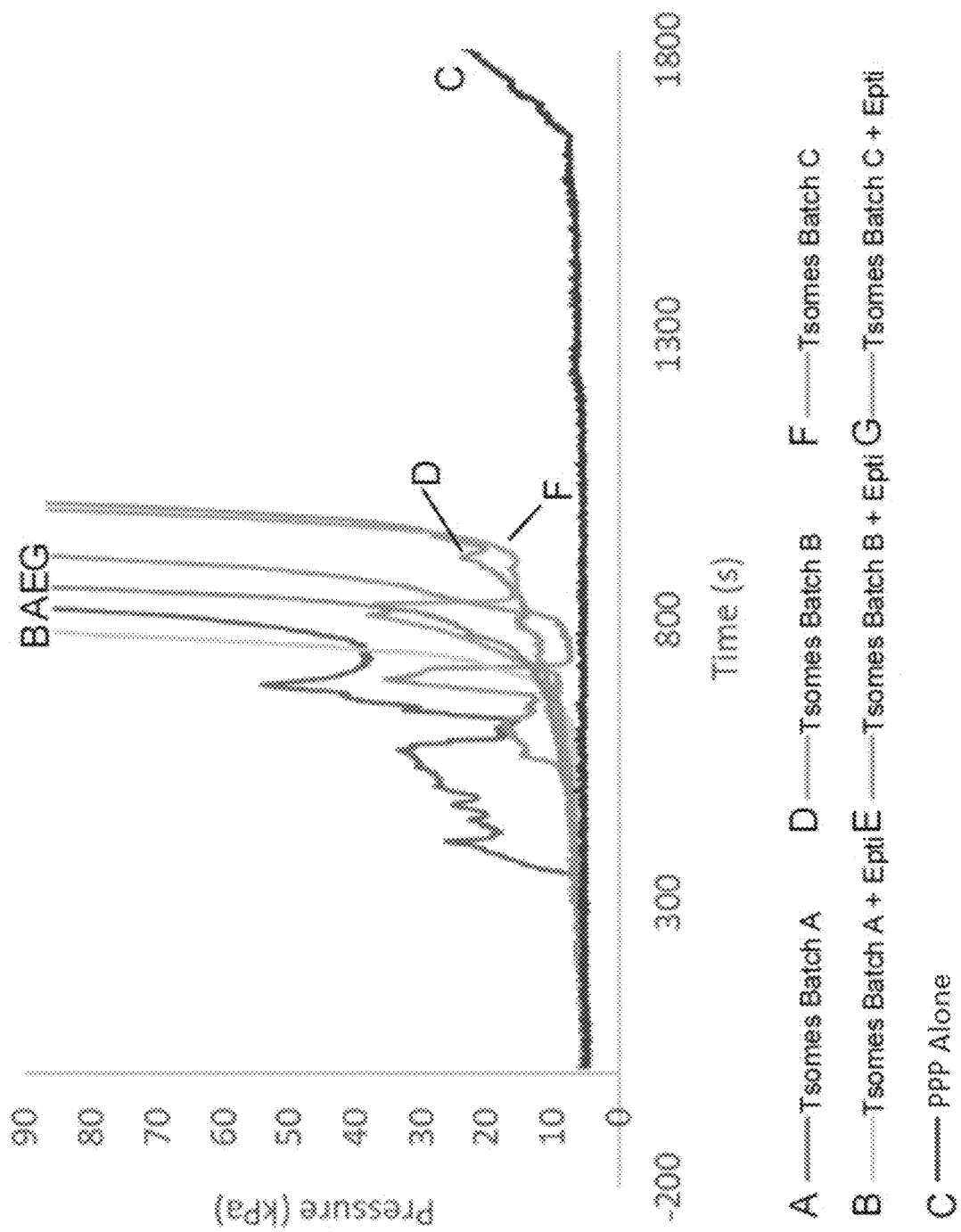
FIG. 13 shows that FDPDs (various lots) occlude in the presence of eptifibatide in platelet-poor plasma (PPP).

FDPDs, unlike platelets, are not inhibited in their ability to occlude under shear in the presence of eptifibatide (FIG. 13). FIG. 13 shows profiles of thrombus formation of various lots of thrombsomes on AR T-TAS® system were unchanged with eptifibatide treatment. FDPDs in platelet poor plasma (PPP) were flowed through the T-TAS® AR Chip with and without 6 uM eptifibatide. There was no effect of eptifibatide on thrombosome adhesion and occlusion. All thrombosome concentrations were approximately 300,000/µL.

Figure 14:
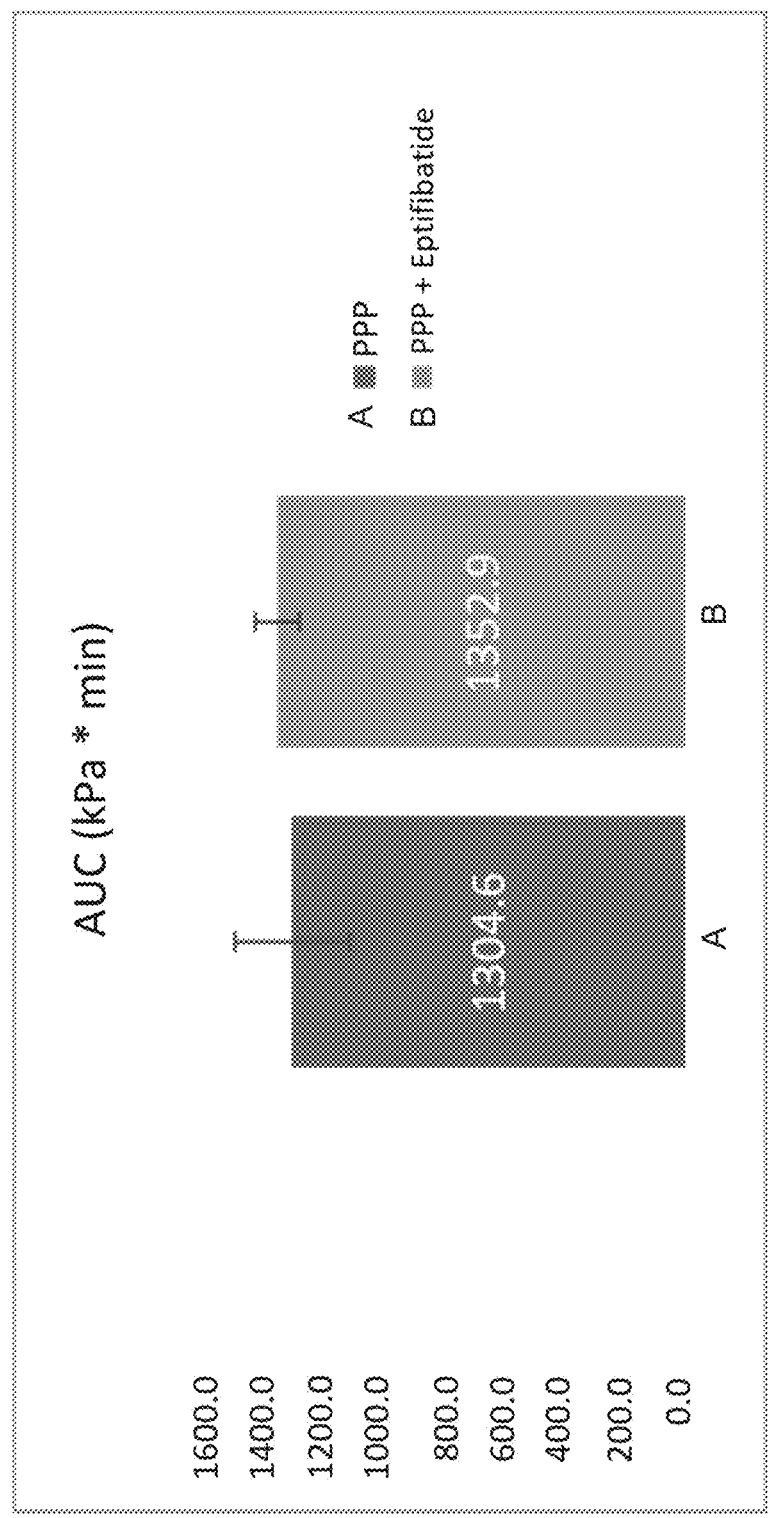
FIG. 14 is a bar plot of the AUC for data sets from FIG. 13. Replicate data sets from FIG. 13 are shown as averages.
Figure 15:
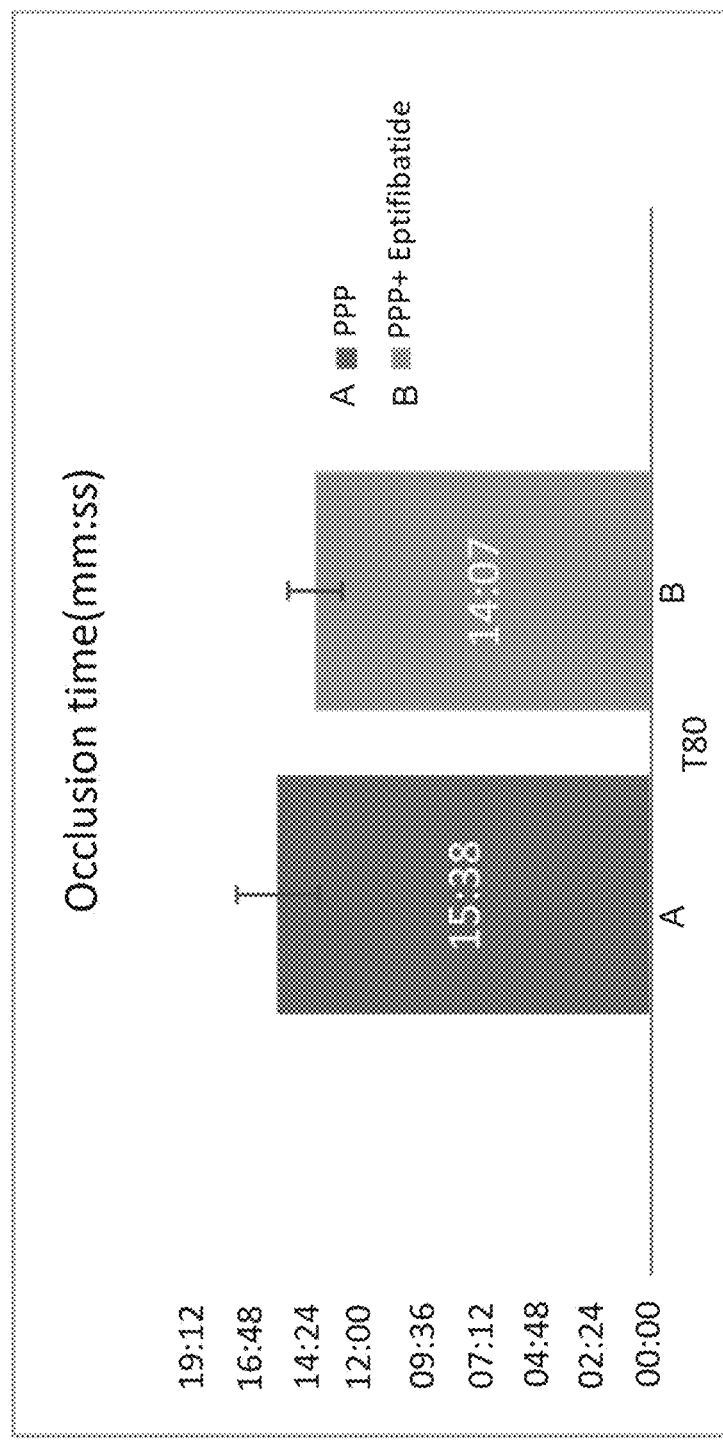
FIG. 15 is a bar plot of the occlusion time for the data sets from FIG. 13. Replicate data sets from FIG. 13 are shown as averages.

The AUC and occlusion values by T-TAS for FDPDs (approximately 300,000/µL) in plasma was the same with and without eptifibatide (FIG. 14-15). FIG. 14 shows the area under the curve values were indicative of thrombus formation, and no changes were observed with eptifibatide in platelet-poor plasma. There was no effect of 6 uM eptifibatide on AUC of FDPDs T-TAS® AR Chip occlusion. FIG. 15 shows the time to occlusion of the FDPDs on AR T-TAS® chip was unchanged with eptifibatide. There was no significant influence from 6 µM eptifibatide on FDPDs occlusion time of the T-TAS® AR Chip in platelet-poor plasma.

Example 3. COX Inhibitors

The results that follow demonstrate the impact of FDPDs in an in vitro model of a patient taking a COX inhibitor. Aspirin, a common antiplatelet drug, blocks the COX1 enzyme in platelets. COX1 is responsible for converting arachidonic acid to prostaglandin.

Aspirin is an irreversible cyclooxygenase (COX) inhibitor. The COX enzyme in platelets is responsible for synthesis of thromboxane A2, prostaglandin E2, and prostacyclin (PGI2). Aspirin permanently inactivates the COX enzyme within platelets, and since platelets do not have the nuclear material to synthesize new enzyme, new platelets must be produced to overcome the aspirin effect. Without thromboxane A2, prostaglandin E2 and prostacyclin (PGI2) platelets are limited in their pro-aggregation activity. Many people are maintained on a low dose of aspirin to prevent unwanted clotting events. Aspirin bioavailability largely varies with administration route, with a single 500 mg dose IV at peaks of 500 µM and the same dose orally at 44 µM.

FDPDs were prepared consistent with the procedure in Example 4. Transmission light aggregometry and T-TAS® experiments were carried out according to Example 4.

Figure 16:
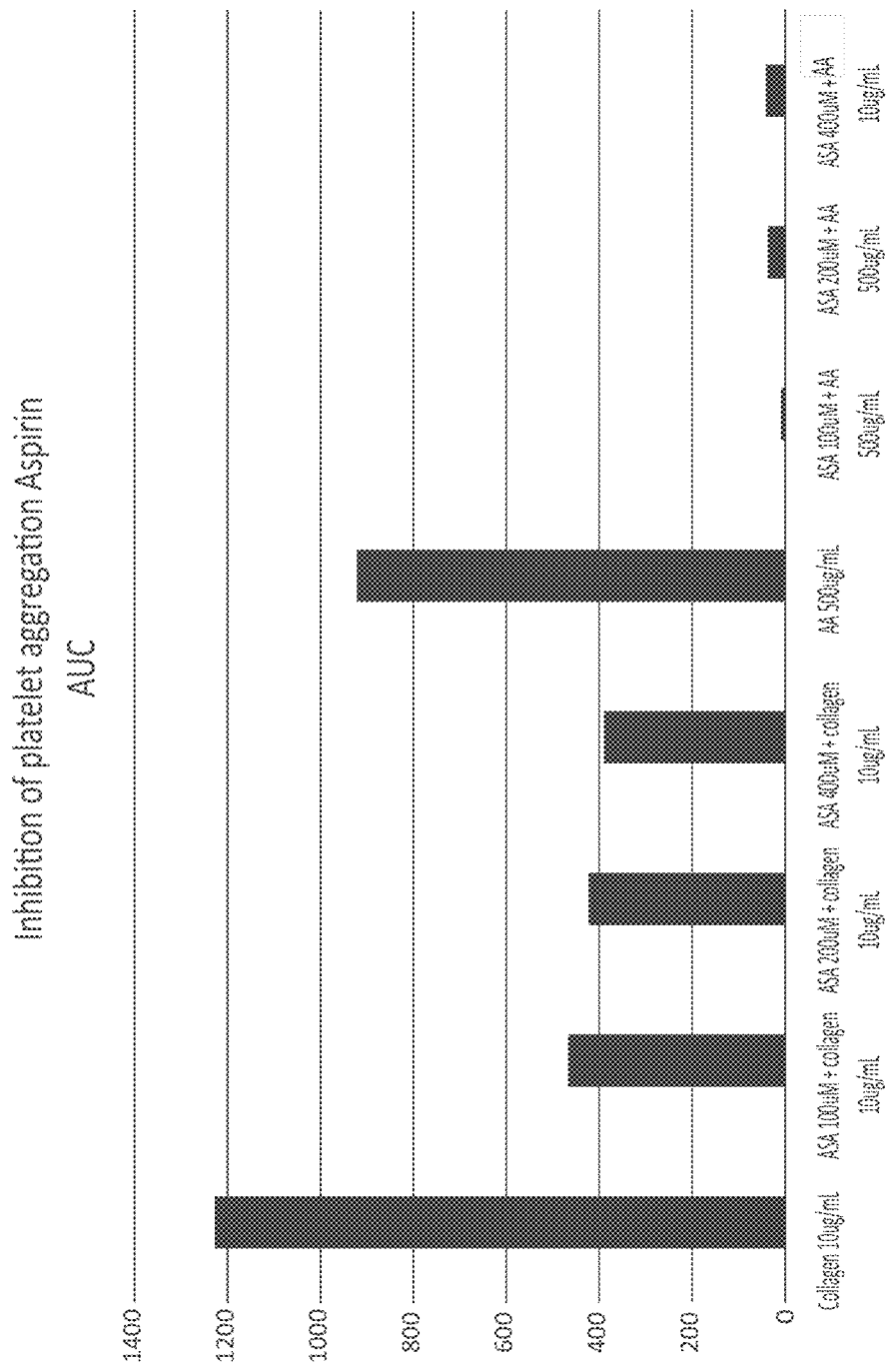
FIG. 16 is a bar plot of the AUC from aggregation experiments for platelets treated with collagen (10 µg/mL) or arachidonic acid ("AA"; 500 µg/mL) with and without various concentrations of aspirin ("ASA").
Figure 17:
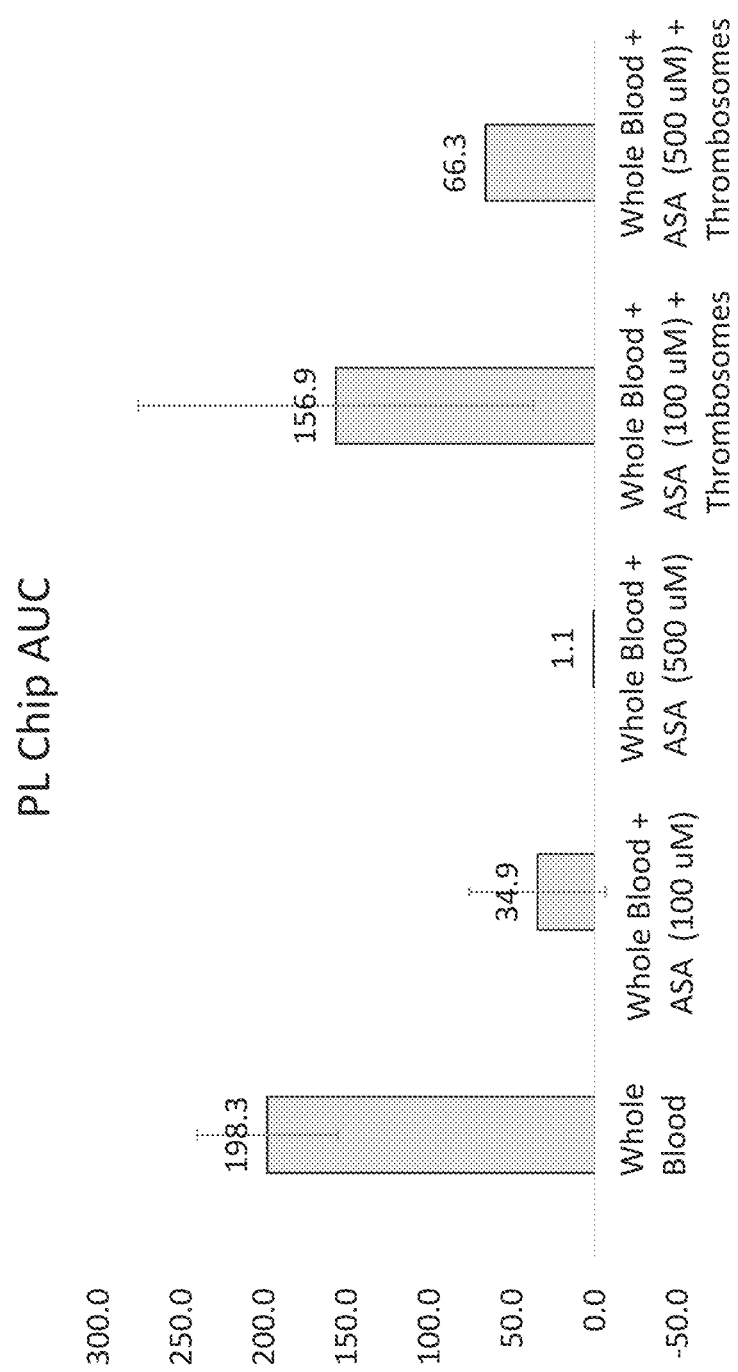
FIG. 17 is a bar plot of the occlusion time for whole blood, whole blood treated with various concentrations of aspirin (ASA), and whole blood treated with various concentrations of aspirin and supplemented with FDPDs (approximately 200,000-400,000/μL) as measured by response to collagen coated plastic under shear using T-TAS® technology.

Platelets will aggregate with collagen and arachidonic acid stimulation. Stimulation by arachidonic acid can be completely inhibited whereas collagen stimulation aggregation can only be partially inhibited at concentrations of 100-400 µM aspirin (FIG. 16). FIG. 16 shows light transmission aggregometry in PRP with collagen (10 ug/mL) and arachidonic acid (AA; 500 ug/mL), which induced platelet aggregation, and that aggregation was inhibited by all doses of aspirin (ASA) tested. Aspirin eliminated arachidonic acid induced platelet aggregation entirely. The PL chip system on the T-TAS® was used to emulate in vitro platelet binding and aggregation due to the exposure of collagen in the vasculature under shear conditions. This action of platelets was largely limited in the presence of 100 and 500 µM of aspirin but can be at least partially returned in the presence of FDPDs (approximately 200,000 to 400,000/µL; FIG. 17). FIG. 17 shows via area under the curve measurement of whole blood that thrombus formation on the PL T-TAS® chip was inhibited by aspirin with partial return of thrombus formation with FDPDs.

Example 4. Protocols

Generation of FDPDs. FDPDs were prepared consistent with the procedures described in U.S. Pat. No. 8,486,617 (such as, e.g., Examples 1-5) and U.S. Pat. No. 8,097,403 (such as, e.g., Examples 1-3), incorporated herein by reference in their entirety.

Transmission Light Aggregometry

Plasma samples with platelet or FDPDs or combination of both are loaded into cuvettes and placed into the aggregometry chambers. The chambers warm the sample and provide constant stirring. The initiation of aggregation can be done by multiple types of inhibitor agents not limited to thrombin, ADP, collagen and any agent know to stimulate platelet aggregation. The samples can also have been taken as ex-vivo, or in-vitro supplemented with inhibitors. The instrument begins the assay by first recording the light transmission previous to stimulation for 2 minutes. The stimulant of interest is then introduced by the technician and the change in light transmission is recorded overtime. The increase in light transmission corresponds to increase in platelet aggregation.

Evaluation by T-TAS® using an AR chip. AR chips are characterized by a single channel containing collagen and tissue factor; they can be used to analyze clotting and platelet function.

The T-TAS® instrument was prepared for use according to the manufacturer's instructions. AR Chips (Diapharma Cat. #TC0101) and AR Chip Calcium Corn Trypsin Inhibitor (CaCTI; Diapharma Cat. #TR0101) were warmed to room temperature. 300 µL of rehydrated FDPDs were transferred to a 1.7 mL microcentrifuge tube and centrifuged at 3900 g×10 minutes to pellet. The FDPDs pellet was resuspended in George King (GK) pooled normal human plasma or autologous plasma with or without autologous platelets to a concentration of approximately 100,000-450,000/uL, as determined by AcT counts (Beckman Coulter AcT Diff 2 Cell Counter). 20 µL of CaCTI with 480 µL of FDPDs sample in GK plasma were mixed with gentle pipetting. The sample was loaded and run on the T-TAS® according to the manufacturer's instructions.

Evaluation by T-TAS® Using a PL Chip

PL chips are run similarly to AR chips but this chip is only coated with collagen alone.

Thrombin Generation

Reagent Preparation. For thrombin generation, the following materials were used from manufacturers, as follows: FluCa Kit (Diagnostica Stago, Cat. No. 86197), Thrombin calibrator (Diagnostica Stago, Cat. No. 86197), PRP Reagent (Diagnostica Stago, Cat. No. 86196), OCTOPLAS®, a solvent detergent treated human pooled plasma (Octapharma, Cat. No. 8-68209-952-04). All frozen reagents were thawed in a 37° C. water bath before use. All reagents were rehydrated with sterile water using the volume printed on the reagent labels. Approximately 2 min after rehydration, the reagents were mixed by inverting vials 5 times, so no chunks or powder left; vortexing was not used. This procedure was repeated approximately 10 minutes after rehydration. All reagents were incubate at room temperature for another approximately 10 minutes (total of approximately 20 min after rehydration). A 30% solution of OCTOPLAS® was prepared by mixing 4.66 ml of FDPDs control buffer (Table B) with 2 ml of OCTOPLAS®.

TABLE B

| Component | FDPDs Control Buffer Concentration (mg/mL, except where otherwise indicated) |
|---|---|
| NaCl | 6.08 |
| KCl | 0.28 |
| HEPES | 2.47 |
| NaHCO$_3$ | 0.77 |
| Dextrose | 0.41 |
| Trehalose | 28.83 |
| Ethanol | 0.76% (v/v) |

Sample Analysis—Plate preparation and testing. For experiments containing FDPDs, a FDPDs dilution series was generated (dilutions of 194.4K, 64.8K, 21.6K, and 7.2K per µL were typically used; cell counts are determined by flow cytometry) for each the experimental FDPDs and the reference FDPDs. FDPDs were rehydrated unless indicated otherwise. The highest-concentration dilution (e.g., 194.4 k FDPDs) was prepared by combining FDPDs, OCTAPLAS®, and FDPDs Control Buffer. The rest of the dilution series was prepared by serial 1:3 dilutions in OCTAPLAS®. For each test sample, 20 uL of PRP reagent was added to each sample well (of Immulon 2HB Clear, round-bottom 96-well plate (VWR, Cat. No. 62402-954)) and 20 µL of Thrombin Calibrator was added to each calibrator well. To each sample well and calibrator well, 80 µL of the each of the FDPDs dilution series was added. Continue until the last dilution. The plate was then incubated in the Fluoroskan Ascent 96 well fluorescent plate reader (Thrombinoscope) (ThermoFisher Scientific) for 10 minutes. During this incubation phase, the FluCa solution was prepared by adding 40 µL of FluCa substrate to the 1.6 ml of thawed Fluo-Buffer, vortexing, and returning the solution to the water bath. When incubation was complete, the FluCa solution was added to the Fluroskan instrument according to the manufacturer's instructions. The plate fluorescence was monitored for 75 minutes at an interval of 20 seconds and a temperature of 40-41° C.

Example 5

Additional experiments were carried out with cangrelor and aspirin. FDPDs were prepared consistent with the procedure in Example 4. Transmission light aggregometry, T-TAS®, and thrombin generation experiments were carried out according to Example 4.

Figure 18:
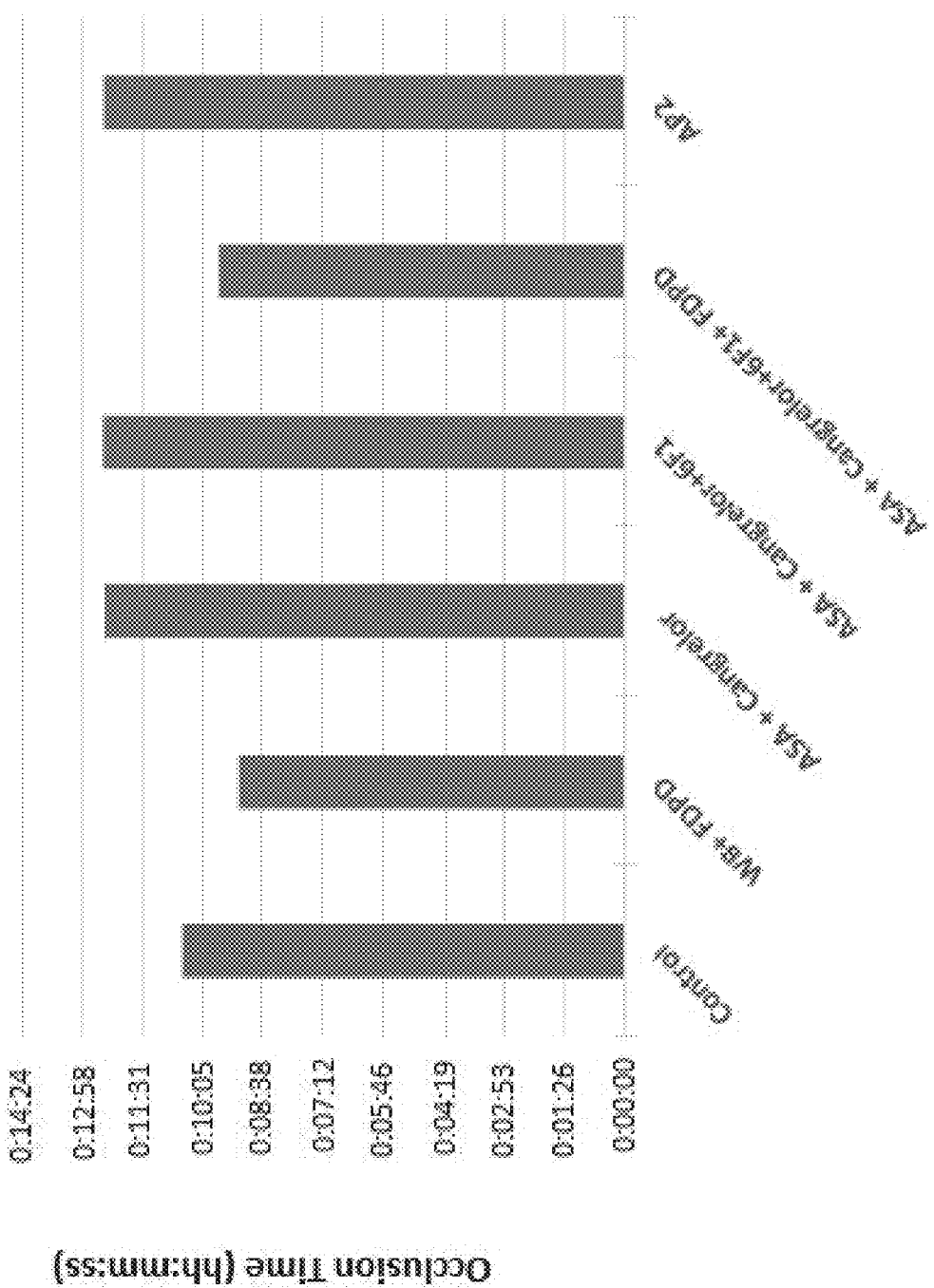
FIG. 18 shows the recovery of thrombus formation promoted by FDPDs in whole blood in the presence of ASA (200 micromolar), cangrelor (1 micromolar), AP2 6F1 (40 micrograms), as measured by occlusion time on the T-TAS AR chip coated with thromboplastin and collagen.
Figure 19:
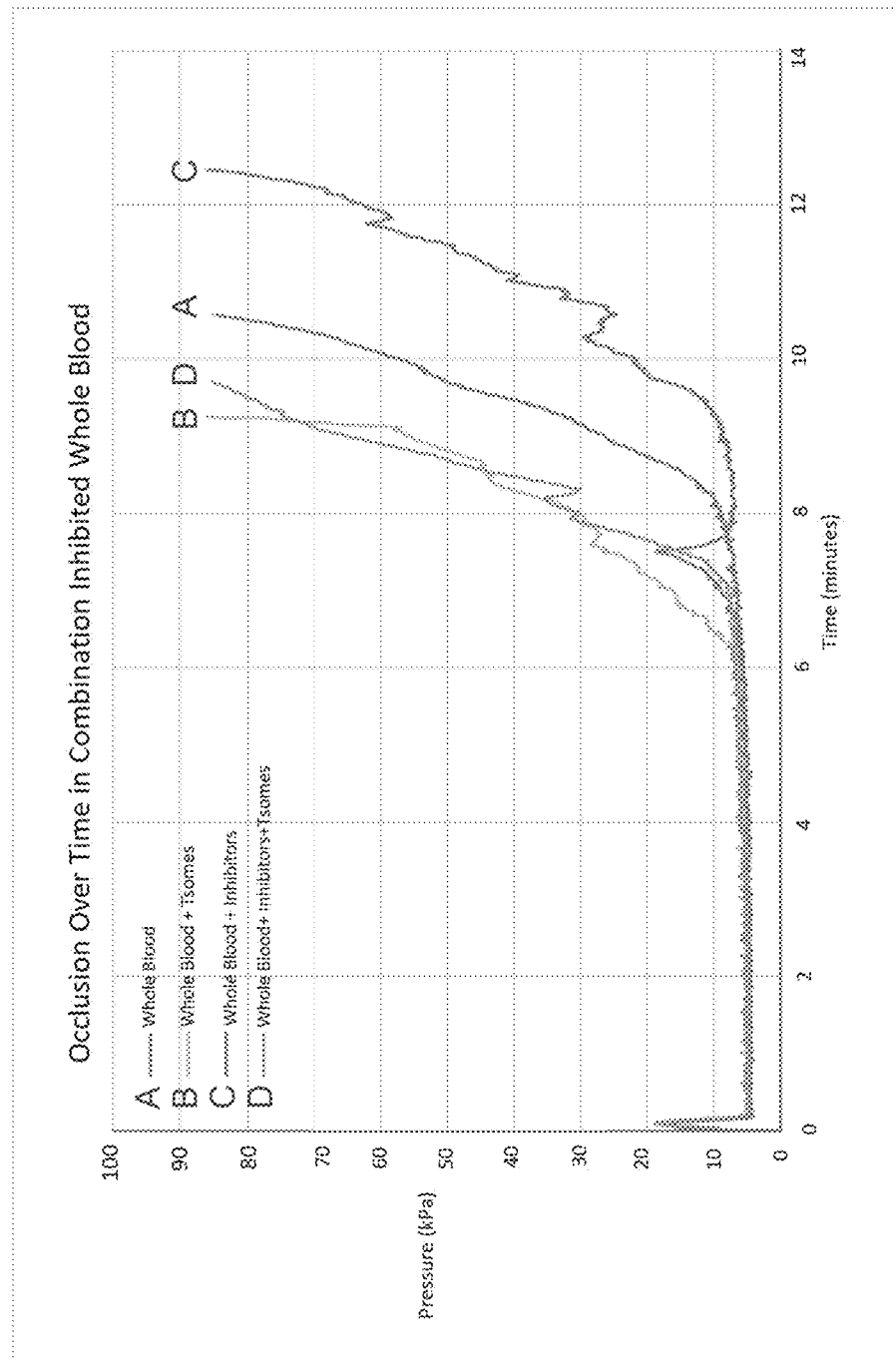
FIG. 19 shows the recovery of thrombus formation promoted by FDPDs in whole blood in the presence of ASA (200 micromolar), cangrelor (1 micromolar) and 6F1 (40 micrograms/mL), as measured by occlusion (pressure) over time.

The effect of FDPDs on the recovery of thrombus formation was evaluated using T-TAS® technology and an AR chip. FIG. 18 shows the occlusion time of whole blood treated with various combinations of FDPDs (at a concentration of 250,000 FDPDs per µL), aspirin (200 µM), cangrelor (1 µM), anti-Integrin alpha-2 (CD49B) antibody 6F1 (40 pg; see dshb.biology.uiowa.edu/integrin-alpha-2-alpha2beta1?sc=7&category=-107 for product/manufacturer information), and anti-GPIIb/IIIa receptor antibody AP2 (20 ug/mL; see kerafast.com/product/2010/anti-glycoprotein-gpiiiagpiib-complex-ap-2-antibody for product/manufacturer information). FIG. 19 shows the occlusion over time of untreated whole blood and whole blood treated with FDPDs (at a concentration of 250,000 FDPDs per µL), a mixture containing 6F1 (40 ug/mL; anti-CD49b), ASA (aspirin; 200 uM), and cangrelor (1 uM); or a combination thereof.

Figure 20:
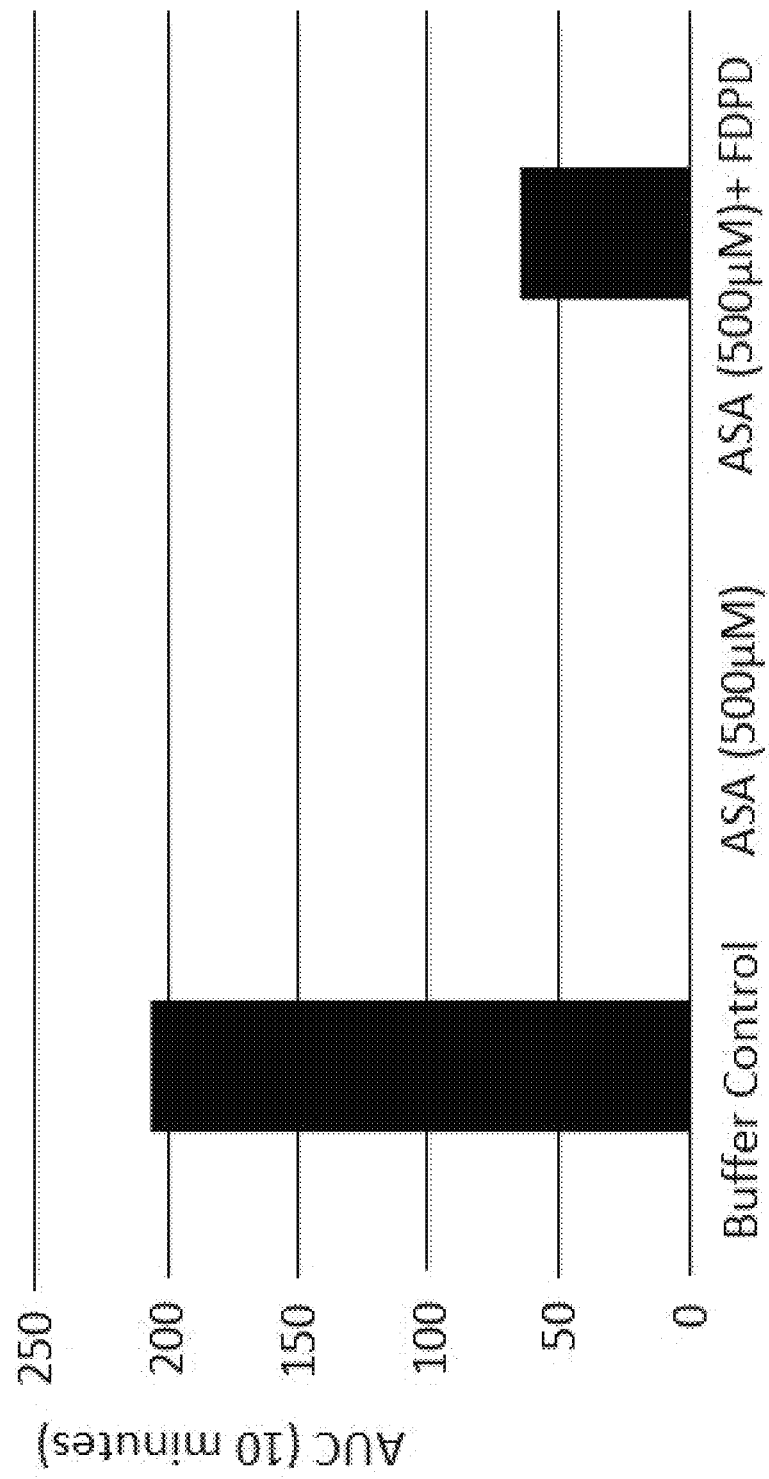
FIG. 20 shows the effect of FDPDs supplementation to aspirin-(ASA-)inhibited whole blood (500 micromolar) on the interaction with plastic immobilized porcine collagen under high shear, as measured by AUC.
Figure 21:
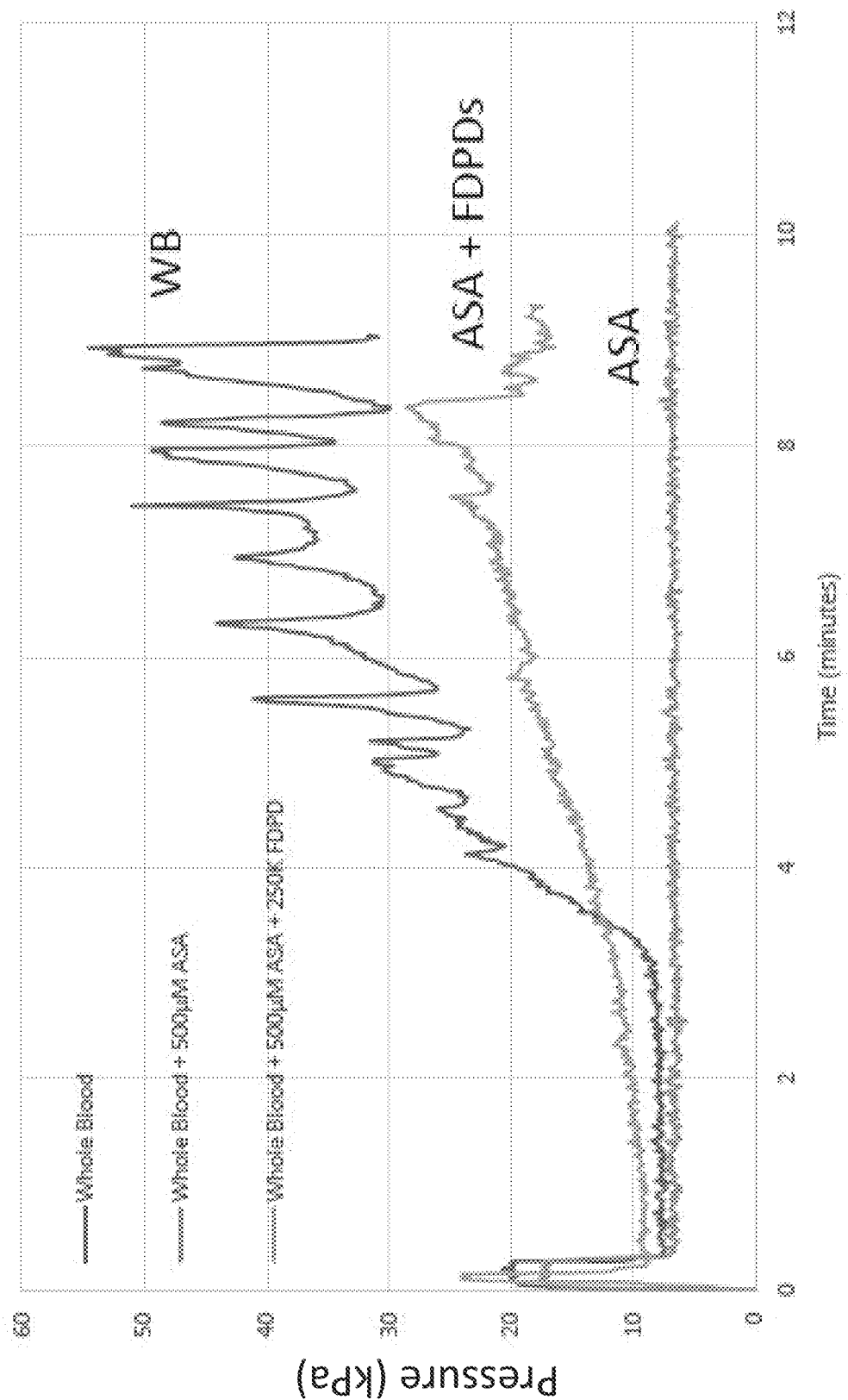
FIG. 21 shows the effect of FDPDs supplementation to aspirin-(ASA-)inhibited whole blood (500 micromolar) on the interaction with plastic immobilized porcine collagen under high shear, as measured by occlusion (pressure) over time.
Figure 22:
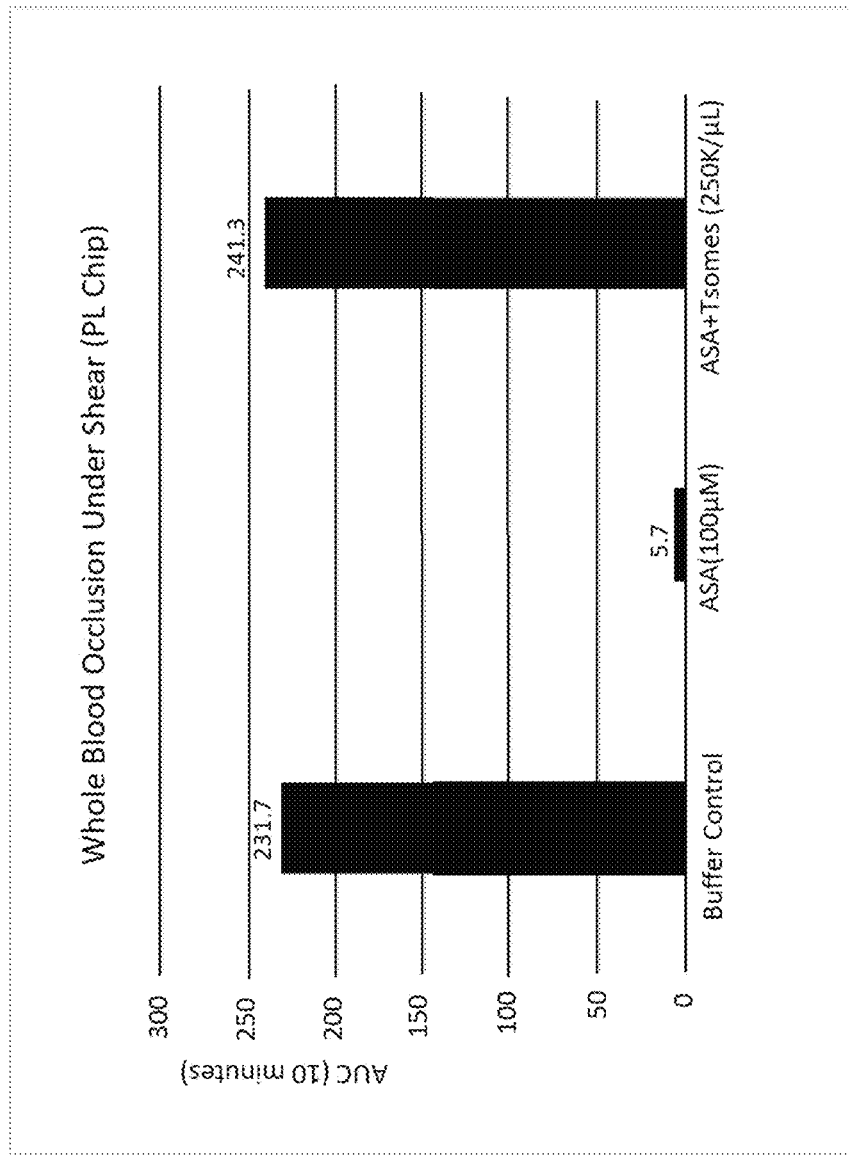
FIG. 22 shows the effect of FDPDs supplementation to aspirin-(ASA-)inhibited whole blood (100 micromolar) on the interaction with plastic immobilized porcine collagen under high shear, as measured by AUC.
Figure 23:
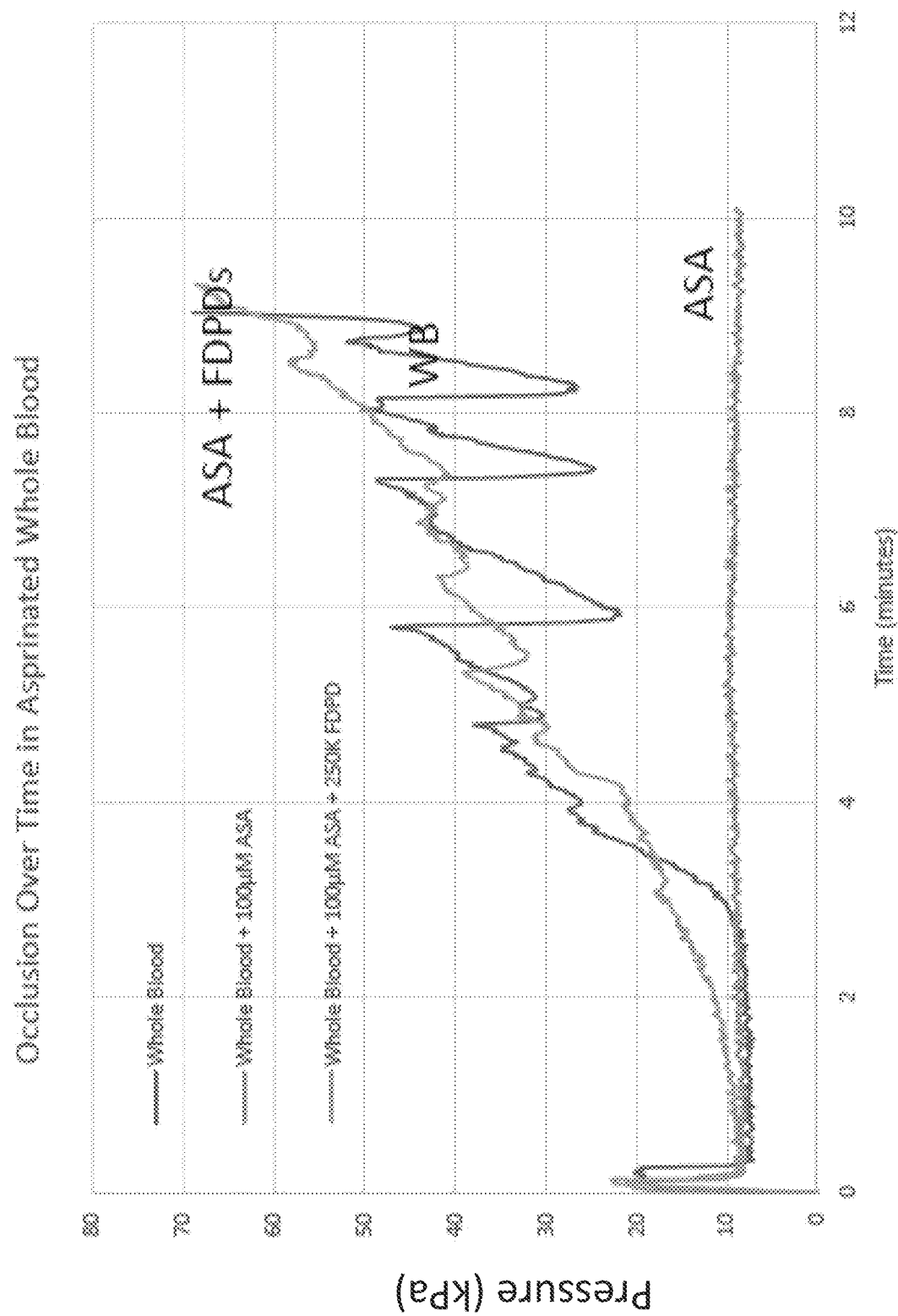
FIG. 23 shows the effect of FDPDs supplementation to aspirin-(ASA-)inhibited whole blood (100 micromolar) on the interaction with plastic immobilized porcine collagen under high shear, as measured by occlusion (pressure) over time.

The effect of FDPDs on the recovery of thrombus formation was also evaluated using T-TAS® technology and a PL chip. FIG. 20 shows the occlusion time of whole blood treated only with buffer, aspirin (500 µM), or aspirin (500 µM) and FDPDs (at a concentration of 250,000 FDPDs per µL). FIG. 21 shows the occlusion over time of whole blood, whole blood treated with aspirin (500 µM), or aspirin (500 µM) and FDPDs (250,000/µL). FIGS. 22 and 23 show similar experimental data using 100 µM aspirin instead of 500 µM aspirin.

Figure 24:
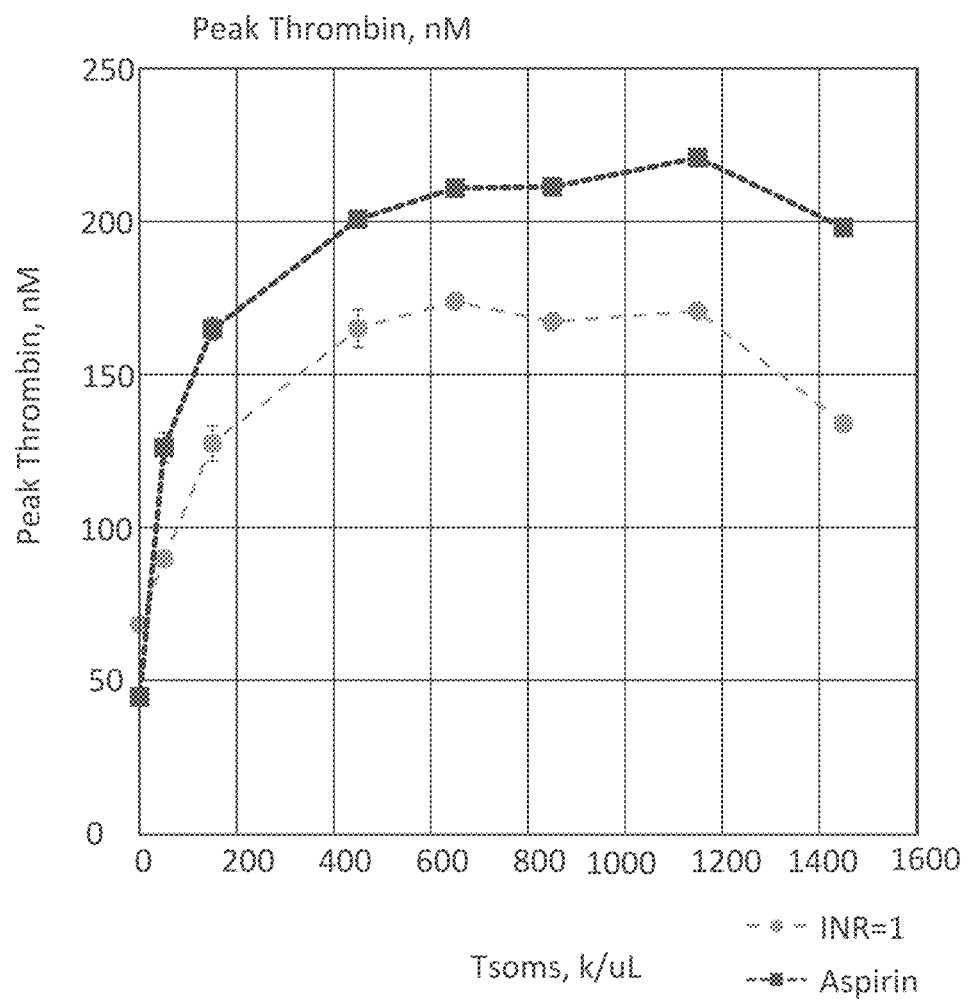
FIG. 24 shows the effect on peak thrombin of FDPD supplementation to normal and aspirin-inhibited plasma.

The effect of aspirin treatment (concentration) on thrombin generation was measured. FDPDs were evaluated at concentrations 1450, 1150, 850, 650, 450, 150, 50, and 0 k/uL in PPP from patients taking baby aspirin daily and standard plasma (INR=1). FIG. 24 shows that the peak thrombin value of the aspirin plasma in absence of FDPDs was below the normal range (about 45 nM; normal range is about 66-166 nM), but with FDPDs addition, it came back to being within the normal range at even the lowest FDPDs concentration used (50 k/µL). The values again were saturated at about 800 k FDPDs and went up to 220 nM—5 times the value of this plasma in absence of FDPDs (increase from 45 to 220 nM).

Example 6. FDPDs Reversed Prolonged PRP Occlusion Times Induced by Cangrelor

Additional experiments were carried out with cangrelor. FDPDs were prepared consistent with the procedure in Example 4. T-TAS® was carried out according to Example 4.

Figure 25A:
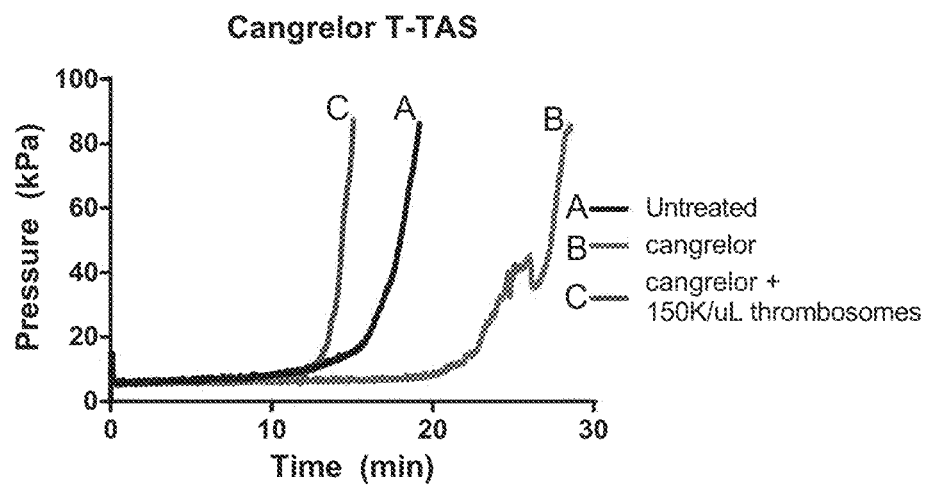
FIG. 25A shows the effect of cangrelor alone or cangrelor plus FDPDs on platelet occlusion using T-TAS® technology.
Figure 25B:
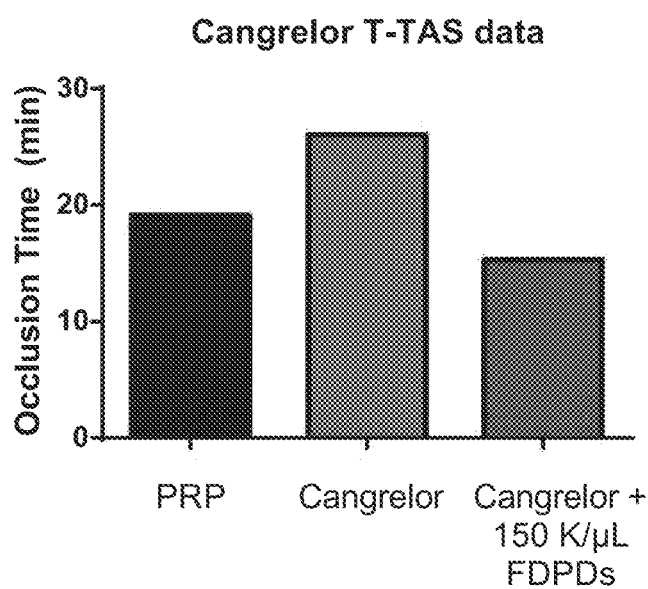
FIG. 25B is a bar plot of the occlusion time for data sets from FIG. 25A.

FIGS. 25A and 25B show that platelet rich plasma treated with 100 ng/mL cangrelor and ADP extended occlusion times from 19 to 26 minutes on the T-TAS® flow system (collagen and tissue factor coated channel). The addition of 150 k/µL FDPDs decreased the time back to 15.3 minutes.

Example 7. FDPDs but not Random Donor Platelets (RDP) Reversed Extended Occlusion Times Induced by Tirofiban in PRP Additional experiments were carried out with tirofiban. FDPDs were prepared consistent with the procedure in Example 4. T-TAS® was carried out according to Example 4. Random donor platelets were prepared from whole blood.

Figure 26A:
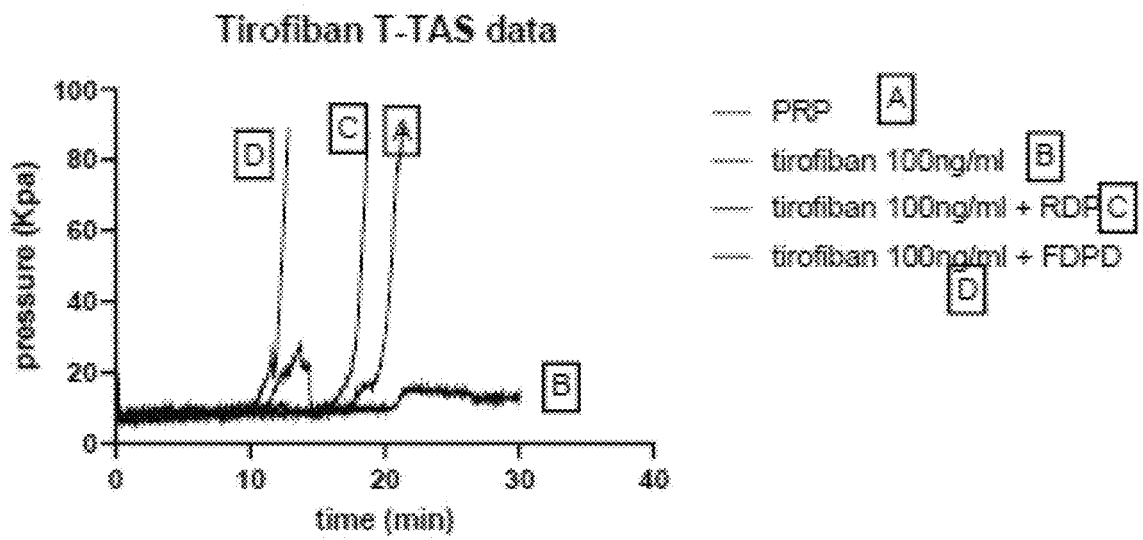
FIG. 26A shows the effect of tirofiban alone, or with random donor platelets (RDP) or FDPDs on platelet occlusion using T-TAS® technology.
Figure 26B:
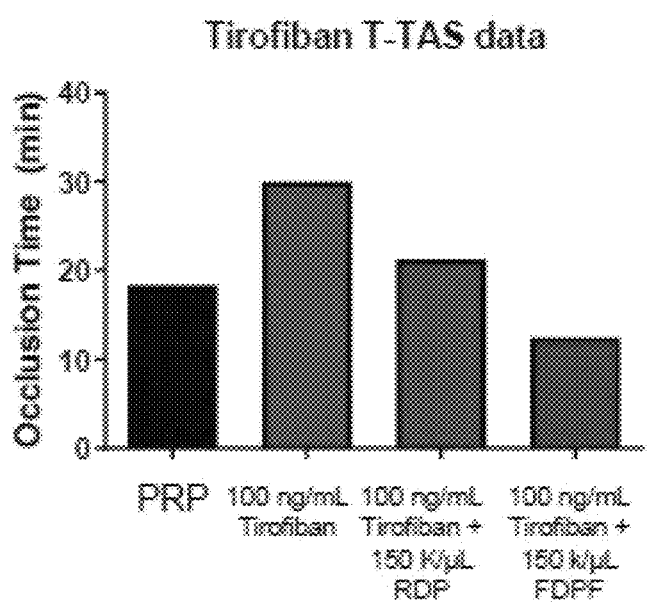
FIG. 26B is a bar plot of the occlusion time for data sets from FIG. 26A.

FIGS. 26A and 26B show that platelet rich plasma treated with 100 ng/mL tirofiban extended occlusion times from 18.43 to no occlusion on the T-TAS® flow system (collagen and tissue factor coated channel). The addition of 150 k/µL of FDPDs decreased the time back to 12.94 minutes but RDP only partially recovered at the same count.

Example 8. FDPDs but not Random Donor Platelets Reversed Extended Occlusion Times Induced by Eptifibatide in PRP Additional experiments were carried out with eptifibatide. FDPDs were prepared consistent with the procedure in Example 4. T-TAS® was carried out according to Example 4. Random donor platelets were prepared from whole blood.

Figure 27A:
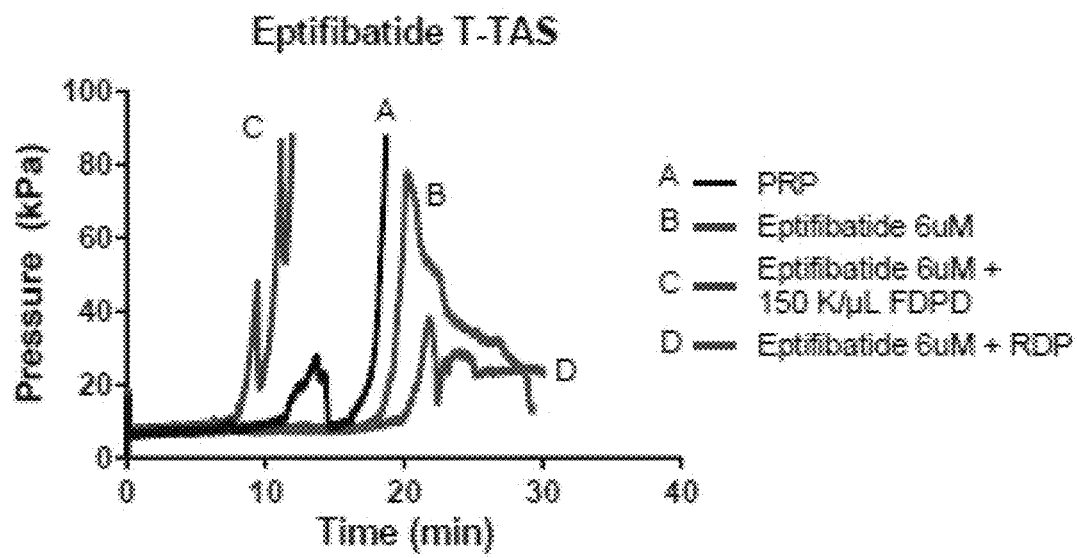
FIG. 27A shows the effect of eptifibatide alone, or with RDP or FDPDs on platelet occlusion using T-TAS® technology.
Figure 27B:
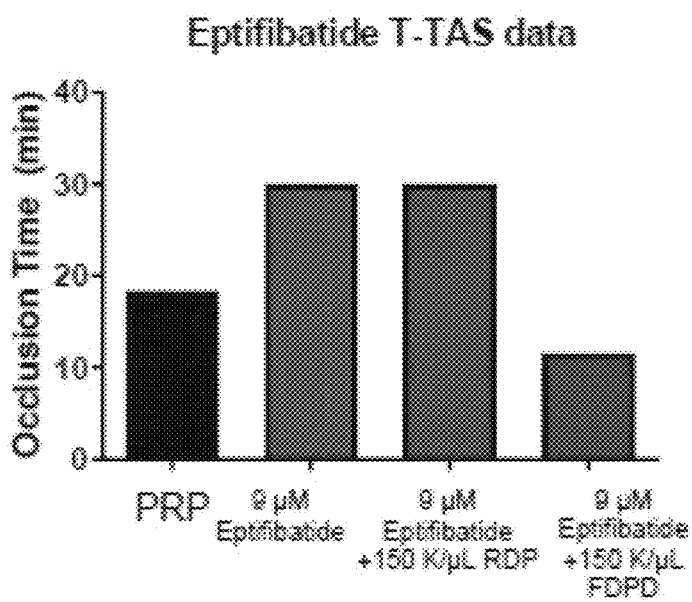
FIG. 27B is a bar plot of the occlusion time for data sets from FIG. 27A.

FIGS. 27A and 27B show that platelet rich plasma treated with 9 µM eptifibatide extended occlusion times from 18.43 to over 30 minutes on the T-TAS® flow system (collagen and tissue factor coated channel). The addition of 150 k/µL of FDPDs decreased the time back to 11.56 minutes but not occlusion seen with same number of RDP.

Example 9. FDPDs Reversed Extended Occlusion Times Induced by AP2 (anti-GpIIb/IIIa) in PRP Additional experiments were carried out with AP2. FDPDs were prepared consistent with the procedure in Example 4. T-TAS® was carried out according to Example 4. Random donor platelets were prepared from whole blood.

Figure 28A:
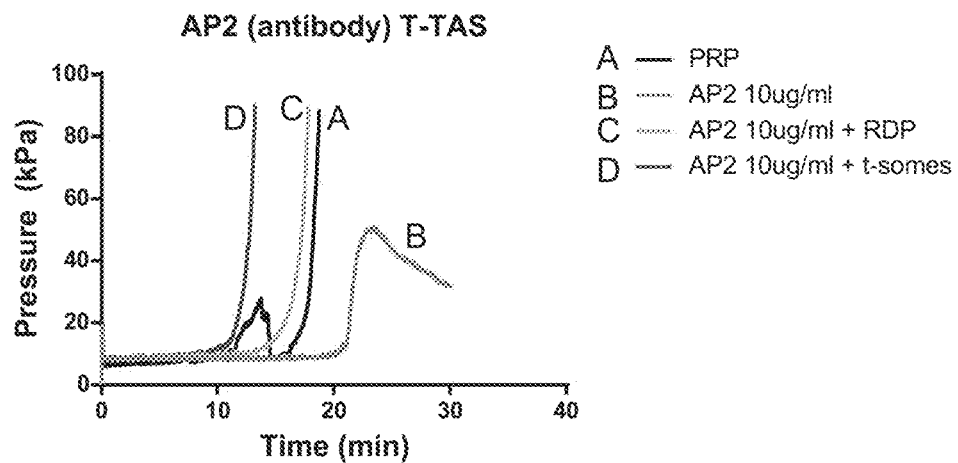
FIG. 28A shows the effect of AP2 alone, or with RDP or FDPDs on platelet occlusion using T-TAS® technology.
Figure 28B:
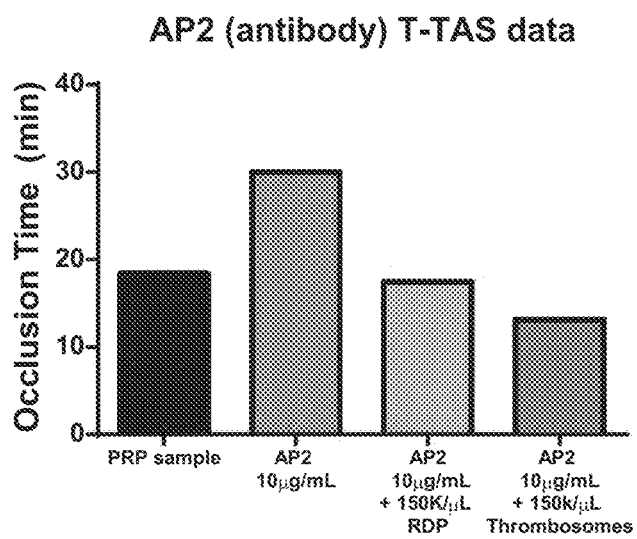
FIG. 28B is a bar plot of the occlusion time for data sets from FIG. 28A.

FIGS. 28A and 28B show that platelet rich plasma treated with 10 µg/mL AP-2 extended occlusion times from 18.43 to over 30 minutes on the T-TAS® flow system (collagen and tissue factor coated channel). The addition of 150 k/µL of FDPDs decreased the time back to 13.14 minutes and occlusion was seen at 17.43 minutes same number of RDP.

Example 10. FDPDs Reversed Prolonged Occlusion in PRP from Subjects on Aspirin Therapy Additional experiments were carried out with aspirin. FDPDs were prepared consistent with the procedure in Example 4. T-TAS® was carried out according to Example 4. Random donor platelets were prepared from whole blood. The subject was on a standard dose of 81 mg/day of aspirin.

Figure 29A:
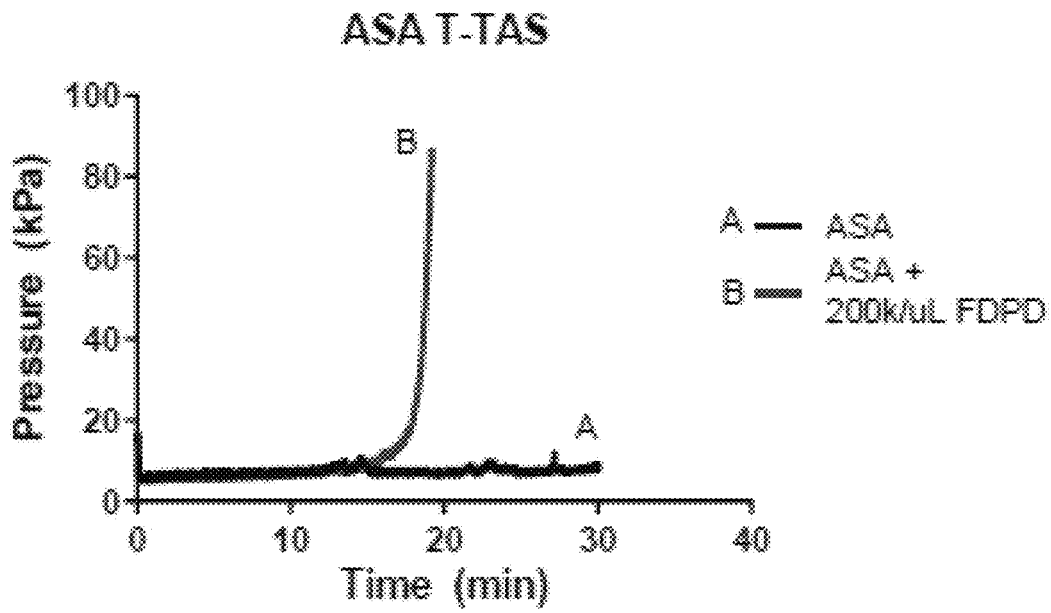
FIG. 29A shows the effect of FDPDs on PRP taken from a subject on aspirin therapy using T-TAS® technology.
Figure 29B:
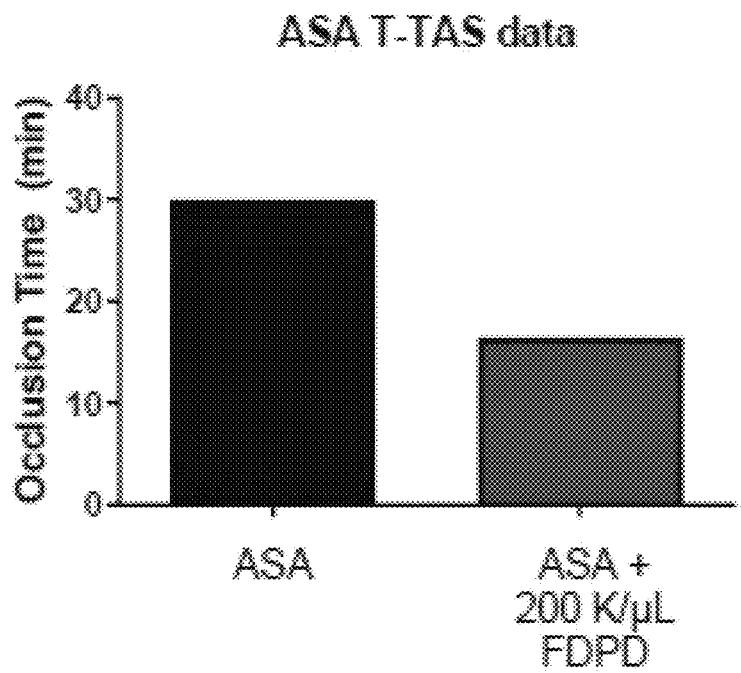
FIG. 29B is a bar plot of the occlusion time for data sets from FIG. 29A.

FIGS. 29A and 29B show that platelet rich plasma taken from an aspirin patient failed to occlude on the T-TAS® flow system (collagen and tissue factor coated channel). The addition of 200 k/µL of FDPDs returned to normal occlusion time to 16 minutes.

Example 11. FDPDs Restore Thrombin Generation in Ex-Vivo Aspirin Platelet Rich Plasma Additional experiments were carried out with aspirin. FDPDs were prepared consistent with the procedure in Example 4. Thrombin generation was carried out according to Example 4.

Figure 30A:
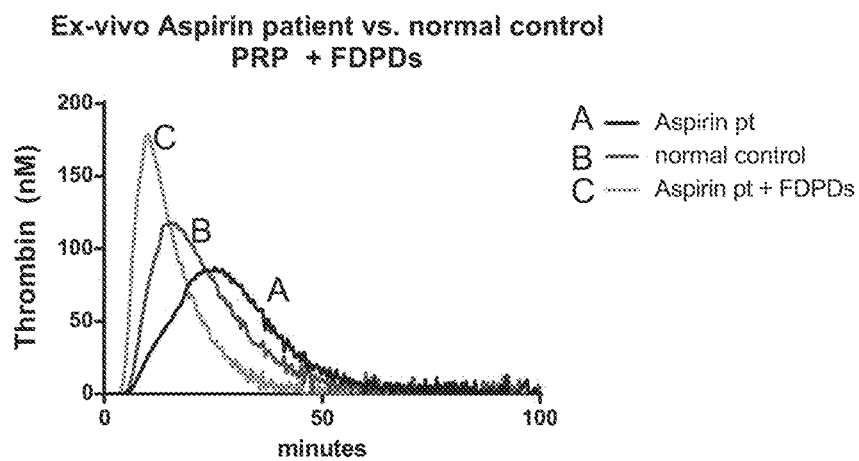
FIG. 30A shows the effect of FDPDs on PRP taken from a subject on aspirin therapy on thrombin generation.
Figure 30B:
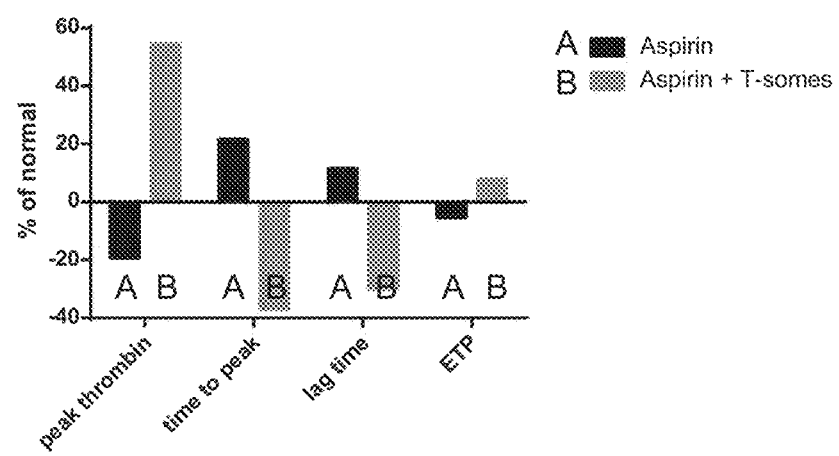
FIG. 30B is a bar plot of thrombin generation parameters for PRP taken from a subject on aspirin therapy, with or without added FDPDs.

FIG. 30A shows Thrombin generation of platelet rich plasma from aspirin patient verses normal stimulated with PRP reagent was reversed with 50 k/μL of FDPDs. FIG. 30B shows the change from and return to normal thrombin production, time to peak production, and lag time in three repeat aspirin ex-vivo samplings with FDPDs (50 k/μL). (n=3 thrombosome lots, n=2 individuals).

Example 12. FDPDs Restore Hemostasis in PRP from Subject on NSAID Ibuprofen Therapy Additional experiments were carried out with ibuprofen, an NSAID. FDPDs were prepared consistent with the procedure in Example 4. Aggregometry and T-TAS® were carried out according to Example 4.

Figure 31A:
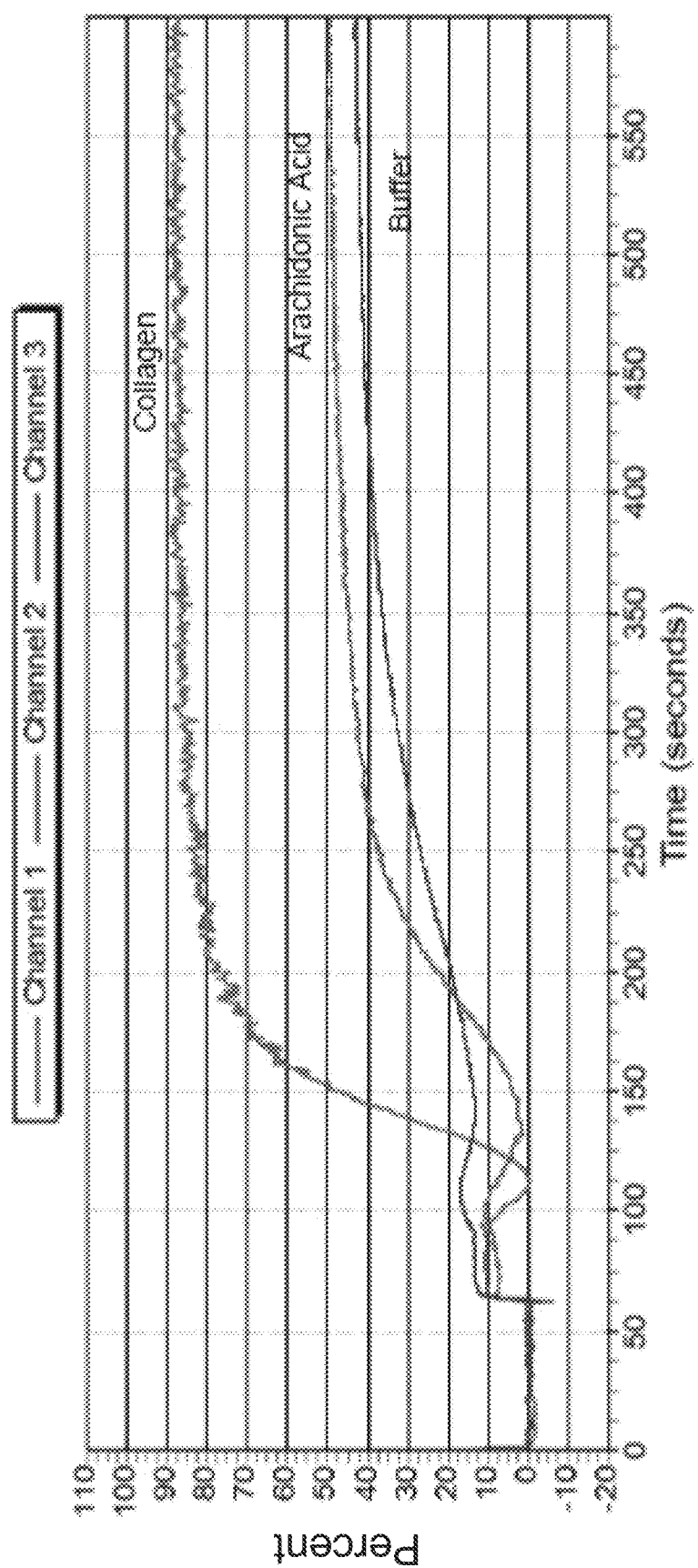
FIG. 31A shows aggregometry of PRP taken from a subject on ibuprofen therapy, with added buffer, arachidonic acid, or collagen.
Figure 31B:
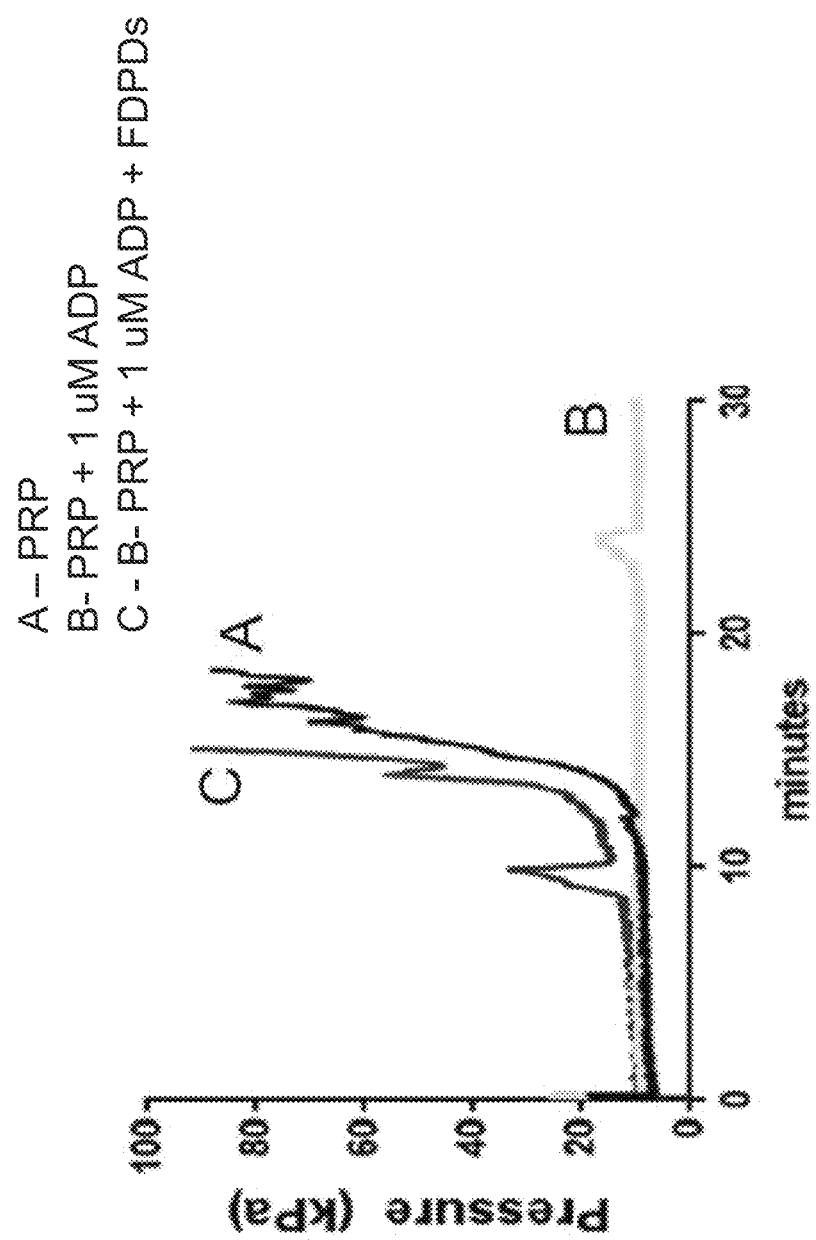
FIG. 31B shows the effect of ADP on PRP taken from a subject on ibuprofen therapy, with or without FDPDs.

Platelet rich plasma was taken from subject on 800 mg ibuprofen. FIG. 31A shows that a lack of aggregation in response to arachidonic acid confirms NSAID presence in the PRP. FIG. 31B shows occlusion on the T-TAS® flow system (collagen and tissue factor coated channel); PRP from the ibuprofen patient demonstrated occlusion, while addition of ADP abolished occlusion. The addition of 150 k/μL thrombosome restored occlusion.

Example 13. FDPDs® Restore Bleeding Time in NOD-SCID Mice Treated with Supra-Pharmacologic Clopidogrel Additional experiments were carried out with clopidogrel. FDPDs were prepared consistent with the procedure in Example 4.

The mouse was treated with clopidogrel for 5 days. The mouse was anesthetized, the tail end was snipped off followed by FDPDs being immediately administered. The time from tail snip to tail stop bleeding was recorded by visual inspection.

Figure 32:
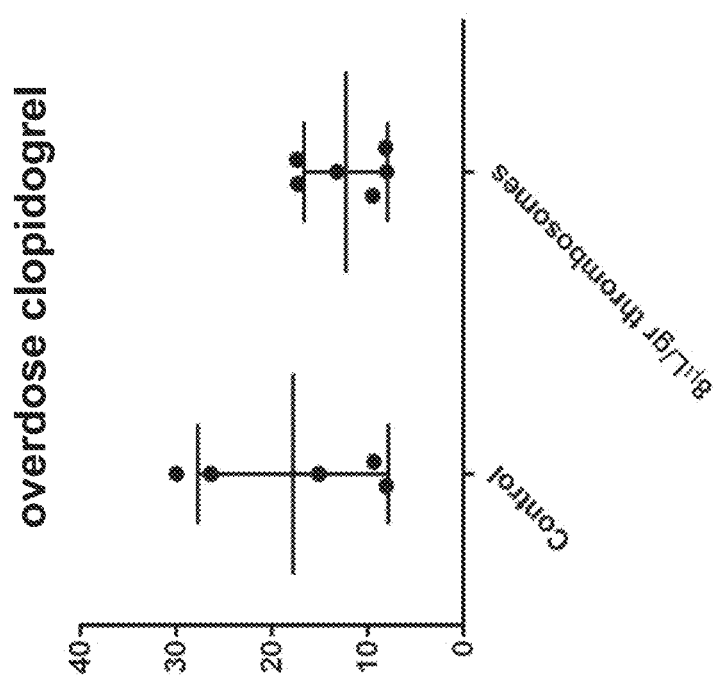
FIG. 32 shows the effect of dosing FDPDs on the bleeding time of mice treated with a superpharmacologic dose of clopidogrel.

NOD/SCID mice were treated with ~3 times the clinical dose of clopidogrel for 5 days then assessed in the tail-snip bleed model. The bleed time (min) was extended to 17.8 minutes with clopidogrel treatment verses untreated at 9 minutes (data not shown). Treatment with 8 μL/gram of FDPDs (1.8×10^9 particles/mL at 200 μL) decreased bleeding to 12.31 minutes (FIG. 32).

Example 14. Reproducibly of FDPD Reversal of Ticagrelor and Cangrelor Inhibition of Occlusion Human freeze-dried platelet derivatives (FDPDs), also called lyophilized human platelets (LHP), were prepared according to the procedure in Example 15. T-TAS® experiments, to measure occlusion time, using AR chips were carried out according to Example 4.

Figure 33A:
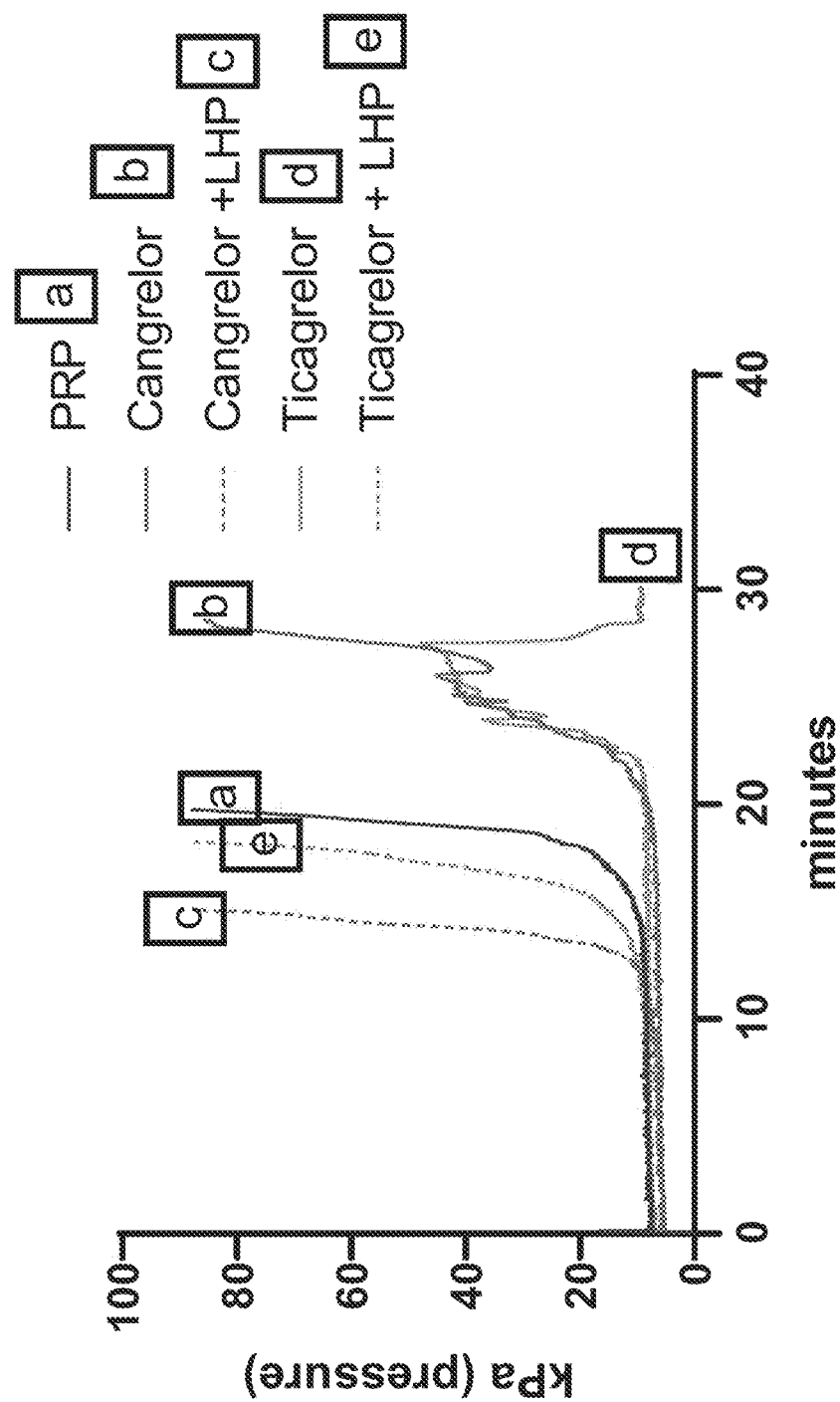
FIG. 33A shows the effect of cangrelor and ticagrelor on the occlusion time of Platelet Rich Plasma (PRP) with and without FDPD
Figure 33B:
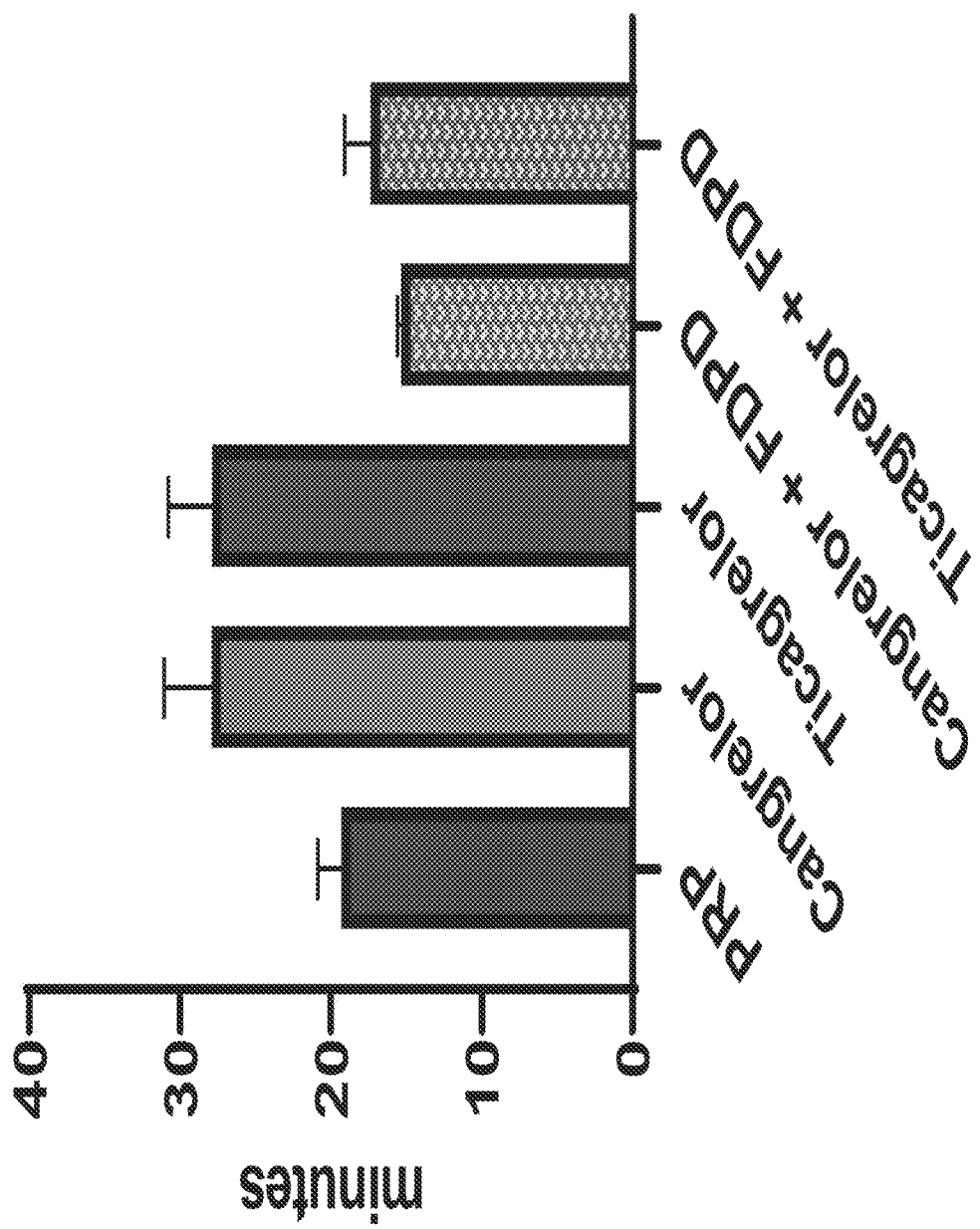
FIG. 33B shows the effect of cangrelor and ticagrelor on the occlusion time of Platelet Rich Plasma (PRP) with and without FDPD

The effect of cangrelor and ticagrelor on occlusion time of Platelet Rich Plasma (PRP) with and without FDPDs was assessed using the T-TAS® assay. The concentrations of the agents were as follows: cangrelor at 1 μM, ticagrelor at 500 ng/mL, FDPDs at 150 k/μL, and ADP at 2 μM. The results are shown in FIGS. 33A and 33B. Adenosine diphosphate (ADP) stimulated PRP samples showed occlusion at 19.5±1.5 minutes (n=4) which increased to 28.0±3.0 minutes with cangrelor (n=4) or 28.0±3.0 minutes with ticagrelor (n=5) treatment (FIGS. 33A-33B). The addition of 150 k/μL lyophilized human platelets to P2Y12-inhibited PRP reduced time to thrombus formation to lower than PRP alone; 15.5±0.5 minutes in the presence of cangrelor (n=3) versus 17.5±1.5 minutes in the presence of ticagrelor (n=5) (FIG. 33). The number of trials per each assay is listed as the "(n=_)" values.

These results demonstrate that occlusion of platelets on the T-TAS® AR Chip in the presence of human FDPDs is not affected by the antiplatelet effect of cangrelor and ticagrelor. These results suggest that human FDPDS will maintain expected function when infused into patients receiving cangrelor, ticagrelor, and/or similar agents.

Example 15. Tangential Flow Filtration (TFF) Method of Platelet Derivative Preparation Apheresis platelets underwent tangential flow filtration in accordance with a standard operating procedure, including the following process steps: platelet dilution, platelet concentration and platelet washing.

The platelet donor units were initially pooled into a common vessel. The platelets may or may not be initially diluted with an acidified washing buffer (e.g., a control buffer) to reduce platelet activation during processing. The platelets can undergo two processing pathways; 1) either washed with control buffer until a desired residual component is reached (e.g., donor plasma) before being concentrated to a final product concentration or 2) the platelets are concentrated to a final product concentration before being washed with control buffer until a desired residual component is reached (e.g., donor plasma). TFF processed platelets are then filled into vials, lyophilized and thermally treated.

One particular protocol follows.

For all steps of the TFF process in this Example, Buffer F was used. The process was carried out at a temperature of 18-24° C.

| Buffer F | |
|---|---|
| Component | Value (±1%) |
| HEPES | 7.6 mM |
| NaCl | 60 mM |
| KCl | 3.84 mM |
| Dextrose | 2.4 mM |
| NaHCO$_3$ | 9.6 mM |
| Trehlaose | 80 mM |
| Ethanol | 0.8% |
| Polysucrose | 6% (w/v) |
| pH | 6.6-6.8 |

Platelets were loaded onto the TFF (PendoTECH controller system (PendoTECH® Princeton, NJ; https://www.pendotech.com), which was prepared with a Repligen TFF Cassette (XPM45L01E). The TFF process was performed using a membrane with a pore size of 0.45 μm. The platelets were diluted with an equal weight (±10%) of Buffer F. The platelets were concentrated to about 2250×10$^3$ cells/μL (±250×10$^3$) and then washed with approximately 2 diavolumes (DV) of Buffer F. The target plasma percentage was typically less than 15% relative plasma (as determined by plasma protein content). Removal of plasma proteins was monitored through 280 nm UV absorbance against known correlations.

In some cases, samples were drawn at UV absorbance readings correlating to about 51% relative plasma volume, about 8.1% relative plasma volume, about 6.0% relative plasma volume, and about 1.3% relative plasma volume. Low volume aliquots were sampled throughout each processing step with the about 6.0% and under samples.

Following washing, if the concentration of the cells was not 2000×10$^3$ cells/µL (±300×10$^3$), the cells were either diluted with Buffer F or were concentrated to fall within this range. Under all circumstances whenever the cells were contacted with the Buffer F, it was done at a temperature in the range of 18-24° C. For a better clarity, the cells were loaded with the reagents of the Buffer F at a temperature in the range of 18-24° C. The cells were typically then freeze-dried (I.e. lyophilized) and subsequently heated (thermally treated) at 80° C. for 24 hours, thereby forming Freeze-dried platelet derivatives (FDPDs), which are also called THROMBOSOMES® when prepared by Cellphire, Inc. For clinical or commercial use.

The lyophilization procedure used to prepare the human FDPDs is presented in Table LA2.

TABLE LA2

LYOPHILIZER RECIPE

| | 30 g Fill | | | | 10 g Fill | | |
|---|---|---|---|---|---|---|---|
| | | | | Freezing | | | |
| Ramp to | −40° C. | 0 mins | omTorr | Ramp to | −40° C. | 0 mins | 0 mTorr |
| Hold at | −40° C. | 180 mins | 0 mTorr | Hold at | −40° C. | 180 mins | O mTorr |
| | | | | Final Freezing | | | |
| Hold at | −40° C. | 0 mins | 100 mTorr | Hold at | −40° C. | O mins | 100 mTorr |
| | | | | Primary Drying | | | |
| Ramp to | .5° C. | 420 mins | O mTorr | Ramp to | −10° C. | 360 mins | O mTorr |
| Hold at | .5° C. | 1200 mins | 0 mTorr | Hold at | −10° C. | 360 mins | o mTorr |
| Ramp to | +5° C. | 120 mins | 0 mTorr | Ramp to | +S° C. | 180 mins | O mTorr |
| Hold at | +S° C. | 1380 mins | 0 mTorr | Hold at | +S° C. | 360 mins | 0 mTorr |
| Ramp to | +30° C. | 300 mins | 0 mTorr | Ramp to | +30° C. | 300 mins | 0 mTorr |
| Hold at | +30° C. | 720 mins | 0 mTorr | Hold at | +30° C. | 720 mins | 0 mTorr |
| Hold at | +30° C. | 720 mins | 200 mTorr | Hold at | +30° C. | 720 mins | 200 mTorr |
| Hold at | +30° C. | 60 mins | 0 mTorr | Hold at | +30° C. | 60 mins | 0 mTorr |
| | | | | Secondary Drying | | | |
| Hold at | +30° C. | 9999 mins | 0 mTorr | Hold at | +30° C. | 9999 mins | 0 mTorr |
| | Total Recipe Time 1a −85 hours | | | | Total Recipe Time 1a −54 hours | | |

To perform studies such as thrombin generation studies (TGPU), and aggregation studies, FDPDs were typically rehydrated with water over 10 minutes at room temperature. In general, the rehydration volume is equal to the volume used to fill each vial with cells prior to drying. The platelet derivatives which were heated (thermally treated) after lyophilization are also referred to as baked FDPDs. Whereas the FDPDs which were not heated (thermally treated) after lyophilization are referred to as unbaked FDPDs.

Human FDPDs, obtained after lyophilization in the form of a powder can be used for commercial applications, such as providing the human FDPDs (e.g. THROMBOSOMES®) in dried form in vials to, for example, a medical practitioner who can rehydrate the vials with an appropriate amount of a liquid.

Example 16. FDPDS Restore Bleeding Time in NOD-SCID Mice Treated with Supra-Pharmacologic Clopidogrel Human FDPDs were prepared consistent with the procedure in Example 15.

Mice were treated with clopidogrel at 5 mg/kg for 3 days. The mice were anesthetized, the tail end was snipped off at 1 mm diameter and submerged in warm saline and time to clot recorded. Animals were syringe injected, into a vein or artery, with saline or 1.6×10$^9$/kg of FDPDs, at the same time the tail was snipped, and the tail snip trial commenced. The time from tail snip to tail stop bleeding was recorded by visual inspection of cessation of blood loss.

Figure 34:
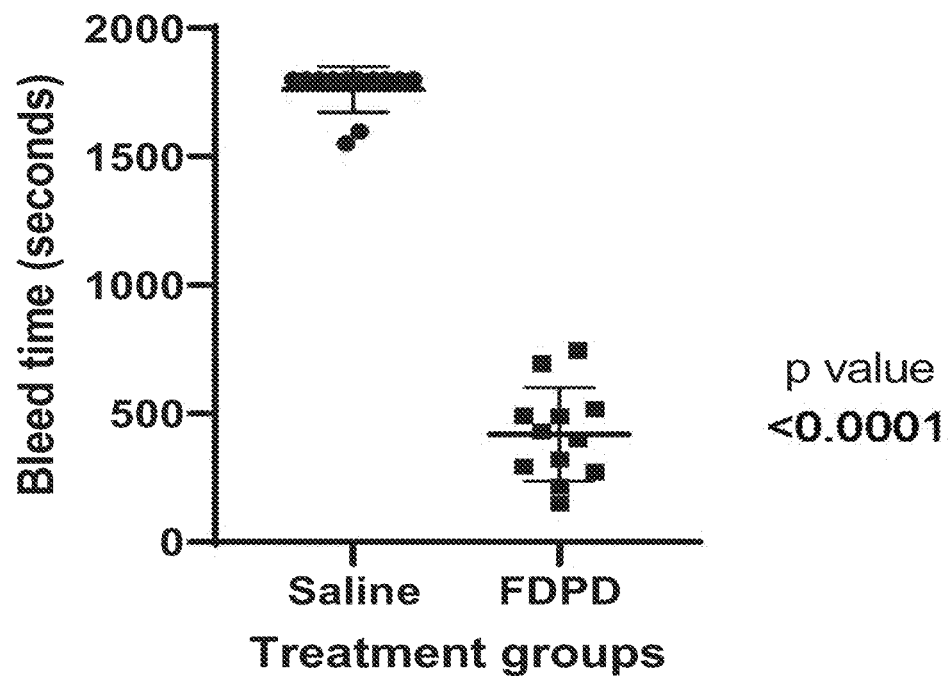
FIG. 34 shows the tail snip test for depicting the ability of FDPDs to restore bleeding time in NOD-SCID mice treated with supra-pharmacologic clopidogrel.

The results for this experiment are shown in FIG. 34. The bleed time (seconds) was extended to 1661+/−257.9 seconds with clopidogrel treatment verses untreated at 758.6+/−623.4 seconds. Treatment with 1.6×10$^9$/kg FDPDS decreased bleeding to 417.9+/−166.6 seconds. One-way ANOVA software, was utilized for analysis of the data.

These results demonstrate that human FDPDs are resistant to clopidogrel effects and restore hemostasis in a mice tail snip model. Human FDPDs have the potential to be an effective clinical tool to stop bleeding in a patient population being treated with clopidogrel.

Example 17. FDPDs Restore Bleeding Time in New Zealand White Rabbits Treated with Supra-Pharmacologic Clopidogrel Additional experiments were carried out with clopidogrel treated New Zealand White Rabbits. Human FDPDs were prepared consistent with the procedure in Example 15.

Rabbits were treated with clopidogrel at 23 mg/kg for 5 days. The rabbits were anesthetized, the ear was bled and time to clot recorded. Animals were treated, injected into a vein or artery, with saline or 1.6×10$^9$/kg of human FDPDs, at the same time the ear was bled, and the ear bleed trial commenced. The time from ear bleed to stop bleeding was recorded by visual inspection.

Figure 35:
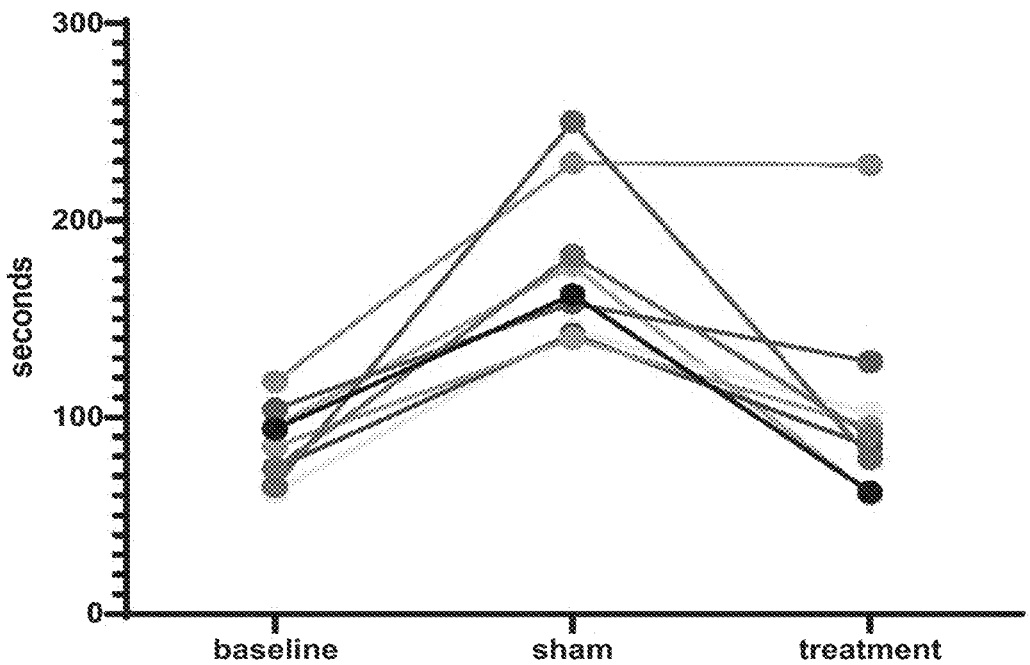
FIG. 35 shows the ability of FDPDs to restore bleeding time in New Zealand White Rabbits treated with supra-pharmacologic clopidogrel. Each line represents a different rabbit dosed under identical conditions and with the same dose.

Results of this experiment are shown in FIG. 35. The bleed time (seconds) was extended to 206.8+/−104.2 seconds with clopidogrel treatment verses untreated at 87.1+/−18.2 seconds. Treatment with 1.6×10$^9$/kg FDPDS decreased bleeding to 417.9+/−166.6 seconds (FIG. 35). One-way ANOVA was utilized for analysis of the data.

These results demonstrate that human FDPDs are resistant to clopidogrel effects and restore hemostasis in a rabbit ear bleed model. Lyophilized human platelets have the potential to be an effective clinical tool to stop bleeding in a patient population being treated with clopidogrel.

Example 18. FDPDs Contribution to Thrombin Generation in the Presence of 25 ng/mL Rivaroxaban Treated OCTAPLAS® PRPs Reagent Human FDPDs were prepared according to the method as described in Example 15. The OCTAPLAS® plasma used in this example is a solvent/detergent treated, pooled human plasma available from Octapharma USA, Inc., 117 W. Century Road Paramus, NJ 07652; www.octapharmausa.com.

A Thrombin Generation Assay (TGA) was performed to detect thrombin generation and endogenous thrombin potential in (1) OCTAPLAS® with platelet rich plasma (PRP) and incrementally increasing FDPD concentration (0, 10, 20, 40, 80, 160)×$10^3$/µL and (2) OCTAPLAS® with platelet rich plasma reagent (PRP), 25 ng/mL rivaroxaban, and incrementally increasing FDPD concentration (0, 10, 20, 40, 80, 160)×$10^3$/µL. A 25 ng/mL dose of Rivaroxaban is within the physiological dose range and is an effective dose to inhibit thrombin generation.

Figure 36A:
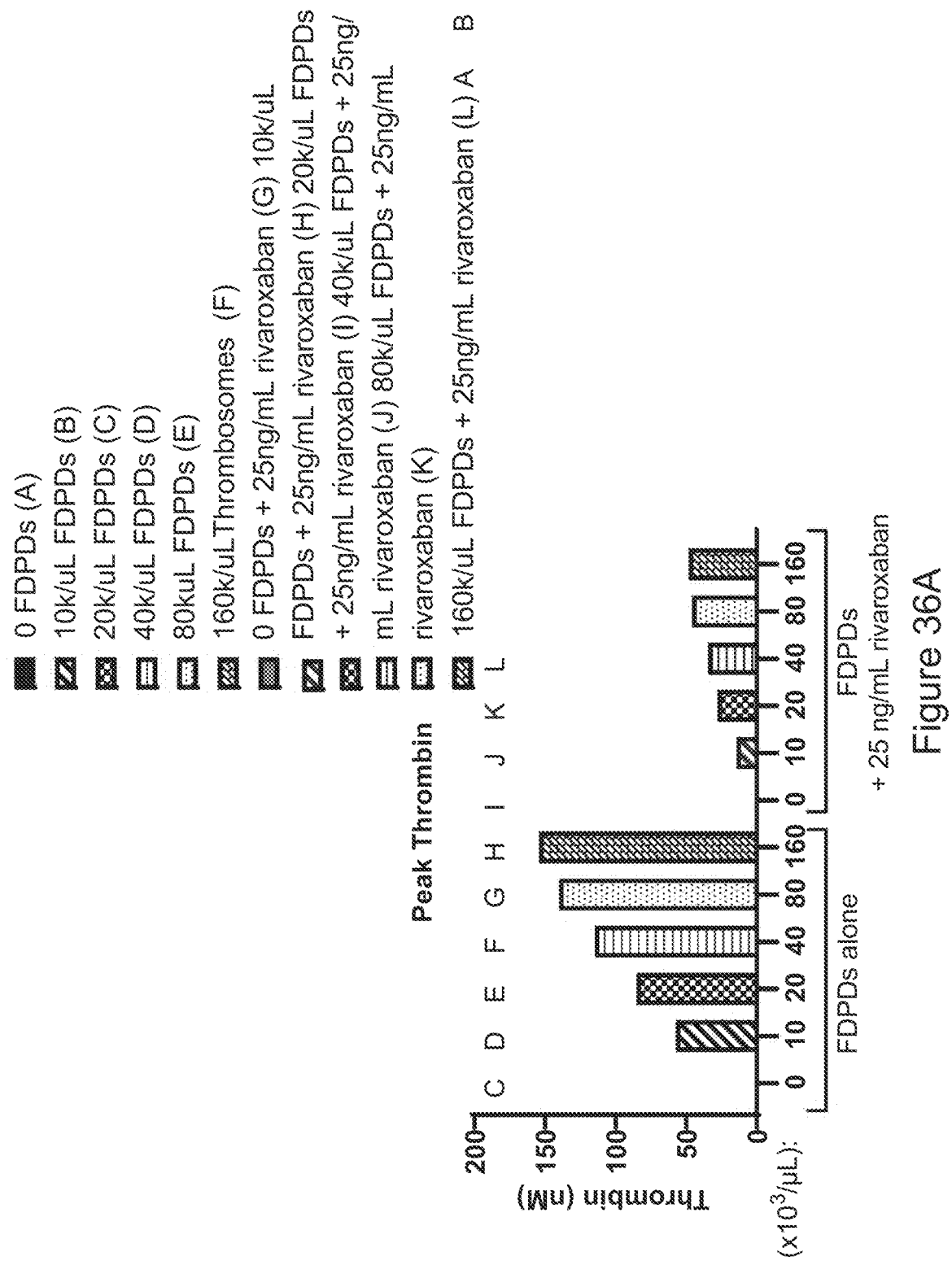
FIG. 36A shows that FDPDs are capable of catalyzing thrombin generation in the presence of 25 ng/ml rivaroxaban.
Figure 36B:
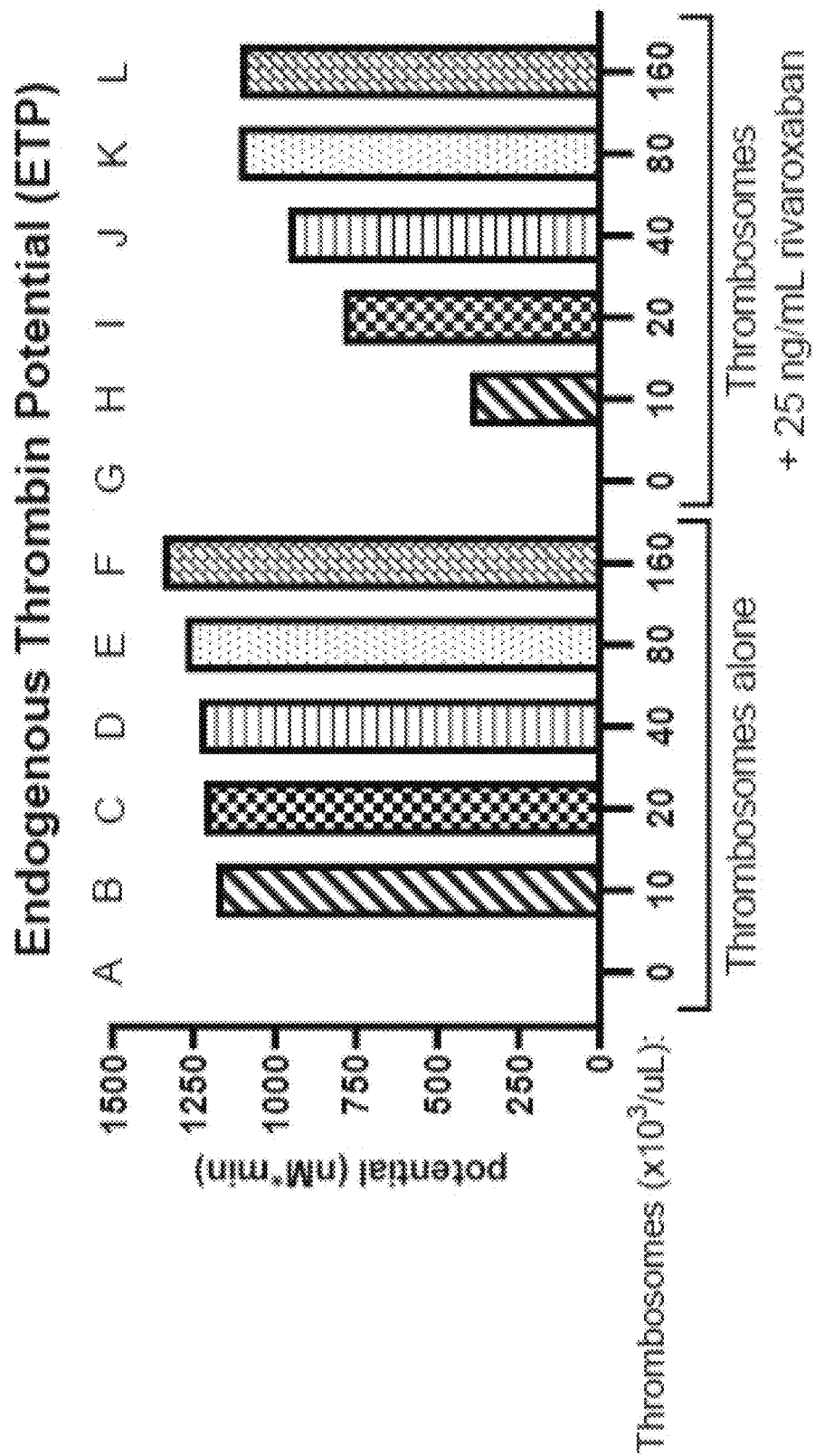
FIG. 36B shows that FDPDs are capable of partially recovering the endogenous thrombin potential in the presence of 25 ng/ml rivaroxaban.

The results of this experiment are shown in FIGS. 36A and 36B. These results demonstrated that even low doses of FDPDs are capable of catalyzing some thrombin generation (FIG. 36A) and partially recovering the endogenous thrombin potential (FIG. 36B) in the presence of 25 ng/mL dose of rivaroxaban in OCTAPLAS® with PRP reagent.

Example 19. Addition of FDPDs Shows Partial Recovery of Occlusion Time of 25 ng/mL Rivaroxaban Treated Whole Blood (WB)

Occlusion time was measured on the Total Thrombin formation Analysis System (T-TAS®) 01 using AR chips (Collagen and Tissue FactorF stimulant). The T-TAS® 01 (Diapharma®, https://diapharma.com) instrument was prepared for use according to the manufacturer's instructions. AR Chips (Diapharma #19001) and Calcium Corn Trypsin Inhibitor (CaCTI; Diapharma Cat. #TR0101) were warmed to 37° C. or room temperature, respectively. Whole blood was collected in sodium citrate tubes 30 minutes prior to the start of the assay. FDPDS were rehydrated, counted (Beckman Coulter AcT Diff 2 Cell Counter), and added to whole blood at the indicated final concentration. Rivaroxaban (Cayman Chemical cat #16043) was dissolved in 100% DMSO to make a 10 µg/mL stock solution and added to the sample at the indicated final concentration, yielding a final DMSO content of 0.25/6, 480 µL of sample was mixed with 20 µL of calcium CTI reagent and run on the AR chip on T-TAS® 01.

FDPDs were prepared according to the procedures of Example 15. The TAS® 01 assays using AR chips general method and OCTAPLAS® plasma are described in Example 18 above. The TAS®°01 assays were run with no rivaroxaban, 25 ng/mL rivaroxaban, and 25 ng/mL rivaroxaban and 20 k/µL FDPDs.

Figure 37:
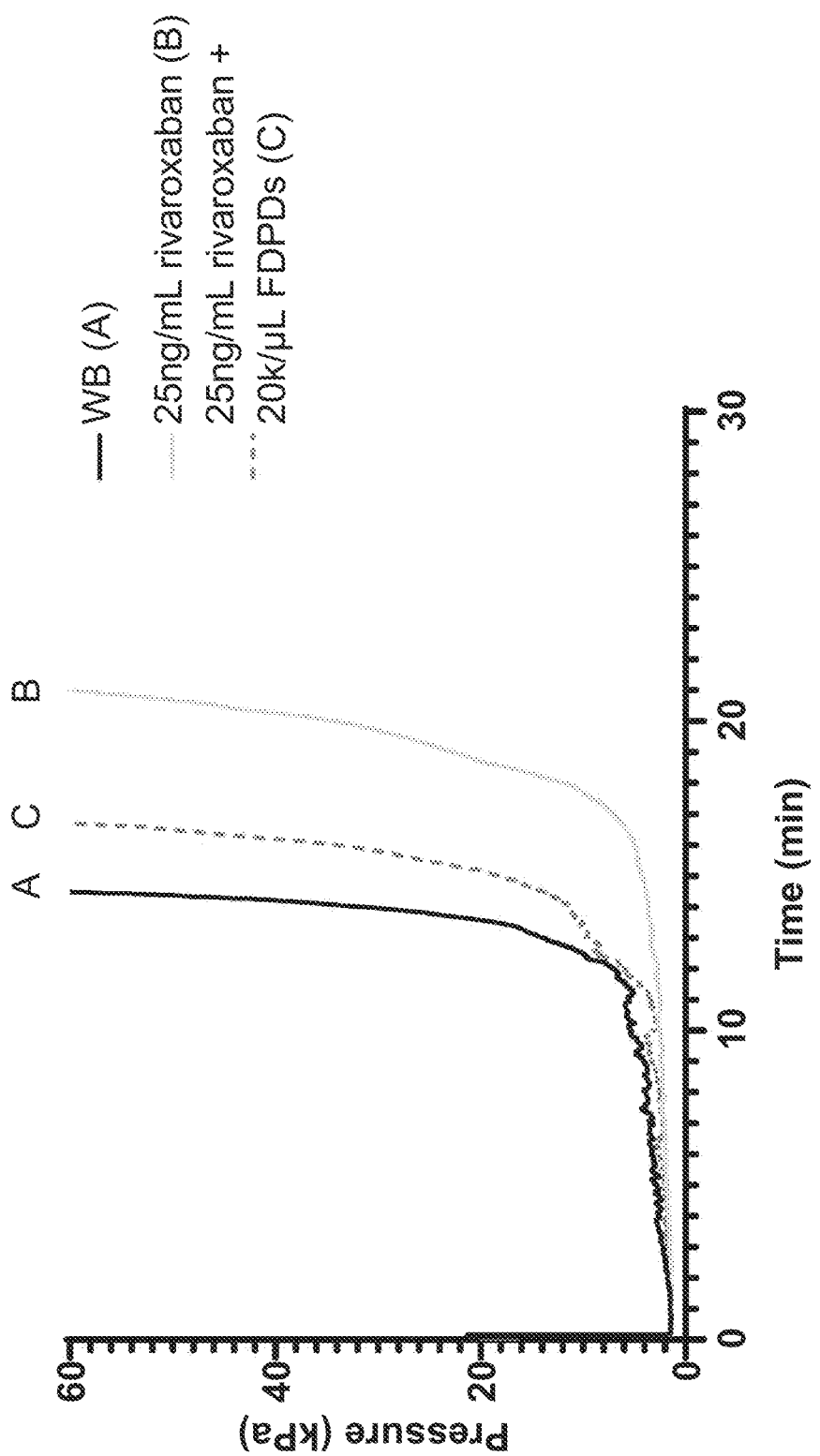
FIG. 37 shows the occlusion time was partially restored with the addition of FDPDs into rivaroxaban treated whole blood.

The pressure over time is shown in FIG. 37 with pressure increase being indicative of occlusion. The results show that Occlusion time was partially restored with the addition of FDPDs into rivaroxaban treated whole blood.

Example 20. The Addition of FDPDs to Rivaroxaban Treated OCTAPLAS® or Rivaroxaban Treated Fresh PRP Show the Recovery of Fibrin and Thrombin Generation Using Thrombodynamics Analyser System (T2T)

The Thrombodynamics® Analyser System (T2T) (Diapharma®, https://diapharma.com) was used to detect thrombin generation and fibrin formation. Human FDPDs were prepared according to the procedure in Example 15.

Thrombodynamics set-up and sample prep were performed according to manufacturer's recommendation EXCEPT a phospholipid reagent was not added. The experiment was performed with either OCTAPLAS® or fresh PRP. OCTAPLAS® and PRP were each incubated with 300 ng/mL rivaroxaban for 2 minutes, FDPDSs were added to the sample, and then the sample was added to Reagent 1 (contact pathway inhibitor and thrombin fluorescent substrate of the T2T assay); 20 k/µL FDPDSs were added for OCTAPLAS® run and 2 k/µL for PRP run. The sample was incubated at 37° C. for 3 min (PRP) or 15 min (OCTAPLAS®) according to instrument protocol. Following the incubation, the sample was added into a cuvette containing TF-coated plastic insert and the run was started. The concentrations of the components in the fresh PRP run are decreased in order to see the dynamic response when using fresh platelets versus OCTAPLAS®, a detergent-treated plasma.

Figure 38A:
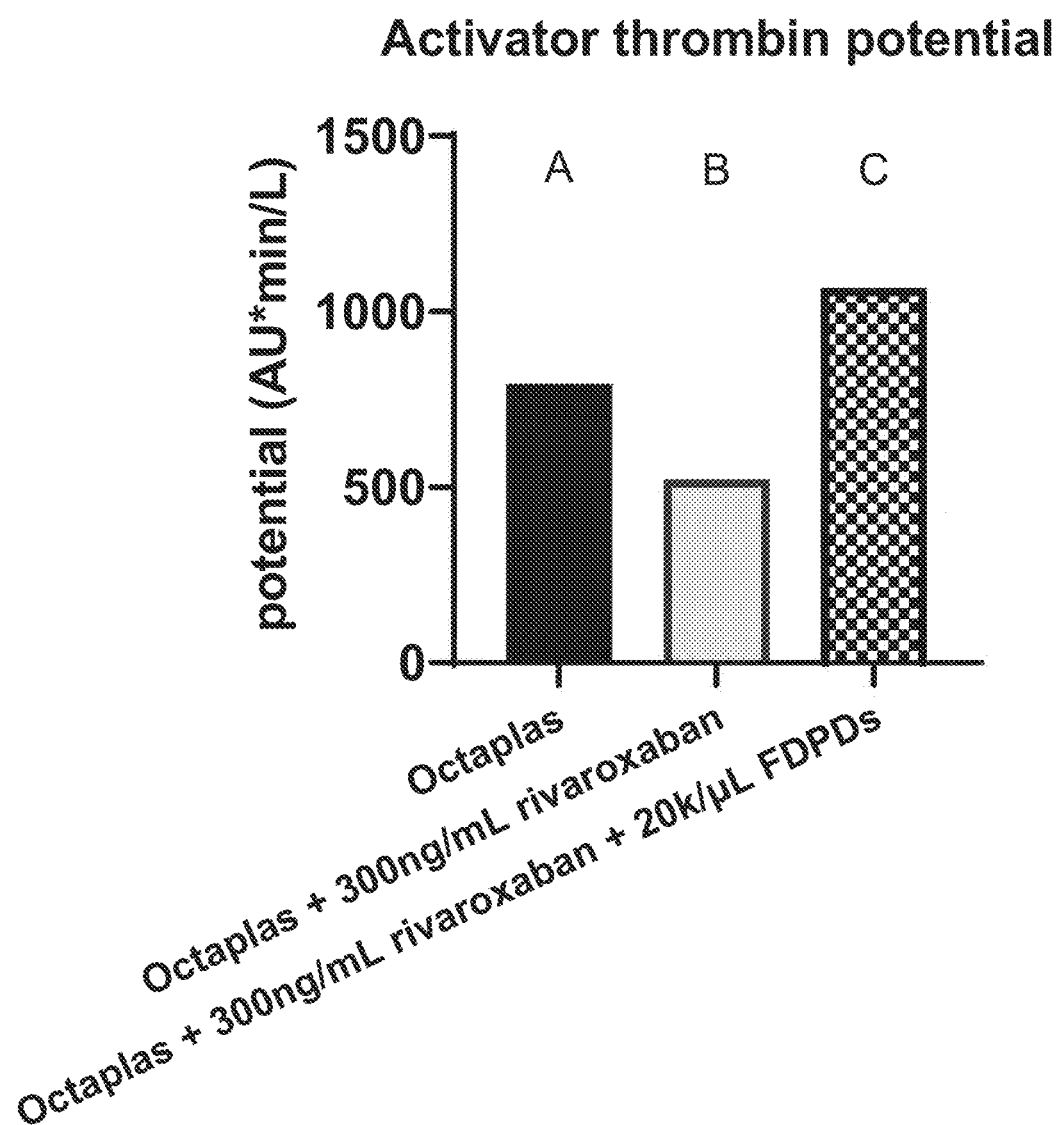
FIG. 38A shows the activator thrombin potential by FDPDs in rivaroxaban treated Octaplas.
Figure 38B:
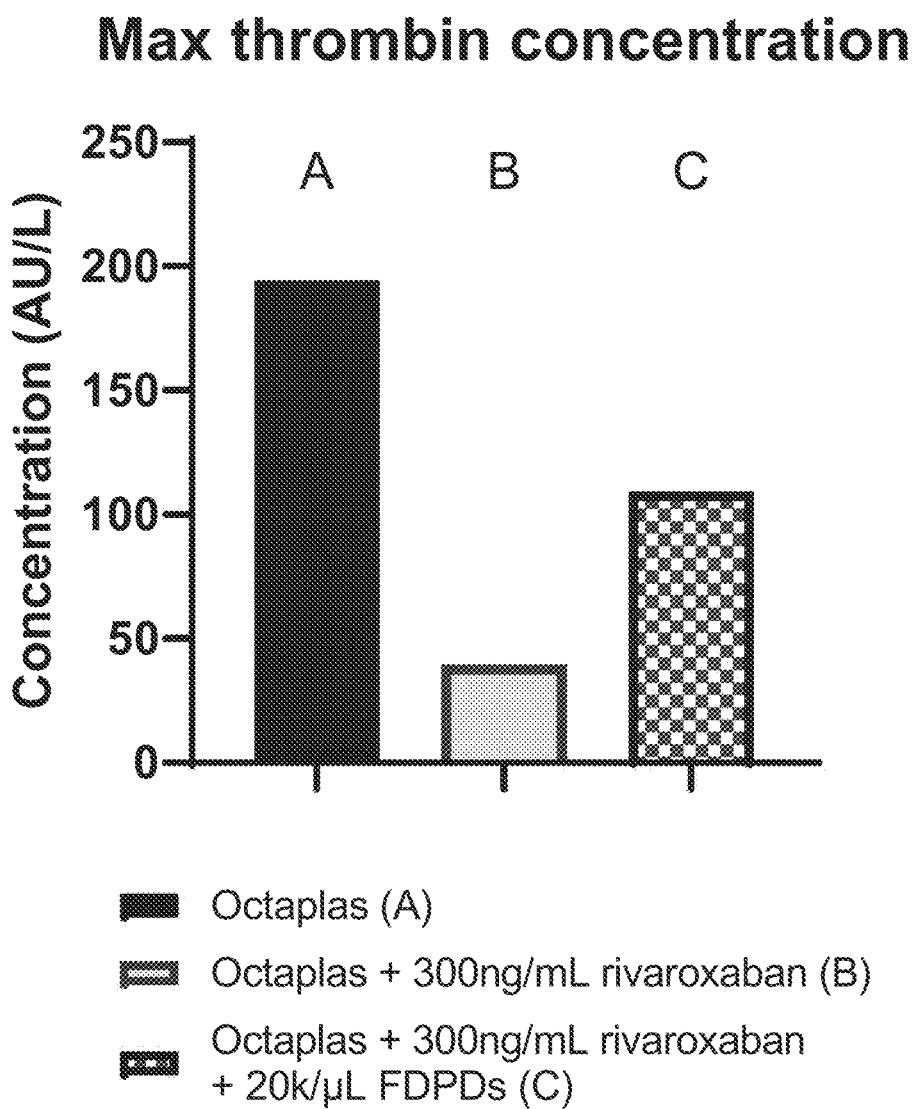
FIG. 38B shows the maximum thrombin concentration by FDPDs in rivaroxaban treated Octaplas.
Figure 38C:
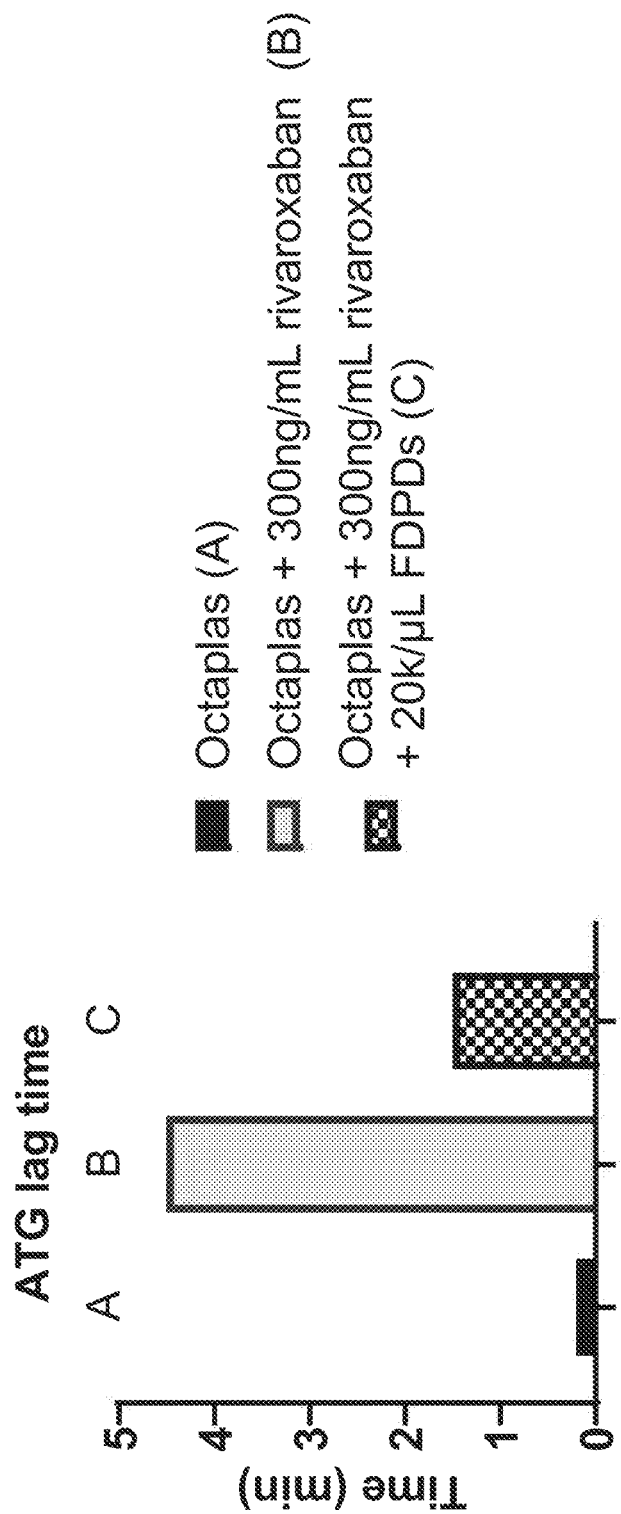
FIG. 38C shows the ATG lag time by FDPDs in rivaroxaban treated Octaplas.
Figure 39A:
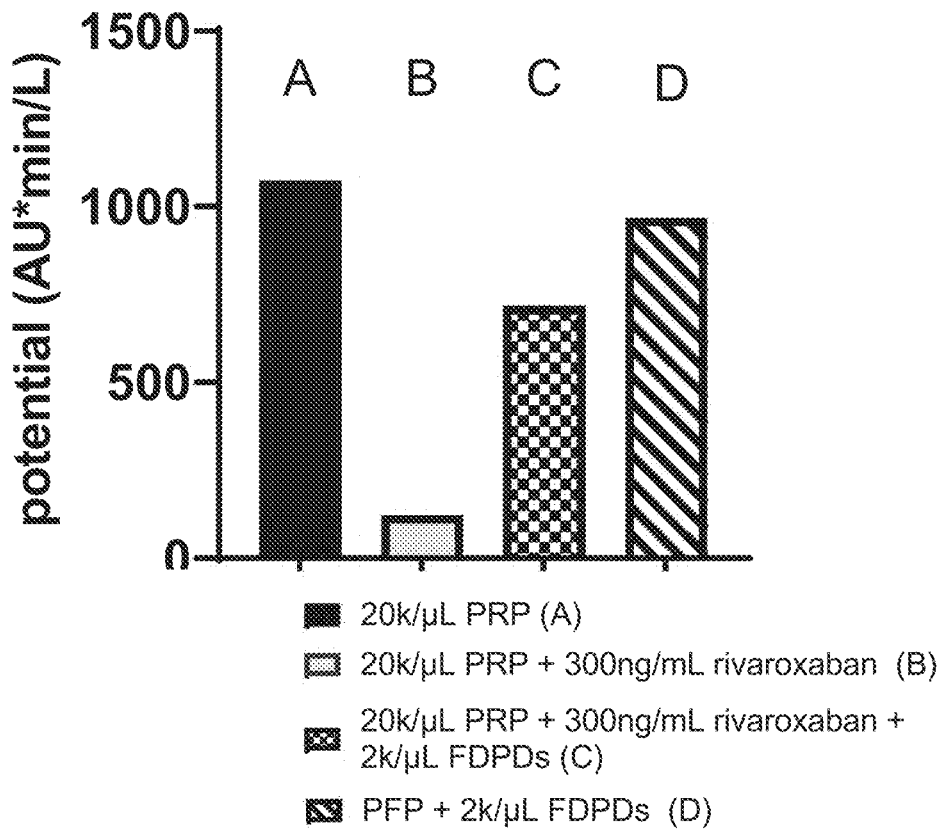
FIG. 39A shows the activator thrombin potential by FDPDs in rivaroxaban treated fresh Platelet Rich Plasma (PRP).
Figure 39B:
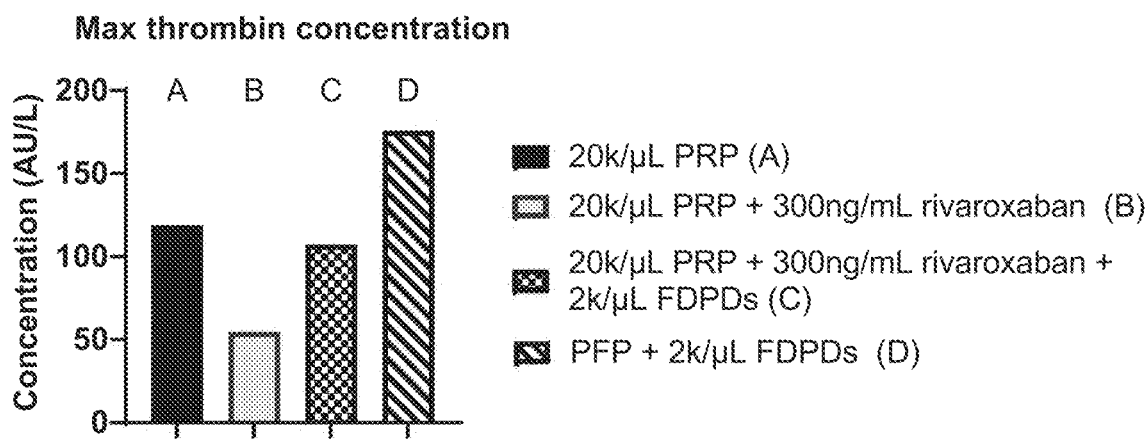
FIG. 39B shows the maximum thrombin concentration by FDPDs in rivaroxaban treated fresh Platelet Rich Plasma (PRP).
Figure 39C:
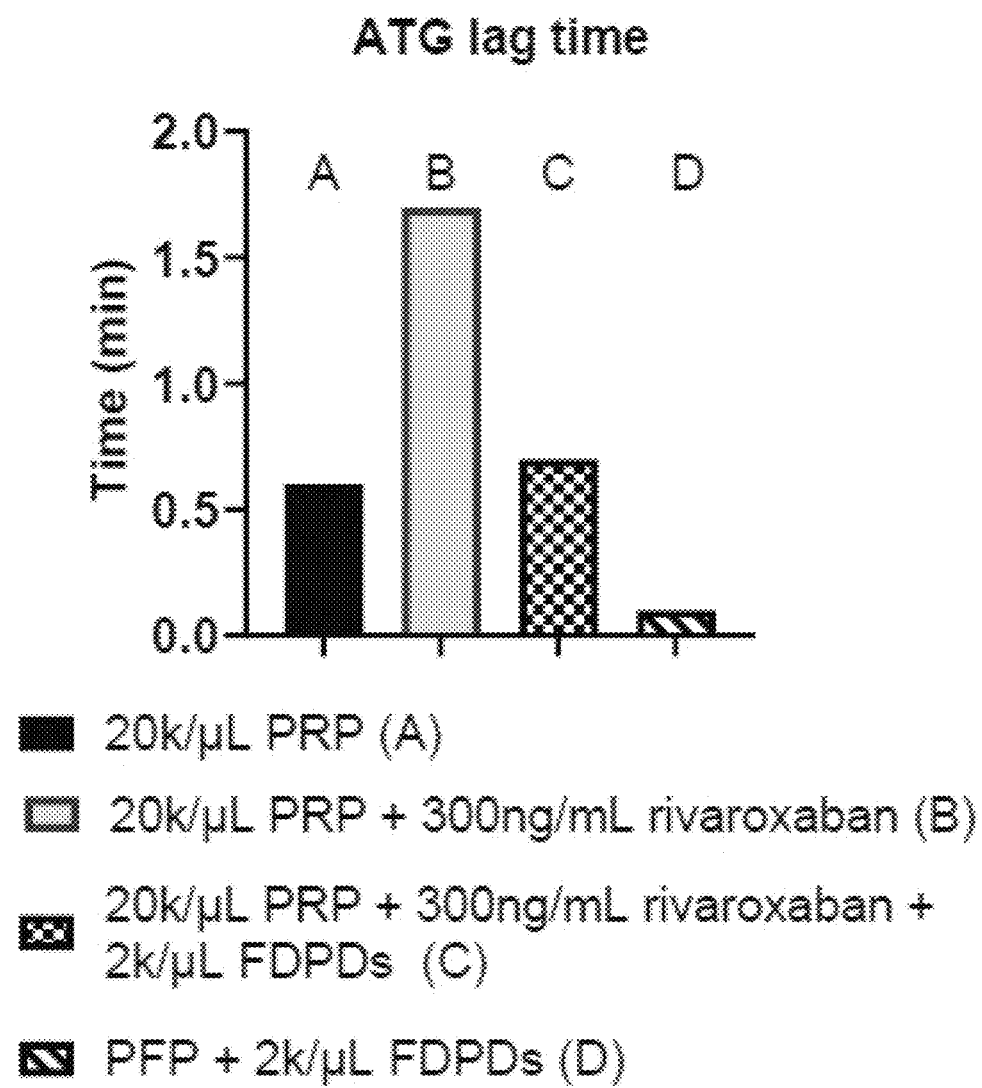
FIG. 39C shows the ATG lag time by FDPDs in rivaroxaban treated Platelet Rich Plasma (PRP).

This results of this experiment showed recovery of fibrin and thrombin generation by FDPDs in rivaroxaban treated Octaplas (FIGS. 38A-38C). The results also showed the partial recovery of fibrin and thrombin generation in a rivaroxaban-treated fresh PRP sample (FIGS. 39A-39C) at the physiological ratios of endogenous platelets: FDPDs FDPDS FDPDS that would be expected if using clinically.

Example 21 Addition of FDPDSs Rescues Clot Forming Capacity of a Heparin Treated Sample with Less than Clinically Suggested Dose of Protamine This experiment assessed how clinical proportions of Heparin and Protamine affect FDPD function. FDPDs were prepared according to the procedure in Example 15. An Activating Clotting Time (ACT) assay was performed to measure time to clot and TGA was performed to measure thrombin generation. An initial Heparin titration run was performed using ACT to find the minimum Heparin dose needed to reach abnormal clot time. Results showed a minimum of 0.8 U/mL Heparin is needed to reach abnormal clot formation.

Figure 40:
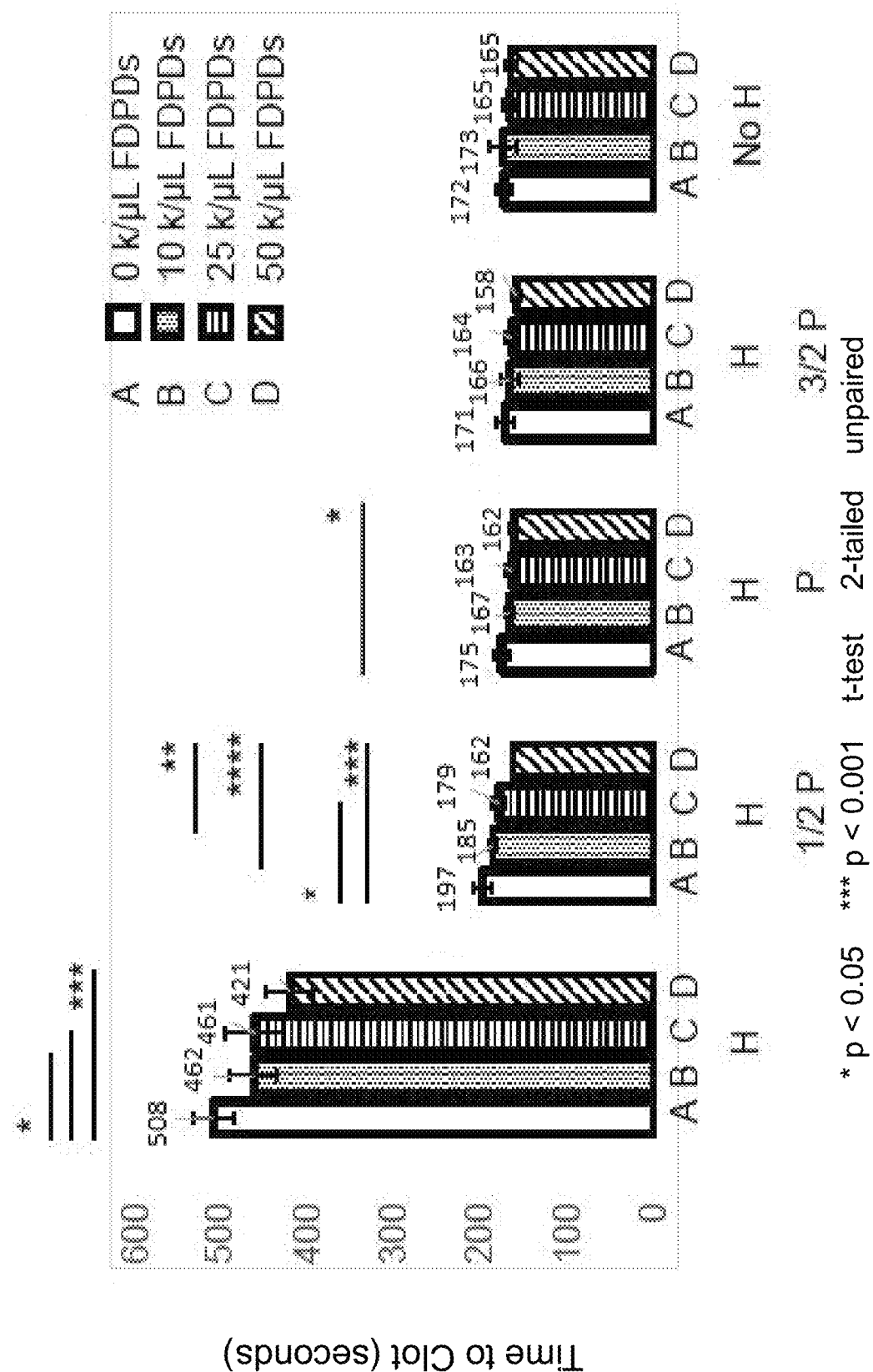
FIG. 40 shows the effect of FDPDs on time to clot in the presence of anticoagulants using the ACT test.

FIG. 40 shows the effect of FDPDs on time to clot in the presence of anticoagulants using the ACT test. Activated clotting time was measured using pooled normal plasma with heparin (H) and protamine (P) as labeled on the x-axis; ½ P, P, and ³⁄₂ P represent protamine doses of 4, 8, and 12 µg/ml, respectively. FDPDs, (referred to as "Tsomes" in FIG. 40) were added at 10, 25 or 50 K/µl. Samples labeled "0" Tsomes had an equal volume of control buffer added to pooled normal plasma. "K" in the legend stands for $10^3$ FDPDS. All samples were run in duplicate. N=2. The experiment was repeated on separate days to improve statistical relevance.

Figure 41A:
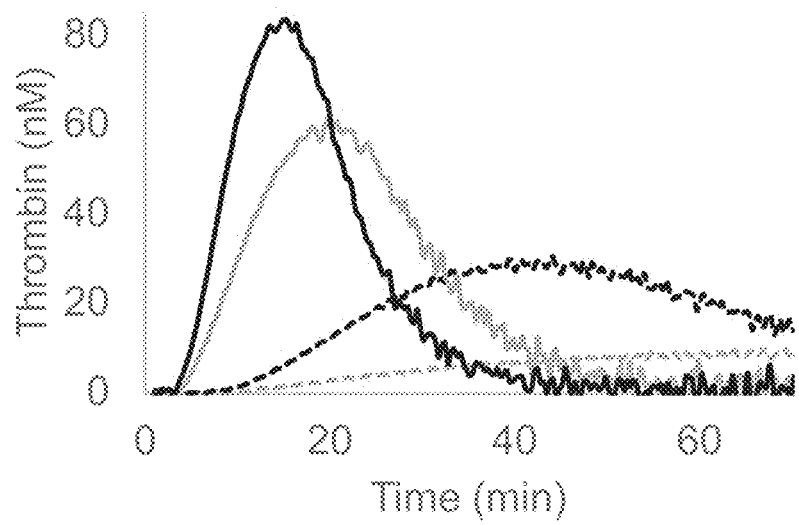
FIG. 41A shows the effect of 0.1 U heparin on thrombin generation, in pooled normal plasma, comparing apheresis units (APU) with FDPDs at 5K and 50K platelets per μL.
Figure 41B:
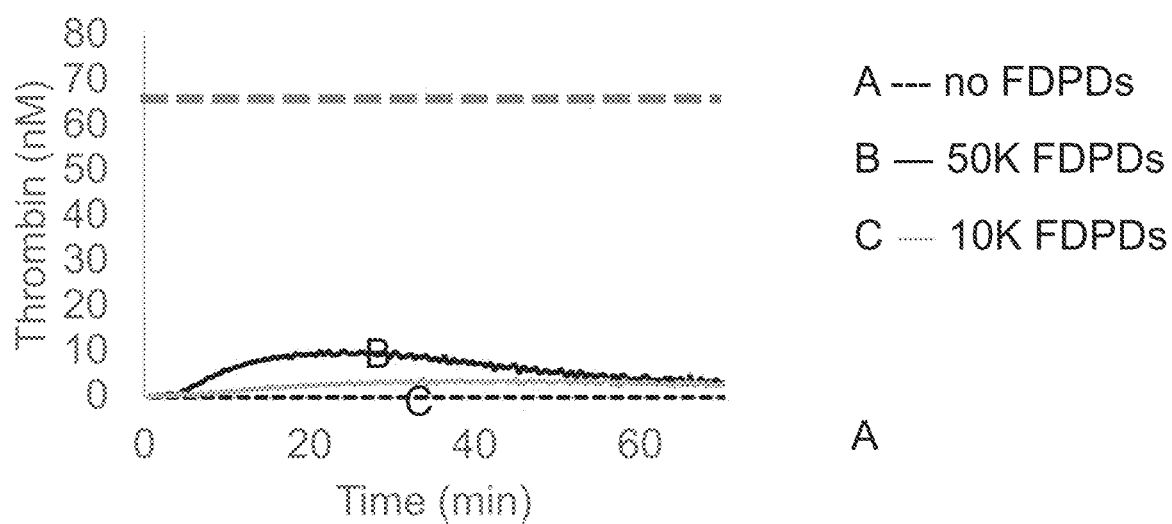
FIG. 41B shows the impact of 0.8 U/mL heparin reversed by 4 μg/ml protamine (½ of the recommended reversal doses) with FDPDs at 10K and 50K platelets per μL.
Figure 41C:
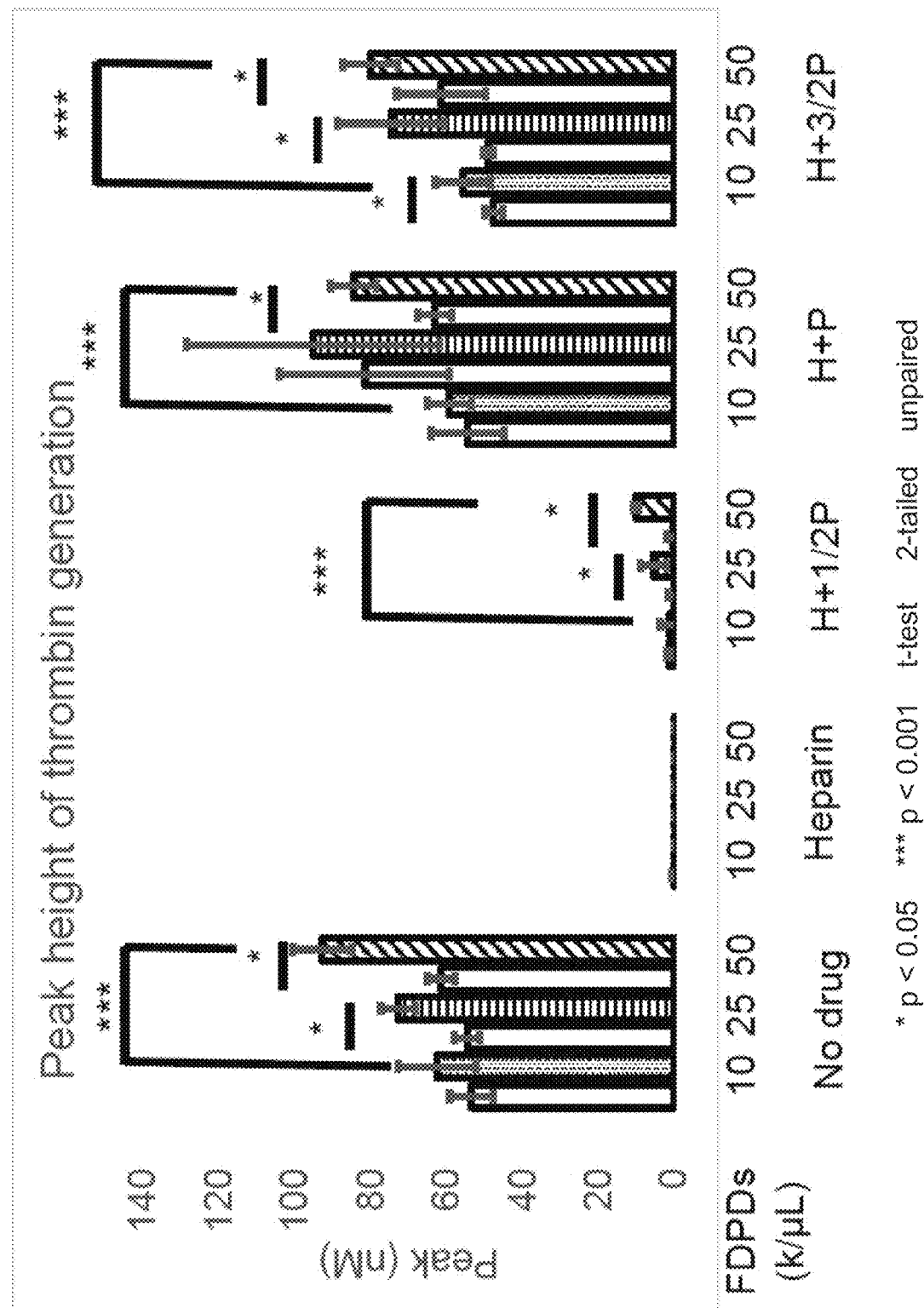
FIG. 41C shows peak height of thrombin generation of samples which were treated with heparin and protamine as described on the x-axis.

FIG. 41A-C show that FDPDs retain thrombin generation peak in the presence of heparin and protamine using TGA. FIG. 41A shows the effect of 0.1 U heparin on thrombin generation, in pooled normal plasma, comparing apheresis units (APU) with FDPDs at 5K and 50K platelets per µL. FIG. 41B shows the impact of 0.8 U/mL heparin reversed by 4 µg/ml protamine (½ of the recommended reversal doses) with FDPDs at 10K and 50K platelets per µL. TGA of FIG. 41A and FIG. 41B is initiated by PRP reagent containing a mixture of phospholipids and tissue factor. The dashed line in FIGS. 41A and 41B denotes the typical thrombin peak seen in this assay. FIG. 41C shows peak height of thrombin generation of samples which were treated with heparin and protamine as described on the x-axis. Empty (white fill) bars represent samples that were diluted with control buffer, and filled bars represent samples that were treated with FDPDs. All samples were run in triplicate. The experiment was repeated on separate days to improve statistical relevance.

The results of this experiment demonstrate that if there is a less than clinical dose of protamine present in a heparin treated sample, then FDPDs impose a dose dependent decrease of time to clot (ACT) and increase of thrombin peak height (TGA)

Example 22. Reproducibly of FDPD Reversal of Aspirin (ASA) Inhibition of Occlusion Human freeze-dried platelet derivatives (FDPDs) were prepared according to the procedure in Example 15. T-TAS® experiments using AR chips were carried out according to Example 4.

Figure 42:
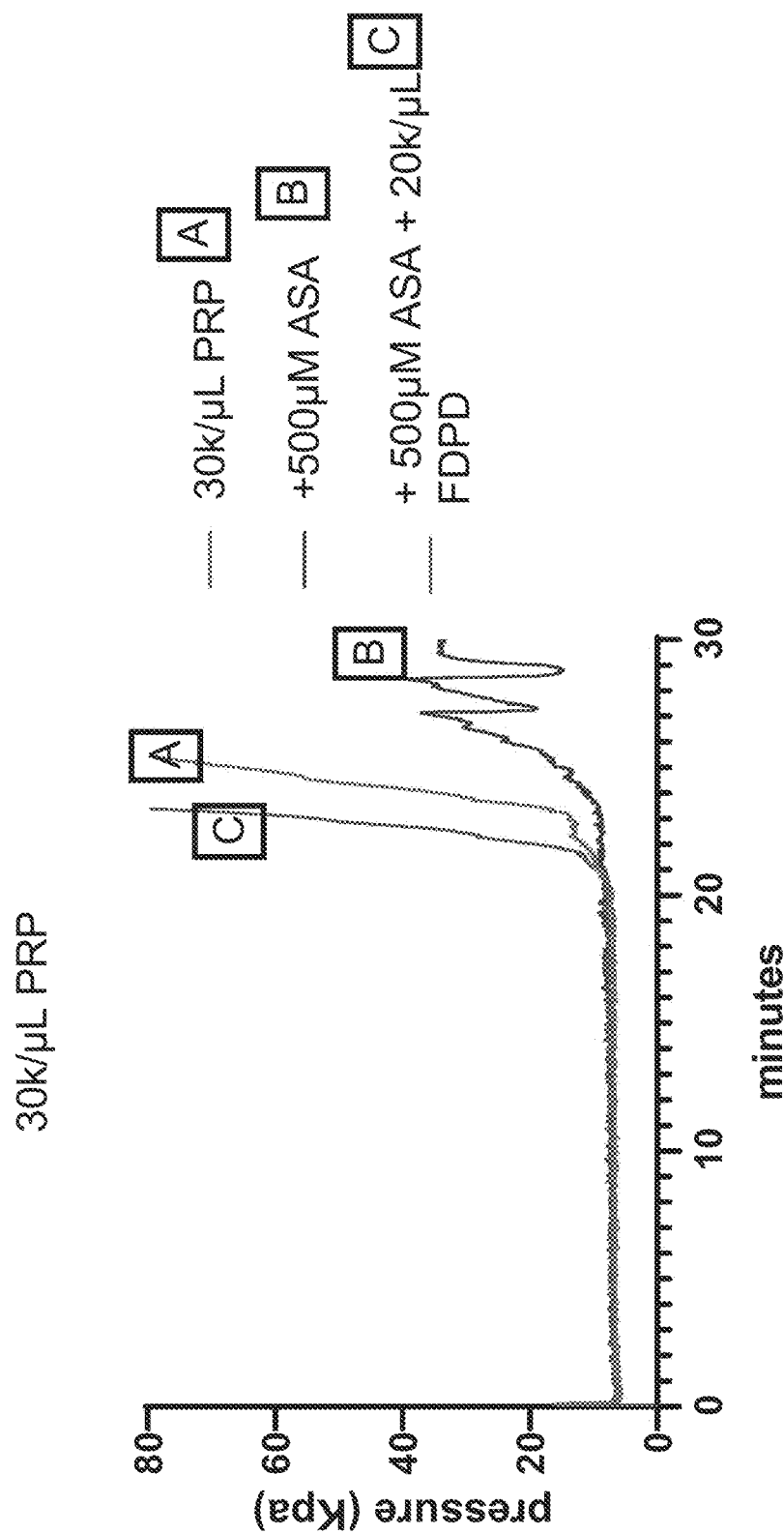
FIG. 42 shows the occlusion time with aspirin treatment in the presence of FDPDs versus PRP alone.

The effect of aspirin on the occlusion time of PRP with and without FDPDs was assessed using a T-TAS assay. The concentrations of the agents are as follows: PRP at 30K/μL, aspirin at 500M, and FDPDs at 20 k/μL. The results are shown in FIG. 42 PRP samples showed occlusion of >30 minutes with aspirin treatment versus a PRP alone time of 25:56 minutes; the addition of 20 k/μL FDPDs to P2Y12-inhibited PRP reduced time to thrombus formation to lower than PRP alone; 23:29 minutes in the presence of aspirin (FIG. 42).

These results demonstrate that the occlusion of platelets on the T-TAS® AR Chip in the presence of human FDPDs is unaffected by the antiplatelet effect of aspirin. This suggests that human FDPDS will maintain expected function when infused into patients receiving aspirin and/or similar agents.

Example 23. Reproducibly of FDPD Reversal of Ticagrelor and Aspirin (ASA) Combined Inhibition of Occlusion Human freeze-dried platelet derivatives (FDPDs) were prepared according to the procedure in Example 15. T-TAS® experiments using AR chips were carried out according to Example 4.

Figure 43:
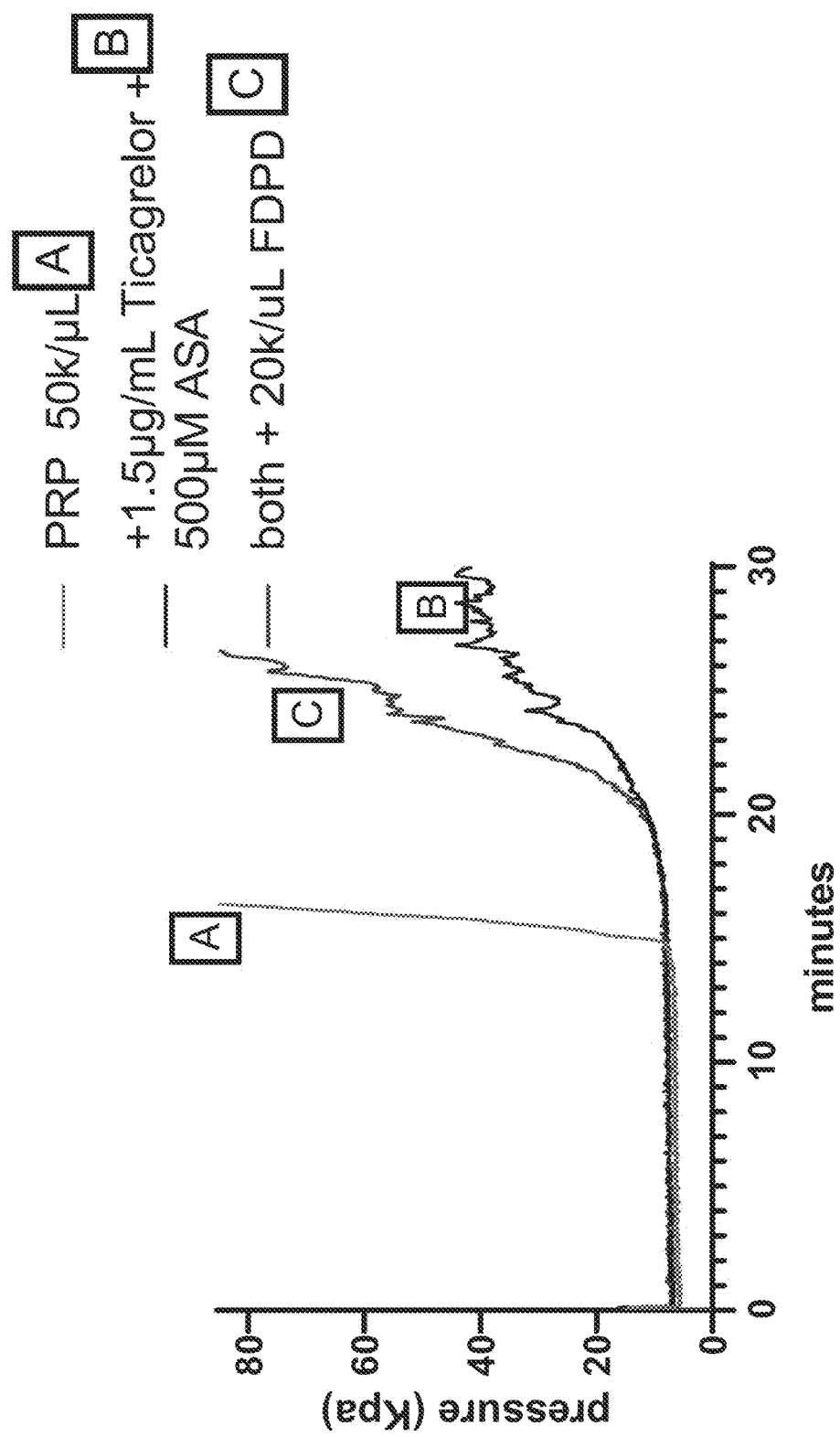
FIG. 43 shows the occlusion time with both ticagrelor and aspirin in the presence of FDPDs versus PRP alone.

The effect of ticagrelor and aspirin together on the occlusion time of PRP with and without FDPDs was assessed using a T-TAS assay. The concentrations of the agents are as follows: PRP at 50K/μL, ticagrelor at 1.5 μg/mL, aspirin at 500 μM, and FDPDs at 50 k/μL. The results are shown in FIG. 43. The addition of 20 k/μL FDPDs to the combined ticagrelor and aspirin treated PRP reduced time to thrombus formation to 19:36 minutes versus a >30 minutes occlusion time in the presence of combined ticagrelor and aspirin alone.

These results demonstrate that the occlusion effect of platelets on the T-TAS® AR Chip in the presence of human FDPDs unaffected by the combined antiplatelet effect of ticagrelor and aspirin. This suggests that human FDPDS will maintain expected function when infused into patients receiving combined ticagrelor and aspirin treatment.

Example 24. Inability of FDPDs to Aggregate in the Presence of Agonists and Absence of Fresh Platelets Light transmission aggregometry (LTA) was used to observe FDPD aggregation in the presence of known platelet aggregation agonists. The FDPD aggregation data was compared to aggregation data of fresh platelets.

FDPDs, also referred as "TFF-FDPDs", were produced by the TFF method described in Example 15. Fresh platelets in Platelet Rich Plasma (PRP) were prepared from whole blood collected in acid-citrate-dextrose (ACD) collection tubes (BD Vacutainer ACD Solution A Blood Collection Tubes ref #364606). Platelet rich plasma (PRP) was prepared by centrifugation of ACD-whole-blood at 180 g for 15 minutes at 22° C. using a Beckman Coulter Avanti J-15R centrifuge. Platelet poor plasma (PPP) was prepared by centrifugation of ACD-whole-blood at 2000 g for 20 minutes at 22° C.

Figure 44A:
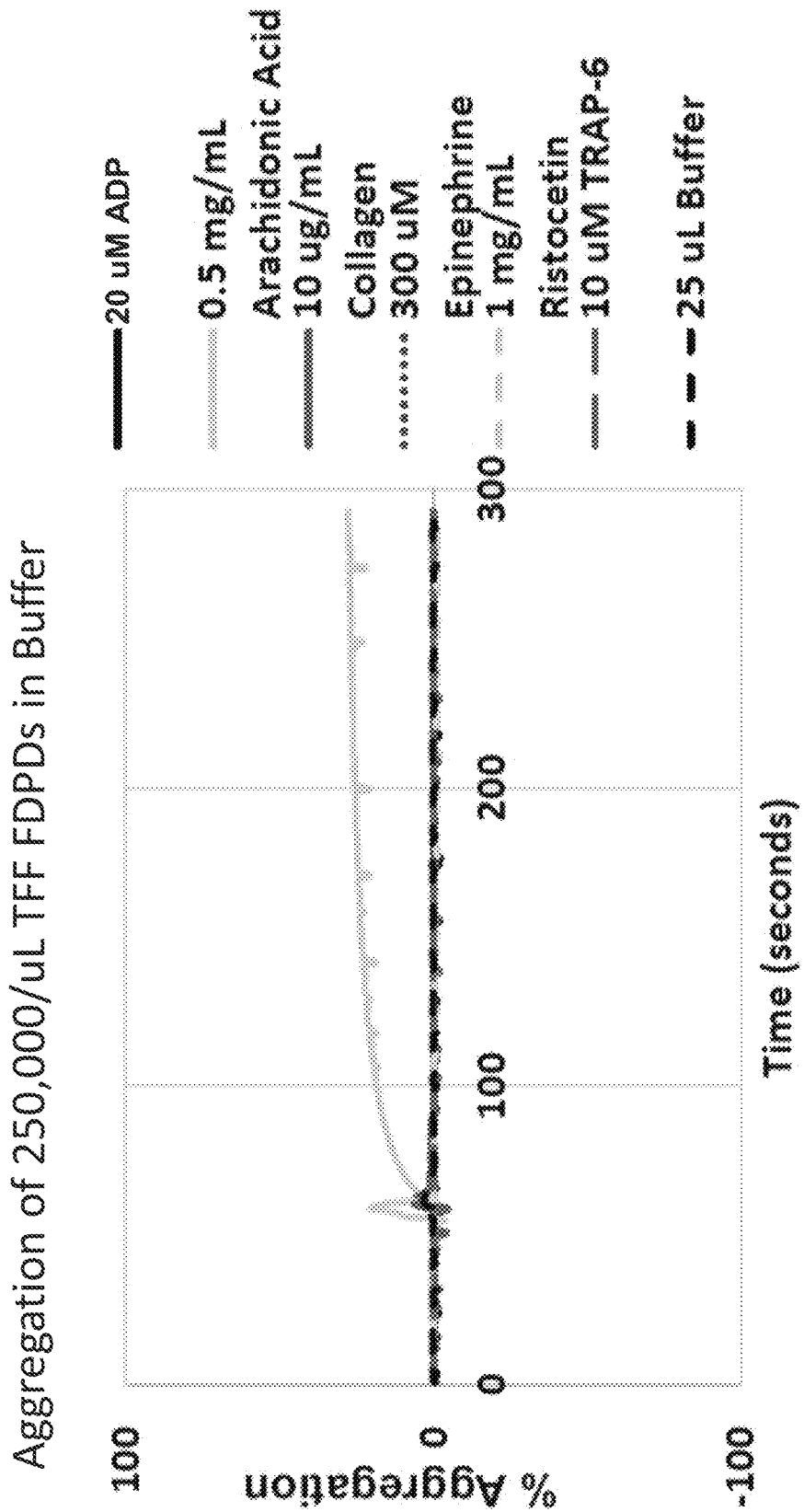
FIG. 44A shows the aggregation response of FDPDs in the presence of agonists, but in the absence of fresh platelets.

For sample preparation for aggregometry studies, PRP was diluted with PPP to a platelet concentration (plt count) of 250,000 plts/uL. Platelet count was determined using a Coulter Ac•T diff2 Hematology Analyzer. TFF FDPDs, lyophilized and thermally treated, were prepared using tangential flow filtration as described in Example 15. A 30 mL vial of FDPDs was rehydrated using 30 mL of cell culture grade water (Corning Cat #25-055-CI). The vial was incubated at room temperature for a total of 10 minutes. During the 10-minute rehydration period, the vial was gently swirled at 0, 5, and 10 minutes to promote dissolution of the lyophilizate. The aggregometry studies as per the present Example was carried out in the absence of fresh platelets. Therefore, the aggregometry studies supported only aggregation ability of the FDPDs, but not the co-aggregation ability. For sample preparation for aggregometry studies, rehydrated FDPDs were diluted in a buffer to a platelet count of 250,000/μL. FDPDs sample preparations used for ristocetin aggregation studies were composed of 20% citrated plasma (George King Bio-Medical, Inc. Pooled Normal Plasma product #0010-1) and buffer. Light transmission aggregometry (LTA) (Bio/Data PAP-8E Platelet Aggregometer catalog #106075) at 37° C. was used to observe the aggregation response of FDPDs (FIG. 44A) and PRP samples (FIG. 44B) from a final concentration of 20 μM ADP, 10 μg/mL collagen, 200 μM epinephrine (ADP, collagen, and epinephrine reagents from Helena Laboratories Platelet Aggregation Kit cat. #5369), 0.5 mg/mL arachidonic acid (Helena Arachidonic Acid Reagent cat.), 1 mg/mL ristocetin (Helena Ristocetin for Aggregation Assays cat.), and 10 μM thrombin receptor activator peptide 6 (TRAP-6) (Sigma Aldrich Cat #T1573-5MG). PPP, buffer, or buffer with 20% citrated plasma were used as blanks for the PRP, FDPDs, and FDPDs with 20% citrated plasma samples, respectively. Prior to agonist treatment, 225 μL of FDPDs or PRP sample was reverse pipetted in a test tube containing a stir bar. The test tube was then placed into the aggregometer's non-stirred incubation well for 1 minute. The sample was then placed into a stirred incubation well for 1 minute. The sample was then placed into the stirred test well and the aggregation test was initiated. After 1-minute of baseline observation the sample was treated with agonist and the aggregation response was recorded. Using the same procedure as the test runs, a negative control of 25 μL buffer was included simultaneously with all runs to determine spontaneous baseline-aggregation responses of all sample groups.

Figure 44B:
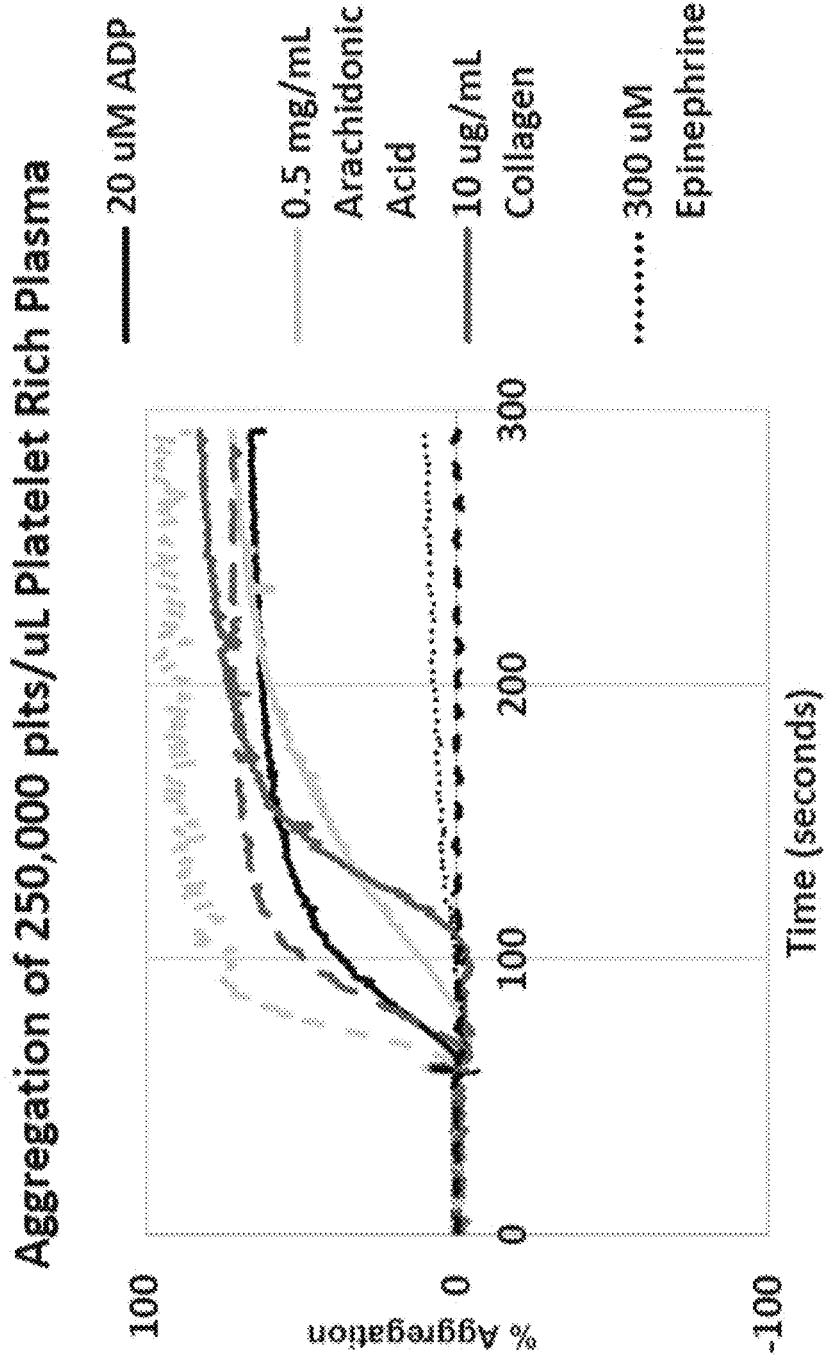
FIG. 44B shows the aggregation response of platelet-rich plasma (PRP) in the presence of agonists, but in the absence of fresh platelets.
Figure 44C:
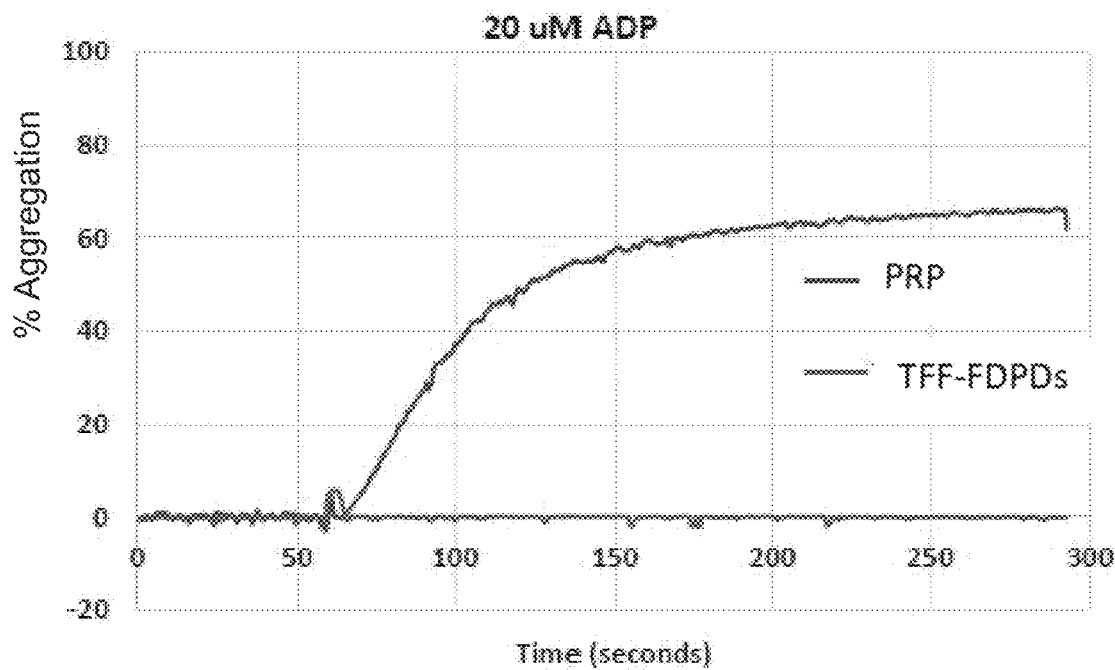
FIG. 44C shows the comparison of aggregation of FDPDs and PRP in the presence of 20 μM ADP.
Figure 44D:
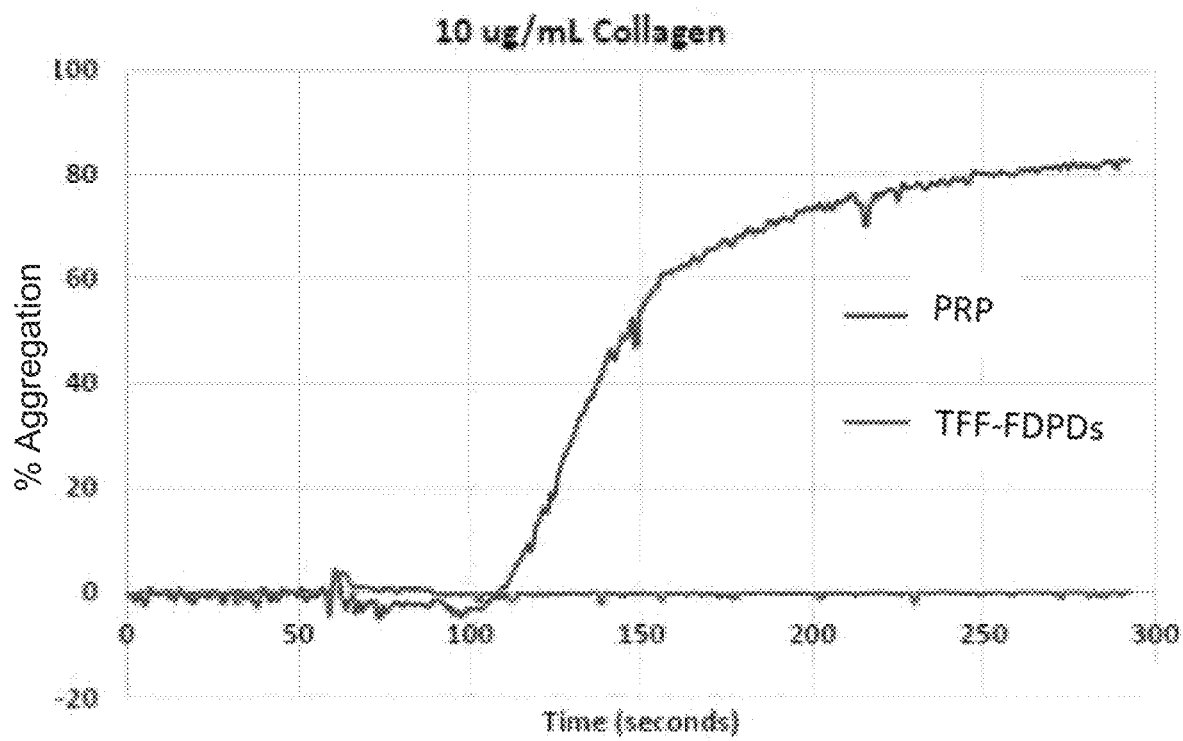
FIG. 44D shows the comparison of aggregation of FDPDs and PRP in the presence of 10 μg/ml collagen.
Figure 44E:
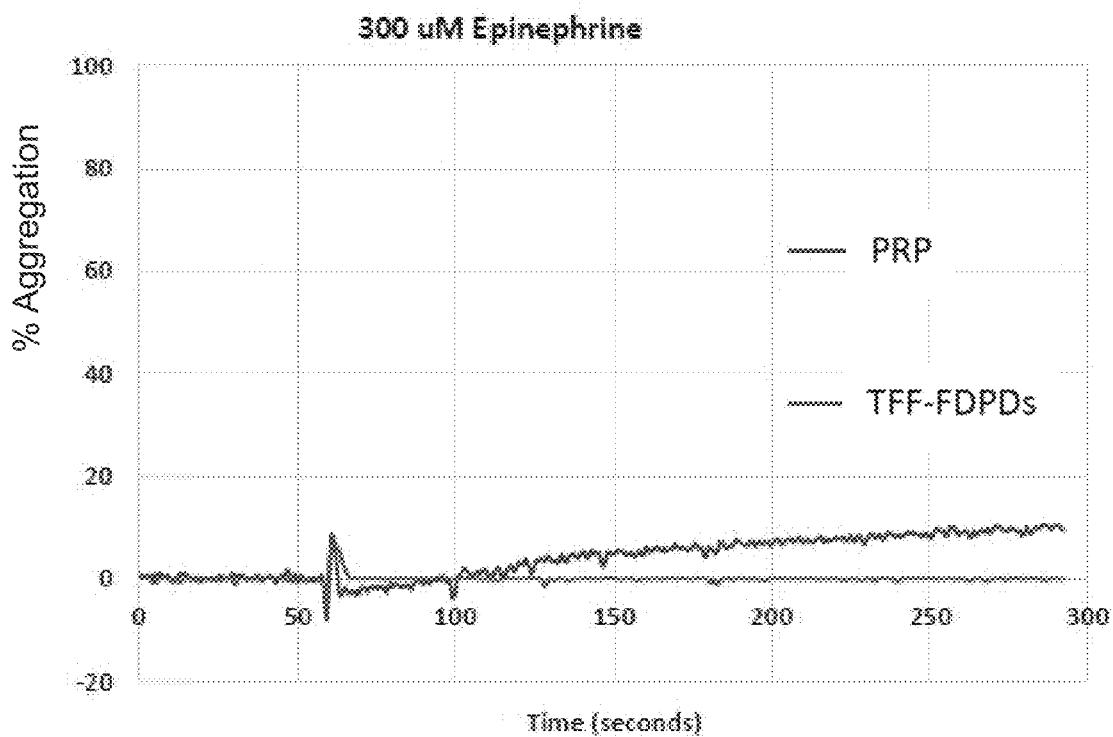
FIG. 44E shows the comparison of aggregation of FDPDs and PRP in the presence of 300 μM epinephrine.
Figure 44F:
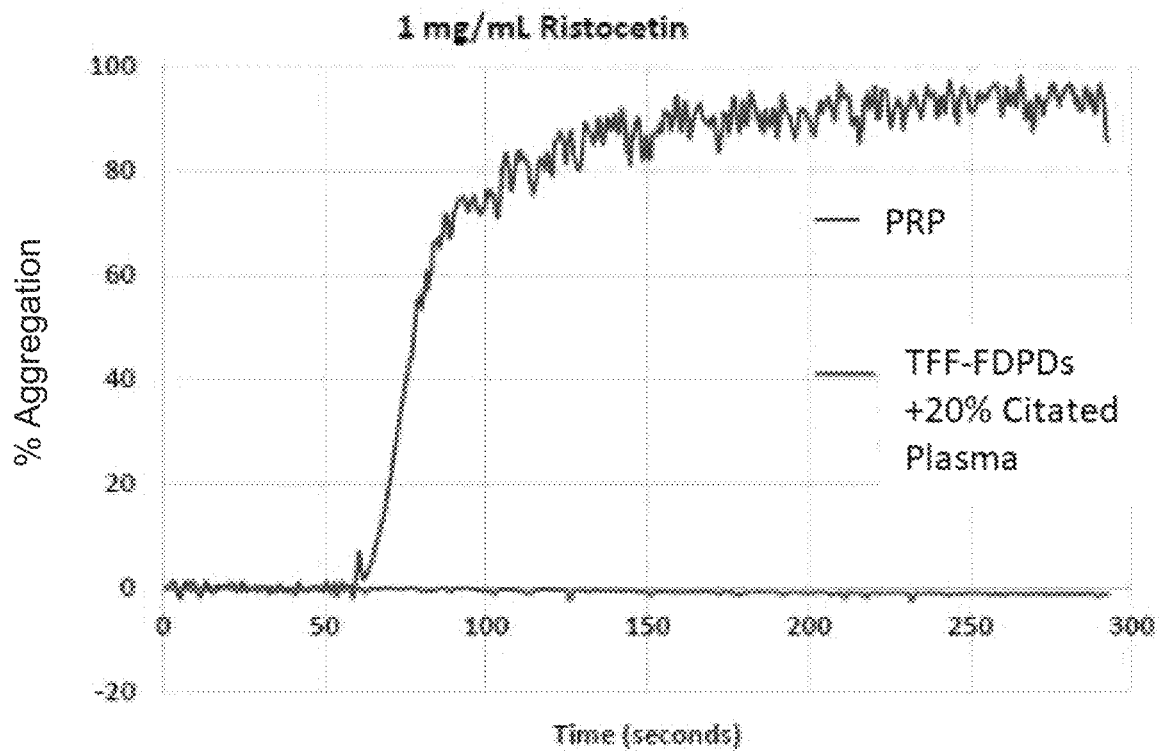
FIG. 44F shows the comparison of aggregation of FDPDs and PRP in the presence of 1 mg/ml ristocetin.
Figure 44G:
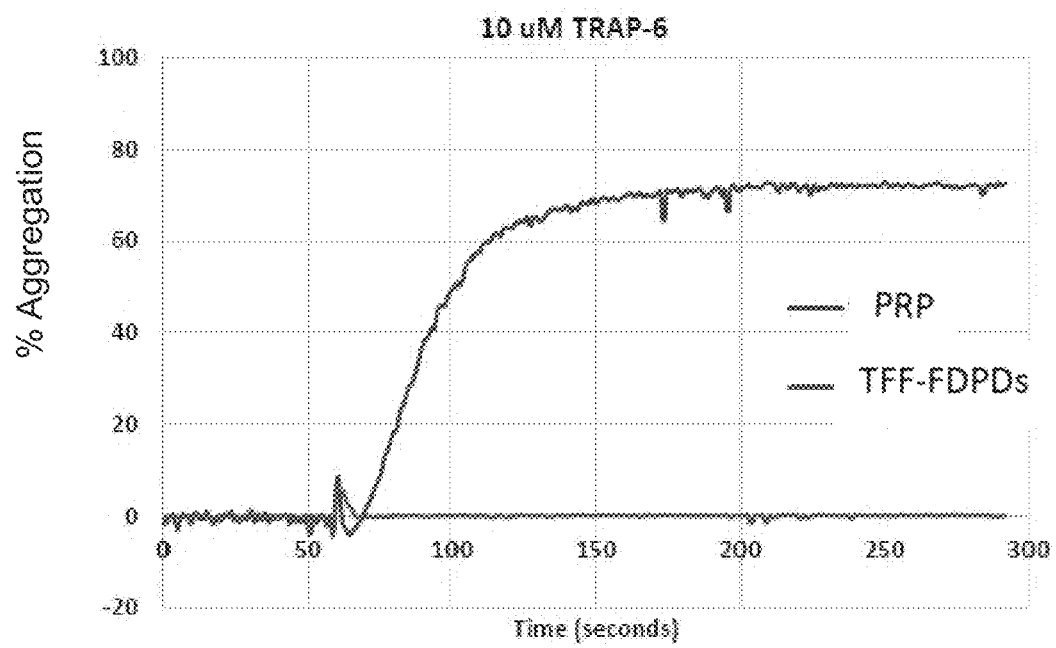
FIG. 44G shows the comparison of aggregation of FDPDs and PRP in the presence of 10 μM TRAP-6.
Figure 44H:
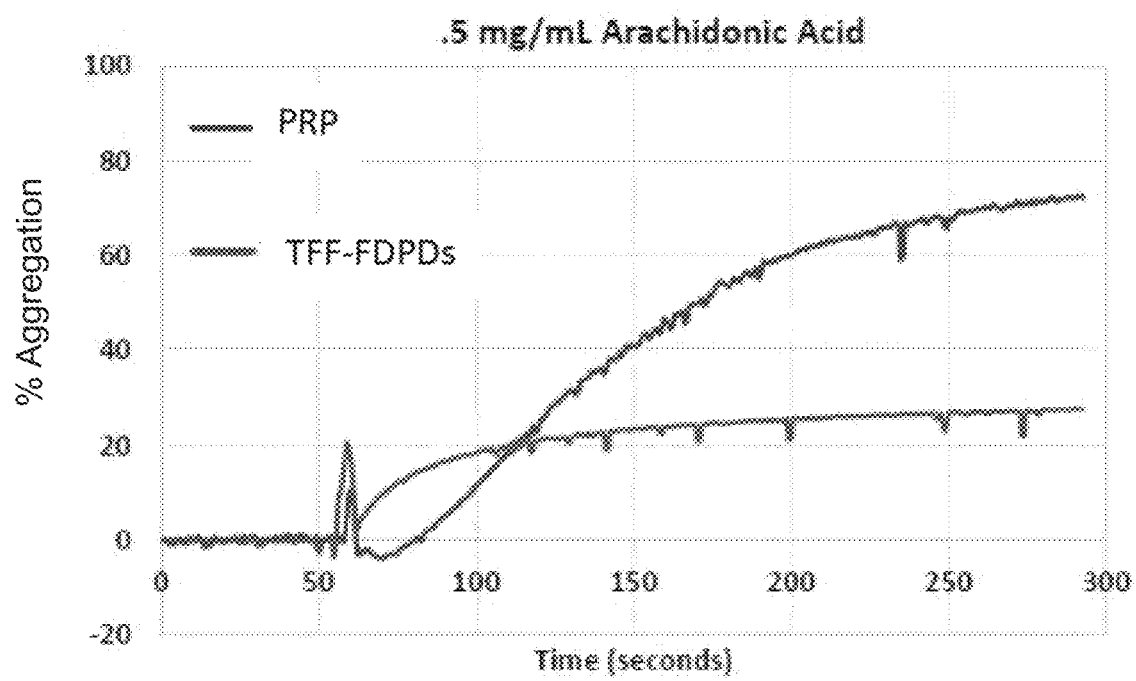
FIG. 44H shows the comparison of aggregation of FDPDs and PRP in the presence of 0.5 mg/ml arachidonic acid.

FDPD sample preparations in 1.7 mL microcentrifuge tubes, at room temperature, were treated with an agonist at a final agonist concentration of 20 μM ADP, 0.5 mg/mL arachidonic acid, 10 μg/mL collagen, 200 μM epinephrine, 1 mg/mL ristocetin, and 10 μM TRAP-6 or 25 μL buffer. FDPD counts were determined prior to and 5-minutes after agonist treatment. ADP (FIG. 44C), collagen (FIG. 44D), epinephrine (FIG. 44E), ristocetin (FIG. 44F), and TRAP-6 (FIG. 44G) did not cause an aggregation response in TFF FDPDs when measured by LTA. TFF FDPDs' response from the aforementioned agonists was equivalent to baseline aggregation values that would be obtained from no agonist or a negative control of buffer. When TFF FDPDs were treated with arachidonic acid (AA) and observed by LTA (FIG. 44H) there was an apparent aggregation response, however after visual inspection of the aggregometry cuvette it was observed that the solution had become visibly clear and aggregates were not observed, indicating that the apparent aggregation response was from lysis of FDPDs and not AA induced aggregation. Determining aggregation by cell count for TFF FDPDs produced similar results to the LTA results for all agonists. Agonists' functionality was confirmed by performing LTA on fresh PRP (FIG. 44B). ADP, arachidonic acid, collagen, epinephrine, ristocetin and TRAP-6 caused normal aggregation profiles and magnitudes that are representative of a strong aggregation response in PRP. The aggregation response from epinephrine in PRP was reduced, however epinephrine was still able to elicit an aggregation response that was above baseline aggregation. The negative control of buffer in PRP indicated that the PRP was not activated prior to agonists additions. Visual inspection of the PRP samples after the aggregation tests indicated that no cell lysis had occurred and platelet aggregates were visually observed in the aggregation cuvettes for all agonists, indicating that all aggregations responses were from platelet aggregation. The aggregation percentage of FDPDs and fresh PRP observed in the presence of the aforementioned agonists have been captured in Table 6.

TABLE 6

| Agonist | TFF FDPDs % Aggregation (n = 3) | PRP % Aggregation(n = 2) |
|---|---|---|
| 20 µM ADP | 1% | 66% |
| 0.5 mg/mL Arachidonic Acid | 28%* | 73% |
| 10 µg/mL Collagen | 2% | 83% |
| 300 µM Epinephrine | 1% | 11% |
| 1 mg/mL Ristocetin | 0% | 98% |
| 10 µM TRAP-6 | 1% | 73% |
| 25 µL Buffer | 1% | 2% |

*Due to lysis of FDPDs and not aggregation

Example 25. FDPDs are Maximally Activated—Binding of Annexin V to FDPDs in the Presence of TRAP FDPDs, prepared using the TFF process and treated with TRAP-6, were tested for the presence of phosphatidylserine (PS), indicative of an activated platelet, on the surface of the FDPDs. The presence of PS was assessed by analysis of Annexin V (AV) binding to the FDPDs.

One 30 mL vial of FDPDs prepared using the TFF process as described in the Example 15 was rehydrated using 30 mL of cell culture grade water (Corning Cat #25-055-CI). After water was added to the vial, the vial was incubated for 10 minutes at room temperature. Gentle swirling of the vial was performed every 2 minutes during the 10-minute period to promote full dissolution of the cake. Once the FDPDs were fully rehydrated, two 475 µL aliquots were transferred to two separate 1.7 mL microcentrifuge tubes. Twenty-five microliters of HEPES Modified Tryode's Albumin buffer (HMTA) (Cellphire RGT-004) was added to the sample in the first tube to generate FDPDs without TRAP-6. Twenty-five microliters of 400 µM Thrombin Receptor Activating Peptide 6 (TRAP-6) (Sigma Aldrich Cat #T1573-5MG) was added to the second tube to generate FDPDs with TRAP-6. The final concentration of TRAP-6 during incubation was 20 µM. Both tubes were inverted 5 times to mix and incubated at room temperature for 10 minutes.

After incubation with HMTA buffer or TRAP-6, the samples were further diluted 1:20 by adding 10 µL of the FDPD sample to 190 µL HMTA. These diluted samples of FDPDs incubated with HMTA and FDPDs incubated with TRAP-6 were both stained in 1.7 mL microcentrifuge tubes as follows: unstained control samples were generated by combining 10 µL of FDPDs and 20 µL HMTA; calcium free control samples were generated by combining 10 µL of FDPDs, 5 µL of Annexin V-ACP (BD Pharmingen Cat #550475), and 15 µL HMTA; Annexin V (AV) stained test samples were generated by combining 10 µL of FDPDs, 5 µL of AV-ACP, and 15 µL HMTA supplemented with 9 mM $CaCl_2$ (Cellphire RGT-012 Lot #LAB-0047-21). The final concentration of $CaCl_2$ in the AV-stained test samples was 3 mM. All stained samples for both FDPDs incubated with HMTA and FDPDs incubated with TRAP-6 were generated in triplicate. The samples were incubated at room temperature, protected from light, for 20 minutes.

After incubation, 500 µL of HEPES buffered saline (HBS) (Cellphire RGT-017) was added to all unstained control and calcium free control samples. Five hundred microliters of HBS supplemented with 3 mM $CaCl_2$ was added to the AV-stained test samples. One hundred microliters from each sample was transferred to an individual well in a 96 well plate, and the samples were analyzed using an Agilent Quanteon flow cytometer.

TRAP-6 activity was confirmed by measuring CD62P expression in human apheresis platelets with and without exposure to TRAP-6. Two 475 µL aliquots of apheresis platelets were transferred to two separate 1.7 mL microcentrifuge tubes. Twenty-five microliters of HMTA buffer was added to the sample in the first tube to generate apheresis platelets without TRAP-6. Twenty-five microliters of 400 µM TRAP-6 was added to the second tube to generate FDPDs with TRAP-6. The final concentration of TRAP-6 during incubation was 20 µM. Both tubes were inverted 5 times to mix and incubated at room temperature for 10 minutes.

After incubation with HMTA buffer or TRAP-6, the samples were further diluted 1:20 by adding 10 µL of apheresis platelets to 190 µL HMTA. These diluted samples of apheresis platelets incubated with HMTA and apheresis platelets incubated with TRAP-6 were both stained in 1.7 mL microcentrifuge tubes as follows: unstained control samples were generated by combining 10 µL of apheresis platelets and 20 µL HMTA; Anti-CD62P stained test samples were generated by combining 10 µL of apheresis platelets, 5 µL of anti-CD62P-PE antibody (BD Pharmingen Cat #550561 Lot #6322976), and 15 µL HMTA. All stained samples for both apheresis platelets incubated with HMTA and apheresis platelets incubated with TRAP-6 were generated in triplicate. The samples were incubated at room temperature, protected from light, for 20 minutes.

After incubation, 500 µL of phosphate buffered saline (PBS) (Corning Cat #21-040-CV1) was added to all samples. One hundred microliters from each sample was transferred to an individual well in a 96 well plate, and the samples were analyzed using an Agilent Quanteon flow cytometer.

Figure 45A:
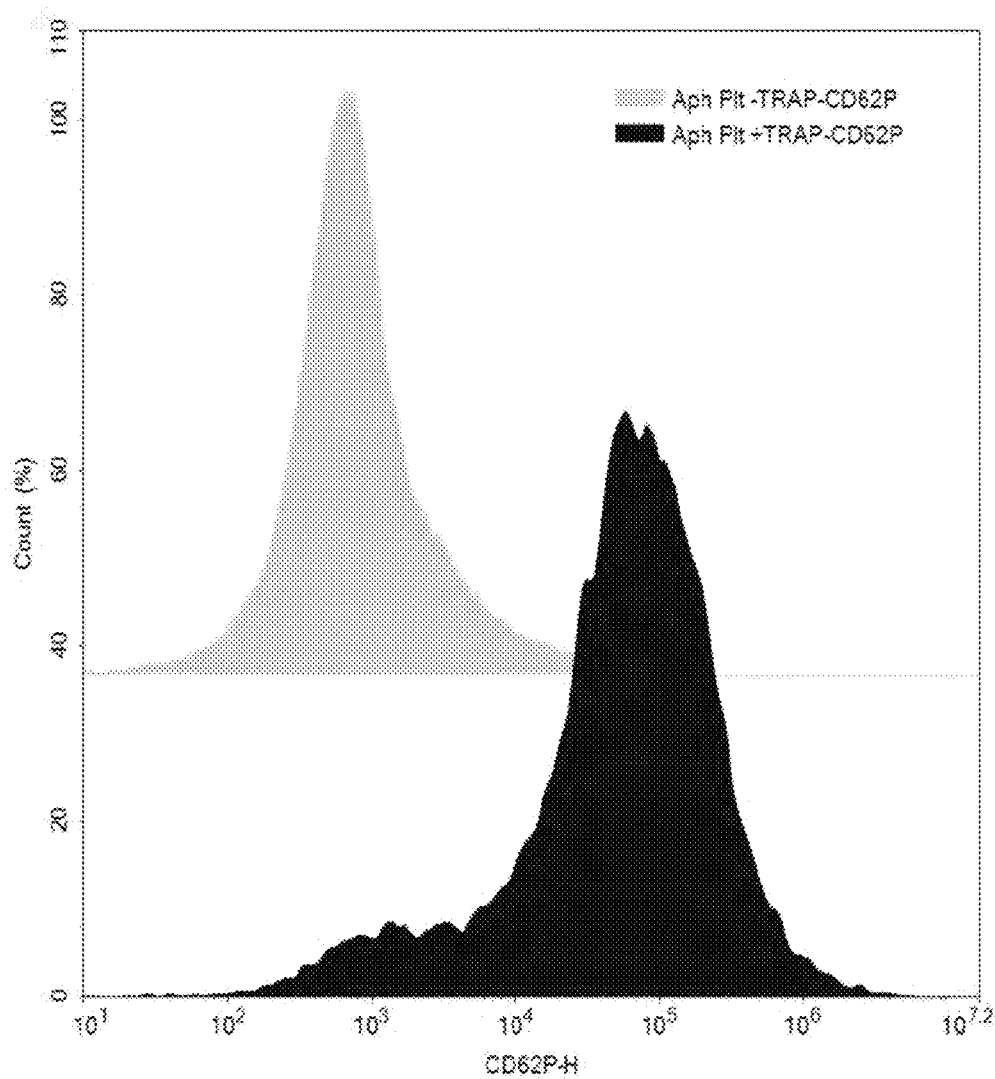
FIG. 45A shows that TRAP-6 peptide is capable of promoting platelet activation by observing expression of CD62P on the apheresis platelets.
Figure 45B:
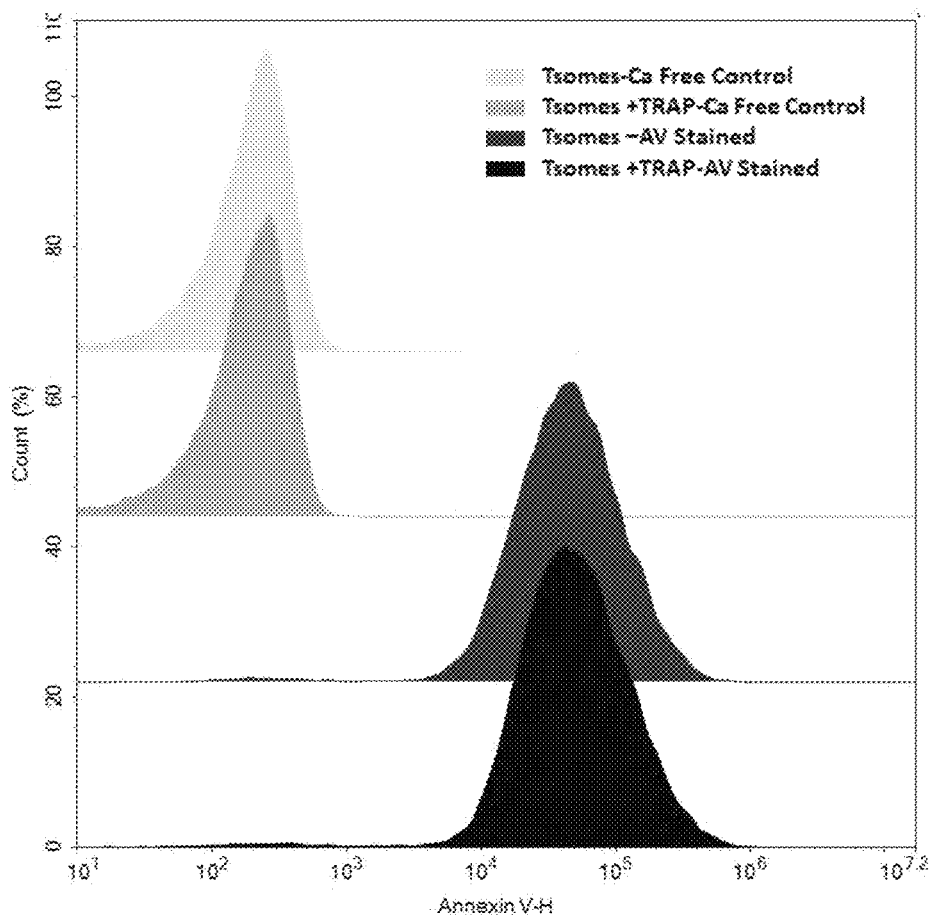
FIG. 45B shows that TRAP-6 peptide is not able to increase the expression of CD62P on FDPDs.

FDPDs manufactured using the TFF process were incubated with either TRAP-6 or buffer and stained with Annexin V (AV) to determine the relative presence of phosphatidylserine (PS). Apheresis platelets were used to confirm TRAP-6 activity (FIG. 45A, and Table 7), and increased expression of CD62P after the exposure to TRAP-6 confirms that TRAP-6 is capable of promoting platelet expression. PS expression on the exterior membrane leaflet is a hallmark of platelet activation and increases in membrane expression of PS result in greater amounts of AV binding. Unstained samples and samples stained with AV but without the addition of calcium were analyzed on the flow cytometer as negative controls. Unstained samples generated little to no fluorescent signal, indicating that FDPDs were not auto fluorescent at the wavelength selected to measure AV (FIG. 45B). The calcium free control samples also generated little to no fluorescent signal. Since AV binding to PS is dependent on the presence of calcium ions, a lack of signal from the calcium free control samples demonstrates that the AV-ACP conjugate was not associating with the FDPD membrane in a nonspecific manner. All samples stained with AV in the presence of calcium provided a strong fluorescent signal that was, on average, approximately 695 times brighter than the unstained controls. This result indicates that all FDPDs samples were expressing, or comprised, PS. Incubating the FDPDs with TRAP-6 did not cause a notable increase in AV binding as measured by mean fluorescent intensity (MFI) (FIG. 45B). The average MFI values for FDPDs incubated with buffer and FDPDs incubated with TRAP-6 were 68,179 and 68,783, respectively (Table 8).

TABLE 7

Apheresis Platelet CD62P MFI

| Sample Type | −TRAP | +TRAP |
| --- | --- | --- |
| Unstained | 100 | 107 |
| CD62P Stained | 2,351 | 126,598 |

TABLE 8

FDPD Annexin V MFIs

| Sample Type | −TRAP | +TRAP |
| --- | --- | --- |
| Unstained | 98 | 99 |
| Calcium Free Control | 203 | 198 |
| AV Stained | 68,179 | 68,783 |

FDPDs, manufactured using the TFF process, were shown to contain phosphatidylserine (PS) on the membrane as evident by the binding of Annexin V (AV) to the FDPDs. The binding of AV to activated platelets is a calcium dependent binding and therefore the calcium ion dependency of AV binding to the rehydrated FDPDs provides further support that the AV conjugate was not associating with the membrane of the FDPD in a nonspecific manner.

While TRAP-6 was shown to activate apheresis platelets, as evident by increased CD62P expression, and increased the binding of AV to the activated platelet, it was not the case for the FDPDs. The FDPDs with or without a TRAP-6 incubation exhibited same high level of AV binding, and indicate that TRAP-6 does not promote further surface expression of PS for FDPDs, likely because the FDPDs are maximally activated during the lyophilization and/or rehydration process, and further stimulation/activation is not possible.

Example 26. Presence of Thrombospondin (TSP1) on the Surface of the FDPDs

Thrombospondin (TSP1), a glycoprotein typically found to coat external membranes of activated platelets, was found to coat FDPDs without activation. The presence of TSP1 was detected by fluorescence of anti-Thrombospondin-1 (TSP-1) antibody.

Fresh platelet rich plasma (PRP) was isolated by centrifuging whole blood collected in acid citrate dextrose (ACD) at 180 g for 10 minutes. Isolated PRP was centrifuged again at 823 g for an additional 10 minutes. The plasma was then removed and discarded, and the platelet pellet was resuspended in HEPES Modified Tyrode's Albumin (HMTA) buffer. An aliquot of the resulting washed platelet sample was activated by incubated the platelets at room temperature for 10 minutes in the presence of 2 mM GPRP peptide (BaChem Cat #H-1998.0025), 2 mM $CaCl_2$, 0.5 U/mL thrombin (EDM Millipore Cat #605190-1000U), and 0.5 µg/mL collagen (ChronoPar Cat #385). A separate aliquot of washed platelets was set aside to be used as a resting negative control.

All samples of FDPDs were manufactured using the TFF process as described in Example 15. The FDPDs studied in this example were baked FDPDs which were heated after lyophilization at 80° C. for 24 hours. All vials were rehydrated using the appropriate amount of cell culture grade water. After water was added, the vials were incubated for 10 minutes at room temperature. Gentle swirling of the vials was performed every 2 minutes during the 10-minute period to promote full dissolution of the cake. Once rehydrated, samples of FDPDs from each vial, along with samples from both the resting and activated fresh washed platelet aliquots, were diluted 1:500 in triplicate using phosphate buffered saline (PBS) (Corning Cat #21-040-CV). The diluted samples were analyzed on the Quanteon flow cytometer and the concentrations of the platelets and FDPDs were determined. Based on these concentrations, an aliquot of each FDPDs or fresh platelet sample was diluted to a concentration of 100,000 FDPDs per microliter.

Stained samples from each vial of FDPDs and the resting and activated fresh platelets were generated by adding 10 µL of diluted FDPDs or platelets to 20 µL of HMTA containing 4 µg/mL of anti-Thrombospondin-1 (TSP-1) antibody (Santa Cruz Biotech Cat #sc-59887 AF594). Unstained control samples were generated by adding 10 µL of diluted FDPDs or platelets to 20 µL of HMTA. All The samples were incubated at room temperature, protected from light, for 20 minutes. After incubation, 500 µL of PBS was added to all samples. One hundred microliters from each sample were transferred to an individual well in a 96 well plate, and the samples were analyzed using an Agilent Quanteon flow cytometer.

Figure 46:
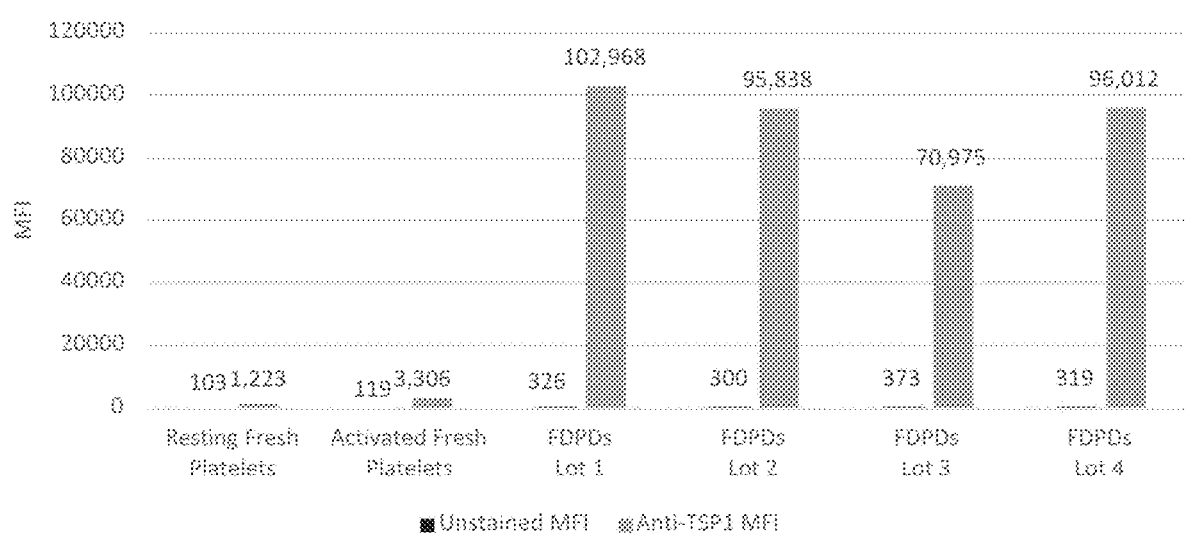
FIG. 46 shows the measurement of thrombospondin (TSP-1) by flow cytometry in terms of mean fluorescent intensity (MFI) in resting fresh platelets, activated fresh platelets, and different lots of FDPDs.

Unstained samples of fresh platelets and FDPDs generated little to no fluorescent signal, indicating that the samples were not auto fluorescent at the wavelength selected to measure TSP-1 expression or presence. Binding of the anti-TSP-1 antibody to fresh platelets increased slightly after activation with collagen and thrombin as shown by an increase in mean fluorescent intensity (MFI) when analyzed using flow cytometry (1,223 vs 3,306). Expression or presence of TSP-1 on FDPD samples varied from lot to lot with an average MFI value of 91,448 (FIG. 46). For all FDPD samples tested, the fluorescent signal was significantly higher than the signal generated by either resting or fresh platelets, indicating high amounts of TSP-1 may be bound to the surface of rehydrated FDPDs. This data suggests that the FDPDs without the requirement of an activation step exhibit properties which in certain embodiments and applications are superior to activated platelet properties.

Example 27. Presence of Von Willebrand Factor (vWF) on the Surface of the FDPDs

Fresh platelet rich plasma (PRP) was isolated by centrifuging whole blood collected in acid citrate dextrose (ACD) at 180 g for 10 minutes. Isolated PRP was centrifuged again at 823 g for an additional 10 minutes. The plasma was then removed and discarded, and the platelet pellet was resuspended in HEPES Modified Tyrode's Albumin (HMTA) buffer. An aliquot of the resulting washed platelet sample was activated by incubating the platelets at room temperature for 10 minutes in the presence of 2 mM GPRP peptide (BaChem Cat #H-1998.0025), 2 mM $CaCl_2$), 0.5 U/mL thrombin (EDM Millipore Cat #605190-1000U), and 0.5 µg/mL collagen (ChronoPar Cat #385). A separate aliquot of washed platelets was set aside to be used as a resting negative control. All samples of FDPDs were prepared using the TFF process as described in the Example 15. The FDPDs studied in this example were baked FDPDs which were heated after lyophilization at 80° C. for 24 hours. All vials were rehydrated using the appropriate amount of cell culture grade water (Corning Cat #25-055-CI). After water was added, the vials were incubated for 10 minutes at room temperature. Gentle swirling of the vials was performed every 2 minutes during the 10-minute period to promote full dissolution of the cake. Once rehydrated, samples of FDPDs from each vial, along with samples from both the resting and activated fresh washed platelet aliquots, were diluted 1:500 in triplicate using phosphate buffered saline (PBS). The diluted samples were analyzed on the Quanteon flow cytometer and the concentrations were determined. Based on these concentrations, an aliquot of each FDPDs or fresh platelet sample was diluted to a concentration of 100,000 FDPDs per microliter.

Prior to staining, the anti-Von Willebrand Factor antibody (Novus Biologicals Cat #NBP2-54379PE) was diluted by a factor of 10. Stained samples from each vial of FDPDs and the resting and activated fresh platelets were generated by adding 10 µL of diluted FDPDs or platelets to 10 µL of diluted antibody and 10 µL of HMTA. Unstained control samples were generated by adding 10 µL of diluted FDPDs or platelets to 20 µL of HMTA. All The samples were incubated at room temperature, protected from light, for 20 minutes. After incubation, 500 µL of PBS was added to all samples. One hundred microliters from each sample was transferred to an individual well in a 96 well plate, and the samples were analyzed using an Agilent Quanteon flow cytometer.

Figure 47:
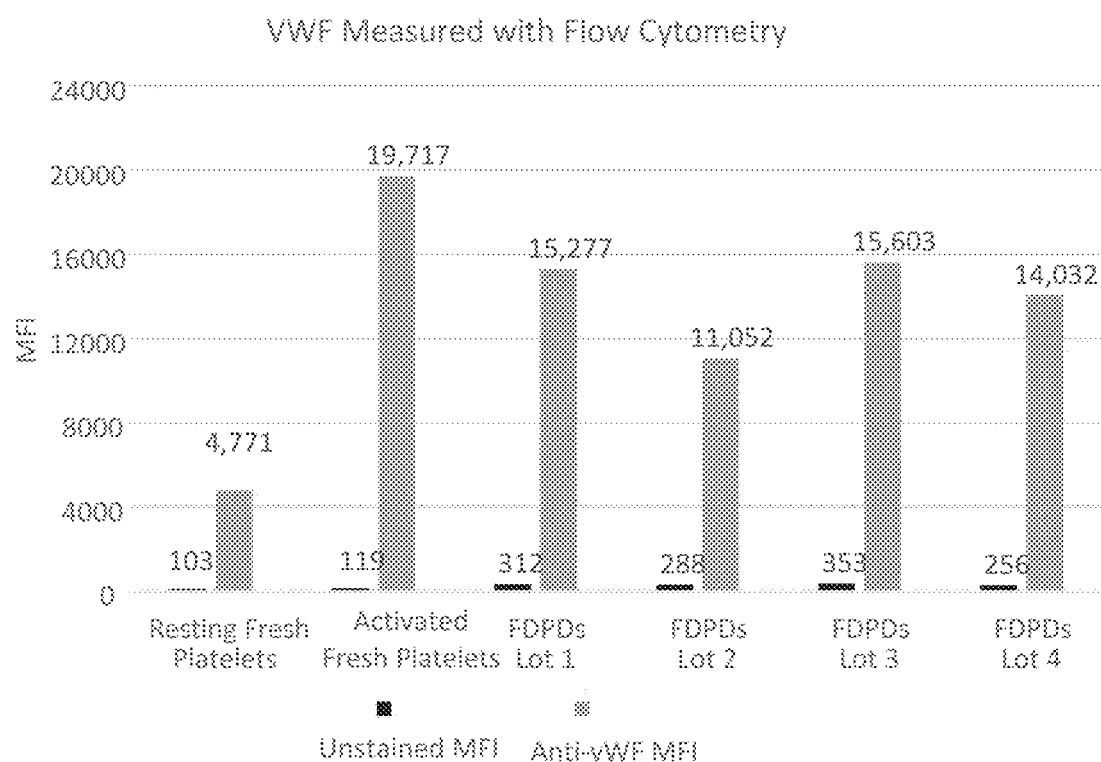
FIG. 47 shows the measurement of von Willebrand factor (vWF) by flow cytometry in terms of mean fluorescent intensity (MFI) in resting fresh platelets, activated fresh platelets, and different lots of FDPDs.

Unstained samples of fresh platelets and FDPDs generated little to no fluorescent signal, indicating that the samples were not auto fluorescent at the wavelength selected to measure vWF expression or presence. Binding of the anti-vWF antibody to fresh platelets increased after activation with collagen and thrombin as shown by an increase in mean fluorescent intensity (MFI) when analyzed using flow cytometry (4,771 vs 19,717). Expression or presence of vWF on FDPD samples varied from lot to lot with an average MFI value of 13,991 (FIG. 47). For all FDPD samples tested, the fluorescent signal fell between the signals generated by resting and activated platelets. This suggests that vWF is present on the surface of rehydrated FDPDs, and that the amount of vWF present is greater than that seen on resting platelets. The data suggests that even in the absence of any activation, the FDPDs exhibit properties that is superior to resting platelets and similar to the activated platelets.

Example 28. FDPDs—Compromised Membrane

Membrane integrity of FDPDs, either heated at 80° C. for 24 hours (baked FDPDs) or not heated (unbaked FDPDs) after lyophilization, was tested. The baked and unbaked FDPDs of the standard formulation were analyzed by forward scatter against pre-lyophilization material and by the use of an antibody against a stable intracellular antigen, β-tubulin, to determine if FDPDs were permeable to IgGs (150 kDa). Forward scatter is a flow cytometry measurement of laser scatter along the path of the laser. Forward scatter (FSC) is commonly used as an indication of cell size as larger cells will produce more scattered light. However, forward scatter also can indicate the membrane integrity of the sample via optical density (i.e., light transmission); a cell with less cytosolic material and a porous membrane would transmit more light (have a lower FSC) than the same cell if intact, despite being the same size.

The FDPDs of Example 15 were studied to determine if FDPDs were permeable to IgGs (150 kDa) by the use of an antibody against a stable intracellular antigen, β-tubulin. Fresh platelets, unbaked FDPDs, and baked FDPDs were fixed and stained with anti-β tubulin IgG with and without cell permeabilization. Fresh platelets showed a dramatic increase in IgG binding with permeabilization, whereas both baked and unbaked FDPDs showed no change in response to permeabilization (Table 9). Results from fresh platelets and FDPDs that were fixed and then either permeabilized with 0.2% Triton-X 100 or not permeabilized and then stained with anti-β tubulin IgG conjugated to the fluorophore AF594. Unstained samples are included for background fluorescence.

TABLE 9

| Sample | Mean FSC-H | AF594 MFI |
|---|---|---|
| Platelets Unstained | 120,301 | 115 |
| Platelets | 118,782 | 636 |
| Permeabilized Platelets | 49,062 | 9,009 |
| Unbaked FDPDs Unstained | 23,140 | 75 |
| Unbaked FDPDs | 23,280 | 546 |
| Permeabilized Unbaked FDPDs | 7,069 | 562 |
| Baked FDPDs Unstained | 49,740 | 362 |
| Baked FDPDs | 49,587 | 2,720 |
| Permeabilized Baked FDPDs | 27,527 | 2,523 |

The IgG binding studies suggest that the membrane integrity of FDPDs is severely impaired such that large molecules can pass through the cell membrane. Of additional note, permeabilization induced decreases in forward scatter value, corroborating the proposed relationship between membrane integrity and optical density for particles of the same size.

Additionally, the mean intensity of forward light scattering of FDPDs prepared by TFF method as described in Example 15 was compared to in-date human platelet apheresis units. The method is as described below.

All samples of FDPDs were manufactured using the TFF process. All vials were rehydrated using the appropriate amount of cell culture grade water (Corning Cat #25-055-CI). After water was added, the vials were incubated for 10 minutes at room temperature. Gentle swirling of the vials was performed every 2 minutes during the 10-minute period to promote full dissolution of the cake. Once rehydrated, samples of FDPDs from each vial, along with samples from both in-date human platelet apheresis units, were diluted 1:500 in triplicate using phosphate buffered saline (PBS) (Corning Cat #21-040-CV). The diluted samples were acquired on the Quanteon flow cytometer and the concentrations were determined. Based on these concentrations, an aliquot of each FDPDs or apheresis platelet sample was diluted to a concentration of 100,000 FDPDs per microliter in HEPES Modified Tyrode's Albumin (HMTA) buffer (Cellphire RGT-004).

Unstained samples of FDPDs and human apheresis platelets containing $10^6$ total cells in HMTA were diluted with 500 µL of PB. One hundred microliters from each sample were transferred to an individual well in a 96 well plate, and the samples were analyzed using an Agilent Quanteon flow cytometer.

Figure 48:
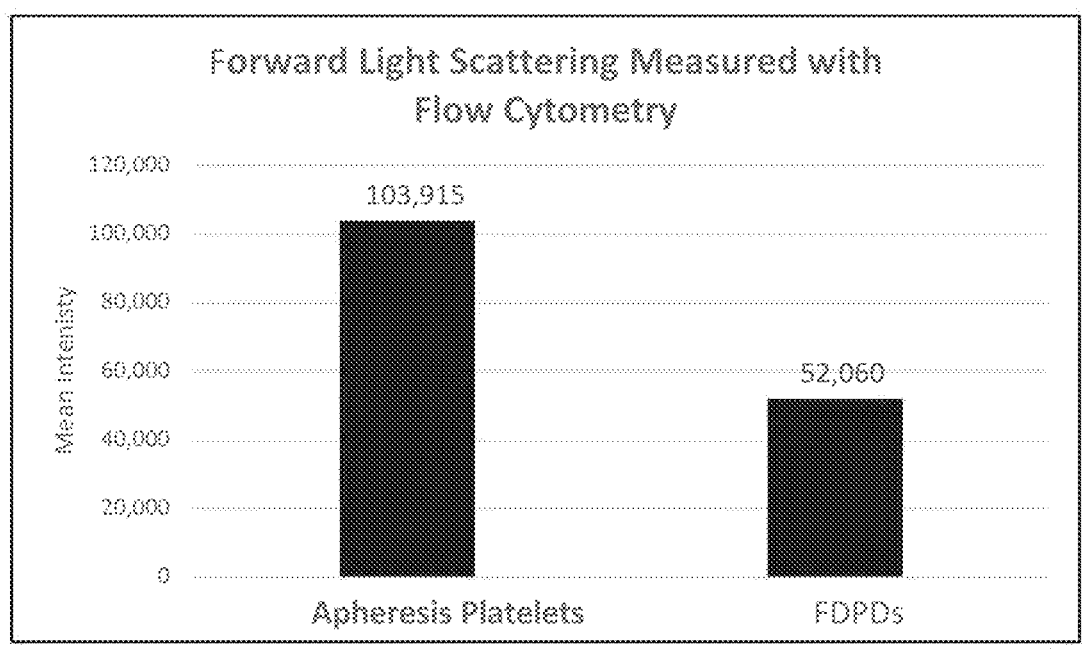
FIG. 48 shows the forward scatter (FSC) measured by flow cytometry of apheresis platelets, and FDPDs.

The mean intensity is depicted in FIG. 48. It can be observed that the mean intensity of forward light scattering measured with flow cytometry is distinctly lower (about 50%) for FDPDs as compared to the apheresis plasma. Therefore, corroborating with the previous result of Table 9 that a cell with less cytosolic material and a porous membrane would transmit more light (have a lower FSC) than the same cell if intact, despite being the same size.

The overall results suggest that membrane integrity is substantially degraded in FDPDs; the platelet intracellular contents have been released (e.g. LDH) and large molecules can enter the cellular cytosol (e.g. anti β-tubulin IgG). The plasma membrane of FDPDs is likely damaged by the drying (sublimation) or rehydration processes as freezing in cryopreserved platelets appears to be insufficient to induce severe membrane dysfunction. These results also imply that signal transduction from the outside of the cell is not possible in FDPDs, which is corroborated by lack of aggregation response (as observed in Example 24). Baking, although it produced an increase in optical density, did not appear to improve membrane integrity significantly (e.g., IgG β-tubulin binding). The results discussed in the present example thus show that the platelet derivatives as disclosed herein have a compromised plasma membrane.

Example 29. Surface Markers and Thrombin Generation

FDPDs batch were produced by the TFF method described in Example 15 and assayed for cell surface marker expression or presence or absence using flow cytometry.

Flow cytometry was used to assess FDPDs for expression or presence or presence of CD41, CD62, and phosphatidylserine (PS). Samples included approximately 270,000/µL FDPDs during staining and were diluted approximately 1:34 before the sample was analyzed in the cytometer. FDPD samples were rehydrated and diluted 1:2 in deionized water. A stock of anti-CD41 was diluted by adding 47.6 µL of antibody to 52.4 µL of HMTA. Samples stained with anti-CD41 were made by adding 10 µL of diluted FDPDs to 10 µL HMTA and 10 µL of diluted CD41 antibody. An anti-CD62 master mix was prepared by combining 12 µL anti-CD62 with 23.8 µL anti-CD41 and 64.2 µL of HMTA. An isotype control mix was made in the same manner. Samples stained with anti-CD62 were made by adding 10 µL of diluted FDPDs to 20 µL of the anti-CD62 master. The isotype master mix was used to make isotype control samples in the same manner. An annexin V (AV) master mix was prepared by combining 11.7 µL of AV with 83.3 µL of anti-CD41 and 80 µL of HMTA. Sample stained with AV were made by adding 20 µL of diluted FDPDs containing 50 mM GPRP to 20 µL of HMTA containing 15 mM $CaCl_2$ and 20 µL of the AV master mix. Negative gating control samples were made in the same manner using HMTA without calcium to prevent AV binding to PS. All samples were incubated at room temperature for 20 minutes. After incubation 1 mL HBS was added to all samples. HBS used to dilute AV test samples contained 5 mM $CaCl_2$ Anti-CD41 binding was used to identify the population of interest. CD62 and PS expression or presence was assessed by anti-CD62 and AV binding within the CD41 positive population.

Figure 49:
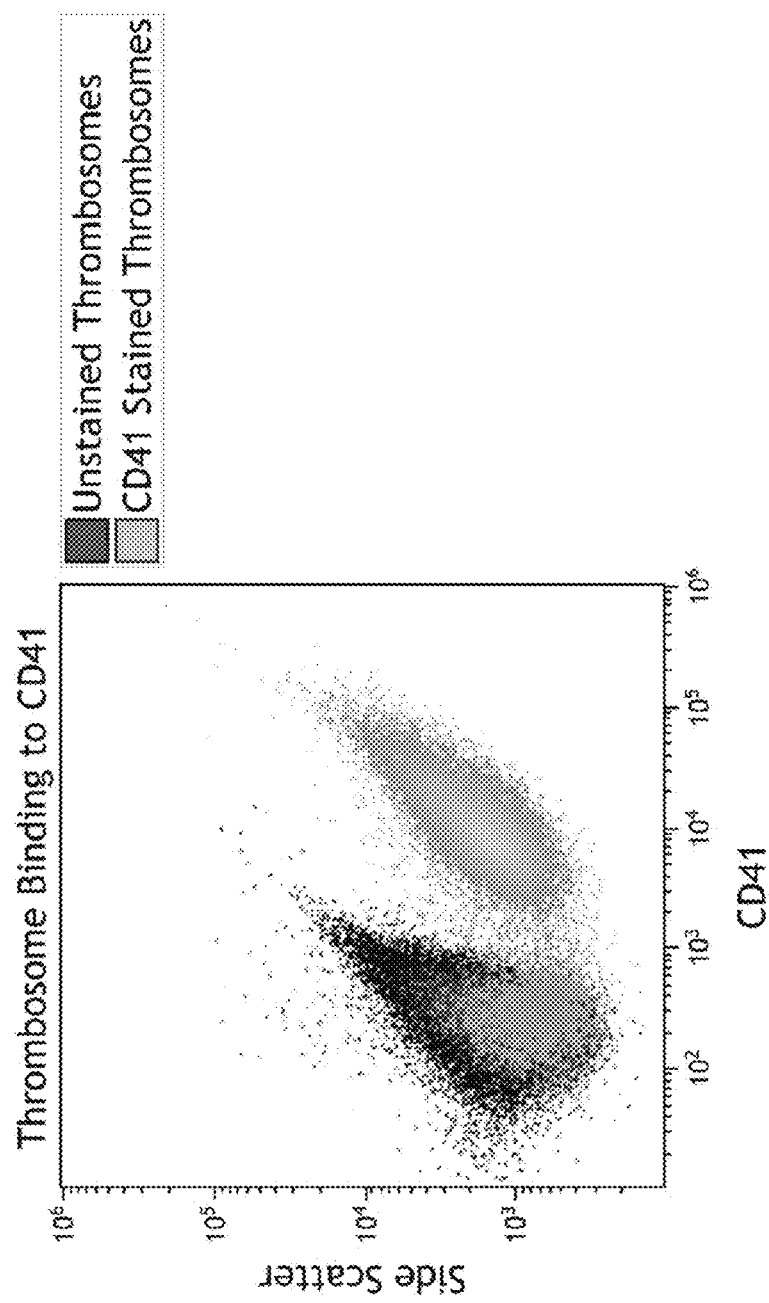
FIG. 49 shows exemplary flow cytometry data of FDPDs unstained (dark data points) or stained (light data points) with an anti-CD-41 antibody.

Glycoprotein IIb (GPIIb, also known as antigen CD41) expression or presence was assayed using an anti-CD41 antibody (4.8 µL, Beckman Coulter part #IM1416U). The assayed FDPDs demonstrated CD41 positivity (Table 10; FIG. 49)

TABLE 10

| Batch | CD41 Positivity (%) |
| --- | --- |
| 1 | 81.5 |
| 2 | 79.4 |
| 3 | 85.7 |
| 4 | 78.2 |
| 5 | 81.5 |
| 6 | 84.0 |
| 7 | 78.5 |
| Mean | 81.3 |

Figure 50:
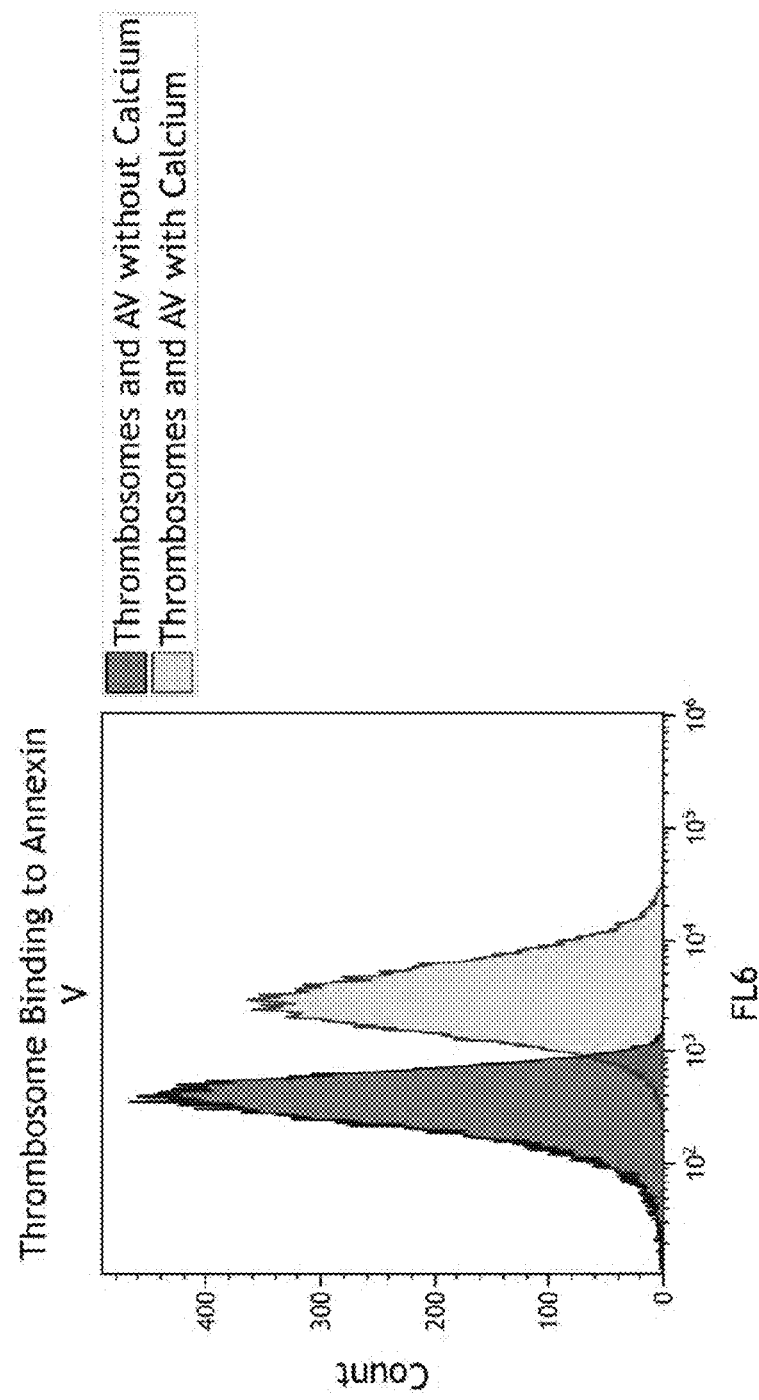
FIG. 50 shows an exemplary histogram of FDPDs incubated with annexin V with (light data points) and without (dark data points) calcium.

Phosphatidylserine (PS) expression or presence was assayed using annexin V (AV) (1.3 µL, BD Biosciences Cat. No. 550475). AV is a calcium-dependent phospholipid binding protein. The assayed FDPDs demonstrated AV positivity (Table 11; FIG. 50).

TABLE 11

| Batch | AV Positivity (%) |
| --- | --- |
| 1 | 96.7 |
| 2 | 89.9 |
| 3 | 95.3 |
| 4 | 95.4 |
| 5 | 95.9 |
| 6 | 96.2 |
| 7 | 93.5 |
| Mean | 94.7 |

Figure 51:
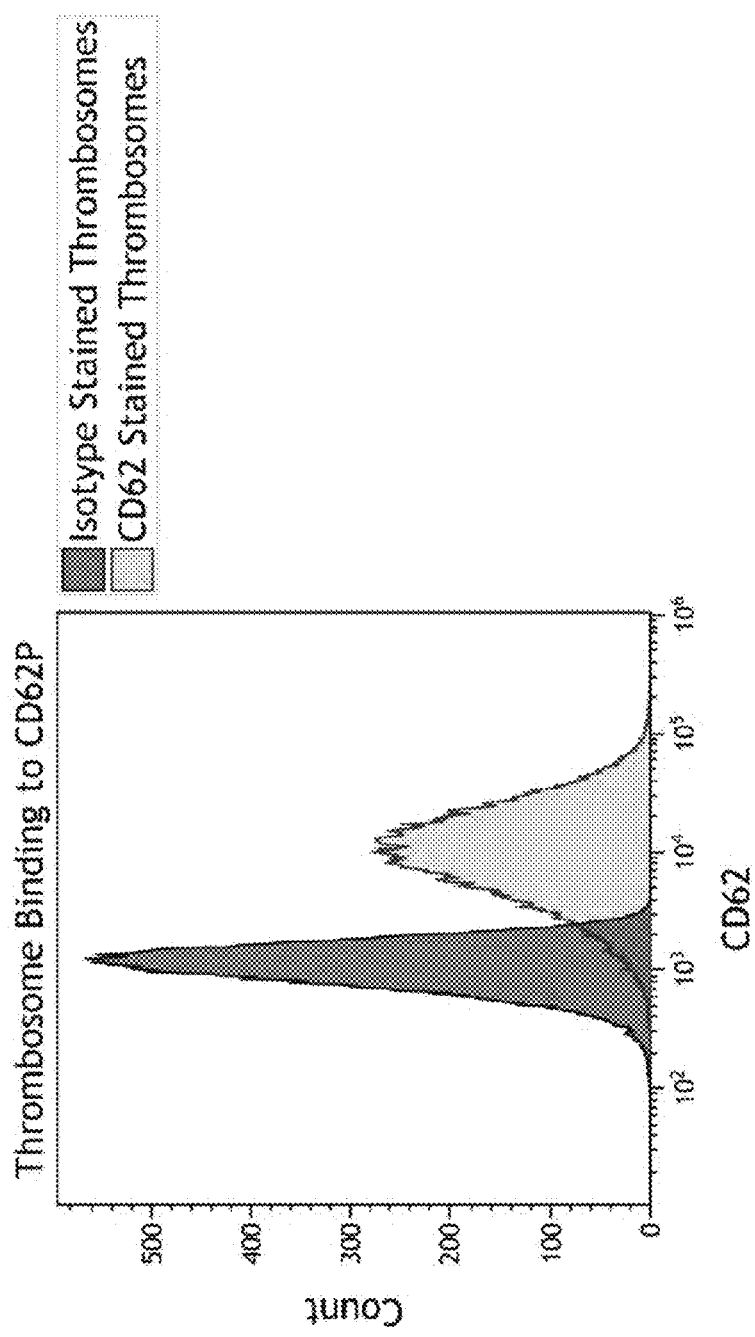
FIG. 51 shows an exemplary histogram of FDPDs incubated with an anti-CD62 antibody (light data points) or with an isotype control (dark data points).

P-selectin (also called CD62P) expression or presence was assayed using an anti-CD62P antibody (2.4 µL, BD Biosciences Cat. No. 550888). The assayed FDPDs demonstrated CD62 positivity (Table 12, FIG. 51)

TABLE 12

| Batch | CD62 Positivity (%) |
| --- | --- |
| 1 | 94.2 |
| 2 | 93.1 |
| 3 | 89.8 |
| 4 | 92.4 |
| 5 | 92.5 |
| 6 | 87.3 |
| 7 | 90.7 |
| Mean | 91.4 |

Figure 52:
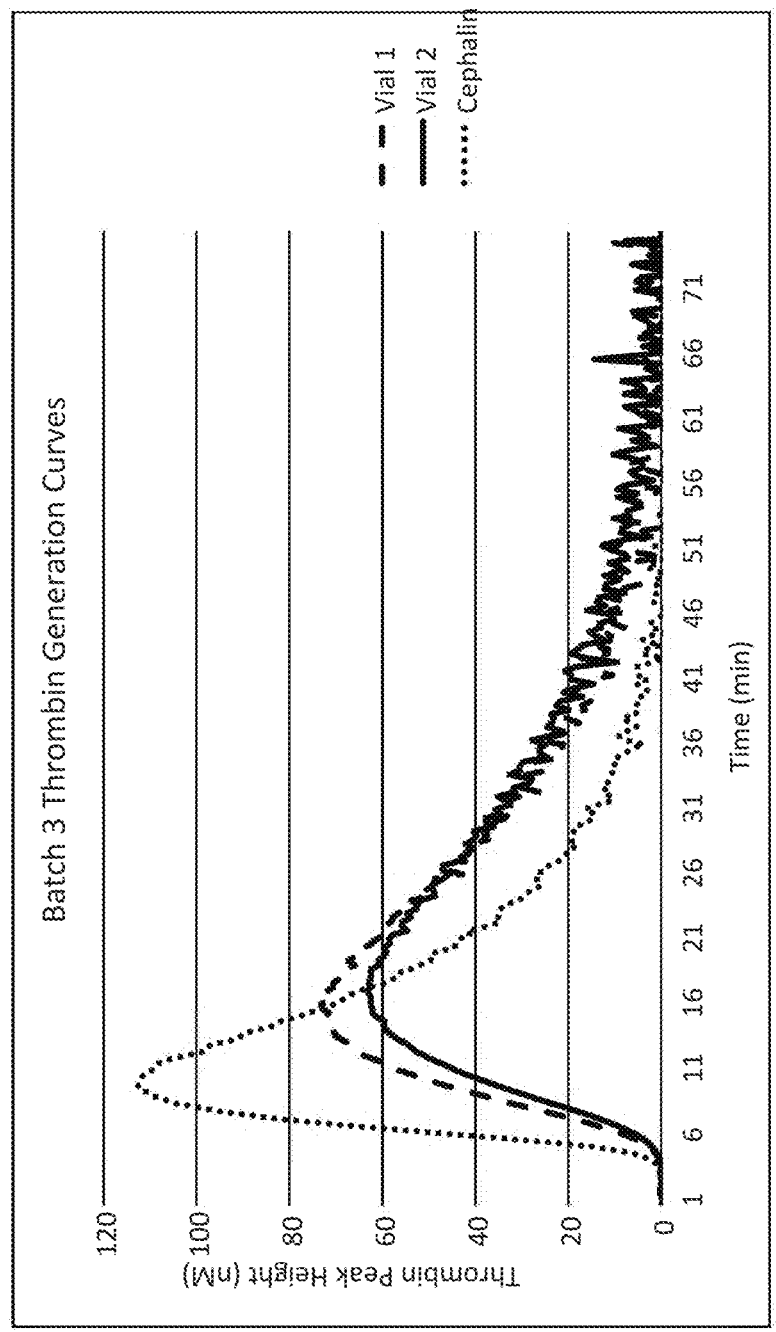
FIG. 52 shows a plot of thrombin peak height for FDPDs in the presence of PRP Reagent containing tissue factor and phospholipids (solid line and long dashes) and control cephalin (dots).

Thrombin generation was measured at $4.8 \times 10^3$ FDPDs/µl in the presence of PRP Reagent containing tissue factor and phospholipids using the below protocol. On average, the Thrombin Peak Height (TPH) for a FDPDs sample was 60.3 nM. Cephalin was used as a positive control. (Table 13; FIG. 52)

For each vial tested, a rehydrated sample of FDPDs was diluted to 7,200 particles per µL based on the flow cytometry particle count using 30% solution of Octaplas in control buffer. In a 96 well plate, sample wells were generated by adding 20 µL of PRP reagent (Diagnostica Stago Catalog No. 86196) and 80 µL of diluted FDPDs. Calibrator wells were generated by adding 20 µL of Thrombin Calibrator reagent (Diagnostica Stago Catalog No. 86197) to 80 µL of diluted FDPDs. The plate was loaded into the plate reader and incubated in the dark at 40° C. for 10 minutes. During sample incubation, FluCa solution was prepared by adding 40 µL of FluCa substrate (Diagnostica Stago Catalog No. 86197) to 1.6 mL of Fluo-Buffer (Diagnostica Stago Catalog No. 86197) warmed to 37° C. and vortexed to mix. The FluCa solution was aspirated in to the dispensing syringe and 20 µL was mechanically dispensed in to each reaction well, bringing the final FDPDs concentration in each well to 4,800 particles per µL and starting the thrombin generation reaction. Thrombin generation was measured via fluorescence in each well over the course of 75 minutes.

An exemplary step-by-step protocol follows:

Open CAT software; set up instrument; and prepare PRP reagent (including Tissue Factor and some phospholipids), calibrator, and fluo-buffer and fluo-substrate according to manufacturer guidelines.

Thaw Octaplas and TGA dilution buffer in 37° C. water bath for 10 minutes.

Add thawed Octaplas to TGA dilution buffer to create a buffer containing 30% Octaplas.

Use the 30% Octaplas mix to dilute reconstituted cephalin 1:50 to be used as a positive control.

Rehydrate FDPDs with cell culture grade water for 10 minutes then dilute with 30% Octaplas to 7,200 FDPDs/µL.

Using a multichannel pipette, add 20 µL of PRP reagent to each test well. Add 20 µL of Calibrator to each calibration well.

Add 80 µL of sample to each test and calibration well. Add 80 µL of 30% Octaplas to negative control wells and 1:50 cephalin to positive control wells.

Insert plate into tray and incubate for 10 minutes at 40° C. After incubation, dispense fluo-buffer and fluo-substrate mixture (including a fluorescent-labeled peptide, that when cleaved by thrombin, generates a fluorescent signal) into active wells.

Read plate for 75 minutes at 20 s intervals to capture full thrombin generation profile.

TABLE 13

| Batch | TPH (nM) |
|---|---|
| 1 | 61.5 |
| 2 | 71.4 |
| 3 | 67.8 |
| 4 | 52.0 |
| 5 | 60.2 |
| 6 | 54.7 |
| 7 | 54.4 |
| Mean | 60.3 |

Data from these assays is summarized in Table 14.

TABLE 14

TFF Batches

| Batch | Average TPH (nM) | Average CD41 Positivity | Average AV Positivity (0.5 µm-2.5 µm)[1] | Average CD62 Positivity (0.5 µm-2.5 µm)[1] |
|---|---|---|---|---|
| Batch B | 61.5 | 81.5 | 96.7 | 94.2 |
| Batch C | 71.4 | 79.4 | 89.9 | 93.1 |
| Batch D | 67.8 | 85.7 | 95.3 | 89.8 |
| Batch E | 52.0 | 78.2 | 95.4 | 92.4 |
| Batch F | 60.2 | 81.5 | 95.9 | 92.5 |
| Batch G | 54.7 | 84.0 | 96.2 | 87.3 |
| Batch H | 54.4 | 78.5 | 93.5 | 90.7 |
| Mean | 60.3 | 81.3 | 94.7 | 91.4 |

[1]Particle diameter as assessed using sizing beats on the flow cytometry forward scatter.

Example 30. Microparticle Content Reduction

Figure 53A:
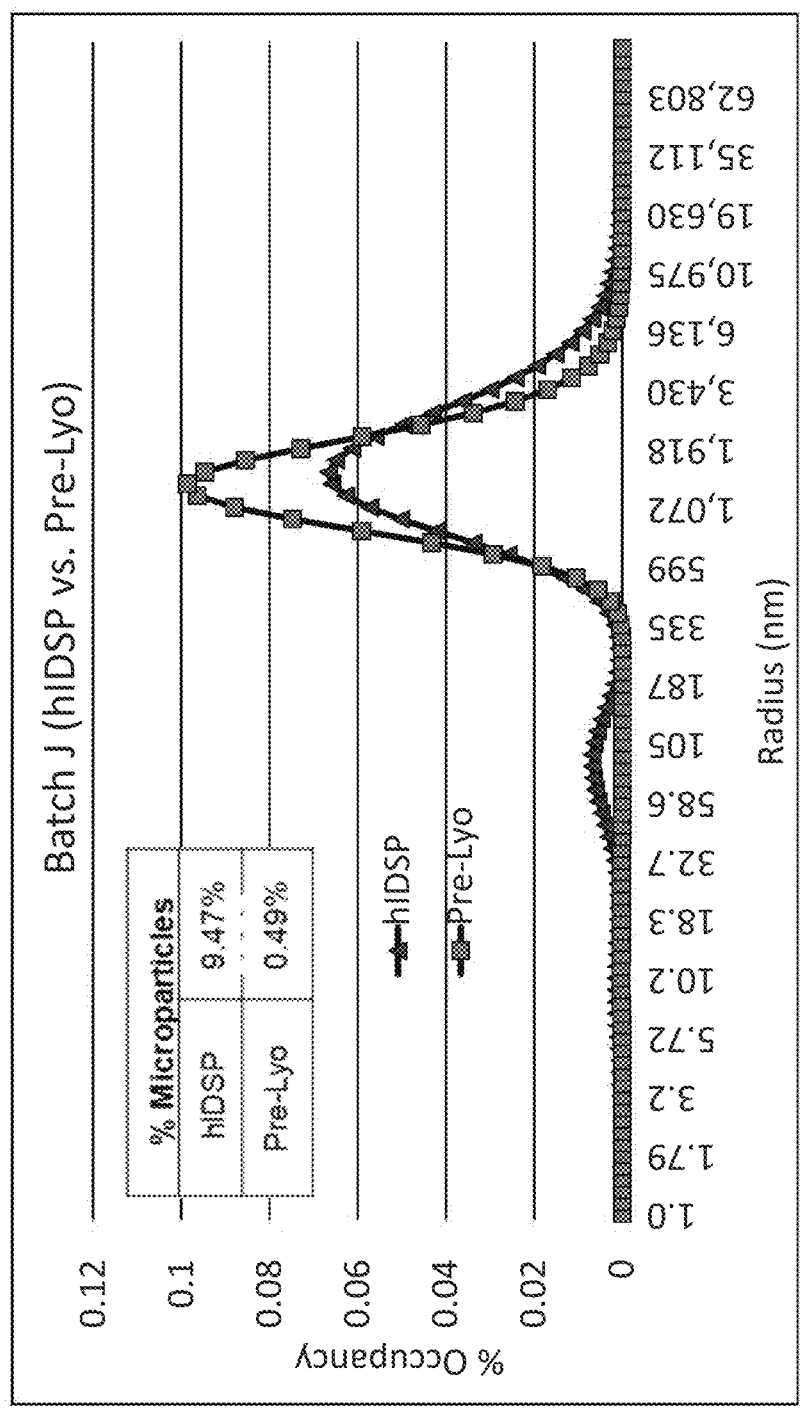
FIG. 53A is a plot of the percent occupancy of particles of different radii in human in-date stored platelets (Batch J) and platelet derivatives (pre-lyophilization) derived therefrom as determined by dynamic light scattering (DLS).
Figure 53B:
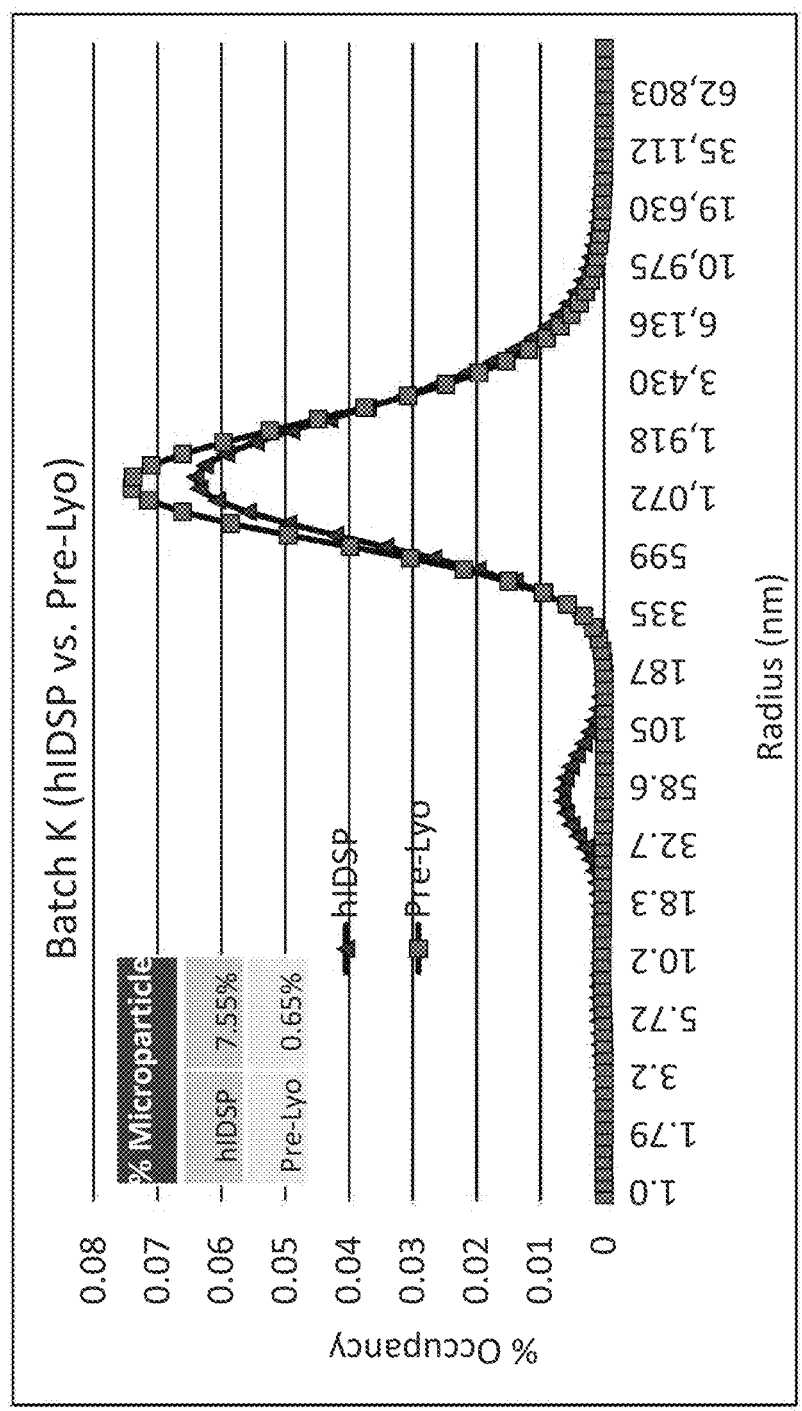
FIG. 53B is a plot of the percent occupancy of particles of different radii in human in-date stored platelets (Batch K) and platelet derivatives (pre-lyophilization) derived therefrom as determined by DLS.
Figure 53C:
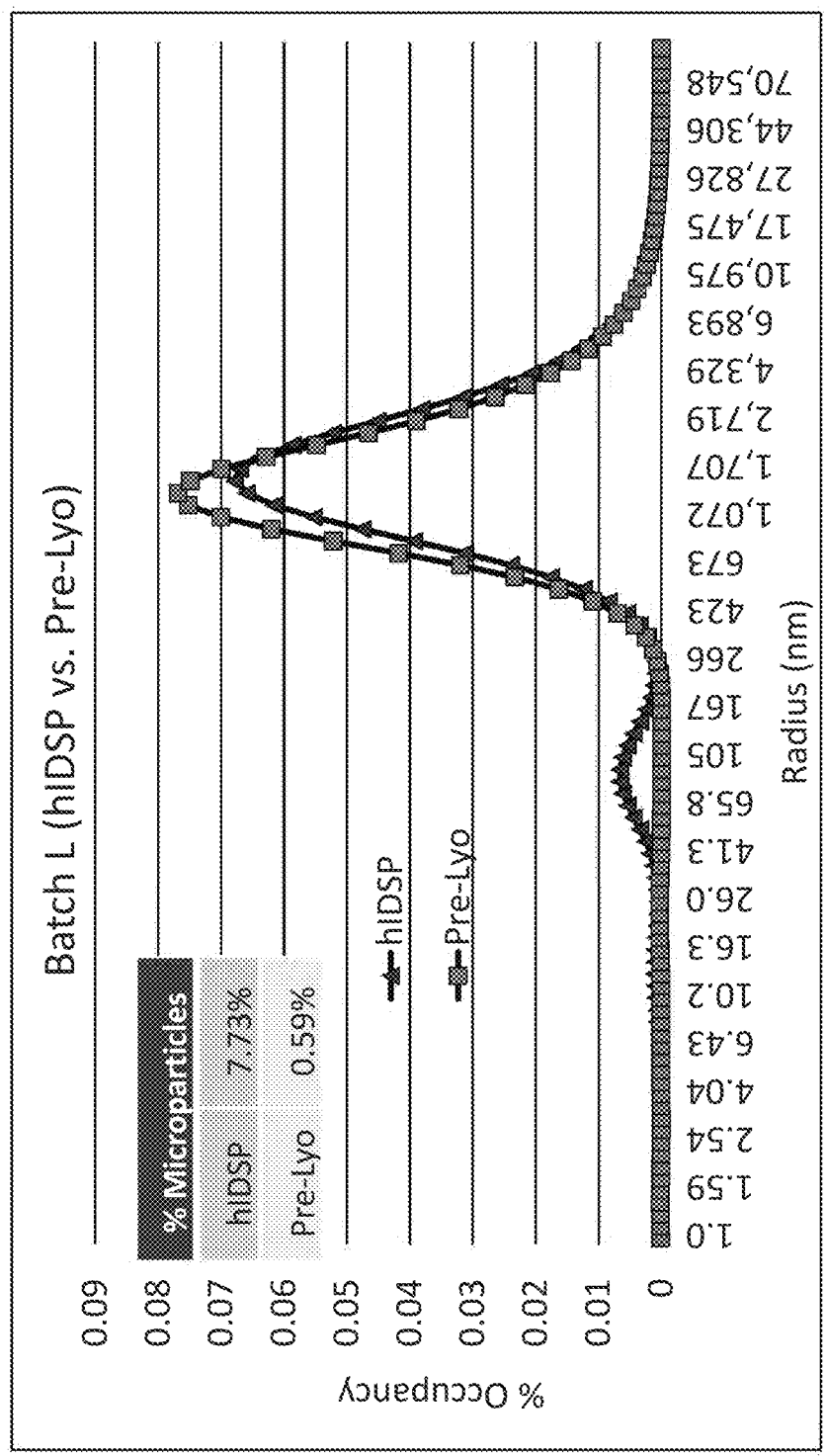
FIG. 53C is a plot of the percent occupancy of particles of different radii in human in-date stored platelets (Batch L) and platelet derivatives (pre-lyophilization) derived therefrom as determined by DLS.

The microparticle content of human in-date stored platelets (hIDSP) compared to FDPDs prepared according to Example 15 (but not lyophilized) were compared using dynamic light scattering. The results are shown in FIGS. 53A-C and Table 15. FIGS. 53A-C are histograms that are normalized to a relative intensity so that the sum of the intensity of each data point equals 1.0. For example, if a particular data point has a y-axis value of 0.1 then it can be typically interpreted that the data point makes up 10% of the scattering intensity of the sample.

A pool of the apheresis units used to manufacture a batch of FDPDs was made for analysis. This sample type is denoted as "hIDSP." A 1 mL aliquot of this hIDSP (human In-Date Stored Platelets) pool was taken for dynamic light scattering (DLS; Thrombolux—Light Integra) analysis. A sample from this aliquot was then drawn into a capillary and inserted into the DLS instrument. The capillary sat in the instrument for 1 minute to allow the temperature and movement to equilibrate. The internal temperature of the machine is 37° C. After 1 minute of equilibration, the viscosity setting for the sample was chosen. The DLS instrument has a built-in viscosity setting for samples that are in plasma, such as apheresis units. This viscosity setting was used for hIDSP samples. The viscosity of this setting is 1.060 cP (centipoise). After the plasma viscosity setting was selected, the sample was analyzed. From the same hIDSP aliquot, a $2^{nd}$ and $3^{rd}$ sample were drawn into a capillary and analyzed with this hIDSP protocol, for triplicate analysis. Microparticle percentage was then determined from the data. "Pre-Lyo" samples are an in-process sample from the FDPDs manufacturing process. This sample type is the material taken right before lyophilization. A viscosity measurement of the sample was taken in order to analysis these samples with DLS. The viscometer (Rheosense µVISC) has a built-in oven that is used to bring the sample to the temperature of the DLS instrument (37° C.). Prior to viscosity analysis of the sample the oven must be heated to 37° C. To determine the viscosity of the pre-lyo sample a 400-350 µL sample was drawn into a syringe and inserted into the viscometer. After inserting the sample into the viscometer, the instrument temperature needs to reach 37° C. again. After the oven reaches 37° C. the sample was analyzed with all settings on AUTO except for "Measurement Volume" which was set to 400 µL. This viscosity was used for the DLS measurement of the same sample. A 1 mL aliquot of this pre-lyo sample was taken for dynamic light scattering (DLS; Thrombolux—LightIntegra) analysis. A sample from this aliquot was then drawn into a capillary and inserted into the DLS instrument.

The capillary sat in the instrument for 1 minute to allow the temperature and movement to equilibrate. The internal temperature of the machine is 37° C. After 1 minute of equilibration, the previously measured viscosity was put into the viscosity setting of the DLS instrument. After the viscosity was entered, the sample was analyzed. From the same pre-lyo aliquot, a $2^{nd}$ and $3^{rd}$ sample were drawn into a capillary and analyzed with this Pre-Lyo Protocol, for triplicate analysis. Microparticle percentage was then determined from the data.

FDPDs were rehydrated according to standard protocol and diluted 1:5 in a mixture of SeraSub (CST Technologies, Inc.) and ACD. The SeraSub/ACD diluent consists of a 1:9 dilution of ACD in SeraSub. 1 mL of the 1:5 dilution of FDPDs was prepared for analysis by DLS. A sample of the FDPDs dilution was drawn into the capillary and inserted into the DLS instrument. The capillary sat in the instrument for 1 minute to allow the temperature and movement to equilibrate. The internal temperature of the machine is 37° C. After 1 minute of equilibration, the viscosity setting for the sample was chosen. The viscosity used for the sample was 1,2000P. After the viscosity was entered, the sample was analyzed. A $2^{nd}$, $3^{rd}$ and $4^{th}$ sample were drawn into a capillary and analyzed with this FDPDs protocol, for quadruplicate analysis. Microparticle percentage was then determined from the data (and platelet radius where applicable).

TABLE 15

| Batch Number | hIDSP % MP | Pre-Lyo % MP |
|---|---|---|
| Batch J | 9.47% | 0.49% |
| Batch K | 7.55% | 0.65% |
| Batch L | 7.73% | 0.59% |
| Average | 8.25% | 0.58% |

Figure 54A:
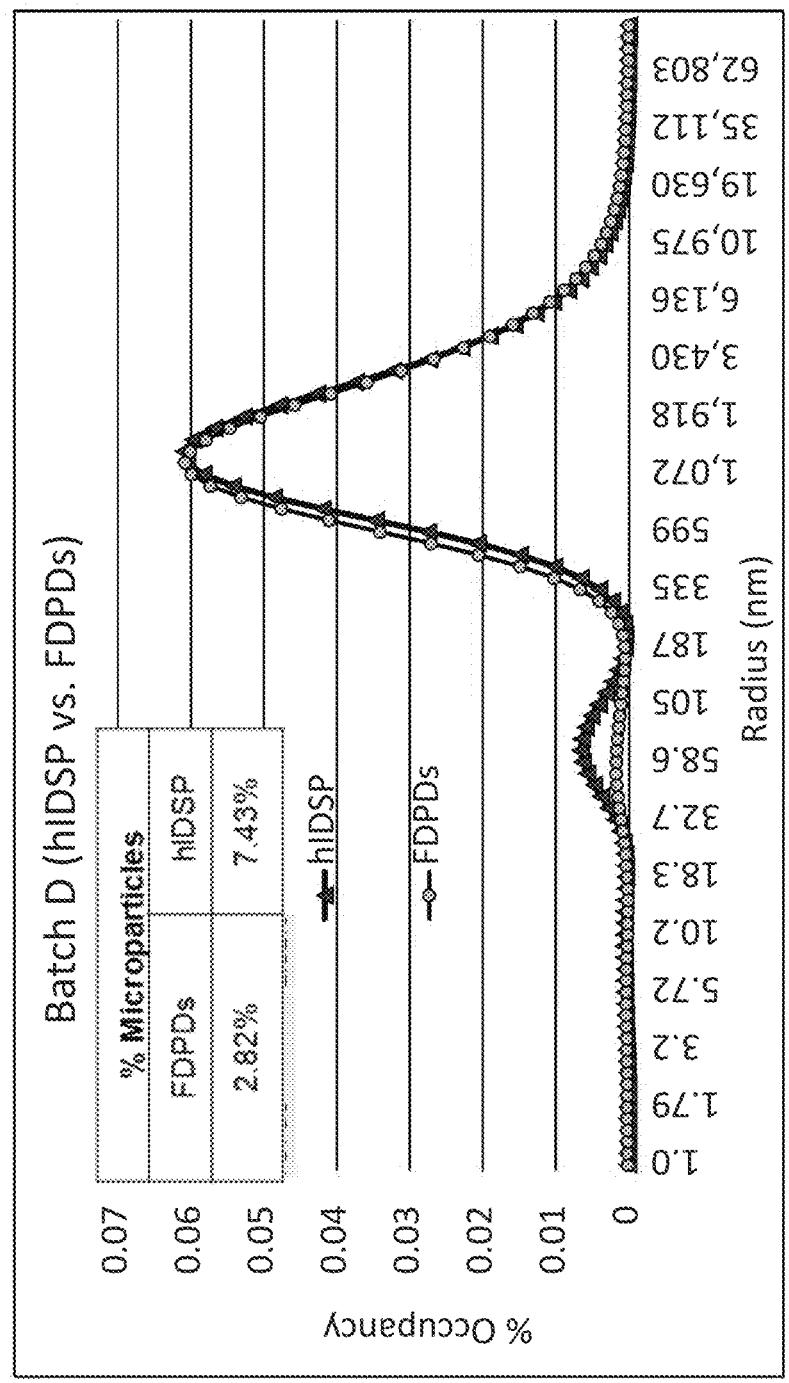
FIG. 54A is a plot of the percent occupancy of particles of different radii in human in-date stored platelets (Batch D) and platelet derivatives (pre-lyophilization) derived therefrom as determined by DLS.
Figure 54B:
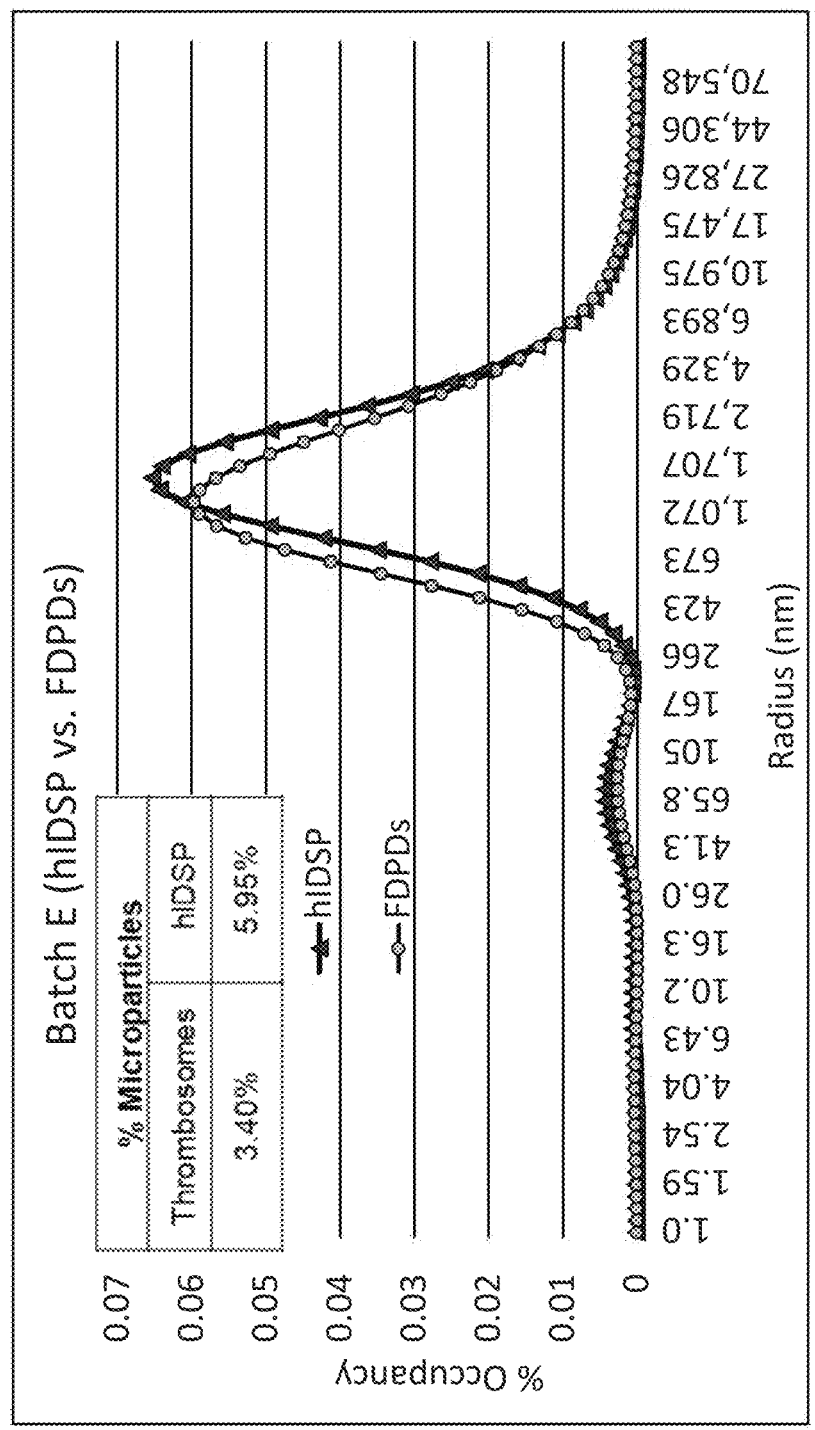
FIG. 54B is a plot of the percent occupancy of particles of different radii in human in-date stored platelets (Batch E) and platelet derivatives (pre-lyophilization) derived therefrom as determined by DLS.
Figure 54C:
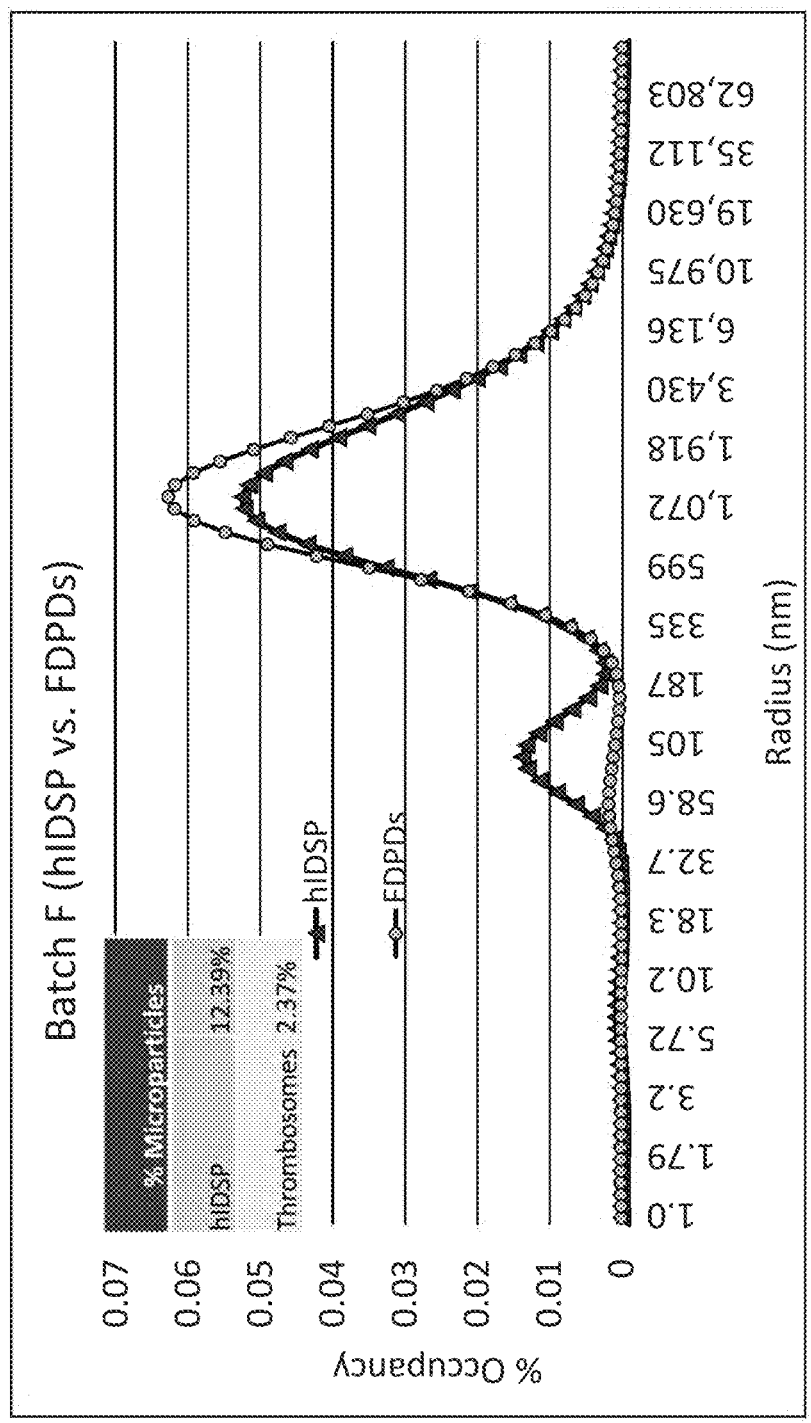
FIG. 54C is a plot of the percent occupancy of particles of different radii in human in-date stored platelets (Batch F) and platelet derivatives (pre-lyophilization) derived therefrom as determined by DLS.

In additional experiments, the microparticle content of human in-date stored platelets (hIDSP) compared to rehydrated FDPDs prepared according to Example 15 were compared using dynamic light scattering (DLS). The results are shown in FIGS. 54A-C and Table 16.

TABLE 16

| Batch Number | hIDSP % MP | FDPDs % MP |
|---|---|---|
| Batch D | 7.43% | 2.82% |
| Batch E | 5.95% | 3.40% |
| Batch F | 12.39% | 2.37% |
| Average | 8.59% | 2.86% |

Example 31. 9F9 and PAC-1 Binding

Aggregation of activated platelets is mediated by the formation of the GRIIb/IM complex, which can bind to fibrinogen (also called Factor 1) and form a clot. GRIIb/MI is a platelet fibrinogen receptor also known as CD41/CD61 complex. In this process, ADP promotes the active form of the GPIIb/IIIa complex. Antibody 9F9 binds to fibrinogen associated with the cell membrane. The presence of fibrinogen on the cell membrane is thus indicative of FDPDs capable of forming clots.

A vial of FDPDs prepared according to Example 15 was rehydrated using 10 mL of deionized water. An aliquot of FDPDs was diluted to a final concentration of $1\times10^5$ particles/μL using HMTA (HEPES Modified Tyrode's Albumin). Samples were prepared as shown in Table 17. Unstained samples were prepared by adding 10 μL of diluted FDPDs to 20 μL of HMTA. FITC isotype control samples were prepared by adding 10 μL of diluted FDPDs to 10 μL of the isotype control antibody (BD Biosciences Cat. No. 555748) and 10 μL of HMTA. Samples stained with 9F9 were prepared by adding 10 μL of diluted FDPDs to 10 μL of the 9F9 antibody (BD Biosciences Cat. No. 340507 and 10 μL of HMTA. Samples stained with PAC-1 were prepared by adding 10 μL of diluted FDPDs to 5 μL of the isotype control antibody and 15 μL of HMTA. All samples were prepared in duplicated using a total of $1\times10^6$ particles per reaction mixture. Samples were incubated at room temperature for 20 minutes away from open light. After incubation, all samples were diluted with 1 mL of HBS and analyzed using the ACEA NovoCyte flow cytometer. The fluorescent signal generated by PAC-1 was used to determine the expression or presence of activated GPIIb/IIIa receptors without bound fibrinogen. The fluorescent signal from 9F9 was used to determine binding of fibrinogen to the surface receptors on FDPDs.

HTMA (HEPES modified Tyrode's albumin).

| Component | Concentration (mM, except where otherwise indicated) |
|---|---|
| HEPES | 9.5 |
| NaCl | 145.0 |
| KCl | 4.8 |
| NaHCO$_3$ | 12.0 |
| Dextrose | 5.0 |
| Bovine Serum Albumin | 0.35% w/v |

TABLE 17

| | Unstained | FITC Iso | 9F9 | PAC-1 |
|---|---|---|---|---|
| Cells (uL) | 10 | 10 | 10 | 10 |
| HMTA (uL) | 20 | 10 | 10 | 15 |
| Antibody (uL) | 0 | 10 | 10 | 5 |

Figure 55:
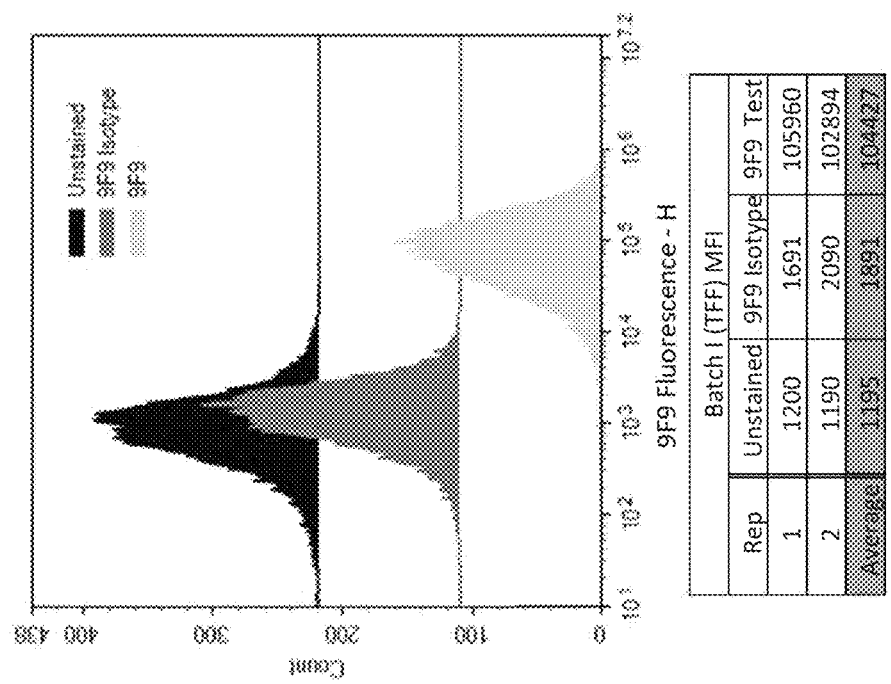
FIG. 55 shows an exemplary histogram comparison of low-plasma FDPDs unstained (black) or stained with an isotype control antibody (dark gray) or a FITC-labeled 9F9 antibody (light gray), and a table showing the mean fluorescence intensity for two replicates.
Figure 56:
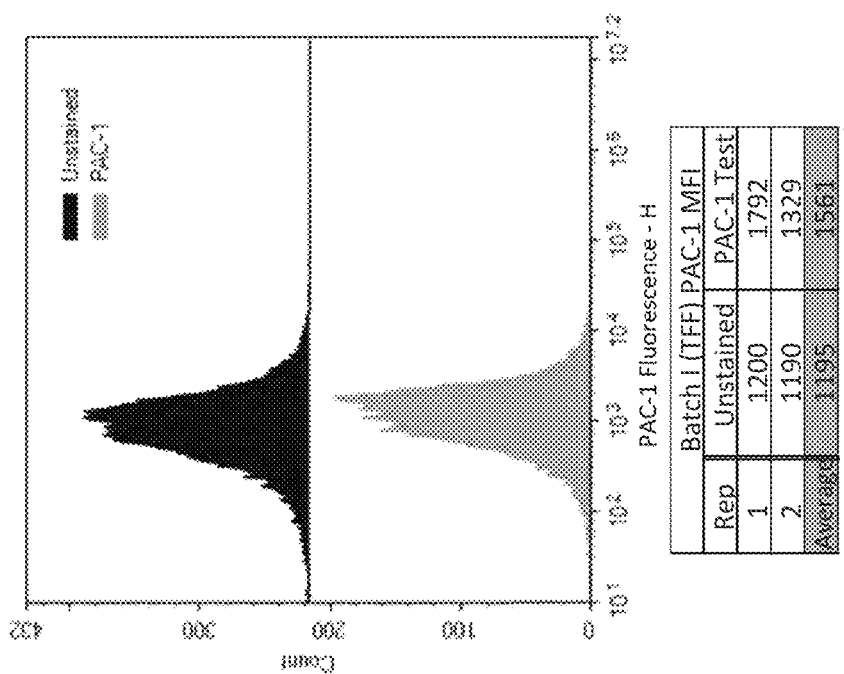
FIG. 56 shows an exemplary histogram comparison of low-plasma FDPDs unstained (black) or stained with an anti-PAC-1 antibody (light gray), and a table showing the mean fluorescence intensity for two replicates.

The samples were assayed by flow cytometry, and it was demonstrated that there is surface-bound fibrinogen post rehydration (FIG. 55), while the anti-PAC-1 antibody shows no significant binding (FIG. 56). This is further evidence that the FDPDs prepared by TFF include fibrinogen bound to the active form of GPIIb/GPIIIa, as PAC-1 binds to the same complex.

Example 32. Pathogen Reduction

The reduction of pathogens is generally desirable in blood products. One method of pathogen reduction involves the use of a photosensitive nucleic acid-intercalating compound to alter the nucleic acids of pathogens upon illumination with an appropriate wavelength.

Figure 57A:
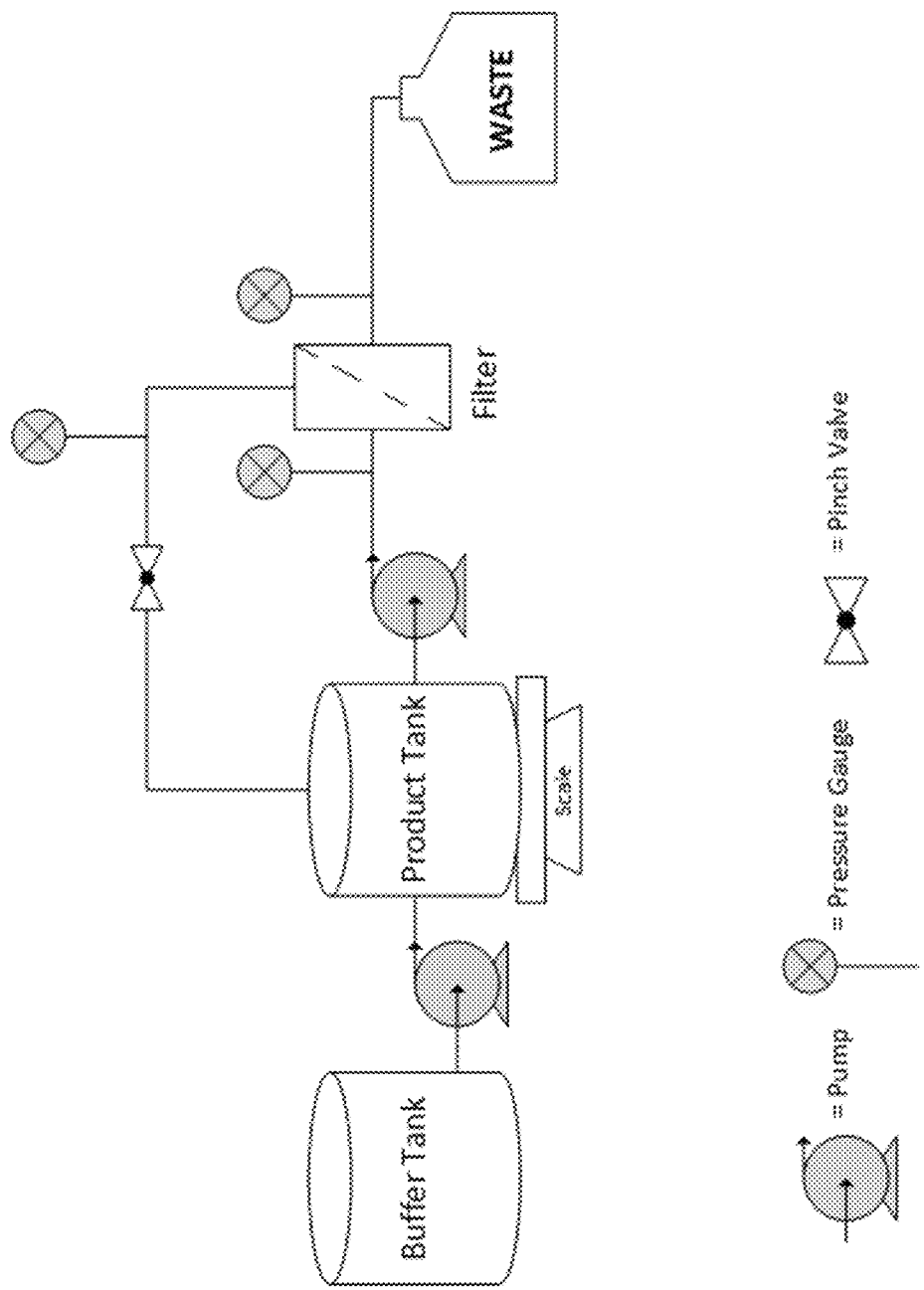
FIG. 57A shows an exemplary schematic of a pathogen reduction system.
Figure 57B:
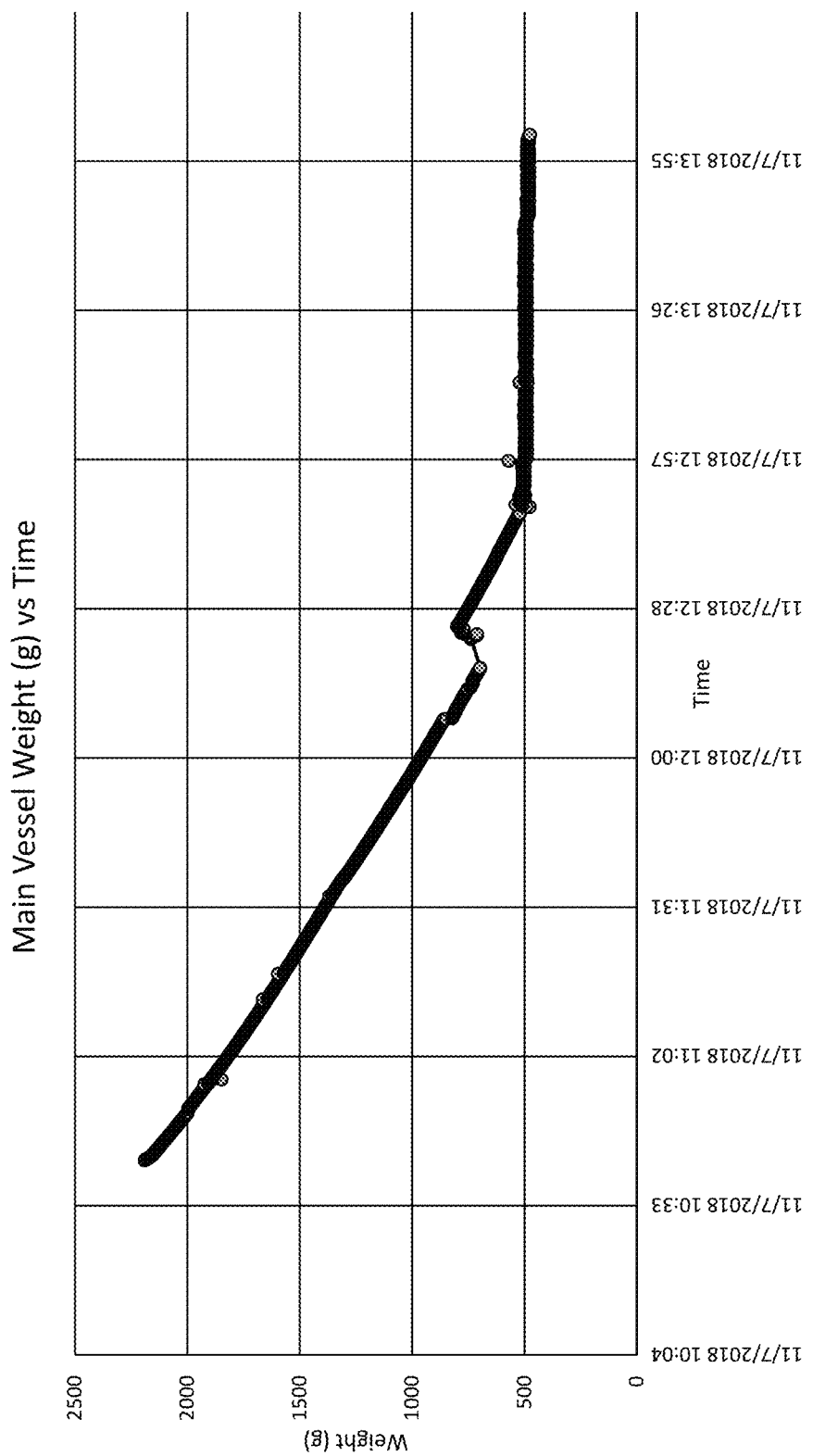
FIG. 57B shows a plot of the weight of a reaction vessel over time.
Figure 57C:
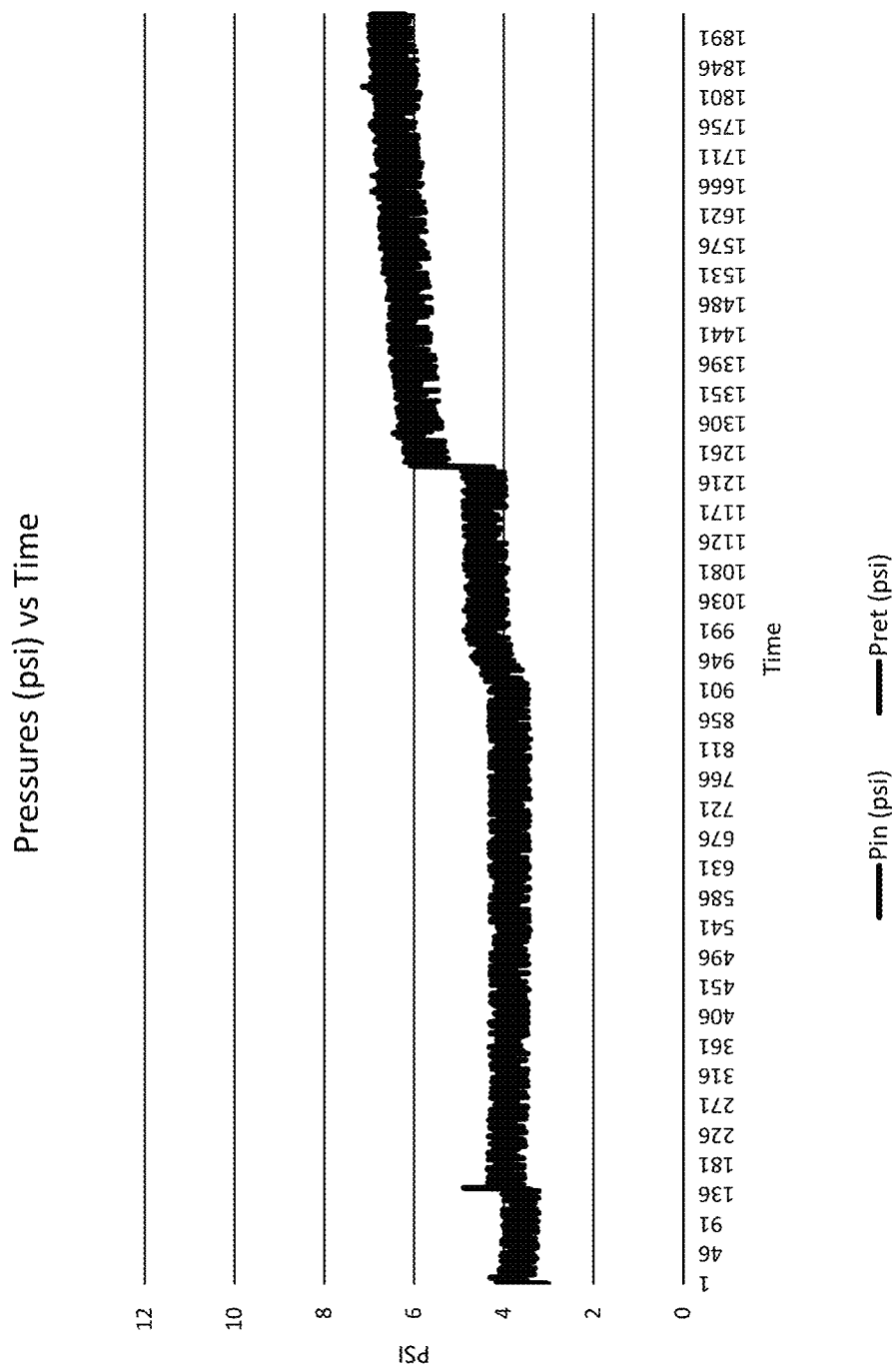
FIG. 57C shows a plot of pressure in a reaction vessel over time.

The INTERCEPT® system (made by Cerus) uses amotosalen, a nucleic acid intercalating compound that forms cross-links in nucleic acid upon illumination with UVA. Exemplary parameters for use of this system are shown in Table 18, and a schematic of the system is shown in FIG. 57A, while exemplary process data are shown in FIGS. 57B-C for 2.6 L of processed material in 198 minutes (approx. 14/min average).

DLS was performed as described in Example 30.

TABLE 18

| Process Parameter | Specification |
|---|---|
| Feed Pump | 600 ml/min (3/8" Tube) |
| Retentate Pressure | Target = 4 to 6 PSI Criteria = 2 to 8 PSI |
| Buffer Pump | 100 ml/min (noncritical) |
| DiaVolumes | X2 DVs |
| Concentration Factor | ~4 (from initial dilution) |

Exemplary comparative data of pH and metabolites of thrombosomes prepared as in Example 15, with or without treatment with the INTERCEPT® system is shown in Table 19.

TABLE 19

| iSTAT CG4+ | Raw Material | | Initial Dilution | | End of Con | | End of DV (Pre-Lyo) | |
|---|---|---|---|---|---|---|---|---|
|  | Control | Treated | Control | Treated | Control | Treated | Control | Treated |
| pH | 7.2 | 7.2 | 7.3 | 7.1 | 7.3 | 7.3 | 7.3 | 7.2 |
| pCO2 (mmHg) | 32.9 | 25.7 | 16.5 | 29.1 | 16.1 | 14.4 | 11.3 | 12.4 |
| pO2 (mmHg) | 67 | 149 | 167 | 150 | 142 | 155 | 145 | 153 |
| HCO3 (mmol/L) | 12.7 | 10.2 | 8.5 | 8.1 | 7.8 | 6.7 | 5.8 | 5.1 |
| TCO2 (mmol/L) | 14 | 11 | 9 | 9 | 8 | 7 | 6 | 5 |
| sO2 (%) | 89 | 99 | 99 | 98 | 99 | 99 | 99 | 99 |
| Lac (mmol/L) | 6.56 | 6.75 | 3.26 | 3.33 | 2.80 | 2.50 | 0.91 | 1.19 |

Exemplary comparative data of functional characterization (AcT count and aggregation parameters) and cell-surface markers are shown in Tables 20 (hIDSPs), 21 (prior to lyophilization) and Table 22 (following lyophilization and rehydration in 10 ml, sterile water for injection to a concentration of approximately $1.8 \times 10^6/\mu L$ (individual sample counts are shown in Table 22).

TABLE 20

|  |  | Raw Material (hIDSP) | |
|---|---|---|---|
|  |  | Batch M "Control" | Batch N "Treated" |
| AcT Counts | AVG (×10^3) | 1212 | 1120 |
| Aggregation (%) or thrombin-induced trapping (%) | Collagen AVG (aggregation) | 22 | 21 |
|  | Plasma—A.Acid AVG (aggregation) | 75 | 84 |
|  | 250k Thrombin AVG (thrombin-induced trapping) | 97 | 97 |
|  | Buffer—A.Acid AVG (aggregation) | 94 | 92 |
| Flow (percent positivity) | CD41 | 93.5 | 97.6 |
|  | CD42 | 91.4 | 95.8 |
|  | Double Positive % | 92.0 | 95.6 |
|  | CD62 | 23.9 | 42.5 |
|  | Annexin V (AV5) | 3.8 | 8.4 |

TABLE 21

|  |  | Pre-Lyophilization | |
|---|---|---|---|
|  |  | Batch M "Control" | Batch N "Treated" |
| AcT Counts | AVG (×10^3) | 1787 | 2057 |
| Aggregation (%) or thrombin-induced trapping (%) | Collagen AVG (aggregation) | 81 | 82 |
|  | Plasma—A.Acid AVG (aggregation) | 93 | 84 |
|  | 250k Thrombin AVG (thrombin-induced trapping) | 97 | 90 |
|  | Buffer—A.Acid AVG (aggregation) | 89 | 95 |
| Flow (percent positivity) | CD41 | 98.4 | 97.0 |
|  | CD42 | 98.2 | 95.4 |
|  | Double Positive % | 97.5 | 94.3 |
|  | CD62 | 26.7 | 41.6 |
|  | AV5 | 10.6 | 13.7 |

TABLE 22

|  |  | Final Product QC | | |
|---|---|---|---|---|
|  |  | Batch M "Control" | | Batch N |
|  |  | V1 | V2 | V1 |
| ACT Counts thrombin-induced trapping (%) | AVG (×10^3) | 1765 | 1767 | 1720 |
|  | 375K Thrombin | 84 | 66 | 74 |
| Flow (percent positivity) | CD41 | 85.5 | 79.5 | 91.2 |
|  | CD42 | 85.1 | 79.2 | 90.6 |
|  | Double Positive % | 84.6 | 78.8 | 90.1 |

TABLE 22-continued

| | | Final Product QC | | |
| --- | --- | --- | --- | --- |
| | | Batch M "Control" | | Batch N |
| | | V1 | V2 | V1 |
| | CD62 | 87.0 | 93.2 | 87.1 |
| | AV5 | 95.4 | 95.0 | 92.6 |
| TGA | 4.8K TPH | 72.3 | 71.5 | 74.8 |
| | Residual Plasma % | 7.0% | | 8.4% |

Figure 58A:
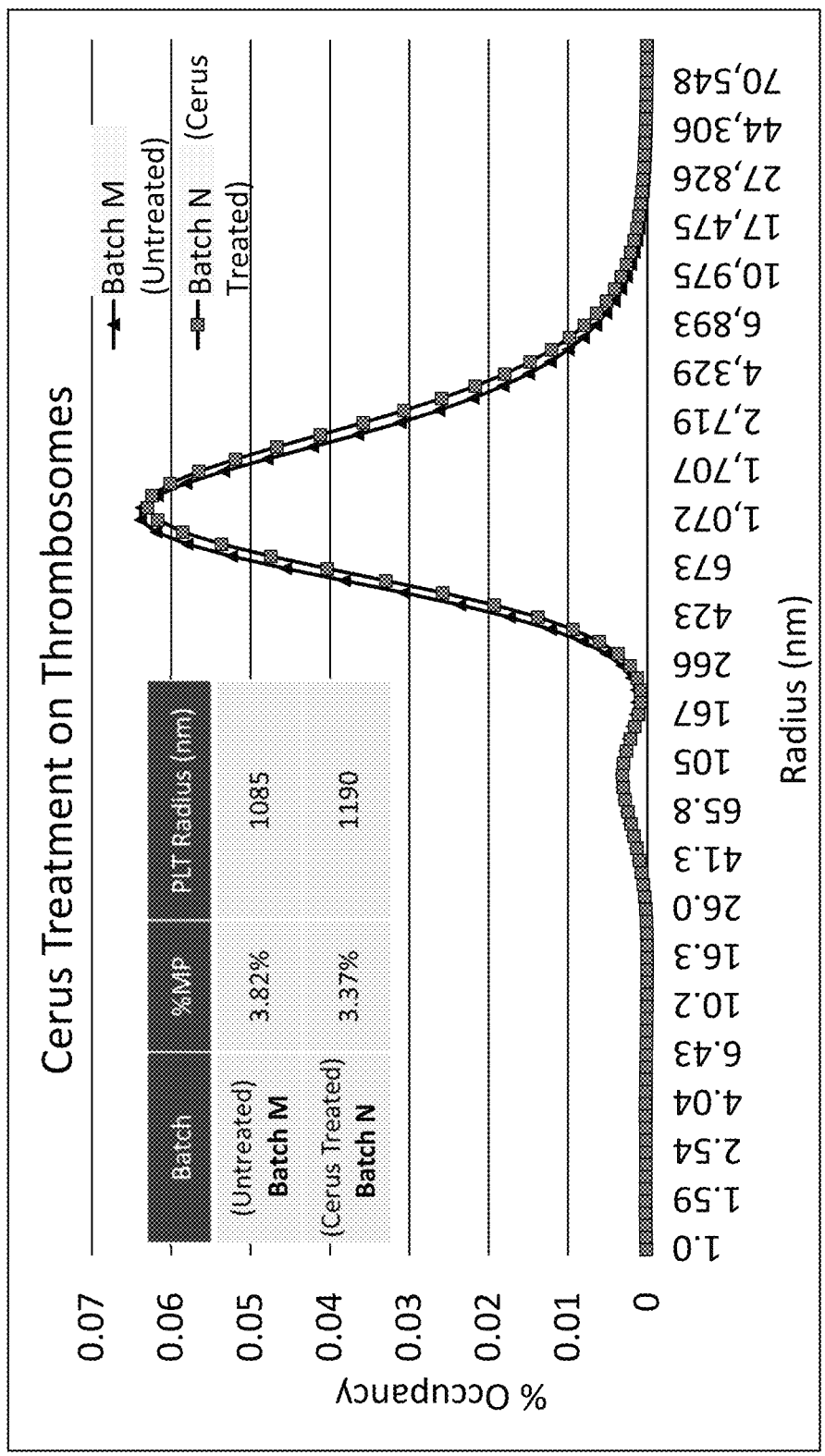
FIG. 58A shows a plot of the percent occupancy of particles of different radii in rehydrated thrombosomes that were (Batch N) or were not (Batch M) treated to remove pathogens, as determined by DLS.
Figure 58B:
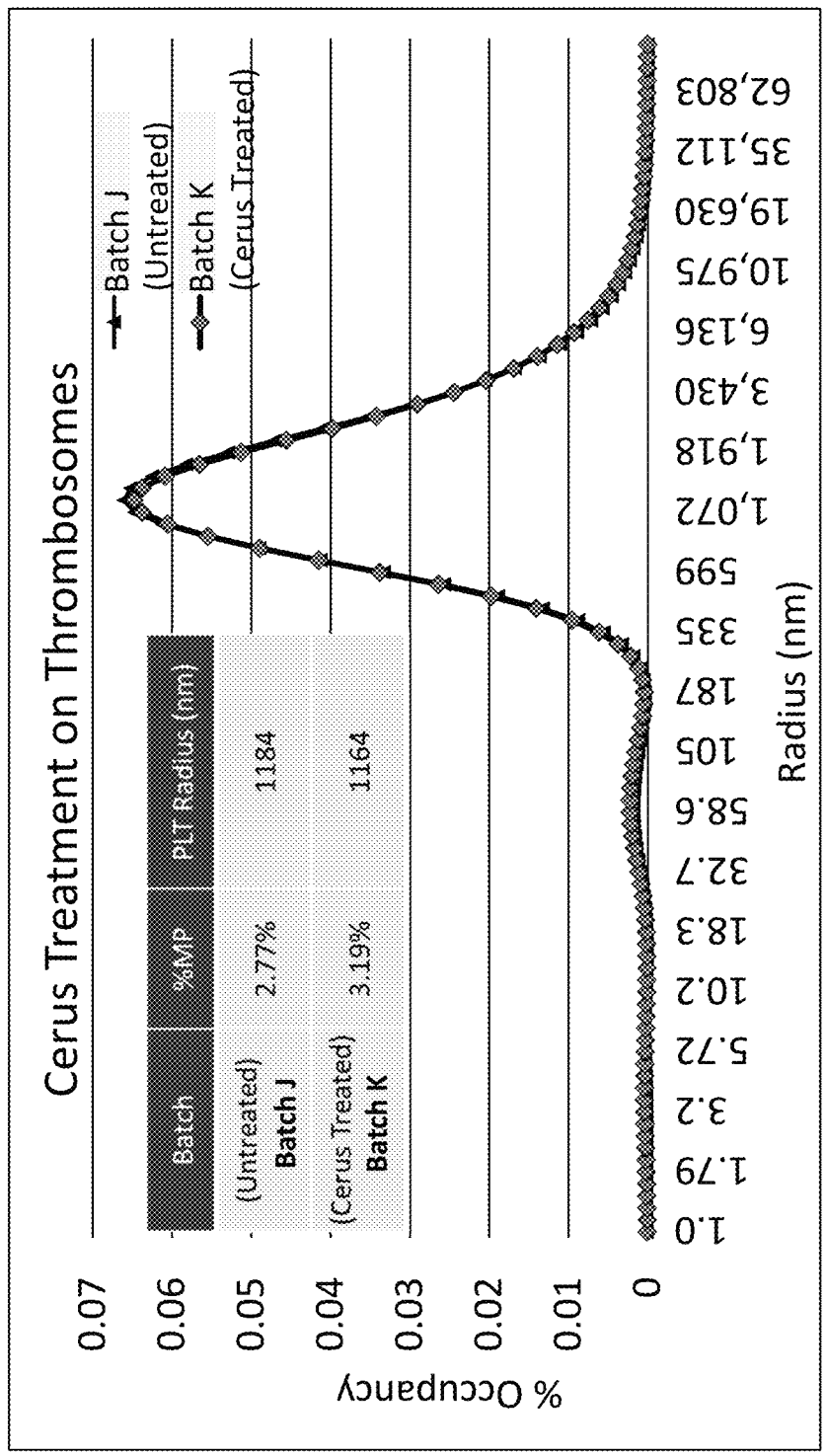
FIG. 58B shows a plot of the percent occupancy of particles of different radii in rehydrated thrombosomes that were (Batch K) or were not (Batch J) treated to remove pathogens, as determined by DLS.
Figure 59A:
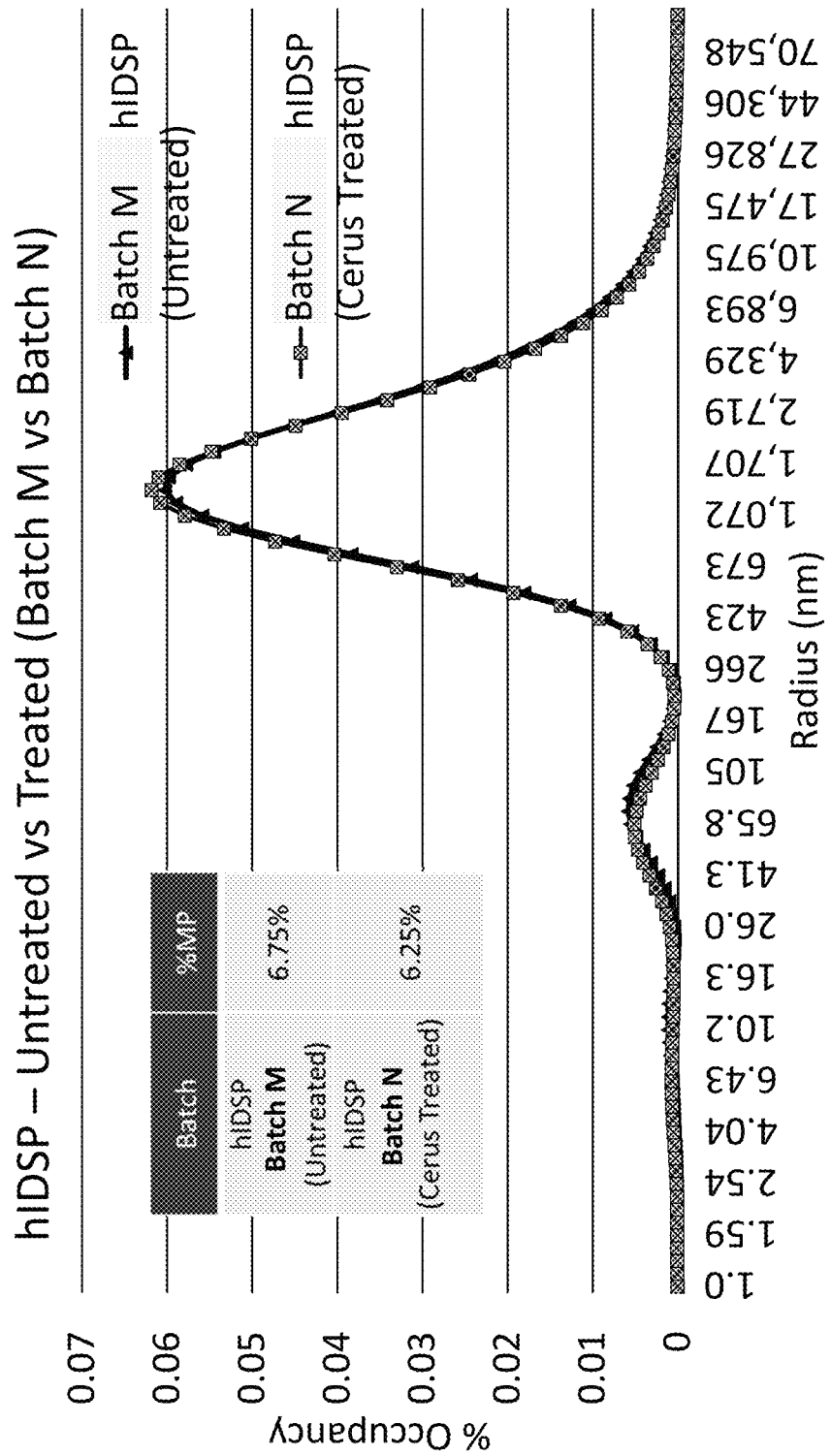
FIG. 59A shows a plot of the percent occupancy of particles of different radii in hIDSPs that were (Batch N) or were not (Batch M) treated to remove pathogens, as determined by DLS.
Figure 59B:
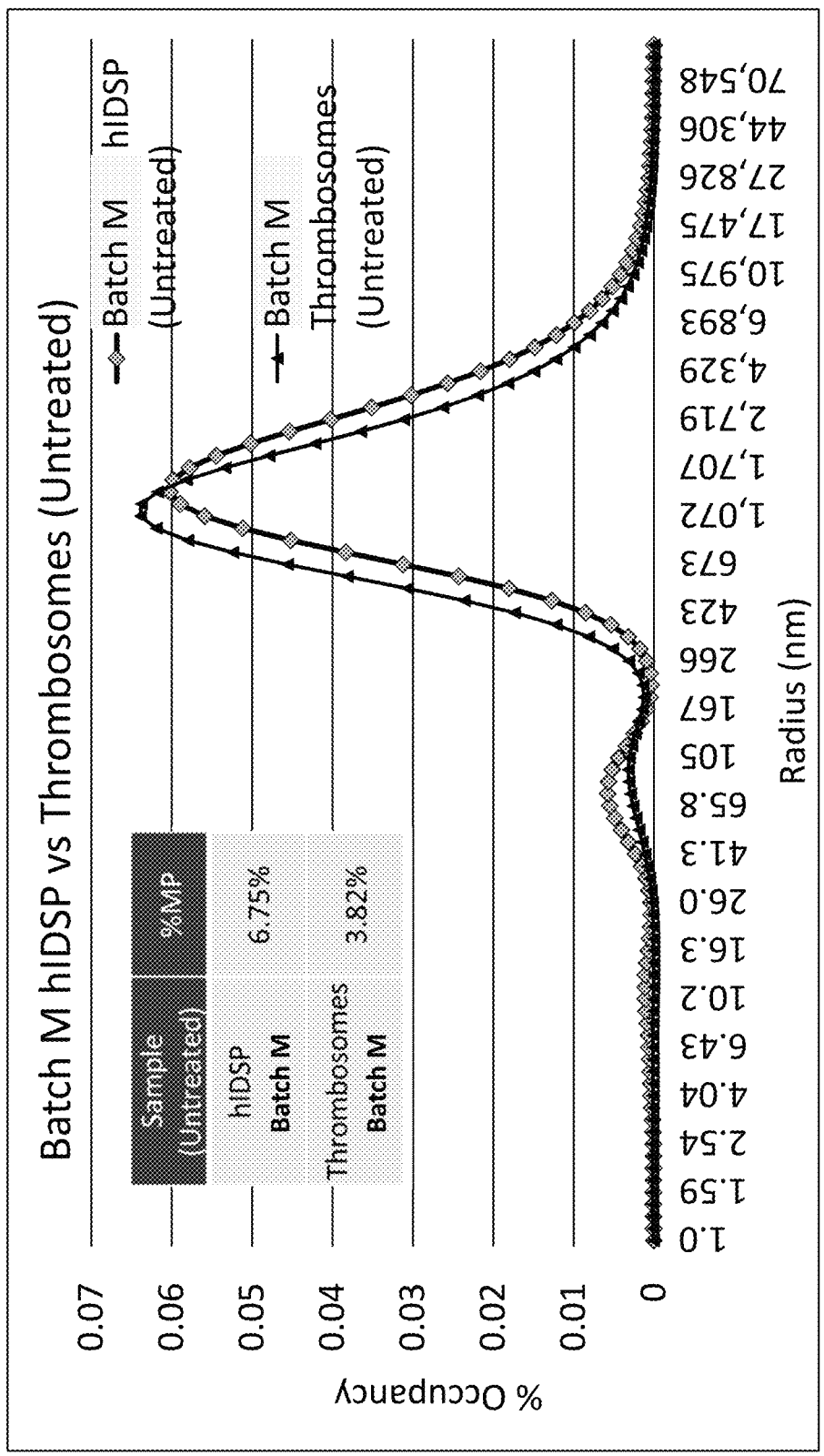
FIG. 59B shows a plot of the percent occupancy of particles of different radii in hIDSPs and thrombosomes derived therefrom (Batch M) that were not treated to remove pathogens, as determined by DLS.
Figure 59C:
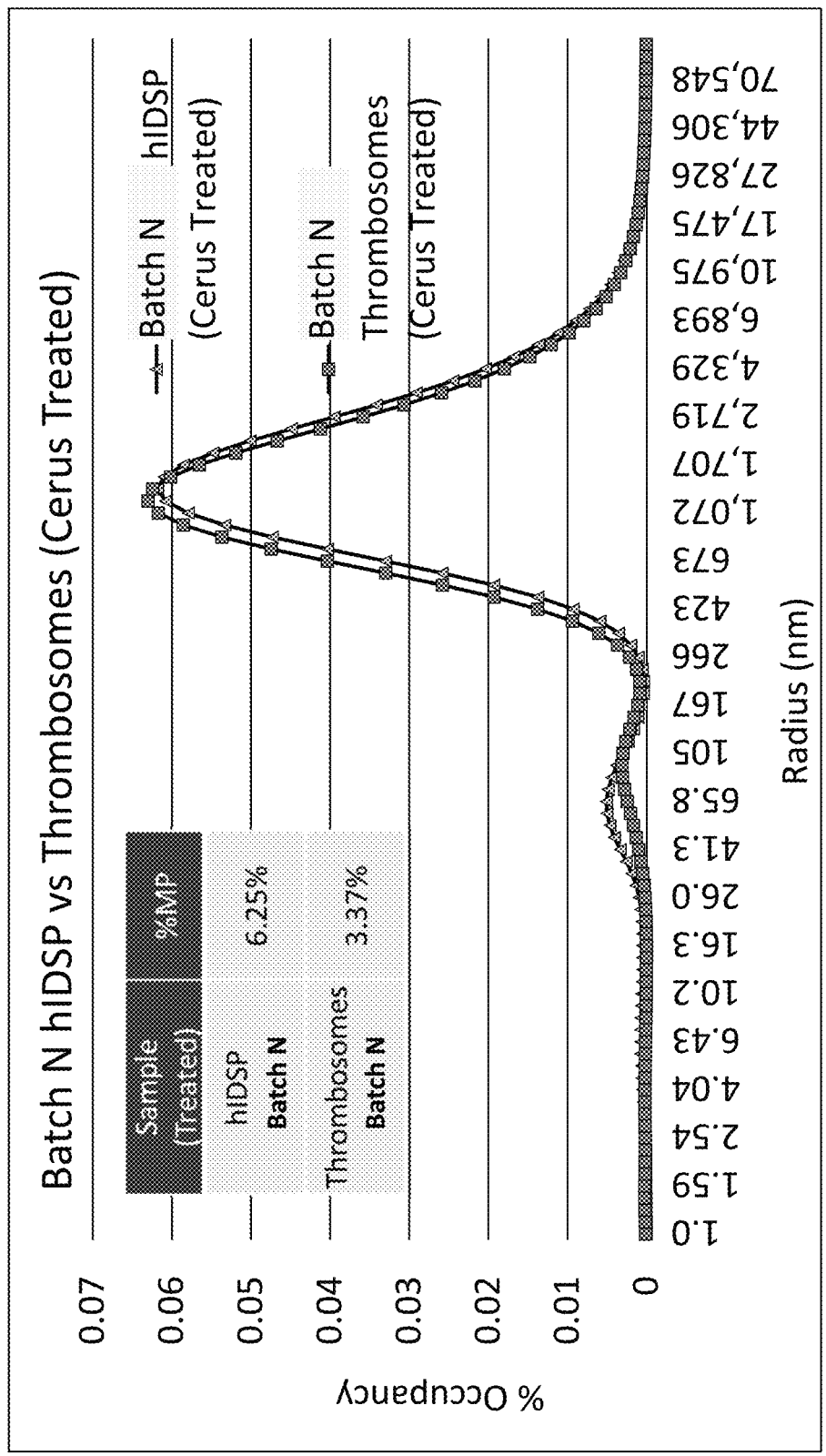
FIG. 59C shows a plot of the percent occupancy of particles of different radii in hIDSPs and thrombosomes derived therefrom (Batch N) that were treated to remove pathogens, as determined by DLS.
Figure 60A:
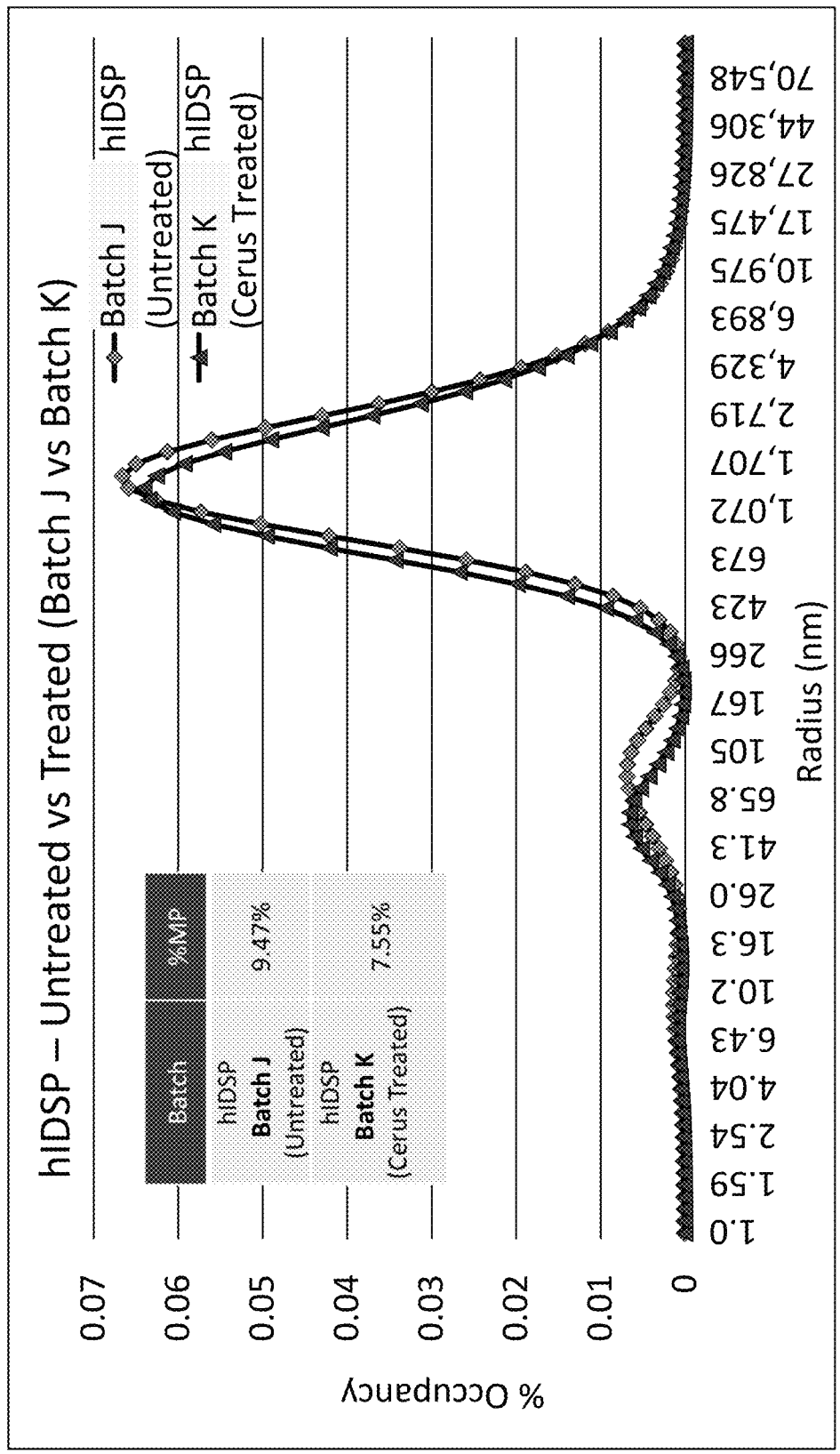
FIG. 60A shows a plot of the percent occupancy of particles of different radii in hIDSPs that were (Batch K) or were not (Batch J) treated to remove pathogens, as determined by DLS.
Figure 60B:
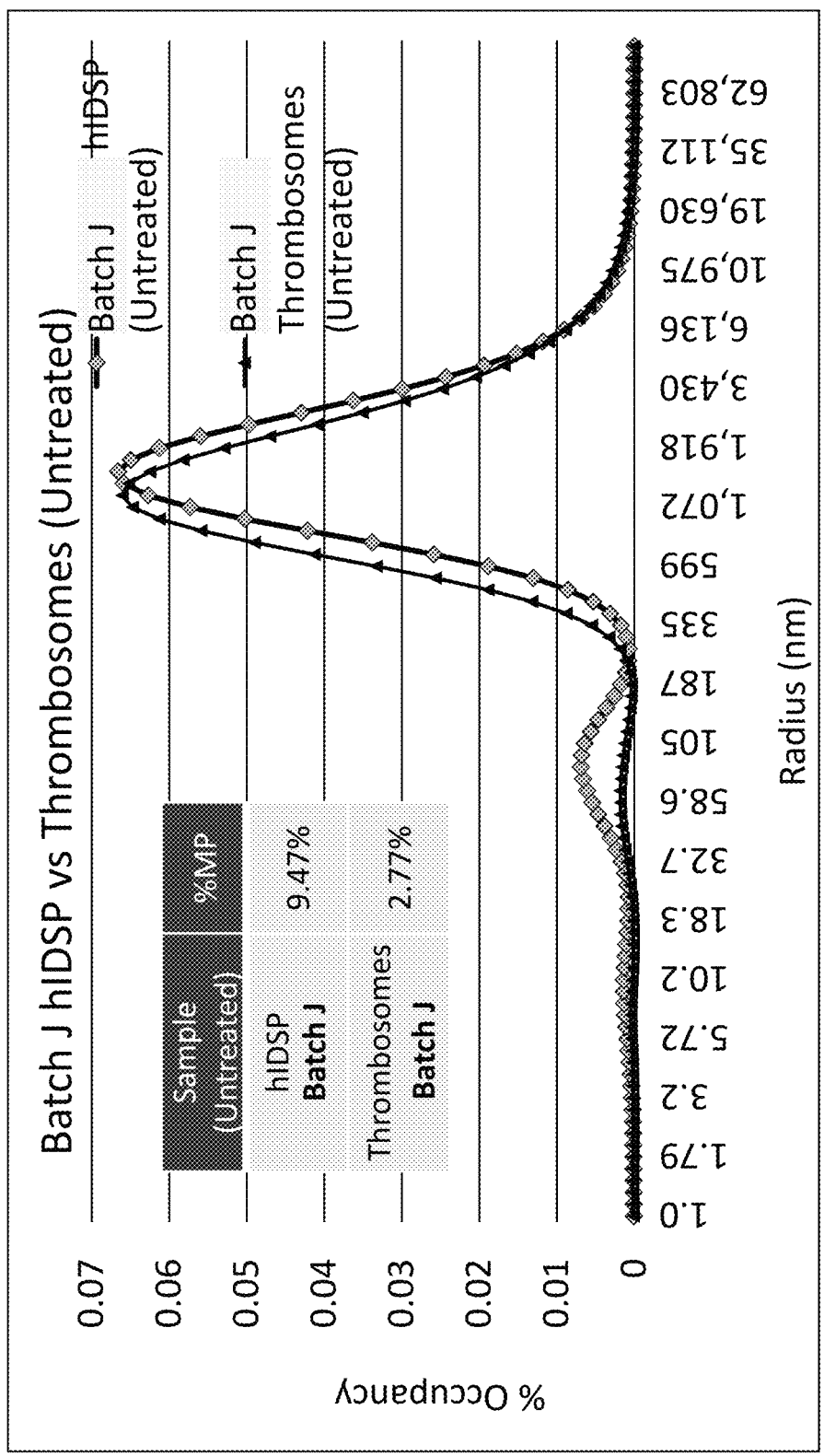
FIG. 60B shows a plot of the percent occupancy of particles of different radii in hIDSPs and thrombosomes derived therefrom (Batch J) that were not treated to remove pathogens, as determined by DLS.
Figure 60C:
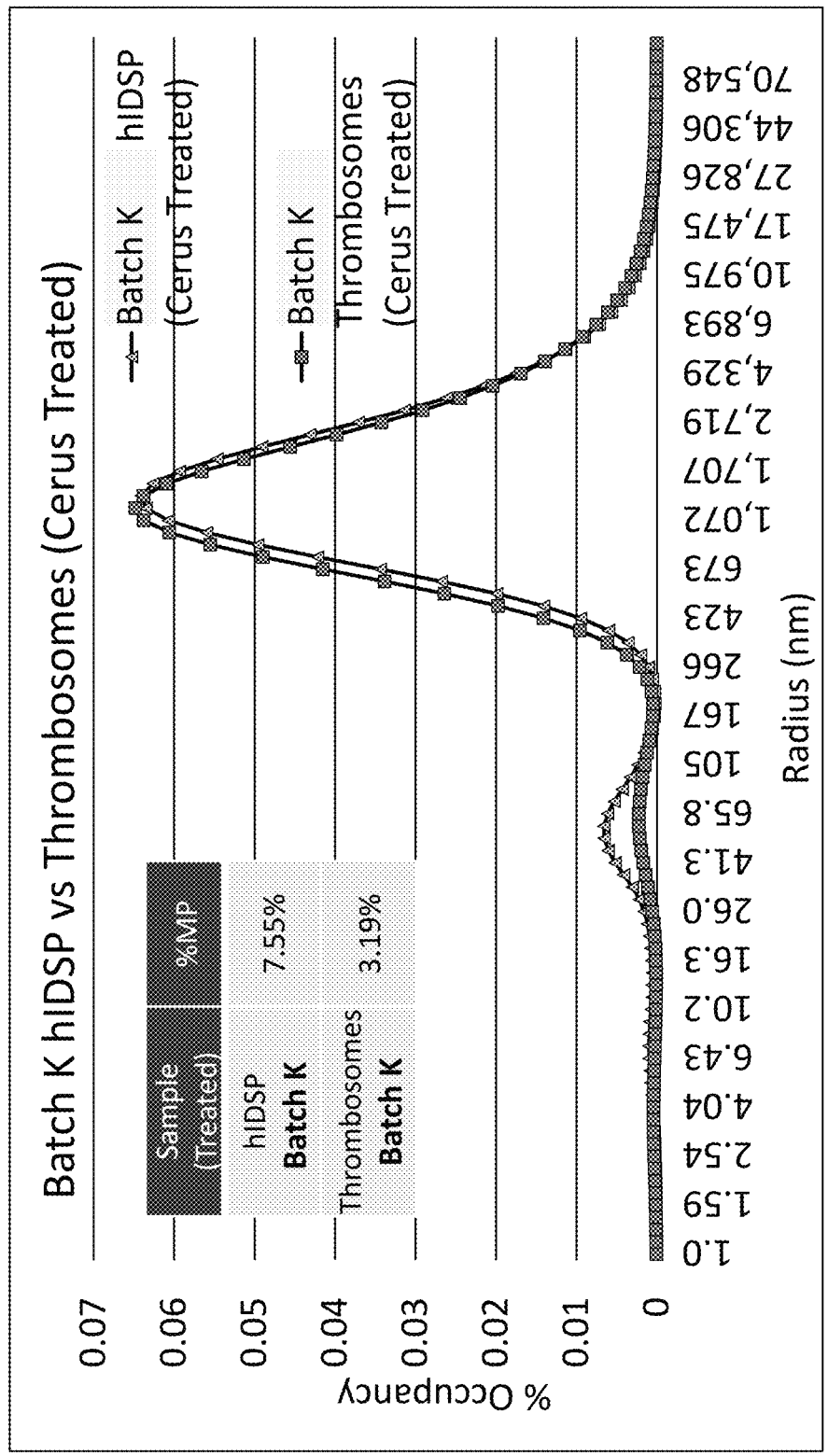
FIG. 60C shows a plot of the percent occupancy of particles of different radii in hIDSPs and thrombosomes derived therefrom (Batch K) that were treated to remove pathogens, as determined by DLS.

The microparticle content at various stages of the preparation of thrombosomes was also determined as described in Example 30. FIGS. 58A-B show the similarity of rehydrated thrombosomes prepared with and without pathogen reduction treatment. A summary of these data is shown in Table 23. FIG. 59A shows the microparticle content of hiDSPs with or without pathogen reduction treatment. FIGS. 59B-C compare the microparticle content of the hiDSPs shown in FIG. 59A and rehydrated thrombosomes prepared therefrom. A summary of these data is shown in Table 24. FIG. 60A shows the microparticle content of hiDSPs with or without pathogen reduction treatment. FIGS. 60B-C compare the microparticle content of the hiDSPs shown in FIG. 60A and rehydrated thrombosomes prepared therefrom. A summary of these data is shown in Table 25.

TABLE 23

| Batch | % MP | Particle Radius (nm) |
| --- | --- | --- |
| (Untreated) Batch M | 3.82% | 1085 |
| (Cerus Treated) Batch N | 3.37% | 1190 |
| (Untreated) Batch J | 2.77% | 1184 |
| (Cerus Treated) Batch K | 3.19% | 1164 |

TABLE 24

| Batch | % MP |
| --- | --- |
| hIDSP Batch M (Untreated) | 6.75% |
| Thrombosomes Batch M (Untreated) | 3.82% |
| hIDSP Batch N (Treated) | 6.25% |
| Thrombosomes Batch N (Treated) | 3.37% |

TABLE 25

| Batch | % MP |
| --- | --- |
| hIDSP Batch J (Untreated) | 9.47% |
| Thrombosomes Batch J (Untreated) | 2.77% |
| hIDSP Batch K (Treated) | 7.55% |
| Thrombosomes Batch K (Treated) | 3.19% |

Example 33. T-TAS® Thrombosome Data

In the Total Thrombus-formation Analysis System (T-TAS®, FUJIMORI KOGYO CO., LTD), the sample is forced through collagen-coated microchannels using mineral oil. Changes in pressure are used to assess thrombus formation. The Occlusion Start Time is time it takes to reach Δ10 kPa, and the Occlusion Time=time it takes to each Δ80 kPa using an AR chip (Zacros Item No, TC0101).

According to FUJIMORI KOGYO CO., LTD, an AR chip can be used for analyzing the formation of a mixed white thrombus consisting chiefly of fibrin and activated platelets. It has a flow path (300 μm wide by 50 μm high) coated with collagen and tissue factors and can be used to analyze the clotting function and platelet function. In comparison, a PL chip can be used for analyzing the formation of a platelet thrombus consisting chiefly of activated platelets. A PL chip has a flow path coated with collagen only and can be used to analyze the platelet function.

T-TAS® reagents (CaCTI, AR Chip) were warmed to 37° C. and thrombosomes were rehydrated according to standard protocol. An aliquot of the rehydrated thrombosomes was washed by centrifugation at 3900 g×10 minutes and resuspended to approximately 300,000 cells/μL in sodium citrate anticoagulated platelet-poor plasma (PPP). CaCTI (20 μL) was mixed with thrombosomes in PPP (480 μL) and run through the T-TAS AR Chip under high shear. Pressure in the system was monitored over 30 minutes or until the maximum backpressure in the channel was achieved.

004 The T-TAS® instrument was prepared for use according to the manufacturer's instructions. AR Chips (Diapharma Cat. #TC0101) and AR Chip Calcium Corn Trypsin Inhibitor (CaCTI; Diapharma Cat. #TR0101) were warmed to room temperature. 300 μL of rehydrated thrombosomes were transferred to a 1.7 mL microcentrifuge tube and centrifuged at 3900 g×10 minutes to pellet. The thrombosomes pellet was resuspended in George King (GK) pooled normal human plasma or autologous plasma with or without autologous platelets to a concentration of approximately 100,000-450,000/uL, as determined by AcT counts (Beckman Coulter AcT Diff 2 Cell Counter). 20 μL of CaCTI with 480 μL of thrombosomes sample in GK plasma were mixed with gentle pipetting. The sample was loaded and run on the T-TAS® according to the manufacturer's instructions.

Table 26 shows T-TAS® results from citrated whole blood, platelet-reduced citrated whole blood supplemented with varying concentrations of thrombosomes as prepared in Example 15, and George King Platelet Poor Plasma (GK PPP) supplemented with varying concentrations of thrombosomes as prepared in Example 15 in experiments run according to the manufacturer's instructions using the AR chip and High Shear instrument settings.

TABLE 26

T-TAS AR Chip Results

| Sample Type | Actual Tsome Concentration (×10^3/μL) | Base Pressure (kPa) | Occlusion Start Time (hh:mm:ss) | Occlusion Time (hh:mm:ss) | Occlusion Speed (kPa/min) | Area Under Curve |
|---|---|---|---|---|---|---|
| Citrated Whole Blood | 0 | 3.2 | 0:11:19 | 0:14:03 | 25.6 | 1393.9 |
| Platelet Reduced Citrated Whole Blood | 0 | 3.3 | 0:12:41 | 0:16:57 | 16.4 | 1180.6 |
|  | 73 | 3.2 | 0:11:11 | 0:13:47 | 26.9 | 1380.9 |
|  | 173 | 3.4 | 0:09:37 | 0:13:22 | 18.7 | 1498.5 |
|  | 255 | 3.4 | 0:08:36 | 0:10:40 | 33.9 | 1653.1 |
| GK PPP | 0 | 2.7 | 0:25:34 | 0:00:00† | 0 | 138.8 |
|  | 45 | 2.8 | 0:27:22 | 0:28:48 | 48.8 | 190.6 |
|  | 193* | 2.9 | 0:12:41 | 0:00:00† | 0 | 775.3 |
|  | 384 | 2.8 | 0:10:54 | 0:12:20 | 48.8 | 1479.8 |

*Test peaked at ~75 kPa before rapidly dropping off. Possible erroneous result.
†Test timed out.

Figure 61A:
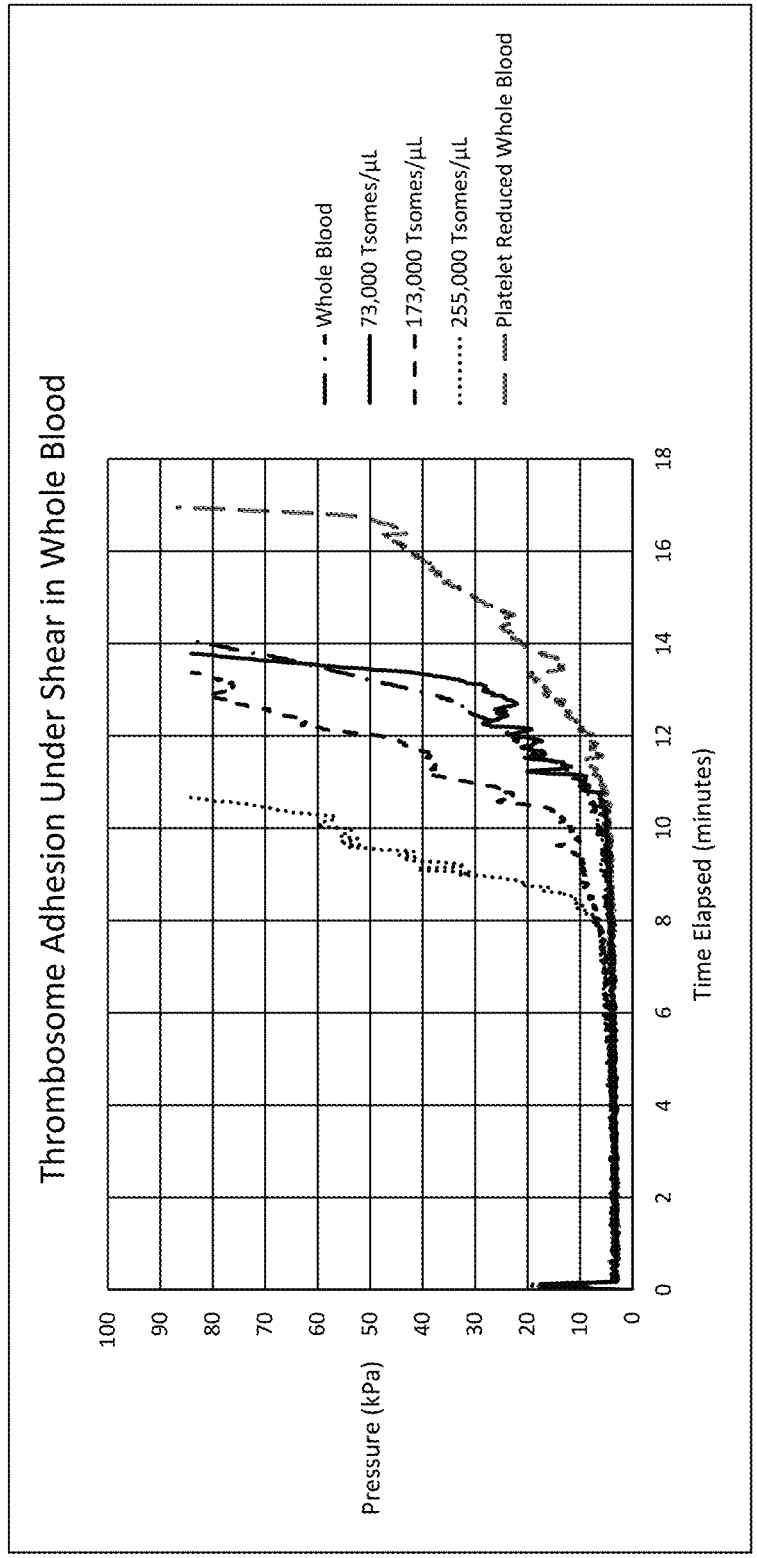
FIG. 61A shows a plot of thrombosome adhesion under shear in whole blood.
Figure 61B:
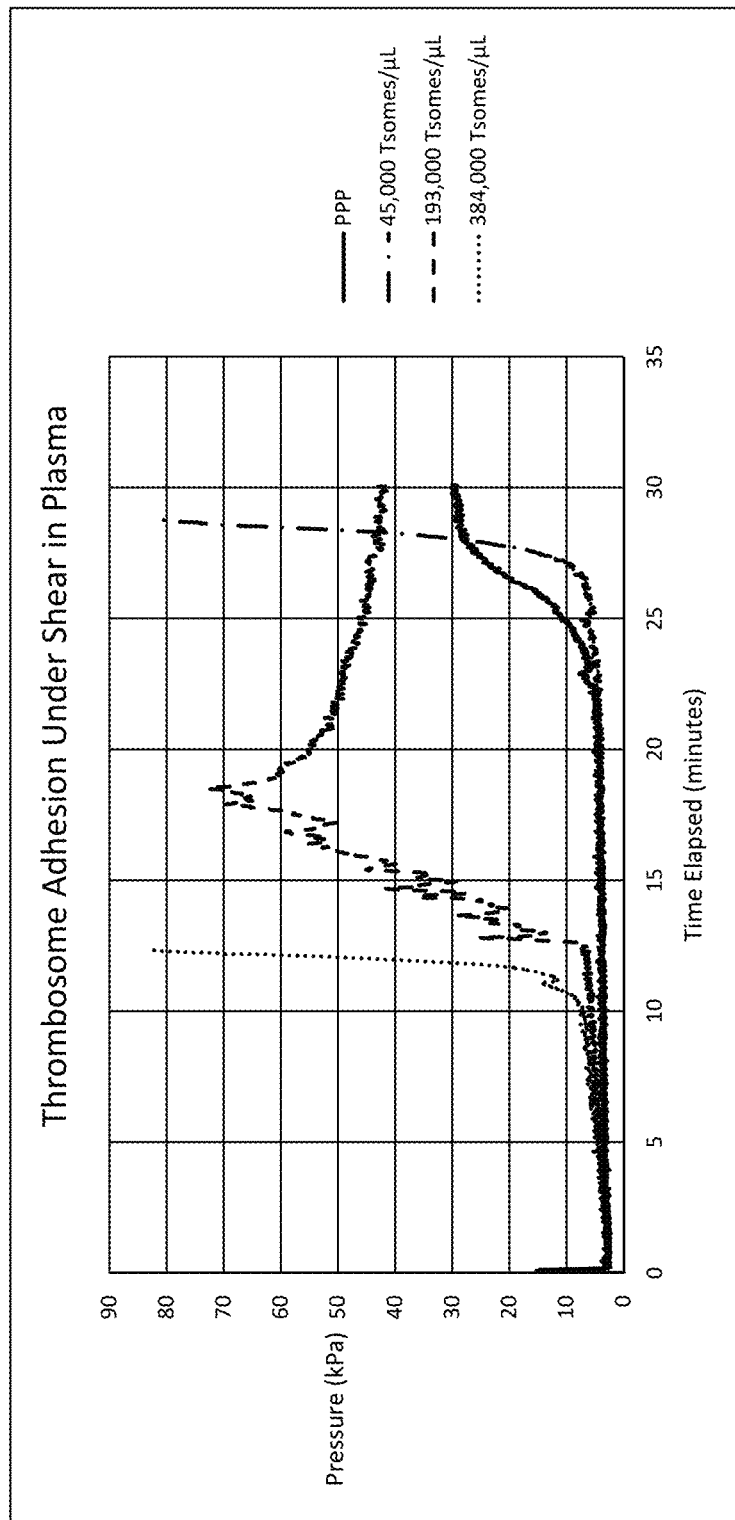
FIG. 61B shows a plot of thrombosome adhesion under shear in plasma.

Time-elapsed results are shown in FIGS. 61A-B. Increasing the concentration of thrombosomes in platelet-reduced whole blood promoted more robust thrombus formation as measured by shortened occlusion times (FIG. 61A). Increasing the concentration of thrombosomes in platelet poor plasma (PPP) promoted more robust thrombus formation as measured by shortened occlusion times (FIG. 61B).

Figure 61C:
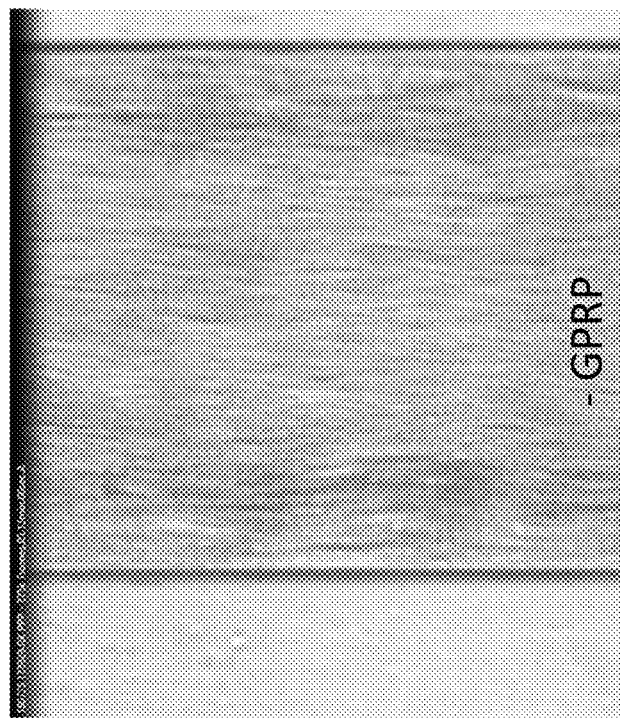
FIG. 61C shows formation of fibrin in a microcapillary channel in the absence of GPRP.
Figure 61D:
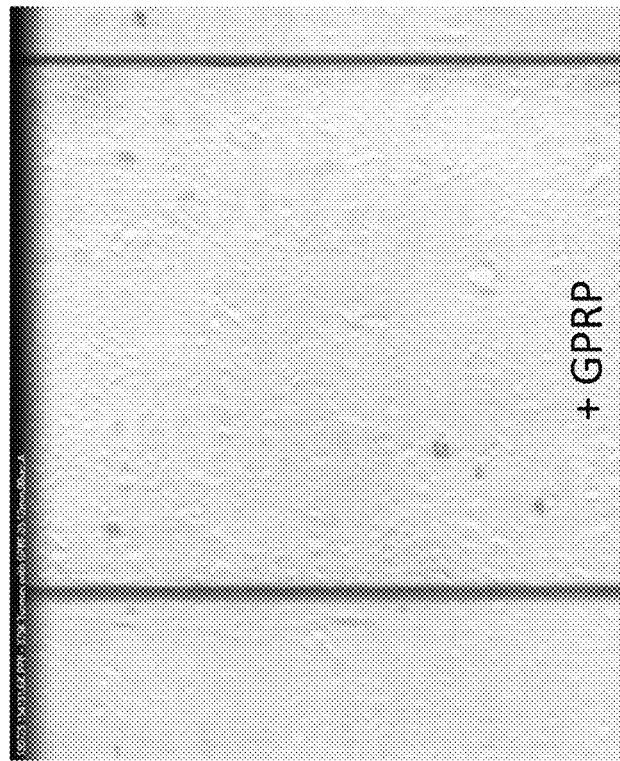
FIG. 61D shows a lack of formation of fibrin in a microcapillary channel in the presence of GPRP.
Figure 61E:
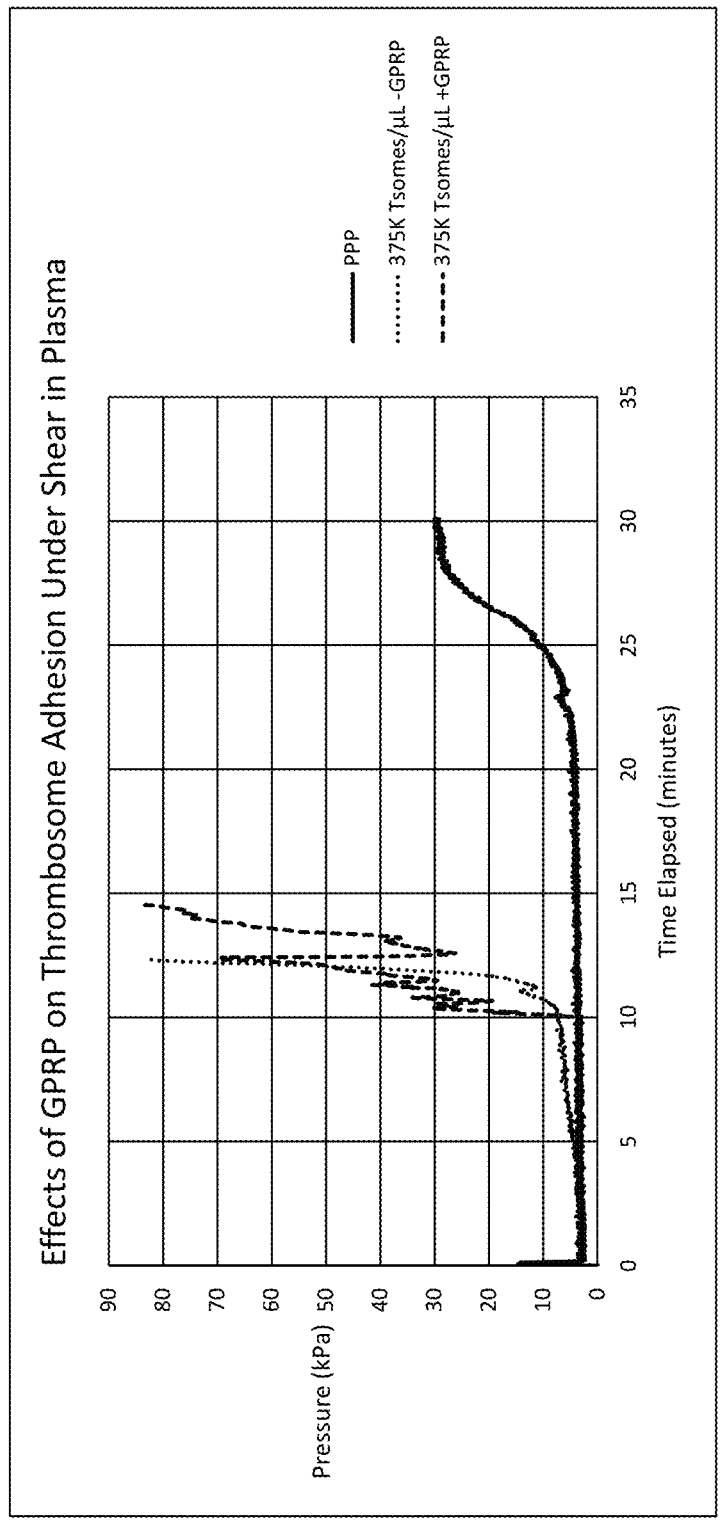
FIG. 61E shows a plot of the effect of GPRP on thrombosome adhesion under shear in plasma.

The effect of GPRP (1 mM) on occlusion activity was also assayed. Table 27 shows T-TAS® results for platelet-poor plasma, with and without thrombosomes in the presence and absence of GPRP. Adding GPRP to prevent fibrinogen formation did not prevent the thrombosome-containing sample from reaching occlusion pressure. While the addition of GPRP to thrombosome samples in plasma prevents the formation of fibrin in the microcapillary channel (FIGS. 61C (no GPRP) and 61D (GPRP), both in GK PPP), the addition of GPRP to thrombosomes PPP did not prevent thrombus formation (FIG. 61E).

TABLE 27

AR Chip: GPRP Comparison

| Sample Type | Actual Tsome Concentration (×10^3/μL) | Base Pressure (kPa) | Occlusion Start Time (hh:mm:ss) | Occlusion Time (hh:mm:ss) | Occlusion Speed (kPa/min) | Area Under Curve |
|---|---|---|---|---|---|---|
| GK PPP (No Tsomes) | 0 | 2.7 | 0:25:34 | 0:00:00† | 0 | 138.8 |
| GK PPP + 1 mM GPRP (No Tsomes) | 0 | 3.5 | 0:00:00 | 0:00:00† | 0 | 52.43 |
| GK PPP + 375 k Tsomes | 384 | 2.8 | 0:10:54 | 0:12:20 | 48.8 | 1479.8 |
| GK PPP + 375 k Tsomes with 1 mM GPRP | 380 | 3.2 | 0:10:09 | 0:14:32 | 16 | 1426.9 |

†Test timed out

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above. Furthermore, one having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. Embodiments of the invention so claimed are inherently or expressly described and enabled herein. In order to determine the metes and bounds of the invention, therefore, reference should be made to the appended claims.

What is claimed is:

1. A method for restoring hemostasis in a subject, wherein the method comprises:

rehydrating a platelet derivative composition in the form of a powder, said composition comprising an effective amount of the platelet derivatives and an incubating agent comprising one or more saccharides, one or more salts, and a buffer to form a rehydrated platelet derivative composition, and administering the rehydrated platelet derivative composition comprising the effective amount of the platelet derivatives to the subject, wherein the subject has been treated or is being treated with at least one antiplatelet agent, wherein at least 70% of the platelet derivatives in the rehydrated platelet derivative composition are CD41 positive platelet derivatives when measured using flow cytometry, and less than 5% of the CD41 positive platelet derivatives are microparticles, wherein at least 70% of the platelet derivatives in the rehydrated platelet derivative composition are CD42 positive platelet derivatives, when measured using flow cytometry, wherein at least 70% of the platelet derivatives in the rehydrated platelet derivative composition are CD62 positive platelet derivatives, when measured using flow cytometry, wherein the platelet derivatives are capable of generating thrombin in an in vitro thrombin formation assay, wherein the platelet derivatives have in vitro occlusion activity, and wherein the platelet derivatives show an inability to increase expression of a platelet activation marker in the presence of an agonist as compared to the expression of the platelet activation marker in the absence of the agonist, and wherein the agonist is thrombin receptor activator peptide 6 (TRAP-6) and the platelet activation marker can be detected by binding of Annexin V to the platelet derivatives.

2. The method of claim 1, wherein the subject is being treated with an antiplatelet agent.

3. The method of claim 2, wherein the one or more saccharides comprise trehalose.

4. The method of claim 3, wherein the platelet derivatives have the in vitro occlusion activity, such that when forced through a collagen-coated microchannel at a concentration of at least $255 \times 10^3$ particles/µL they are capable of attaining a pressure of 80 kPa in less than 14 minutes in platelet-reduced citrated whole blood in an in vitro total thrombus-formation analysis system (T-TAS) assay.

5. The method of claim 3, wherein less than 3.5% of the CD41 positive platelet derivatives are microparticles.

6. The method of claim 3, wherein the one or more saccharides further comprise polysucrose, and wherein the one or more salts are selected from the group consisting of phosphate salts, sodium salts, potassium salts, calcium salts, magnesium salts, and a combination of two or more thereof.

7. The method of claim 6, wherein the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, and sarpogrelate.

8. The method of claim 6, wherein the administering comprises administering intravenously the rehydrated platelet derivative composition comprising the effective amount of the platelet derivatives.

9. The method of claim 6, wherein the antiplatelet agent is selected from the group consisting of cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, and sarpogrelate.

10. The method of claim 9, wherein the subject is being treated with aspirin in addition to the antiplatelet agent.

11. The method of claim 6, wherein the platelet derivatives are capable of generating thrombin in the in vitro thrombin formation assay, such that the platelet derivatives at a concentration of at least $4.8 \times 10^3$ particles/µl generate a thrombin peak height of at least 25 nM in the presence of a reagent containing tissue factor and phospholipids.

12. The method of claim 6, wherein less than 3.5% of the CD41 positive platelet derivatives are microparticles, and wherein the rehydrated platelet derivative composition comprises trehalose in an amount from 50 mM to 200 mM, and polysucrose in amount from 3% to 10%.

13. The method of claim 1, wherein the method is for preparing a subject for surgery.

14. A method for restoring hemostasis in a subject, wherein the method comprises:

rehydrating a platelet derivative composition in the form of a powder, said composition comprising an effective amount of the platelet derivatives and an incubating agent comprising one or more saccharides, one or more salts, and a buffer to form a rehydrated platelet derivative composition, and administering the rehydrated platelet derivative composition comprising the effective amount of the platelet derivatives to the subject, wherein the rehydrated platelet derivative composition comprises a population of platelet derivatives comprising CD 41 positive platelet derivatives, wherein less than 5% of the CD 41 positive platelet derivatives are microparticles, wherein at least 70% of the platelet derivatives in the rehydrated platelet derivative composition are CD42 positive platelet derivatives, when measured using flow cytometry, wherein at least 70% of the platelet derivatives in the rehydrated platelet derivative composition are CD 41 positive platelet derivatives, when measured using flow cytometry, wherein at least 70% of the platelet derivatives in the rehydrated platelet derivative composition are CD62 positive platelet derivatives, when measured using flow cytometry, wherein the platelet derivatives are capable of generating thrombin in an in vitro thrombin formation assay, wherein the platelet derivatives have in vitro occlusion activity, and wherein the platelet derivatives show an inability to increase expression of a platelet activation marker in the presence of an agonist as compared to the expression of the platelet activation marker in the absence of the agonist, and wherein the agonist is thrombin receptor activator peptide 6 (TRAP-6) and the platelet activation marker can be detected by binding of Annexin V to the platelet derivatives.

15. The method of claim 14, wherein the subject has a clotting-related disorder selected from the group consisting of Von Willebrand Disease, hemophilia, thrombasthenia, and thrombocytopenia.

16. The method of claim 15, wherein the one or more saccharides comprise trehalose and polysucrose.

17. The method of claim 16, wherein the trehalose in the rehydrated platelet derivative composition is in an amount from 50 mM to 200 mM, and wherein the polysucrose in the rehydrated platelet derivative composition in amount from 3% to 10%.

18. The method of claim 16, wherein the one or more salts are selected from the group consisting of phosphate salts, sodium salts, potassium salts, calcium salts, magnesium salts, and a combination of two or more thereof.

19. The method of claim 18, wherein the buffer comprises 4-(2-hydroxyethyl)-1-piperazineethanesulfonic acid (HEPES).

20. The method of claim 16, wherein less than 3.5% of the CD 41 positive platelet derivatives are microparticles.

21. The method of claim 16, wherein the platelet derivatives have the in vitro occlusion activity, such that when forced through a collagen-coated microchannel at a concentration of at least 255×10³ particles/µL they are capable of attaining a pressure of 80 kPa in less than 14 minutes in platelet-reduced citrated whole blood in an in vitro total thrombus-formation analysis system (T-TAS) assay.

22. The method of claim 16, wherein the administering comprises administering intravenously the rehydrated platelet derivative composition comprising the effective amount of the platelet derivatives.

23. A method for administering platelet derivatives to a subject,
wherein the method comprises:
rehydrating a platelet derivative composition in the form of a powder, said composition comprising an effective amount of the platelet derivatives and an incubating agent comprising one or more saccharides comprising 10-60% trehalose by weight, one or more salts, and a buffer to form a rehydrated platelet derivative composition, and
administering intravenously the rehydrated platelet derivative composition comprising the effective amount of the platelet derivatives to the subject,
wherein the rehydrated platelet derivative composition comprises a population of platelet derivatives comprising CD 41 positive platelet derivatives, wherein less than 5% of the CD 41 positive platelet derivatives are microparticles,
wherein at least 70% of the platelet derivatives in the rehydrated platelet derivative composition are CD42 positive platelet derivatives, when measured using flow cytometry,
wherein at least 70% of the platelet derivatives in the rehydrated platelet derivative composition are CD41 positive platelet derivatives, when measured using flow cytometry,
wherein at least 70% of the platelet derivatives in the rehydrated platelet derivative composition are CD62 positive platelet derivatives, when measured using flow cytometry,
wherein the platelet derivatives in the rehydrated platelet derivative composition have thrombospondin (TSP) on their surface at a level that is greater than a level of TSP on the surface of resting platelets,
wherein the platelet derivatives in the rehydrated platelet derivative composition have von Willebrand factor (vWF) on their surface at a level that is greater than a level of vWF on the surface of resting platelets,
wherein the platelet derivatives are capable of generating thrombin in an in vitro thrombin formation assay,
wherein the platelet derivatives have in vitro occlusion activity,
wherein the platelet derivatives show an inability to increase expression of a platelet activation marker in the presence of an agonist as compared to the expression of the platelet activation marker in the absence of the agonist, and wherein the agonist is thrombin receptor activator peptide 6 (TRAP-6) and the platelet activation marker can be detected by binding of Annexin V to the platelet derivatives, and
wherein the administering the rehydrated platelet derivative composition restores hemostasis in the subject.

24. The method of claim 23, wherein the one or more saccharides further comprises polysucrose.

25. The method of claim 24, wherein the composition in the form of the powder comprises the trehalose in a range of 20-35% by weight, and the polysucrose in a range of 45-60% by weight.

26. The method of claim 25, wherein the platelet derivative composition in the form of the powder is in a container,
wherein the container is at least one container from a plurality of containers,
wherein the plurality of containers comprise the platelet derivatives from at least 2 different lots in separate containers, and
wherein the amount of microparticles in the powder of any two containers chosen from different lots, differs by less than 10%.

27. The method of claim 23, wherein the platelet derivative composition in the form of the powder is prepared by a process, comprising:
performing tangential flow filtration (TFF) of a platelet composition comprising platelets in a preparation agent comprising a buffering agent, trehalose in an amount in the range of 10 mM to 500 mM, and polysucrose in an amount in the range of 3% to 7%, thereby preparing a TFF-treated composition comprising at least 1000×10³ platelets/µl in an aqueous medium having less than or equal to 7.5% plasma protein and having less than 5.0% microparticles by scattering intensity;
freeze drying the TFF-treated composition comprising platelets in the aqueous medium to form a freeze-dried platelet derivative composition comprising platelet derivatives; and
heating the freeze-dried platelet derivative composition at a temperature in the range of 60° C. to 90° C. for at least 1 hour to not more than 36 hours to thermally treat the platelet derivatives in the freeze-dried platelet derivative composition to form the platelet derivative composition in the form of the powder.

28. The method of claim 17, wherein the platelet derivatives are capable of generating thrombin in the in vitro thrombin formation assay, such that the platelet derivatives at a concentration of at least 4.8×10³ particles/µl generate a thrombin peak height of at least 25 nM in the presence of a reagent containing tissue factor and phospholipids.

29. The method of claim 17, wherein less than 3.5% of the CD 41 positive platelet derivatives are microparticles.

30. The method of claim 14, wherein less than 3.5% of the CD 41 positive platelet derivatives are microparticles.

* * * * *